(12) United States Patent
Gasser et al.

(10) Patent No.: US 12,049,515 B2
(45) Date of Patent: Jul. 30, 2024

(54) AGONISTIC CD28 ANTIGEN BINDING MOLECULES TARGETING HER2

(71) Applicant: Hoffmann-La Roche Inc., Little Falls, NJ (US)

(72) Inventors: Stephan Gasser, Schlieren (CH); Thomas Hofer, Schlieren (CH); Teemu Tapani Junttila, South San Francisco, CA (US); Christian Klein, Schlieren (CH); Christine Kuettel, Schlieren (CH); Jenny Tosca Thom, Schlieren (CH); Pablo Umaña, Schlieren (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 64 days.

(21) Appl. No.: 17/354,409

(22) Filed: Jun. 22, 2021

(65) Prior Publication Data

US 2022/0017637 A1 Jan. 20, 2022

(30) Foreign Application Priority Data

Jun. 23, 2020 (EP) .................................... 20181730

(51) Int. Cl.
*C07K 16/32* (2006.01)
*A61K 39/395* (2006.01)
*A61K 45/06* (2006.01)
*A61P 35/00* (2006.01)
*C07K 16/28* (2006.01)

(52) U.S. Cl.
CPC .......... *C07K 16/32* (2013.01); *A61K 39/3955* (2013.01); *A61K 39/39558* (2013.01); *A61K 45/06* (2013.01); *A61P 35/00* (2018.01); *C07K 16/2809* (2013.01); *C07K 16/2818* (2013.01); *C07K 16/2827* (2013.01); *C07K 2317/31* (2013.01); *C07K 2317/52* (2013.01); *C07K 2317/522* (2013.01); *C07K 2317/55* (2013.01); *C07K 2317/565* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,565,332 A | 10/1996 | Hoogenboom et al. | |
| 5,571,894 A | 11/1996 | Wels et al. | |
| 5,587,458 A | 12/1996 | King et al. | |
| 5,677,171 A | 10/1997 | Hudziak et al. | |
| 5,731,168 A | 3/1998 | Carter et al. | |
| 5,821,337 A | 10/1998 | Carter et al. | |
| 5,869,046 A | 2/1999 | Presta et al. | |
| 6,054,297 A | 4/2000 | Carter et al. | |
| 6,165,464 A | 12/2000 | Hudziak et al. | |
| 6,248,516 B1 | 6/2001 | Winter et al. | |
| 6,339,142 B1 | 1/2002 | Basey et al. | |
| 6,407,213 B1 | 6/2002 | Carter et al. | |
| 6,602,684 B1 | 8/2003 | Umana et al. | |
| 6,639,055 B1 | 10/2003 | Carter et al. | |
| 6,719,971 B1 | 4/2004 | Carter et al. | |
| 6,800,738 B1 | 10/2004 | Carter et al. | |
| 6,818,418 B1 | 11/2004 | Lipovsek et al. | |
| 6,982,321 B2 | 1/2006 | Winter et al. | |
| 7,074,404 B2 | 7/2006 | Basey et al. | |
| 7,087,409 B2 | 8/2006 | Barbas et al. | |
| 7,166,697 B1 | 1/2007 | Galanis et al. | |
| 7,250,297 B1 | 7/2007 | Beste et al. | |
| 7,521,541 B2 | 4/2009 | Eigenbrot et al. | |
| 7,527,791 B2 | 5/2009 | Adams et al. | |
| 7,560,111 B2 | 7/2009 | Kao et al. | |
| 7,695,936 B2 | 4/2010 | Carter et al. | |
| 10,882,922 B2 * | 1/2021 | Yang | A61P 29/00 |
| 2003/0157108 A1 | 8/2003 | Presta et al. | |
| 2004/0093621 A1 | 5/2004 | Shitara et al. | |
| 2004/0132028 A1 | 7/2004 | Stumpp et al. | |
| 2004/0132066 A1 | 7/2004 | Balint et al. | |
| 2007/0224633 A1 | 9/2007 | Skerra et al. | |
| 2008/0139791 A1 | 6/2008 | Lipovsek et al. | |

FOREIGN PATENT DOCUMENTS

| | | |
|---|---|---|
| EP | 0404097 B1 | 9/1996 |
| EP | 1641818 B1 | 12/2008 |
| WO | 93/01161 A1 | 1/1993 |
| WO | 93/16185 A2 | 8/1993 |
| WO | 93/16185 A3 | 8/1993 |
| WO | 97/30087 A1 | 8/1997 |
| WO | 98/525964 A1 | 12/1998 |
| WO | 99/22764 A1 | 5/1999 |
| WO | 02/020565 A2 | 3/2002 |

(Continued)

OTHER PUBLICATIONS

Acuto et al., "CD28-mediated co-stimulation: a quantitative support for TCR signalling." Nat. Rev. Immunol. 3:939-951 (2003).
Ali, S., et al., "Transferrin Trojan Horses as a Rational Approach for the Biological Delivery of Therapeutic Peptide Domains" J Biol Chem 274(34):24066-24073 (Aug. 20, 1999).
Almagro and Fransson, "Humanization of antibodies" Front Biosci 13:1619-1633 (Jan. 1, 2008).
Bahlis et al., "CD28-mediated regulation of multiple myeloma cell proliferation and survival" Blood 109(11):5002-5010 (2007).
Baselga, J., et al., "Phase II study of weekly intravenous recombinant humanized anti-p185HER2 monoclonal antibody in patients with HER2/neu-overexpressing metastatic breast cancer" J Clin Oncol 14(3):737-744 (Mar. 1, 1996).

(Continued)

*Primary Examiner* — Laura B Goddard
*Assistant Examiner* — Sarah A Alsomairy
(74) *Attorney, Agent, or Firm* — Lawrence S. Graham

(57) ABSTRACT

The present invention relates to Her2-targeted bispecific agonistic CD28 antigen binding molecules characterized by monovalent binding to CD28, methods for their production, pharmaceutical compositions containing these antibodies, and methods of using the same.

37 Claims, 11 Drawing Sheets

Specification includes a Sequence Listing.

(56) References Cited

FOREIGN PATENT DOCUMENTS

| WO | 03/011878 A2 | 2/2003 |
|---|---|---|
| WO | 2005/056764 A2 | 6/2005 |
| WO | 2006/050949 A2 | 5/2006 |
| WO | 2006/050949 A3 | 5/2006 |
| WO | 2008/098796 A1 | 8/2008 |
| WO | 2009/089004 A1 | 7/2009 |
| WO | 2012/020006 A2 | 2/2012 |
| WO | 2012/130831 A1 | 10/2012 |
| WO | 2012/143523 A1 | 10/2012 |
| WO | 2015/091738 A1 | 6/2015 |
| WO | 2015/150447 A1 | 10/2015 |
| WO | 2017/180913 A2 | 10/2017 |
| WO | 2017/180913 A3 | 10/2017 |

OTHER PUBLICATIONS

Baselga, J., et al., "Recombinant Humanized Anti-HER2 Antibody (Herceptin™) Enhances the Antitumor Activity of Paclitaxel and Doxorubicin against HER2/neu Overexpressing Human Breast Cancer Xenografts" Cancer Res. 58(13):2825-2831 (Jul. 1, 1998).
Binz, H., et al., "Designing Repeat Proteins: Well-expressed, Soluble and Stable Proteins from Combinatorial Libraries of Consensus Ankyrin Repeat Proteins" J Mol Biol 332(2):489-503 (Sep. 12, 2003).
Boomer and Green et al., "An Enigmatic Tail of CD28 Signaling" Herb Perspect Biol. 2(a002436):1-20 (2010).
Borghouts, C., et al., "Peptide aptamers: recent developments for cancer therapy" Expert Opin Biol Th 5(6):783-797 (Nov. 24, 2005).
Bowie, J. et al., "Deciphering the message in protein sequences: tolerance to amino acid substitutions" Science 247(4948):1306-1310 (Mar. 16, 1990).
Braddock, M., "11th Annual Inflammatory and Immune Diseases Drug Discovery and Development Summit" Expert Opin Inv Drug 16(6):909-917 (Jun. 1, 2007).
Carreno and Collins et al., "The B7 Family of Ligands and Its Receptors: New Pathways for Costimulation and Inhibition of Immune Responses" Annu Rev Immunol(20):29-53 (2002).
Carter et al., "Bispecific human IgG by design" J Immunol Methods 248(1-2):7-15 (Feb. 1, 2001).
Chames et al., "Bispecific antibodies for cancer therapy" MABS 1(6):539-547 (2009).
Chen et al., "Molecular mechanisms of T cell co-stimulation and co-inhibition" Nat. Rev. Immunol. 13:227-242 (2013).
Cho, H.S., et al., "Structure of the extracellular region of HER2 alone and in complex with the Herceptin Fab" Nature 421(6924):756-760 (Feb. 13, 2003).
Clackson, T., et al., "Making antibody fragments using phage display libraries" Nature 352(6336):624-628 (Aug. 15, 1991).
ClinicalTrials.gov, "A Dose-Finding Study of Pertuzumab (Perjeta) in Combination With Trastuzumab (Herceptin) in Healthy Male Participants and Women With Early Breast Cancer (EBC)" (History of Changes for Study: NCT02738970; Submitted: Jul. 1, 2016 (v4); Latest Version: Jun. 11, 2018; Printed: Jun. 2, 2021) pp. 1-12, Retrieved from: https://www.clinicaltrials_gov/ct2/show/NCT02738970.
Coussens, L., et al., "Tyrosine Kinase Receptor with Extensive Homology to EGF Receptor Shares Chromosomal Location with neu Oncogene" Science 230(4730):1132-1139 (Dec. 6, 1985).
Dall'Acqua et al., "Antibody humanization by framework shuffling" Methods 36:43-60 (2005).
Engelhardt et al., "CTLA-4 Overexpression Inhibits T Cell Responses through a CD28-B7-Dependent Mechanism" J. Immunol. 177:1052-1061 (2003).
Esensten et al., "CD28 costimulation: from mechanism to therapy" Immunity 44(5):973-988 (2016).
Franklin et al., "Insights into ErbB signaling from the structure of the ErbB2-pertuzumab complex" Cancer Cell 5:317-328 (Apr. 2004).

Fraser et al., "Regulation of interleukin-2 gene enhancer activity by the T cell accessory molecule CD28" Science 251:313-316 (1991).
Gao, Y., et al., "Comparative Transcriptome Analysis of Fetal Skin Reveals Key Genes Related to Hair Follicle Morphogenesis in Cashmere Goats" PLOS One 11(3 Suppl e0151118):1-20 (Mar. 9, 2016).
Gebauer and Skerra, "Engineered protein scaffolds as next-generation antibody therapeutics" Curr Opin Chem Biol 13(3):245-255 (Jun. 1, 2009).
Genentech, Inc., "Herceptin®—Trastuzumab—Trastuzumab United States Prescribing Information (USPI)" (US FDA-Package Insert; U.S. BLA Supplement: Herceptin®—Genentech, Inc.; 481704; Revised),:1-28 (Aug. 1, 2002).
Genentech, Inc. "Kadcyla® (ado-trastuzumab emtansine) for injection, for intravenous use, Initial U.S. Approval: 2013" Highlights of Prescribing and Full Prescribing Information (Revised: Sep. 2020), pp. 1-34.
Gerngross, T., "Advances in the Production of Human Therapeutic Proteins in Yeasts and Filamentous Fungi" Nat Biotechnol 22(11):1409-1414 (Nov. 22, 2004).
Gerstmayer et al., "Costimulation of T Cell Proliferation by a Chimeric B7-2 Antibody Fusion Protein Specifically Targeted to Cells Expressing the erbB2 Proto-Oncogene" J Immunol 158:4584-4590 (1997).
Harari, D., et al., "Molecular mechanisms underlying ErbB2/HER2 action in breast cancer" Oncogene 19(53):6102-6114 (Dec. 1, 2000).
Heeley, R. et al., "Mutations Flanking the Polyglutamine Repeat in the Modulatory Domain of Rat Glucocorticoid Receptor Lead to an Increase in Affinity for Hormone" Endocr Res 28(3):217-229 (Aug. 1, 2002).
Holliger, P., et al., "Diabodies: Small Bivalent and Bispecific Antibody Fragments" PNAS 90(14):6444-6448 (Jul. 15, 1993).
Hoogenboom, H., et al., "Overview of antibody phage-display technology and its applications" Methods Mol Biol 178:1-37 (2002).
Hotaling, T. et al., "The humanized anti-HER2 antibody rhuMAb HER2 mediates antibody dependent cell-mediated cytotoxicity via FcγR III" Proceedings of the American Association for Cancer Research (Abstract #3215), 37:471 (Mar. 1996).
Hudson, P., et al., "Engineered antibodies" Nat Med 9(1):129-134 (Jan. 1, 2003).
Hudziak, R., et al., "p185HER2 monoclonal antibody has antiproliferative effects in vitro and sensitizes human breast tumor cells to tumor necrosis factor" Mol Cell Biol 9(3):1165-1172 (Mar. 1, 1989).
Hui et al., "T cell costimulatory receptor CD28 is a primary target for PD-1-mediated inhibition" Science 355:1428-1433 (2017).
Hunig et al., "The storm has cleared: lessons from the CD28 superagonist TGN1412 trial" Nat. Rev. Immunol. 12:317-318 (2012).
Huston, J. et al., "Protein Engineering of Single-Chain Fv Analogs and Fusion Proteins" Methods in Enzymology 203:46-96 (1991).
International Search and Written Opinion for PCT/EP2021/066901 mailed Sep. 22, 2021.
Irving, R., et al., "Ribosome display and affinity maturation: from antibodies to single V-domains and steps towards cancer therapeutics" J Immunol Methods 248(1-2):31-45 (Feb. 1, 2001).
Isaacs et al., "T cell immunomodulation—the Holy Grail of therapeutic tolerance" Curr. Opin Pharmacol 7:418-425 (2007).
Jones, P.T., et al., "Replacing the Complementarity-Determining Regions in a Human Antibody with Those From a Mouse" Nature 321(6069):522-525 (May 29, 1986).
June et al., "T-Cell Proliferation Involving the CD28 Pathway Is Associated with Cyclosporine-Resistant Interleukin 2 Gene Expression" Mol. Cell .Biol. 7(12):4472-4481 (1987).
Kam, N., et al., "Carbon nanotubes as multifunctional biological transporters and near-infrared agents for selective cancer cell destruction" PNAS 102(33):11600-11605 (Aug. 16, 2005).
Kamphorst et al., "Rescue of exhausted CD8 T cells by PD-1-targeted therapies is CD28-dependent" Science 355:1423-1427 (2017).
Kashmiri, S., et al., "SDR grafting—a new approach to antibody humanization" Methods 36:25-34 (Jan. 1, 2005).
Klimka, A. et al., "Human anti-CD30 recombinant antibodies by guided phage antibody selection using cell panning" Brit J Cancer 83(2):252-260 (Jun. 15, 2000).

(56) References Cited

OTHER PUBLICATIONS

Kohl, A., et al., "Designed to be stable: Crystal structure of a consensus ankyrin repeat protein" PNAS 100(4):1700-1705 (Feb. 18, 2003).
Lavin et al., "Innate Immune Landscape in Early Lung Adenocarcinoma by Paired Single-Cell Analyses" Cell 169:750-765 (2017).
Lewis, G., et al., "Differential responses of human tumor cell lines to anti-p185HER2 monoclonal antibodies" Cancer Immunol Immunother 37(4):255-263 (Sep. 1, 1993).
Li, H., et al., "Optimization of humanized IgGs in glycoengineered *Pichia pastoris*" Nat Biotechnol 24(2):210-215 (Feb. 1, 2006).
Liljeblad, M., et al., "Analysis of agalacto-IgG in rheumatoid arthritis using surface plasmon resonance" Glycoconjugate J 17:323-329 (Jul. 14, 2000).
Linsley et al., "T-cell antigen CD28 mediates adhesion with B cells by interacting with activation antigen B7/BB-1" Proc. Natl. Acad. Sci. USA 87:5031-5035 (1990).
Lonberg, N., et al., "Fully human antibodies from transgenic mouse and phage display platforms" Curr Opin Immunol 20(4):450-459 (Aug. 1, 2008).
Lonberg, N., et al., "Human antibodies from transgenic animals" Nat Biotechnol 23(9):1117-1125 (Sep. 7, 2005).
Lopez-Albaitero et al., "Overcoming resistance to HER2-targeted therapy with a novel HER2/CD3 bispecific antibody" OncoImmunology 6(3):e1267891-12 (2017).
Malik et al., "Dose-Response Studies of Recombinant Humanized Monoclonal Antibody 2C4 in Tumor Xenograft Models" Pro Am Soc Cancer Res 44:Abstract No. 773 (2003).
McCafferty, J., et al., "Phage Antibodies: Filamentous Phage Displaying Antibody Variable Domains" Nature 348(6301):552-554 (Dec. 6, 1990).
Morrison and Oi, "Genetically Engineered Antibody Molecules" Adv Immunol 44:65-92 (1989).
Morrison et al., "The purification and characterization of fetal liver hematopoietic stem cells" Proc. Natl. Acad. Sci. USA 92(22):10302-10306 (1995).
Morrison et al., "Chimeric human antibody molecules: Mouse antigen-binding domains with human constant region domains" Proc. Natl. Acad. Sci. USA 81(21):6851-6855 (Nov. 1, 1984).
Murray et al., "CD28-mediated pro-survival signaling induces chemotherapeutic resistance in multiple myeloma" Blood 123(24):3770-3779.
Sequence >NP_000724.1 T-cell surface glycoprotein CD3 epsilon chain precursor [*Homo sapiens*] MQSGTHWRVLGLCLLSVGVW GQDGNEEMGGITQTPYKVSISGTTVILTCPQYPGSEILWQHN DKNIGGDEDDKNIGSDEDHLSLKEFSELEQSGYYVCYPRGS KPEDANFYLYLRARVCENCMEMDVMSVATIVIVDICITGGLL LLVYYWSKNRKAKAKPVTRGAGAGGRQRGQNKERPPPVPN PDYEPIRKGQRDLYSGLNQRRI, NCBI, Retrieve from internet on Oct. 1, 2021.
Osbourn, J. et al., "From rodent reagents to human therapeutics using antibody guided selection" Methods 36(1):61-68 (May 1, 2005).
Padlan, E., et al., "A possible procedure for reducing the immunogenicity of antibody variable domains while preserving their ligand-binding properties" Mol Immunol 28(4-5):489-498 (Apr. 30, 1991).
Padlan, E., et al., "Anatomy of the Antibody Molecule" Mol Immunol 31(3):169-217 (Feb. 1, 1994).
Parker, M.H., et al., "Antibody mimics based on human fibronectin type three domain engineered for thermostability and high-affinity binding to vascular endothelial growth factor receptor two" Protein Eng Des Sel 18(9):435-444 (Aug. 8, 2005).

Pegram, M., et al., "Antibody dependent cell-mediated cytotoxicity in breast cancer patients in Phase III clinical trials of a humanized anti-HER2 antibody" P Am Assoc Canc Res (Abstract No. 4044), 38:602 (Mar. 1, 1997).
Pluckthun, A. et al. The Pharmacology of Monoclonal Antibodies "Antibodies from *Escherichia coli*" (Antibodies from *Escherichia coli*), Rosenberg & Moore, vol. 113:269-315 (1994).
Queen, C., et al., "A humanized antibody that binds to the interleukin 2 receptor" PNAS USA 86(24):10029-10033 (Dec. 1, 1989).
Ridgway, J., et al., "'Knobs-into-holes' engineering of antibody CH3 domains for heavy chain heterodimerization" Protein Eng 9(7):617-621 (Jul. 1, 1996).
Riechmann, L., et al., "Reshaping human antibodies for therapy" Nature 332:323-327 (Mar. 24, 1988).
Romer et al., "Preculture of PBMCs at high cell density increases sensitivity of T-cell responses, revealing cytokine release by CD28 superagonist TGN1412" Blood 118(26):6772-6782 (2011).
Silverman, J. et al., "Multivalent avimer proteins evolved by exon shuffling of a family of human receptor domains" Nat Biotechnol 23(12):1556-1561 (Dec. 1, 2005).
Skerra, A. et al., "Review: Lipocalins as a scaffold" Biochim Biophys Acta 1482(1-2):337-350 (Oct. 18, 2000).
Skokos et al., "A class of costimulatory CD28-bispecific antibodies that enhance the antitumor activity of CD3-bispecific antibodies" Sci. Transl. Med. 12(eaaw7888):1-14 (Jan. 8, 2020).
Slamon, D., et al., "Human breast cancer: correlation of relapse and survival with amplification of the HER-2/neuoncogene" Science 235(4785):177-182 (Jan. 9, 1987).
Slamon, D., et al., "Studies of the HER-2/neu proto-oncogene in human breast and ovarian cancer" Science 244(4905):707-712 (May 12, 1989).
Slamon, D., et al., "Use of chemotherapy plus a monoclonal antibody against HER2 for metastatic breast cancer that overexpresses HER2" New Engl J Med 344(11):783-792 (Mar. 15, 2001).
Sliwkowski et al., "Ready to partner" Nat Struct Biol 10(3):158-159 (Mar. 2003).
Sliwkowski, M.X., et al., "Nonclinical studies addressing the mechanism of action of trastuzumab (Herceptin)" Semin Oncol 26(Suppl 4 Suppl 12):60-70 (Aug. 1, 1999).
Stumpp, M., et al., "DARPins: A new generation of protein therapeutics" Drug Discov Today 13(15-16):695-701 (Aug. 1, 2008).
Tai et al., "Induction of autoimmune disease in CTLA-4-/-mice depends on a specific CD28 motif that is required for in vivo costimulation" Proc. Natl. Acad. Sci. USA 104:13756-13761 (2007).
Thompson et al., "CD28 activation pathway regulates the production of multiple T-cell-derived lymphokines/cytokines" P Natl Acad Sci USA 86(4):1333-7 (Feb. 1989).
Van Dijk and Van De Winkel et al., "Human antibodies as next generation therapeutics" Curr Opin Chem Biol 5(4):368-374 (Aug. 2001).
Verhoeyen, M., et al., "Reshaping human antibodies: Grafting an antilysozyme activity" Science 239(4847):1534-1536 (Mar. 25, 1988).
Wikman, M., et al., "Selection and characterization of HER2/neu-binding affibody ligands" Protein Eng Des Sel 17(5):455-462 (Jun. 18, 2004).
Wright, A., et al., "Effect of Glycosylation on Antibody Function: Implications for Genetic Engineering" Trends Biotechnol 15(1):26-32 (Jan. 1, 1997).
Yarden and Sliwkowski, "Untangling the ErbB Signalling Network" Nat Rev Mol Cell Biol, Macmillan Magazines, Ltd. 2:127-137 (Feb. 1, 2001).
Zahnd, C. et al., "A designed ankyrin repeat protein evolved to picomolar affinity to Her2" J Mol Biol 369(4):1015-1028 (Mar. 13, 2007).
Zheng et al., "Landscape of Infiltrating T Cells in Liver Cancer Revealed by Single-Cell Sequencing" Cell 169:1342-1356 (2017).

* cited by examiner

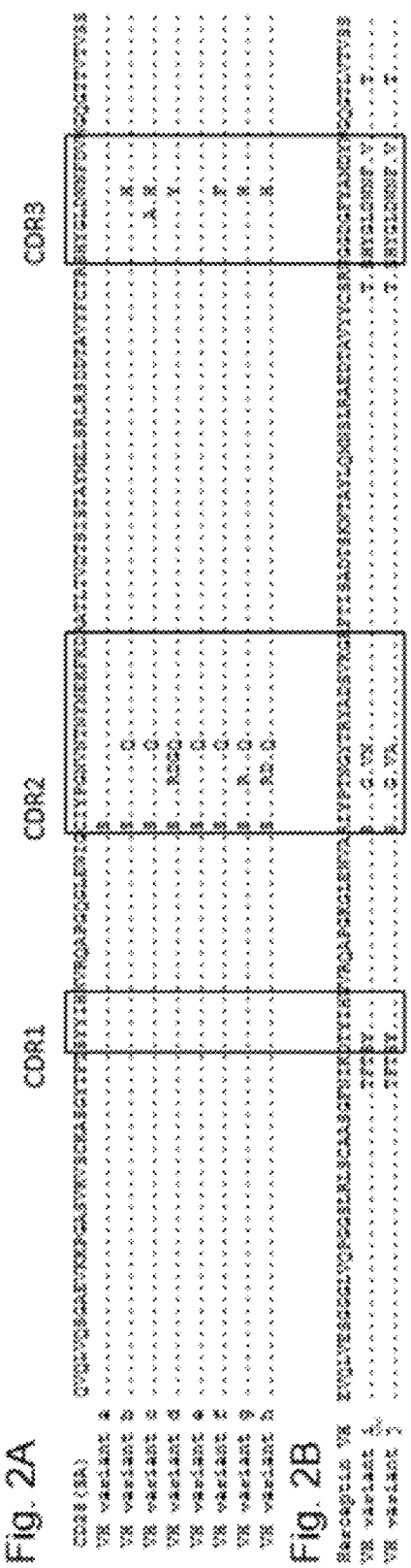
Fig. 2A
Fig. 2B
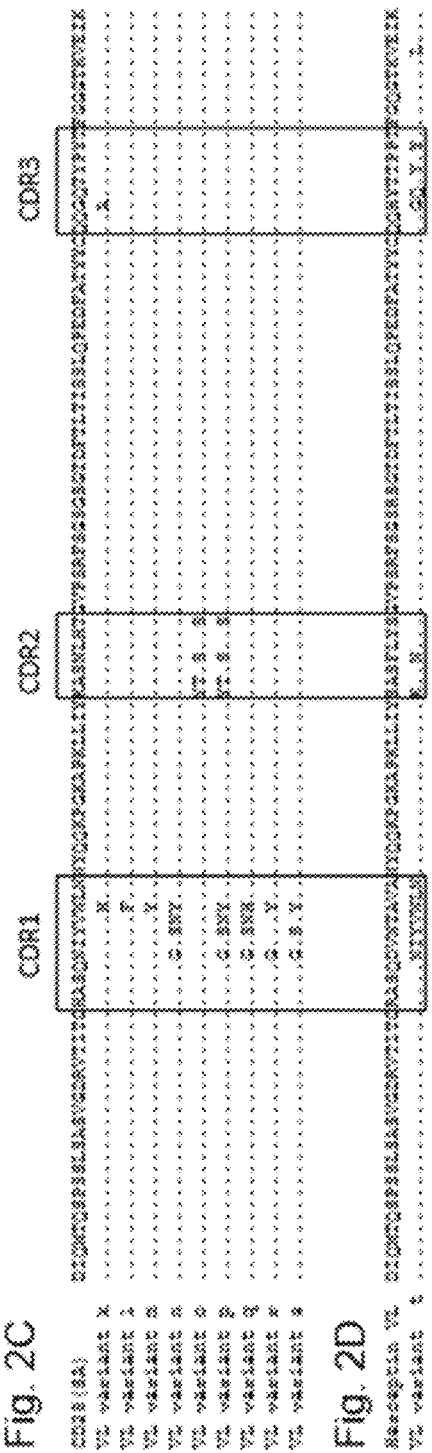
Fig. 2C
Fig. 2D

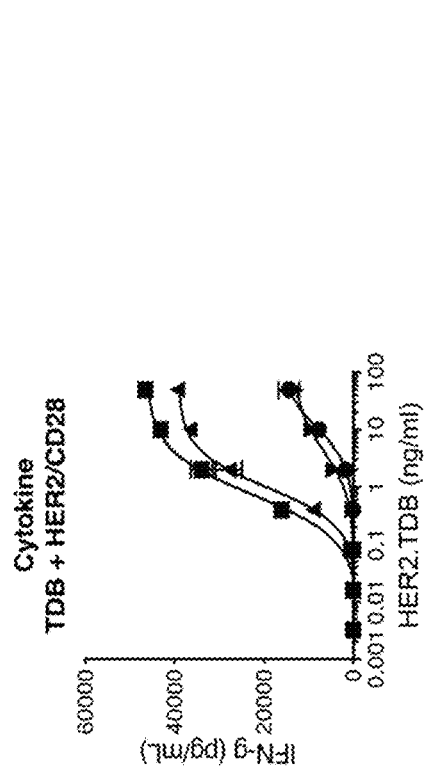
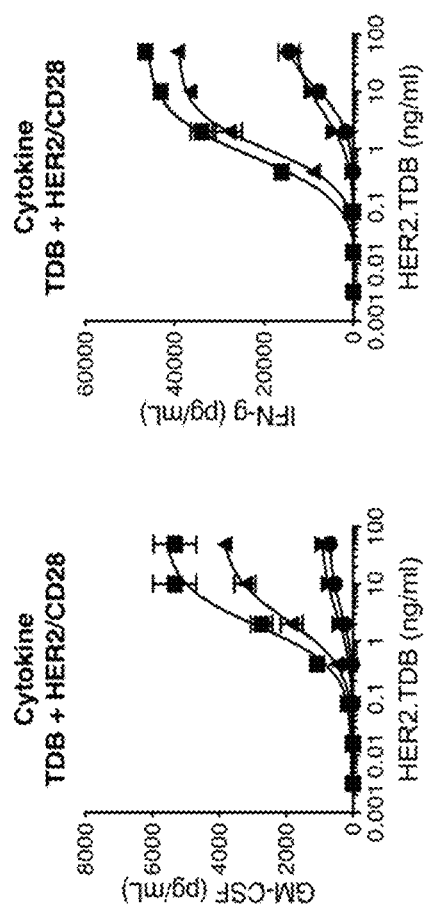
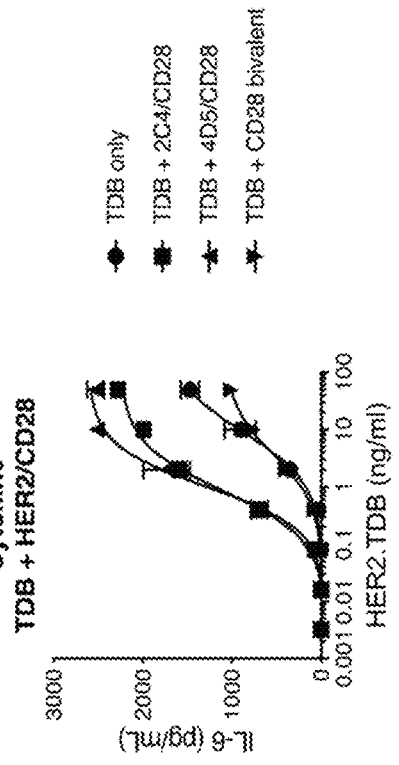
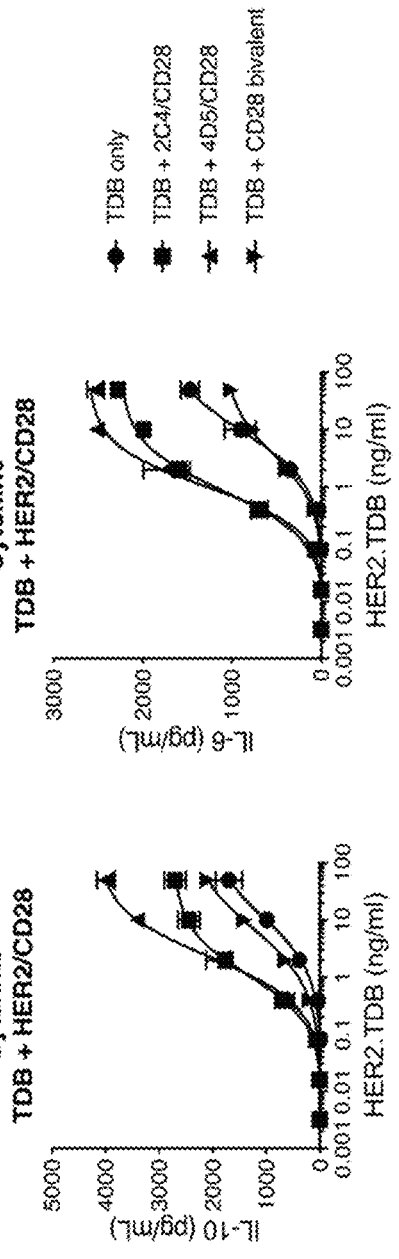

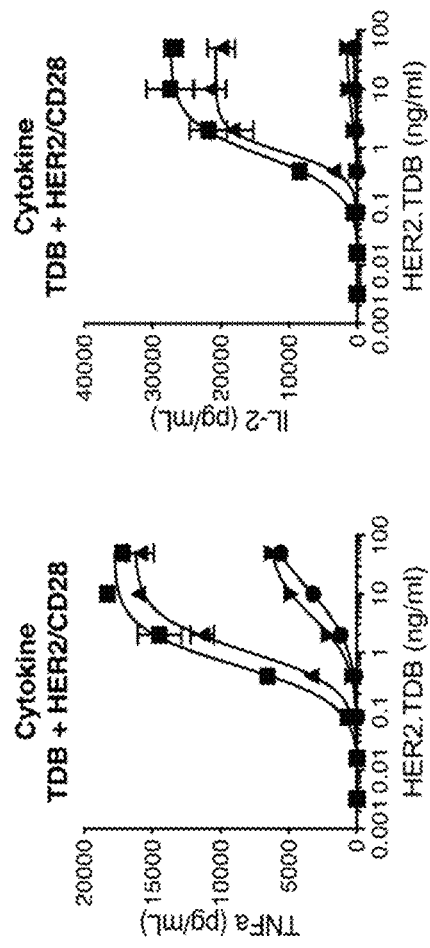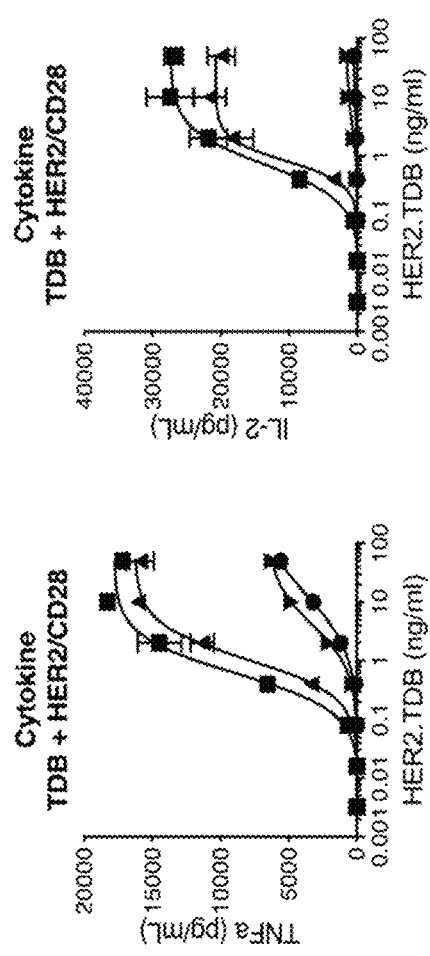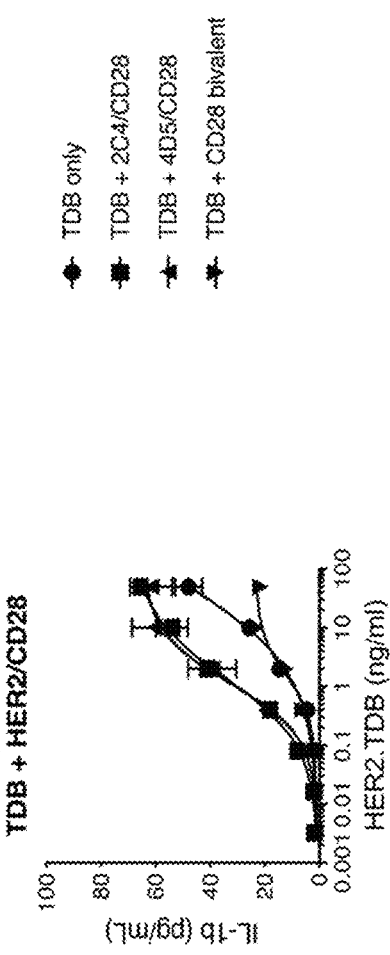

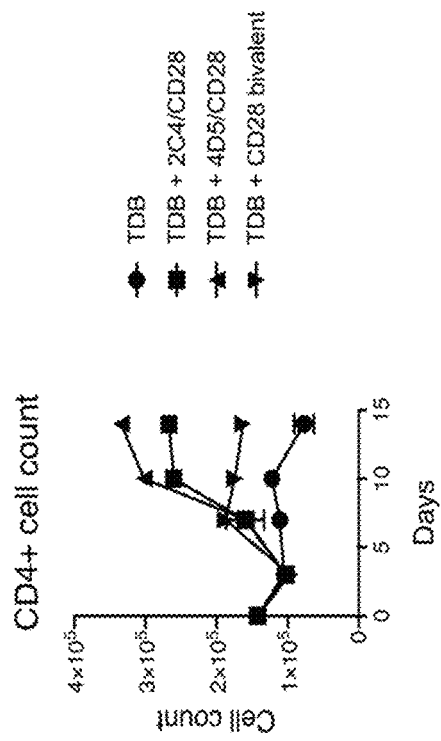
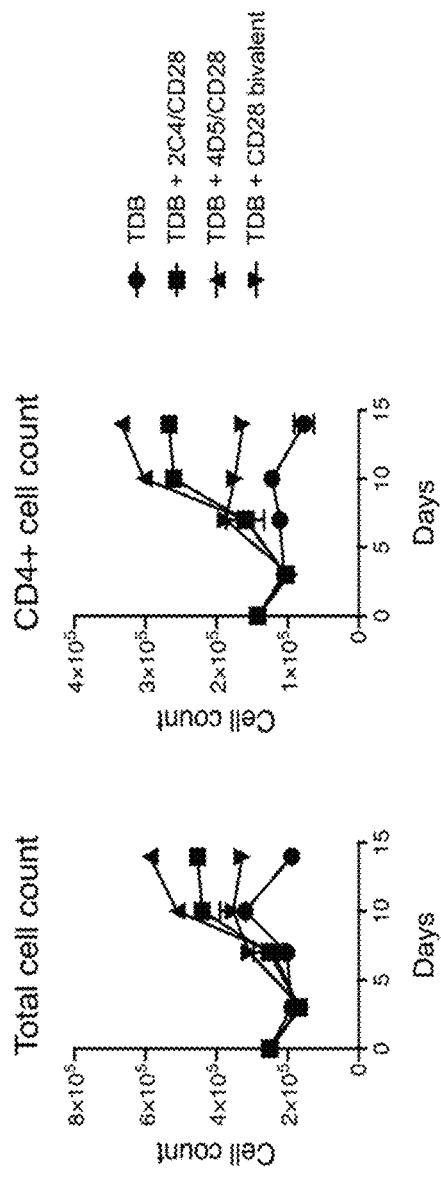
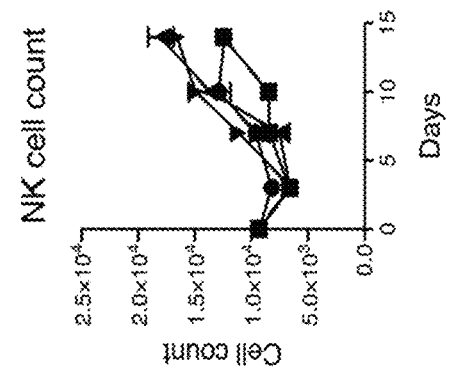
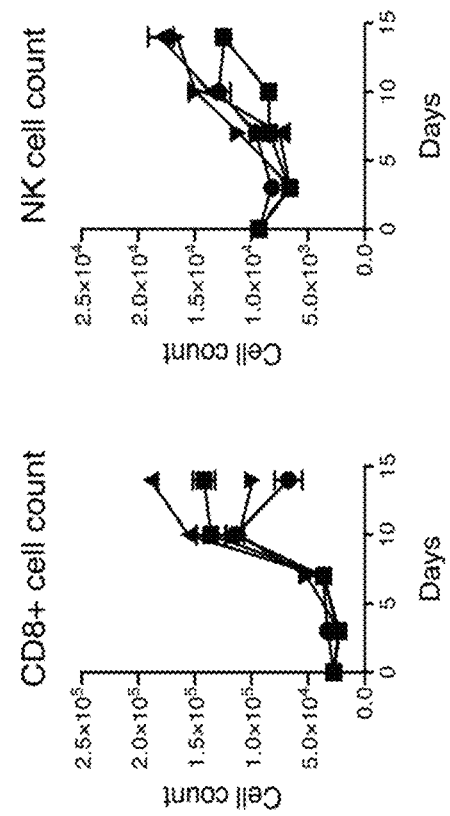

SEQUENCE LISTING

```
<160> NUMBER OF SEQ ID NOS: 189

<210> SEQ ID NO 1
<211> LENGTH: 220
<212> TYPE: PRT
<213> ORGANISM: Homo sapiens

<400> SEQUENCE: 1

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
```

-continued

```
                65                  70                  75                  80

Lys Thr Gly Phe Asn Cys Asp Gly Lys Leu Gly Asn Glu Ser Val Thr
                    85                  90                  95

Phe Tyr Leu Gln Asn Leu Tyr Val Asn Gln Thr Asp Ile Tyr Phe Cys
                    100                 105                 110

Lys Ile Glu Val Met Tyr Pro Pro Tyr Leu Asp Asn Glu Lys Ser
                    115                 120                 125

Asn Gly Thr Ile Ile His Val Lys Gly Lys His Leu Cys Pro Ser Pro
                    130                 135                 140

Leu Phe Pro Gly Pro Ser Lys Pro Phe Trp Val Leu Val Val Gly
                    145                 150                 155                 160

Gly Val Leu Ala Cys Tyr Ser Leu Leu Val Thr Val Ala Phe Ile Ile
                    165                 170                 175

Phe Trp Val Arg Ser Lys Arg Ser Arg Leu Leu His Ser Asp Tyr Met
                    180                 185                 190

Asn Met Thr Pro Arg Arg Pro Gly Pro Thr Arg Lys His Tyr Gln Pro
                    195                 200                 205

Tyr Ala Pro Pro Arg Asp Phe Ala Ala Tyr Arg Ser
                    210                 215                 220

<210> SEQ ID NO 2
<211> LENGTH: 5
<212> TYPE: PRT
<213> ORGANISM: Artificial Sequence
<220> FEATURE:
<223> OTHER INFORMATION: heavy chain CDR-H1, pertuzumab CLC

<400> SEQUENCE: 2

Asp Tyr Thr Met Asp
1               5

<210> SEQ ID NO 3
<211> LENGTH: 17
<212> TYPE: PRT
<213> ORGANISM: Artificial Sequence
<220> FEATURE:
<223> OTHER INFORMATION: heavy chain CDR-H2, pertuzumab CLC

<400> SEQUENCE: 3

Asp Val Asn Pro Asn Ser Gly Gly Ser Ile Val Asn Arg Arg Phe Lys
1               5                   10                  15

Gly

<210> SEQ ID NO 4
<211> LENGTH: 10
<212> TYPE: PRT
<213> ORGANISM: Artificial Sequence
<220> FEATURE:
<223> OTHER INFORMATION: heavy chain CDR-H3, pertuzumab CLC

<400> SEQUENCE: 4

Asn Leu Gly Pro Phe Phe Tyr Phe Asp Tyr
1               5                   10

<210> SEQ ID NO 5
<211> LENGTH: 9
<212> TYPE: PRT
<213> ORGANISM: Artificial Sequence
<220> FEATURE:
<223> OTHER INFORMATION: light chain CDR-L1, pertuzumab CLC

<400> SEQUENCE: 5
```

Lys Ala Ser Gln Asp Val Ser Thr Ala
1               5

<210> SEQ ID NO 6
<211> LENGTH: 7
<212> TYPE: PRT
<213> ORGANISM: Artificial Sequence
<220> FEATURE:
<223> OTHER INFORMATION: light chain CDR-L2, pertuzumab CLC

<400> SEQUENCE: 6

Ser Ala Ser Phe Arg Tyr Thr
1               5

<210> SEQ ID NO 7
<211> LENGTH: 9
<212> TYPE: PRT
<213> ORGANISM: Artificial Sequence
<220> FEATURE:
<223> OTHER INFORMATION: light chain CDR-L3, pertuzumab CLC

<400> SEQUENCE: 7

Gln Gln His Tyr Thr Thr Pro Pro Thr
1               5

<210> SEQ ID NO 8
<211> LENGTH: 119
<212> TYPE: PRT
<213> ORGANISM: Artificial Sequence
<220> FEATURE:
<223> OTHER INFORMATION: heavy chain variable domain VH, pertuzumab CLC

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Val Asn Arg Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Phe Phe Tyr Phe Asp Tyr Trp Gly Gln Gly
            100                 105                 110

Thr Leu Val Thr Val Ser Ser
        115

<210> SEQ ID NO 9
<211> LENGTH: 107
<212> TYPE: PRT
<213> ORGANISM: Artificial Sequence
<220> FEATURE:
<223> OTHER INFORMATION: light chain variable domain VL, pertuzumab CLC

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

```
Val Ala Trp Tyr Gln Gln Lys Pro Gly Lys Ala Pro Lys Leu Leu Ile
         35                  40                  45

Tyr Ser Ala Ser Phe Arg Tyr Thr Gly Val Pro Ser Arg Phe Ser Gly
         50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys
            100                 105

<210> SEQ ID NO 10
<211> LENGTH: 10
<212> TYPE: PRT
<213> ORGANISM: Artificial Sequence
<220> FEATURE:
<223> OTHER INFORMATION: heavy chain CDR-H1, trastuzumab CLC

<400> SEQUENCE: 10

Gly Phe Asn Ile Lys Asp Thr Tyr Ile His
1               5                   10

<210> SEQ ID NO 11
<211> LENGTH: 17
<212> TYPE: PRT
<213> ORGANISM: Artificial Sequence
<220> FEATURE:
<223> OTHER INFORMATION: heavy chain CDR-H2, trastuzumab CLC

<400> SEQUENCE: 11

Arg Ile Tyr Pro Thr Asn Gly Tyr Thr Arg Tyr Ala Asp Ser Val Lys
1               5                   10                  15

Gly

<210> SEQ ID NO 12
<211> LENGTH: 11
<212> TYPE: PRT
<213> ORGANISM: Artificial Sequence
<220> FEATURE:
<223> OTHER INFORMATION: heavy chain CDR-H3, trastuzumab CLC

<400> SEQUENCE: 12

Trp Gly Gly Glu Gly Phe Tyr Ala Met Asp Tyr
1               5                   10

<210> SEQ ID NO 13
<211> LENGTH: 9
<212> TYPE: PRT
<213> ORGANISM: Artificial Sequence
<220> FEATURE:
<223> OTHER INFORMATION: light chain CDR-L1, trastuzumab CLC

<400> SEQUENCE: 13

Lys Ala Ser Gln Asp Val Ser Thr Ala
1               5

<210> SEQ ID NO 14
<211> LENGTH: 7
<212> TYPE: PRT
<213> ORGANISM: Artificial Sequence
<220> FEATURE:
<223> OTHER INFORMATION: light chain CDR-L2, trastuzumab CLC

<400> SEQUENCE: 14
```

```
Ser Ala Ser Phe Arg Tyr Thr
1               5

<210> SEQ ID NO 15
<211> LENGTH: 9
<212> TYPE: PRT
<213> ORGANISM: Artificial Sequence
<220> FEATURE:
<223> OTHER INFORMATION: light chain CDR-L3, trastuzumab CLC

<400> SEQUENCE: 15

Gln Gln His Tyr Thr Thr Pro Pro Thr
1               5

<210> SEQ ID NO 16
<211> LENGTH: 120
<212> TYPE: PRT
<213> ORGANISM: Artificial Sequence
<220> FEATURE:
<223> OTHER INFORMATION: heavy chain variable domain VH, trastuzumab CLC

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Glu Gly Phe Tyr Ala Met Asp Tyr Trp Gly Gln
            100                 105                 110

Gly Thr Leu Val Thr Val Ser Ser
        115                 120

<210> SEQ ID NO 17
<211> LENGTH: 107
<212> TYPE: PRT
<213> ORGANISM: Artificial Sequence
<220> FEATURE:
<223> OTHER INFORMATION: light chain variable domain VL, trastuzumab CLC

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Arg Tyr Thr Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95
```

Thr Phe Gly Gln Gly Thr Lys Val Glu Ile Lys
            100                 105

<210> SEQ ID NO 18
<211> LENGTH: 5
<212> TYPE: PRT
<213> ORGANISM: Artificial Sequence
<220> FEATURE:
<223> OTHER INFORMATION: CD28(SA) CDR-H1

<400> SEQUENCE: 18

Ser Tyr Tyr Ile His
1               5

<210> SEQ ID NO 19
<211> LENGTH: 17
<212> TYPE: PRT
<213> ORGANISM: Artificial Sequence
<220> FEATURE:
<223> OTHER INFORMATION: CD28(SA) CDR-H2

<400> SEQUENCE: 19

Cys Ile Tyr Pro Gly Asn Val Asn Thr Asn Tyr Asn Glu Lys Phe Lys
1               5                   10                  15

Asp

<210> SEQ ID NO 20
<211> LENGTH: 11
<212> TYPE: PRT
<213> ORGANISM: Artificial Sequence
<220> FEATURE:
<223> OTHER INFORMATION: CD28(SA) CDR-H3

<400> SEQUENCE: 20

Ser His Tyr Gly Leu Asp Trp Asn Phe Asp Val
1               5                   10

<210> SEQ ID NO 21
<211> LENGTH: 11
<212> TYPE: PRT
<213> ORGANISM: Artificial Sequence
<220> FEATURE:
<223> OTHER INFORMATION: CD28(SA) CDR-L1

<400> SEQUENCE: 21

His Ala Ser Gln Asn Ile Tyr Val Trp Leu Asn
1               5                   10

<210> SEQ ID NO 22
<211> LENGTH: 7
<212> TYPE: PRT
<213> ORGANISM: Artificial Sequence
<220> FEATURE:
<223> OTHER INFORMATION: CD28(SA) CDR-L2

<400> SEQUENCE: 22

Lys Ala Ser Asn Leu His Thr
1               5

<210> SEQ ID NO 23
<211> LENGTH: 9
<212> TYPE: PRT
<213> ORGANISM: Artificial Sequence
<220> FEATURE:
<223> OTHER INFORMATION: CD28(SA) CDR-L3

<400> SEQUENCE: 23

```
Gln Gln Gly Gln Thr Tyr Pro Tyr Thr
  1               5
```

```
<210> SEQ ID NO 24
<211> LENGTH: 120
<212> TYPE: PRT
<213> ORGANISM: Artificial Sequence
<220> FEATURE:
<223> OTHER INFORMATION: CD28(SA) VH

<400> SEQUENCE: 24

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Tyr Ile His Trp Val Arg Gln Ala Pro Gly Gln Gly Leu Glu Trp Ile
             35                  40                  45

Gly Cys Ile Tyr Pro Gly Asn Val Asn Thr Asn Tyr Asn Glu Lys Phe
 50                  55                  60

Lys Asp Arg Ala Thr Leu Thr Val Asp Thr Ser Ile Ser Thr Ala Tyr
 65                  70                  75                  80

Met Glu Leu Ser Arg Leu Arg Ser Asp Asp Thr Ala Val Tyr Phe Cys
                 85                  90                  95

Thr Arg Ser His Tyr Gly Leu Asp Trp Asn Phe Asp Val Trp Gly Gln
            100                 105                 110

Gly Thr Thr Val Thr Val Ser Ser
            115                 120
```

```
<210> SEQ ID NO 25
<211> LENGTH: 107
<212> TYPE: PRT
<213> ORGANISM: Artificial Sequence
<220> FEATURE:
<223> OTHER INFORMATION: CD28(SA) VL

<400> SEQUENCE: 25

Asp Ile Gln Met Thr Gln Ser Pro Ser Ser Leu Ser Ala Ser Val Gly
  1               5                  10                  15

Asp Arg Val Thr Ile Thr Cys His Ala Ser Gln Asn Ile Tyr Val Trp
                 20                  25                  30

Leu Asn Trp Tyr Gln Gln Lys Pro Gly Lys Ala Pro Lys Leu Leu Ile
             35                  40                  45

Tyr Lys Ala Ser Asn Leu His Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Gln Thr Tyr Pro Tyr
                 85                  90                  95

Thr Phe Gly Gly Gly Thr Lys Val Glu Ile Lys
            100                 105
```

```
<210> SEQ ID NO 26
<211> LENGTH: 5
<212> TYPE: PRT
<213> ORGANISM: Artificial Sequence
<220> FEATURE:
<223> OTHER INFORMATION: CD28 CDR-H1 consensus

<400> SEQUENCE: 26
```

Ser Tyr Tyr Ile His
1               5

<210> SEQ ID NO 27
<211> LENGTH: 17
<212> TYPE: PRT
<213> ORGANISM: Artificial Sequence
<220> FEATURE:
<223> OTHER INFORMATION: CD28 CDR-H2 consensus
<220> FEATURE:
<221> NAME/KEY: VARIANT
<222> LOCATION: (5)..(5)
<223> OTHER INFORMATION: Gly or Arg
<220> FEATURE:
<221> NAME/KEY: VARIANT
<222> LOCATION: (6)..(6)
<223> OTHER INFORMATION: Asn or Asp
<220> FEATURE:
<221> NAME/KEY: VARIANT
<222> LOCATION: (7)..(7)
<223> OTHER INFORMATION: Val or Gly
<220> FEATURE:
<221> NAME/KEY: VARIANT
<222> LOCATION: (8)..(8)
<223> OTHER INFORMATION: Asn, Gln or Ala

<400> SEQUENCE: 27

Ser Ile Tyr Pro Xaa Xaa Xaa Xaa Thr Asn Tyr Asn Glu Lys Phe Lys
1               5                   10                  15
Asp

<210> SEQ ID NO 28
<211> LENGTH: 11
<212> TYPE: PRT
<213> ORGANISM: Artificial Sequence
<220> FEATURE:
<223> OTHER INFORMATION: CD28 CDR-H3 consensus
<220> FEATURE:
<221> NAME/KEY: VARIANT
<222> LOCATION: (5)..(5)
<223> OTHER INFORMATION: Leu or Ala
<220> FEATURE:
<221> NAME/KEY: VARIANT
<222> LOCATION: (7)..(7)
<223> OTHER INFORMATION: Trp, His, Tyr or Phe

<400> SEQUENCE: 28

Ser His Tyr Gly Xaa Asp Xaa Asn Phe Asp Val
1               5                   10

<210> SEQ ID NO 29
<211> LENGTH: 11
<212> TYPE: PRT
<213> ORGANISM: Artificial Sequence
<220> FEATURE:
<223> OTHER INFORMATION: CD28 CDR-L1 consensus
<220> FEATURE:
<221> NAME/KEY: VARIANT
<222> LOCATION: (1)..(1)
<223> OTHER INFORMATION: His or Arg
<220> FEATURE:
<221> NAME/KEY: VARIANT
<222> LOCATION: (5)..(5)
<223> OTHER INFORMATION: Asn or Gly
<220> FEATURE:
<221> NAME/KEY: VARIANT
<222> LOCATION: (7)..(7)
<223> OTHER INFORMATION: Tyr or Ser
<220> FEATURE:
<221> NAME/KEY: VARIANT
<222> LOCATION: (8)..(8)
<223> OTHER INFORMATION: Val or Asn
<220> FEATURE:

```
<221> NAME/KEY: VARIANT
<222> LOCATION: (9)..(9)
<223> OTHER INFORMATION: Trp, His, Phe or Tyr

<400> SEQUENCE: 29

Xaa Ala Ser Gln Xaa Ile Xaa Xaa Xaa Leu Asn
1               5                   10

<210> SEQ ID NO 30
<211> LENGTH: 7
<212> TYPE: PRT
<213> ORGANISM: Artificial Sequence
<220> FEATURE:
<223> OTHER INFORMATION: CD28 CDR-L2 consensus
<220> FEATURE:
<221> NAME/KEY: VARIANT
<222> LOCATION: (1)..(1)
<223> OTHER INFORMATION: Lys or Tyr
<220> FEATURE:
<221> NAME/KEY: VARIANT
<222> LOCATION: (2)..(2)
<223> OTHER INFORMATION: Ala or Gly
<220> FEATURE:
<221> NAME/KEY: VARIANT
<222> LOCATION: (4)..(4)
<223> OTHER INFORMATION: Asn or Ser
<220> FEATURE:
<221> NAME/KEY: VARIANT
<222> LOCATION: (6)..(6)
<223> OTHER INFORMATION: His or Tyr
<220> FEATURE:
<221> NAME/KEY: VARIANT
<222> LOCATION: (7)..(7)
<223> OTHER INFORMATION: Thr or Ser

<400> SEQUENCE: 30

Xaa Xaa Ser Xaa Leu Xaa Xaa
1               5

<210> SEQ ID NO 31
<211> LENGTH: 9
<212> TYPE: PRT
<213> ORGANISM: Artificial Sequence
<220> FEATURE:
<223> OTHER INFORMATION: CD28 CDR-L3 consensus
<220> FEATURE:
<221> NAME/KEY: VARIANT
<222> LOCATION: (3)..(3)
<223> OTHER INFORMATION: Gly or Ala

<400> SEQUENCE: 31

Gln Gln Xaa Gln Thr Tyr Pro Tyr Thr
1               5

<210> SEQ ID NO 32
<211> LENGTH: 120
<212> TYPE: PRT
<213> ORGANISM: Artificial Sequence
<220> FEATURE:
<223> OTHER INFORMATION: CD28 VH variant a

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Ser Ile Tyr Pro Gly Asn Val Asn Thr Asn Tyr Asn Glu Lys Phe
```

```
                50                  55                  60
Lys Asp Arg Ala Thr Leu Thr Val Asp Thr Ser Ile Ser Thr Ala Tyr
 65                  70                  75                  80

Met Glu Leu Ser Arg Leu Arg Ser Asp Thr Ala Val Tyr Phe Cys
                    85                  90                  95

Thr Arg Ser His Tyr Gly Leu Asp Trp Asn Phe Asp Val Trp Gly Gln
                100                 105                 110

Gly Thr Thr Val Thr Val Ser Ser
            115                 120

<210> SEQ ID NO 33
<211> LENGTH: 120
<212> TYPE: PRT
<213> ORGANISM: Artificial Sequence
<220> FEATURE:
<223> OTHER INFORMATION: CD28 VH variant b

<400> SEQUENCE: 33

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Tyr Ile His Trp Val Arg Gln Ala Pro Gly Gln Gly Leu Glu Trp Ile
            35                  40                  45

Gly Ser Ile Tyr Pro Gly Asn Val Gln Thr Asn Tyr Asn Glu Lys Phe
        50                  55                  60

Lys Asp Arg Ala Thr Leu Thr Val Asp Thr Ser Ile Ser Thr Ala Tyr
 65                  70                  75                  80

Met Glu Leu Ser Arg Leu Arg Ser Asp Thr Ala Val Tyr Phe Cys
                    85                  90                  95

Thr Arg Ser His Tyr Gly Leu Asp His Asn Phe Asp Val Trp Gly Gln
                100                 105                 110

Gly Thr Thr Val Thr Val Ser Ser
            115                 120

<210> SEQ ID NO 34
<211> LENGTH: 120
<212> TYPE: PRT
<213> ORGANISM: Artificial Sequence
<220> FEATURE:
<223> OTHER INFORMATION: CD28 VH variant c

<400> SEQUENCE: 34

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Tyr Ile His Trp Val Arg Gln Ala Pro Gly Gln Gly Leu Glu Trp Ile
            35                  40                  45

Gly Ser Ile Tyr Pro Gly Asn Val Gln Thr Asn Tyr Asn Glu Lys Phe
        50                  55                  60

Lys Asp Arg Ala Thr Leu Thr Val Asp Thr Ser Ile Ser Thr Ala Tyr
 65                  70                  75                  80

Met Glu Leu Ser Arg Leu Arg Ser Asp Thr Ala Val Tyr Phe Cys
                    85                  90                  95

Thr Arg Ser His Tyr Gly Ala Asp His Asn Phe Asp Val Trp Gly Gln
                100                 105                 110
```

```
Gly Thr Thr Val Thr Val Ser Ser
        115                 120
```

<210> SEQ ID NO 35
<211> LENGTH: 120
<212> TYPE: PRT
<213> ORGANISM: Artificial Sequence
<220> FEATURE:
<223> OTHER INFORMATION: CD28 VH variant d

<400> SEQUENCE: 35

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Ser Ile Tyr Pro Arg Asp Gly Gln Thr Asn Tyr Asn Glu Lys Phe
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Thr Arg Ser His Tyr Gly Leu Asp Tyr Asn Phe Asp Val Trp Gly Gln
            100                 105                 110

Gly Thr Thr Val Thr Val Ser Ser
        115                 120
```

<210> SEQ ID NO 36
<211> LENGTH: 120
<212> TYPE: PRT
<213> ORGANISM: Artificial Sequence
<220> FEATURE:
<223> OTHER INFORMATION: CD28 VH variant e

<400> SEQUENCE: 36

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Ser Ile Tyr Pro Gly Asn Val Gln Thr Asn Tyr Asn Glu Lys Phe
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Thr Arg Ser His Tyr Gly Leu Asp Trp Asn Phe Asp Val Trp Gly Gln
            100                 105                 110

Gly Thr Thr Val Thr Val Ser Ser
        115                 120
```

<210> SEQ ID NO 37
<211> LENGTH: 120
<212> TYPE: PRT
<213> ORGANISM: Artificial Sequence
<220> FEATURE:
<223> OTHER INFORMATION: CD28 VH variant f

```
<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Ser Ile Tyr Pro Gly Asn Val Gln Thr Asn Tyr Asn Glu Lys Phe
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Thr Arg Ser His Tyr Gly Leu Asp Phe Asn Phe Asp Val Trp Gly Gln
            100                 105                 110

Gly Thr Thr Val Thr Val Ser Ser
        115                 120

<210> SEQ ID NO 38
<211> LENGTH: 120
<212> TYPE: PRT
<213> ORGANISM: Artificial Sequence
<220> FEATURE:
<223> OTHER INFORMATION: CD28 VH variant g

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Ser Ile Tyr Pro Arg Asn Val Gln Thr Asn Tyr Asn Glu Lys Phe
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Thr Arg Ser His Tyr Gly Leu Asp His Asn Phe Asp Val Trp Gly Gln
            100                 105                 110

Gly Thr Thr Val Thr Val Ser Ser
        115                 120

<210> SEQ ID NO 39
<211> LENGTH: 120
<212> TYPE: PRT
<213> ORGANISM: Artificial Sequence
<220> FEATURE:
<223> OTHER INFORMATION: CD28 VH variant h

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45
```

```
Gly Ser Ile Tyr Pro Arg Asp Val Gln Thr Asn Tyr Asn Glu Lys Phe
        50                  55                  60

Lys Asp Arg Ala Thr Leu Thr Val Asp Thr Ser Ile Ser Thr Ala Tyr
 65                  70                  75                  80

Met Glu Leu Ser Arg Leu Arg Ser Asp Asp Thr Ala Val Tyr Phe Cys
                 85                  90                  95

Thr Arg Ser His Tyr Gly Leu Asp His Asn Phe Asp Val Trp Gly Gln
            100                 105                 110

Gly Thr Thr Val Thr Val Ser Ser
            115                 120

<210> SEQ ID NO 40
<211> LENGTH: 120
<212> TYPE: PRT
<213> ORGANISM: Artificial Sequence
<220> FEATURE:
<223> OTHER INFORMATION: CD28 VH variant i

<400> SEQUENCE: 40

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Ser Tyr
             20                  25                  30

Tyr Ile His Trp Val Arg Gln Ala Pro Gly Lys Gly Leu Glu Trp Val
         35                  40                  45

Ala Ser Ile Tyr Pro Gly Asn Val Asn Thr Arg Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Thr Arg Ser His Tyr Gly Leu Asp Trp Asn Phe Asp Val Trp Gly Gln
            100                 105                 110

Gly Thr Thr Val Thr Val Ser Ser
            115                 120

<210> SEQ ID NO 41
<211> LENGTH: 120
<212> TYPE: PRT
<213> ORGANISM: Artificial Sequence
<220> FEATURE:
<223> OTHER INFORMATION: CD28 VH variant j

<400> SEQUENCE: 41

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Ser Tyr
             20                  25                  30

Tyr Ile His Trp Val Arg Gln Ala Pro Gly Lys Gly Leu Glu Trp Val
         35                  40                  45

Ala Ser Ile Tyr Pro Gly Asn Val Ala Thr Arg Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Thr Arg Ser His Tyr Gly Leu Asp Trp Asn Phe Asp Val Trp Gly Gln
            100                 105                 110
```

```
Gly Thr Thr Val Thr Val Ser Ser
        115                 120

<210> SEQ ID NO 42
<211> LENGTH: 107
<212> TYPE: PRT
<213> ORGANISM: Artificial Sequence
<220> FEATURE:
<223> OTHER INFORMATION: CD28 VL variant k

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val His
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Gln Thr Tyr Pro Tyr
                85                  90                  95

Thr Phe Gly Gly Gly Thr Lys Val Glu Ile Lys
            100                 105

<210> SEQ ID NO 43
<211> LENGTH: 107
<212> TYPE: PRT
<213> ORGANISM: Artificial Sequence
<220> FEATURE:
<223> OTHER INFORMATION: CD28 VL variant l

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val Phe
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys
            100                 105

<210> SEQ ID NO 44
<211> LENGTH: 107
<212> TYPE: PRT
<213> ORGANISM: Artificial Sequence
<220> FEATURE:
<223> OTHER INFORMATION: CD28 VL variant m

<400> SEQUENCE: 44

Asp Ile Gln Met Thr Gln Ser Pro Ser Ser Leu Ser Ala Ser Val Gly
1               5                   10                  15
```

```
Asp Arg Val Thr Ile Thr Cys His Ala Ser Gln Asn Ile Tyr Val Tyr
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys
                100                 105
```

<210> SEQ ID NO 45
<211> LENGTH: 107
<212> TYPE: PRT
<213> ORGANISM: Artificial Sequence
<220> FEATURE:
<223> OTHER INFORMATION: CD28 VL variant n

<400> SEQUENCE: 45

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Gly Ile Ser Asn Tyr
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys
                100                 105
```

<210> SEQ ID NO 46
<211> LENGTH: 107
<212> TYPE: PRT
<213> ORGANISM: Artificial Sequence
<220> FEATURE:
<223> OTHER INFORMATION: CD28 VL variant o

<400> SEQUENCE: 46

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val Trp
            20                  25                  30

Leu Asn Trp Tyr Gln Gln Lys Pro Gly Lys Ala Pro Lys Leu Leu Ile
        35                  40                  45

Tyr Tyr Thr Ser Ser Leu His Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys
                100                 105
```

```
<210> SEQ ID NO 47
<211> LENGTH: 107
<212> TYPE: PRT
<213> ORGANISM: Artificial Sequence
<220> FEATURE:
<223> OTHER INFORMATION: CD28 VL variant p

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys His Ala Ser Gln Gly Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Ser Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys
            100                 105

<210> SEQ ID NO 48
<211> LENGTH: 107
<212> TYPE: PRT
<213> ORGANISM: Artificial Sequence
<220> FEATURE:
<223> OTHER INFORMATION: CD28 VL variant q

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys His Ala Ser Gln Gly Ile Ser Asn His
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys
            100                 105

<210> SEQ ID NO 49
<211> LENGTH: 107
<212> TYPE: PRT
<213> ORGANISM: Artificial Sequence
<220> FEATURE:
<223> OTHER INFORMATION: CD28 VL variant r

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys His Ala Ser Gln Gly Ile Tyr Val Tyr
            20                  25                  30
```

```
Leu Asn Trp Tyr Gln Gln Lys Pro Gly Lys Ala Pro Lys Leu Leu Ile
         35                  40                  45

Tyr Lys Ala Ser Asn Leu His Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Gln Thr Tyr Pro Tyr
                 85                  90                  95

Thr Phe Gly Gly Gly Thr Lys Val Glu Ile Lys
             100                 105

<210> SEQ ID NO 50
<211> LENGTH: 107
<212> TYPE: PRT
<213> ORGANISM: Artificial Sequence
<220> FEATURE:
<223> OTHER INFORMATION: CD28 VL variant s

<400> SEQUENCE: 50

Asp Ile Gln Met Thr Gln Ser Pro Ser Ser Leu Ser Ala Ser Val Gly
 1               5                  10                  15

Asp Arg Val Thr Ile Thr Cys His Ala Ser Gln Gly Ile Ser Val Tyr
             20                  25                  30

Leu Asn Trp Tyr Gln Gln Lys Pro Gly Lys Ala Pro Lys Leu Leu Ile
         35                  40                  45

Tyr Lys Ala Ser Asn Leu His Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Gln Thr Tyr Pro Tyr
                 85                  90                  95

Thr Phe Gly Gly Gly Thr Lys Val Glu Ile Lys
             100                 105

<210> SEQ ID NO 51
<211> LENGTH: 107
<212> TYPE: PRT
<213> ORGANISM: Artificial Sequence
<220> FEATURE:
<223> OTHER INFORMATION: CD28 VL variant t

<400> SEQUENCE: 51

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asn Ile Tyr Val Trp
             20                  25                  30

Leu Asn Trp Tyr Gln Gln Lys Pro Gly Lys Ala Pro Lys Leu Leu Ile
         35                  40                  45

Tyr Lys Ala Ser Asn Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Gln Thr Tyr Pro Tyr
                 85                  90                  95

Thr Phe Gly Gln Gly Thr Lys Leu Glu Ile Lys
             100                 105

<210> SEQ ID NO 52
```

```
<211> LENGTH: 5
<212> TYPE: PRT
<213> ORGANISM: Artificial Sequence
<220> FEATURE:
<223> OTHER INFORMATION: CD28(variant 8) CDR-H1

<400> SEQUENCE: 52

Ser Tyr Tyr Ile His
1               5

<210> SEQ ID NO 53
<211> LENGTH: 17
<212> TYPE: PRT
<213> ORGANISM: Artificial Sequence
<220> FEATURE:
<223> OTHER INFORMATION: CD28(variant 8) CDR-H2

<400> SEQUENCE: 53

Ser Ile Tyr Pro Gly Asn Val Gln Thr Asn Tyr Asn Glu Lys Phe Lys
1               5                   10                  15

Asp

<210> SEQ ID NO 54
<211> LENGTH: 11
<212> TYPE: PRT
<213> ORGANISM: Artificial Sequence
<220> FEATURE:
<223> OTHER INFORMATION: CD28(variant 8) CDR-H3

<400> SEQUENCE: 54

Ser His Tyr Gly Leu Asp Trp Asn Phe Asp Val
1               5                   10

<210> SEQ ID NO 55
<211> LENGTH: 11
<212> TYPE: PRT
<213> ORGANISM: Artificial Sequence
<220> FEATURE:
<223> OTHER INFORMATION: CD28(variant 8) CDR-L1

<400> SEQUENCE: 55

His Ala Ser Gln Asn Ile Tyr Val Tyr Leu Asn
1               5                   10

<210> SEQ ID NO 56
<211> LENGTH: 7
<212> TYPE: PRT
<213> ORGANISM: Artificial Sequence
<220> FEATURE:
<223> OTHER INFORMATION: CD28(variant 8) CDR-L2

<400> SEQUENCE: 56

Lys Ala Ser Asn Leu His Thr
1               5

<210> SEQ ID NO 57
<211> LENGTH: 9
<212> TYPE: PRT
<213> ORGANISM: Artificial Sequence
<220> FEATURE:
<223> OTHER INFORMATION: CD28(variant 8) CDR-L3

<400> SEQUENCE: 57

Gln Gln Gly Gln Thr Tyr Pro Tyr Thr
1               5
```

```
<210> SEQ ID NO 58
<211> LENGTH: 5
<212> TYPE: PRT
<213> ORGANISM: Artificial Sequence
<220> FEATURE:
<223> OTHER INFORMATION: CD28(variant 15) CDR-H1

<400> SEQUENCE: 58

Ser Tyr Tyr Ile His
1               5

<210> SEQ ID NO 59
<211> LENGTH: 17
<212> TYPE: PRT
<213> ORGANISM: Artificial Sequence
<220> FEATURE:
<223> OTHER INFORMATION: CD28(variant 15) CDR-H2

<400> SEQUENCE: 59

Ser Ile Tyr Pro Gly Asn Val Gln Thr Asn Tyr Asn Glu Lys Phe Lys
1               5                   10                  15

Asp

<210> SEQ ID NO 60
<211> LENGTH: 11
<212> TYPE: PRT
<213> ORGANISM: Artificial Sequence
<220> FEATURE:
<223> OTHER INFORMATION: CD28(variant 15) CDR-H3

<400> SEQUENCE: 60

Ser His Tyr Gly Leu Asp Trp Asn Phe Asp Val
1               5                   10

<210> SEQ ID NO 61
<211> LENGTH: 11
<212> TYPE: PRT
<213> ORGANISM: Artificial Sequence
<220> FEATURE:
<223> OTHER INFORMATION: CD28(variant 15) CDR-L1

<400> SEQUENCE: 61

His Ala Ser Gln Asn Ile Tyr Val Phe Leu Asn
1               5                   10

<210> SEQ ID NO 62
<211> LENGTH: 7
<212> TYPE: PRT
<213> ORGANISM: Artificial Sequence
<220> FEATURE:
<223> OTHER INFORMATION: CD28(variant 15) CDR-L2

<400> SEQUENCE: 62

Lys Ala Ser Asn Leu His Thr
1               5

<210> SEQ ID NO 63
<211> LENGTH: 9
<212> TYPE: PRT
<213> ORGANISM: Artificial Sequence
<220> FEATURE:
<223> OTHER INFORMATION: CD28(variant 15) CDR-L3

<400> SEQUENCE: 63

Gln Gln Gly Gln Thr Tyr Pro Tyr Thr
1               5
```

```
<210> SEQ ID NO 64
<211> LENGTH: 5
<212> TYPE: PRT
<213> ORGANISM: Artificial Sequence
<220> FEATURE:
<223> OTHER INFORMATION: CD28(variant 29) CDR-H1

<400> SEQUENCE: 64

Ser Tyr Tyr Ile His
1               5

<210> SEQ ID NO 65
<211> LENGTH: 17
<212> TYPE: PRT
<213> ORGANISM: Artificial Sequence
<220> FEATURE:
<223> OTHER INFORMATION: CD28(variant 29) CDR-H2

<400> SEQUENCE: 65

Ser Ile Tyr Pro Gly Asn Val Asn Thr Asn Tyr Asn Glu Lys Phe Lys
1               5                   10                  15

Asp

<210> SEQ ID NO 66
<211> LENGTH: 11
<212> TYPE: PRT
<213> ORGANISM: Artificial Sequence
<220> FEATURE:
<223> OTHER INFORMATION: CD28(variant 29) CDR-H3

<400> SEQUENCE: 66

Ser His Tyr Gly Leu Asp Trp Asn Phe Asp Val
1               5                   10

<210> SEQ ID NO 67
<211> LENGTH: 11
<212> TYPE: PRT
<213> ORGANISM: Artificial Sequence
<220> FEATURE:
<223> OTHER INFORMATION: CD28(variant 29) CDR-L1

<400> SEQUENCE: 67

His Ala Ser Gln Asn Ile Tyr Val Trp Leu Asn
1               5                   10

<210> SEQ ID NO 68
<211> LENGTH: 7
<212> TYPE: PRT
<213> ORGANISM: Artificial Sequence
<220> FEATURE:
<223> OTHER INFORMATION: CD28(variant 29) CDR-L2

<400> SEQUENCE: 68

Lys Ala Ser Asn Leu His Thr
1               5

<210> SEQ ID NO 69
<211> LENGTH: 9
<212> TYPE: PRT
<213> ORGANISM: Artificial Sequence
<220> FEATURE:
<223> OTHER INFORMATION: CD28(variant 29) CDR-L3

<400> SEQUENCE: 69

Gln Gln Gly Gln Thr Tyr Pro Tyr Thr
1               5
```

```
<210> SEQ ID NO 70
<211> LENGTH: 225
<212> TYPE: PRT
<213> ORGANISM: Artificial Sequence
<220> FEATURE:
<223> OTHER INFORMATION: Fc hole PGLALA

<400> SEQUENCE: 70

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro
225

<210> SEQ ID NO 71
<211> LENGTH: 225
<212> TYPE: PRT
<213> ORGANISM: Artificial Sequence
<220> FEATURE:
<223> OTHER INFORMATION: Fc knob PGLALA

<400> SEQUENCE: 71

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
```

```
                65                  70                  75                  80
Arg Val Val Ser Val Leu Thr Val Leu His Gln Asp Trp Leu Asn Gly
                    85                  90                  95
Lys Glu Tyr Lys Cys Lys Val Ser Asn Lys Ala Leu Gly Ala Pro Ile
                100                 105                 110
Glu Lys Thr Ile Ser Lys Ala Lys Gly Gln Pro Arg Glu Pro Gln Val
                115                 120                 125
Tyr Thr Leu Pro Pro Cys Arg Asp Glu Leu Thr Lys Asn Gln Val Ser
            130                 135                 140
Leu Trp Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
                180                 185                 190
Asp Lys Ser Arg Trp Gln Gln Gly Asn Val Phe Ser Cys Ser Val Met
                195                 200                 205
His Glu Ala Leu His Asn His Tyr Thr Gln Lys Ser Leu Ser Leu Ser
            210                 215                 220
Pro
225

<210> SEQ ID NO 72
<211> LENGTH: 448
<212> TYPE: PRT
<213> ORGANISM: Artificial Sequence
<220> FEATURE:
<223> OTHER INFORMATION: VH (CD28 SA) CH1 (EE)- Fc knob PGLALA

<400> SEQUENCE: 72

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
                20                  25                  30
Tyr Ile His Trp Val Arg Gln Ala Pro Gly Gln Gly Leu Glu Trp Ile
            35                  40                  45
Gly Cys Ile Tyr Pro Gly Asn Val Asn Thr Asn Tyr Asn Glu Lys Phe
        50                  55                  60
Lys Asp Arg Ala Thr Leu Thr Val Asp Thr Ser Ile Ser Thr Ala Tyr
65                  70                  75                  80
Met Glu Leu Ser Arg Leu Arg Ser Asp Asp Thr Ala Val Tyr Phe Cys
                85                  90                  95
Thr Arg Ser His Tyr Gly Leu Asp Trp Asn Phe Asp Val Trp Gly Gln
                100                 105                 110
Gly Thr Thr Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
        130                 135                 140
Leu Gly Cys Leu Val Glu Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
```

```
                195                 200                 205
Pro Ser Asn Thr Lys Val Asp Glu Lys Val Glu Pro Lys Ser Cys Asp
210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

<210> SEQ ID NO 73
<211> LENGTH: 448
<212> TYPE: PRT
<213> ORGANISM: Artificial Sequence
<220> FEATURE:
<223> OTHER INFORMATION: VH (CD28 variant g) CH1- Fc knob PGLALA

<400> SEQUENCE: 73

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Ser Ile Tyr Pro Arg Asn Val Gln Thr Asn Tyr Asn Glu Lys Phe
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Thr Arg Ser His Tyr Gly Leu Asp His Asn Phe Asp Val Trp Gly Gln
            100                 105                 110

Gly Thr Thr Val Thr Val Ser Ser Ala Ser Thr Lys Gly Pro Ser Val
```

```
                115                 120                 125
Phe Pro Leu Ala Pro Ser Ser Lys Ser Thr Ser Gly Gly Thr Ala Ala
        130                 135                 140
Leu Gly Cys Leu Val Glu Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Glu Lys Val Glu Pro Lys Ser Cys Asp
210                 215                 220
Lys Thr His Thr Cys Pro Pro Cys Pro Ala Pro Glu Ala Ala Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Gly Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Cys Arg Asp Glu Leu Thr Lys Asn Gln Val Ser Leu
        355                 360                 365
Trp Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
```

<210> SEQ ID NO 74
<211> LENGTH: 448
<212> TYPE: PRT
<213> ORGANISM: Artificial Sequence
<220> FEATURE:
<223> OTHER INFORMATION: VH (CD28 variant f) CH1- Fc knob PGLALA

<400> SEQUENCE: 74

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Tyr Ile His Trp Val Arg Gln Ala Pro Gly Gln Gly Leu Glu Trp Ile
```

```
            35                  40                  45
Gly Ser Ile Tyr Pro Gly Asn Val Gln Thr Asn Tyr Asn Glu Lys Phe
 50                  55                  60

Lys Asp Arg Ala Thr Leu Thr Val Asp Thr Ser Ile Ser Thr Ala Tyr
 65                  70                  75                  80

Met Glu Leu Ser Arg Leu Arg Ser Asp Asp Thr Ala Val Tyr Phe Cys
                 85                  90                  95

Thr Arg Ser His Tyr Gly Leu Asp Phe Asn Phe Asp Val Trp Gly Gln
                100                 105                 110

Gly Thr Thr Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
130                 135                 140

Leu Gly Cys Leu Val Glu Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Glu Lys Val Pro Lys Ser Cys Asp
210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Cys Arg Asp Glu Leu Thr Lys Asn Gln Val Ser Leu
                355                 360                 365

Trp Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

<210> SEQ ID NO 75
```

<211> LENGTH: 448
<212> TYPE: PRT
<213> ORGANISM: Artificial Sequence
<220> FEATURE:
<223> OTHER INFORMATION: VH (CD28 variant j) CH1- Fc knob PGLALA

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Tyr Ile His Trp Val Arg Gln Ala Pro Gly Lys Gly Leu Glu Trp Val
        35                  40                  45

Ala Ser Ile Tyr Pro Gly Asn Val Ala Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Thr Arg Ser His Tyr Gly Leu Asp Trp Asn Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Glu Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Glu Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

<210> SEQ ID NO 76
<211> LENGTH: 448
<212> TYPE: PRT
<213> ORGANISM: Artificial Sequence
<220> FEATURE:
<223> OTHER INFORMATION: VH (CD28 variant e) CH1- Fc knob PGLALA

<400> SEQUENCE: 76

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Ser Ile Tyr Pro Gly Asn Val Gln Thr Asn Tyr Asn Glu Lys Phe
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Thr Ala Val Tyr Phe Cys
                85                  90                  95

Thr Arg Ser His Tyr Gly Leu Asp Trp Asn Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Glu Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Glu Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
            355                 360                 365

Trp Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

<210> SEQ ID NO 77
<211> LENGTH: 448
<212> TYPE: PRT
<213> ORGANISM: Artificial Sequence
<220> FEATURE:
<223> OTHER INFORMATION: VH (CD28 variant b) CH1- Fc knob PGLALA

<400> SEQUENCE: 77

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Ser Ile Tyr Pro Gly Asn Val Gln Thr Asn Tyr Asn Glu Lys Phe
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Thr Arg Ser His Tyr Gly Leu Asp His Asn Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Glu Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Glu Lys Val Glu Pro Lys Ser Cys Asp
    210                 215                 220

```
Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

<210> SEQ ID NO 78
<211> LENGTH: 448
<212> TYPE: PRT
<213> ORGANISM: Artificial Sequence
<220> FEATURE:
<223> OTHER INFORMATION: VH (CD28 variant a) CH1- Fc knob PGLALA

<400> SEQUENCE: 78

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Ser Ile Tyr Pro Gly Asn Val Asn Thr Asn Tyr Asn Glu Lys Phe
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Thr Arg Ser His Tyr Gly Leu Asp Trp Asn Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

-continued

```
Leu Gly Cys Leu Val Glu Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Glu Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

<210> SEQ ID NO 79
<211> LENGTH: 448
<212> TYPE: PRT
<213> ORGANISM: Artificial Sequence
<220> FEATURE:
<223> OTHER INFORMATION: VH (CD28 variant i) CH1- Fc knob PGLALA

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Tyr Ile His Trp Val Arg Gln Ala Pro Gly Lys Gly Leu Glu Trp Val
        35                  40                  45

Ala Ser Ile Tyr Pro Gly Asn Val Asn Thr Arg Tyr Ala Asp Ser Val
    50                  55                  60
```

```
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Thr Arg Ser His Tyr Gly Leu Asp Trp Asn Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Glu Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Glu Lys Val Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

<210> SEQ ID NO 80
<211> LENGTH: 214
<212> TYPE: PRT
<213> ORGANISM: Artificial Sequence
<220> FEATURE:
```

<223> OTHER INFORMATION: VL-CD28(SA)-CL"RK"

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val Trp
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Arg Lys Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 81
<211> LENGTH: 214
<212> TYPE: PRT
<213> ORGANISM: Artificial Sequence
<220> FEATURE:
<223> OTHER INFORMATION: VL (CD28 variant k)-CL (RK)

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val His
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Gln Thr Tyr Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Arg Lys Leu Lys Ser Gly
        115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 82
<211> LENGTH: 214
<212> TYPE: PRT
<213> ORGANISM: Artificial Sequence
<220> FEATURE:
<223> OTHER INFORMATION: VL (CD28 variant l)-CL (RK)

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val Phe
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Arg Lys Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 83
<211> LENGTH: 214
<212> TYPE: PRT
<213> ORGANISM: Artificial Sequence
<220> FEATURE:
<223> OTHER INFORMATION: VL (CD28 variant m)-CL (RK)

-continued

```
<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val Tyr
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Arg Lys Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 84
<211> LENGTH: 214
<212> TYPE: PRT
<213> ORGANISM: Artificial Sequence
<220> FEATURE:
<223> OTHER INFORMATION: VL (CD28 variant r)-CL (RK)

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys His Ala Ser Gln Gly Ile Tyr Val Tyr
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Arg Lys Leu Lys Ser Gly
        115                 120                 125

Thr Ala Ser Val Val Cys Leu Leu Asn Asn Phe Tyr Pro Arg Glu Ala
```

```
                130              135               140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 85
<211> LENGTH: 214
<212> TYPE: PRT
<213> ORGANISM: Artificial Sequence
<220> FEATURE:
<223> OTHER INFORMATION: VL (CD28 variant s)-CL (RK)

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys His Ala Ser Gln Gly Ile Ser Val Tyr
                20                  25                  30

Leu Asn Trp Tyr Gln Gln Lys Pro Gly Lys Ala Pro Lys Leu Leu Ile
            35                  40                  45

Tyr Lys Ala Ser Asn Leu His Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Arg Lys Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 86
<211> LENGTH: 214
<212> TYPE: PRT
<213> ORGANISM: Artificial Sequence
<220> FEATURE:
<223> OTHER INFORMATION: VL (CD28 variant t)-CL (RK)

<400> SEQUENCE: 86
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Tyr Val Trp
            20                  25                  30

Leu Asn Trp Tyr Gln Gln Lys Pro Gly Lys Ala Pro Lys Leu Leu Ile
            35                  40                  45

Tyr Lys Ala Ser Asn Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Arg Lys Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 87
<211> LENGTH: 225
<212> TYPE: PRT
<213> ORGANISM: Artificial Sequence
<220> FEATURE:
<223> OTHER INFORMATION: Fc hole PGLALA, HYRF

<400> SEQUENCE: 87

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
    130                 135                 140

```
Leu Ser Cys Ala Val Lys Gly Phe Tyr Pro Ser Asp Ile Ala Val Glu
145                 150                 155                 160

Trp Glu Ser Asn Gly Gln Pro Glu Asn Tyr Lys Thr Thr Pro Pro
            165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn Arg Phe Thr Gln Lys Ser Leu Ser Leu Ser
            210                 215                 220

Pro
225

<210> SEQ ID NO 88
<211> LENGTH: 15
<212> TYPE: PRT
<213> ORGANISM: Artificial Sequence
<220> FEATURE:
<223> OTHER INFORMATION: Avi tag

<400> SEQUENCE: 88

Gly Leu Asn Asp Ile Phe Glu Ala Gln Lys Ile Glu Trp His Glu
1               5                   10                  15

<210> SEQ ID NO 89
<211> LENGTH: 437
<212> TYPE: PRT
<213> ORGANISM: Artificial Sequence
<220> FEATURE:
<223> OTHER INFORMATION: CD28(SA) VL-CH1 hu IgG1 Fc knob PGLALA

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val Trp
            20                  25                  30

Leu Asn Trp Tyr Gln Gln Lys Pro Gly Lys Ala Pro Lys Leu Leu Ile
            35                  40                  45

Tyr Lys Ala Ser Asn Leu His Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys Ser Ser Ala Ser Thr
            100                 105                 110

Lys Gly Pro Ser Val Phe Pro Leu Ala Pro Ser Ser Lys Ser Thr Ser
            115                 120                 125

Gly Gly Thr Ala Ala Leu Gly Cys Leu Val Lys Asp Tyr Phe Pro Glu
            130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
            195                 200                 205
```

```
Pro Lys Ser Cys Asp Lys Thr His Thr Cys Pro Pro Cys Pro Ala Pro
    210                 215                 220

Glu Ala Ala Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser His Glu Asp Pro Glu Val Lys Phe Asn Trp Tyr Val Asp
                260                 265                 270

Gly Val Glu Val His Asn Ala Lys Thr Lys Pro Arg Glu Glu Gln Tyr
            275                 280                 285

Asn Ser Thr Tyr Arg Val Val Ser Val Leu Thr Val Leu His Gln Asp
    290                 295                 300

Trp Leu Asn Gly Lys Glu Tyr Lys Cys Lys Val Ser Asn Lys Ala Leu
305                 310                 315                 320

Gly Ala Pro Ile Glu Lys Thr Ile Ser Lys Ala Lys Gly Gln Pro Arg
                325                 330                 335

Glu Pro Gln Val Tyr Thr Leu Pro Pro Cys Arg Asp Glu Leu Thr Lys
                340                 345                 350

Asn Gln Val Ser Leu Trp Cys Leu Val Lys Gly Phe Tyr Pro Ser Asp
            355                 360                 365

Ile Ala Val Glu Trp Glu Ser Asn Gly Gln Pro Glu Asn Asn Tyr Lys
    370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Asn His Tyr Thr Gln Lys Ser
                420                 425                 430

Leu Ser Leu Ser Pro
            435

<210> SEQ ID NO 90
<211> LENGTH: 227
<212> TYPE: PRT
<213> ORGANISM: Artificial Sequence
<220> FEATURE:
<223> OTHER INFORMATION: CD28(SA) VH-Ckappa

<400> SEQUENCE: 90

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Ile His Trp Val Arg Gln Ala Pro Gly Gln Gly Leu Glu Trp Ile
            35                  40                  45

Gly Cys Ile Tyr Pro Gly Asn Val Asn Thr Asn Tyr Asn Glu Lys Phe
        50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Thr Arg Ser His Tyr Gly Leu Asp Trp Asn Phe Asp Val Trp Gly Gln
                100                 105                 110

Gly Thr Thr Val Thr Val Ser Ser Ala Ser Val Ala Ala Pro Ser Val
            115                 120                 125
```

```
Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys
225
```

<210> SEQ ID NO 91
<211> LENGTH: 437
<212> TYPE: PRT
<213> ORGANISM: Artificial Sequence
<220> FEATURE:
<223> OTHER INFORMATION: CD28(SA_Variant 8) VL-CH1 hu IgG1 Fc knob
      PGLALA

<400> SEQUENCE: 91

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val Tyr
                20                  25                  30

Leu Asn Trp Tyr Gln Gln Lys Pro Gly Lys Ala Pro Lys Leu Leu Ile
            35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205

Pro Lys Ser Cys Asp Lys Thr His Thr Cys Pro Pro Cys Pro Ala Pro
    210                 215                 220

Glu Ala Ala Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
```

```
            245                 250                 255
Asp Val Ser His Glu Asp Pro Glu Val Lys Phe Asn Trp Tyr Val Asp
            260                 265                 270

Gly Val Glu Val His Asn Ala Lys Thr Lys Pro Arg Glu Glu Gln Tyr
        275                 280                 285

Asn Ser Thr Tyr Arg Val Val Ser Val Leu Thr Val Leu His Gln Asp
    290                 295                 300

Trp Leu Asn Gly Lys Glu Tyr Lys Cys Lys Val Ser Asn Lys Ala Leu
305                 310                 315                 320

Gly Ala Pro Ile Glu Lys Thr Ile Ser Lys Ala Lys Gly Gln Pro Arg
                325                 330                 335

Glu Pro Gln Val Tyr Thr Leu Pro Pro Cys Arg Asp Glu Leu Thr Lys
            340                 345                 350

Asn Gln Val Ser Leu Trp Cys Leu Val Lys Gly Phe Tyr Pro Ser Asp
        355                 360                 365

Ile Ala Val Glu Trp Glu Ser Asn Gly Gln Pro Glu Asn Asn Tyr Lys
    370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Asn His Tyr Thr Gln Lys Ser
            420                 425                 430

Leu Ser Leu Ser Pro
            435

<210> SEQ ID NO 92
<211> LENGTH: 227
<212> TYPE: PRT
<213> ORGANISM: Artificial Sequence
<220> FEATURE:
<223> OTHER INFORMATION: CD28(SA_Variant 8) VH-Ckappa

<400> SEQUENCE: 92

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Ser Ile Tyr Pro Gly Asn Val Gln Thr Asn Tyr Asn Glu Lys Phe
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Thr Ala Val Tyr Phe Cys
                85                  90                  95

Thr Arg Ser His Tyr Gly Leu Asp Phe Asn Phe Asp Val Trp Gly Gln
            100                 105                 110

Gly Thr Thr Val Thr Val Ser Ser Ala Ser Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
```

```
                        165                 170                 175
Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys
225

<210> SEQ ID NO 93
<211> LENGTH: 437
<212> TYPE: PRT
<213> ORGANISM: Artificial Sequence
<220> FEATURE:
<223> OTHER INFORMATION: CD28(SA_Variant 15) VL-CH1 hu IgG1 Fc knob
      PGLALA

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val Phe
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205

Pro Lys Ser Cys Asp Lys Thr His Thr Cys Pro Pro Cys Pro Ala Pro
    210                 215                 220

Glu Ala Ala Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser His Glu Asp Pro Glu Val Lys Phe Asn Trp Tyr Val Asp
            260                 265                 270

Gly Val Glu Val His Asn Ala Lys Thr Lys Pro Arg Glu Glu Gln Tyr
        275                 280                 285
```

```
Asn Ser Thr Tyr Arg Val Val Ser Val Leu Thr Val Leu His Gln Asp
            290                 295                 300

Trp Leu Asn Gly Lys Glu Tyr Lys Cys Lys Val Ser Asn Lys Ala Leu
305                 310                 315                 320

Gly Ala Pro Ile Glu Lys Thr Ile Ser Lys Ala Lys Gly Gln Pro Arg
                325                 330                 335

Glu Pro Gln Val Tyr Thr Leu Pro Pro Cys Arg Asp Glu Leu Thr Lys
            340                 345                 350

Asn Gln Val Ser Leu Trp Cys Leu Val Lys Gly Phe Tyr Pro Ser Asp
                355                 360                 365

Ile Ala Val Glu Trp Glu Ser Asn Gly Gln Pro Glu Asn Asn Tyr Lys
        370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Asn His Tyr Thr Gln Lys Ser
            420                 425                 430

Leu Ser Leu Ser Pro
        435
```

<210> SEQ ID NO 94
<211> LENGTH: 227
<212> TYPE: PRT
<213> ORGANISM: Artificial Sequence
<220> FEATURE:
<223> OTHER INFORMATION: CD28(SA_Variant 15) VH-Ckappa

<400> SEQUENCE: 94

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Ser Ile Tyr Pro Gly Asn Val Gln Thr Asn Tyr Asn Glu Lys Phe
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Thr Ala Val Tyr Phe Cys
                85                  90                  95

Thr Arg Ser His Tyr Gly Leu Asp Trp Asn Phe Asp Val Trp Gly Gln
            100                 105                 110

Gly Thr Thr Val Thr Val Ser Ser Ala Ser Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205
```

```
Val Thr His Gln Gly Leu Ser Ser Pro Val Thr Lys Ser Phe Asn Arg
    210                 215                 220

Gly Glu Cys
225
```

```
<210> SEQ ID NO 95
<211> LENGTH: 227
<212> TYPE: PRT
<213> ORGANISM: Artificial Sequence
<220> FEATURE:
<223> OTHER INFORMATION: CD28(SA_Variant 29) VH-Ckappa

<400> SEQUENCE: 95

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Ser Ile Tyr Pro Gly Asn Val Asn Thr Asn Tyr Asn Glu Lys Phe
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Thr Arg Ser His Tyr Gly Leu Asp Trp Asn Phe Asp Val Trp Gly Gln
            100                 105                 110

Gly Thr Thr Val Thr Val Ser Ser Ala Ser Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys
225
```

```
<210> SEQ ID NO 96
<211> LENGTH: 447
<212> TYPE: PRT
<213> ORGANISM: Artificial Sequence
<220> FEATURE:
<223> OTHER INFORMATION: Her2 (pertuzumab CLC) hu IgG1 VH-CH1 "EE" Fc
      hole wildtype

<400> SEQUENCE: 96

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asp Tyr
            20                  25                  30

Thr Met Asp Trp Val Arg Gln Ala Pro Gly Lys Gly Leu Glu Trp Val
```

```
                35                  40                  45
Ala Asp Val Asn Pro Asn Ser Gly Ser Ile Val Asn Arg Arg Phe
 50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Leu Gly Pro Phe Phe Tyr Phe Asp Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
                130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Glu Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Cys Thr
                340                 345                 350

Leu Pro Pro Ser Arg Asp Glu Leu Thr Lys Asn Gln Val Ser Leu Ser
                355                 360                 365

Cys Ala Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro
                435                 440                 445

<210> SEQ ID NO 97
```

<211> LENGTH: 214
<212> TYPE: PRT
<213> ORGANISM: Artificial Sequence
<220> FEATURE:
<223> OTHER INFORMATION: Her2 (pertuzumab CLC) VL-Ckappa "RK"

<400> SEQUENCE: 97

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Arg Tyr Thr Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Arg Lys Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 98
<211> LENGTH: 447
<212> TYPE: PRT
<213> ORGANISM: Artificial Sequence
<220> FEATURE:
<223> OTHER INFORMATION: Her2 (pertuzumab CLC) hu IgG1 VH-CH1 "EE" Fc
      hole PGLALA

<400> SEQUENCE: 98

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Val Asn Arg Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Arg Asn Leu Gly Pro Phe Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445
```

<210> SEQ ID NO 99
<211> LENGTH: 437
<212> TYPE: PRT
<213> ORGANISM: Artificial Sequence
<220> FEATURE:
<223> OTHER INFORMATION: Her2 (pertuzumab CLC) VL-CH1 hu IgG1 Fc knob
      PGLALA

<400> SEQUENCE: 99

```
Asp Ile Gln Met Thr Gln Ser Pro Ser Ser Leu Ser Ala Ser Val Gly
1               5                   10                  15
```

```
Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Arg Tyr Thr Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205

Pro Lys Ser Cys Asp Lys Thr His Thr Cys Pro Pro Cys Pro Ala Pro
    210                 215                 220

Glu Ala Ala Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser His Glu Asp Pro Glu Val Lys Phe Asn Trp Tyr Val Asp
            260                 265                 270

Gly Val Glu Val His Asn Ala Lys Thr Lys Pro Arg Glu Glu Gln Tyr
        275                 280                 285

Asn Ser Thr Tyr Arg Val Val Ser Val Leu Thr Val Leu His Gln Asp
    290                 295                 300

Trp Leu Asn Gly Lys Glu Tyr Lys Cys Lys Val Ser Asn Lys Ala Leu
305                 310                 315                 320

Gly Ala Pro Ile Glu Lys Thr Ile Ser Lys Ala Lys Gly Gln Pro Arg
                325                 330                 335

Glu Pro Gln Val Cys Thr Leu Pro Pro Ser Arg Asp Glu Leu Thr Lys
            340                 345                 350

Asn Gln Val Ser Leu Ser Cys Ala Val Lys Gly Phe Tyr Pro Ser Asp
        355                 360                 365

Ile Ala Val Glu Trp Glu Ser Asn Gly Gln Pro Glu Asn Asn Tyr Lys
    370                 375                 380

Thr Thr Pro Pro Val Leu Asp Ser Asp Gly Ser Phe Phe Leu Val Ser
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Asn His Tyr Thr Gln Lys Ser
            420                 425                 430
```

```
Leu Ser Leu Ser Pro
        435
```

<210> SEQ ID NO 100
<211> LENGTH: 226
<212> TYPE: PRT
<213> ORGANISM: Artificial Sequence
<220> FEATURE:
<223> OTHER INFORMATION: Her2 (pertuzumab CLC) VH-Ckappa

<400> SEQUENCE: 100

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Val Asn Arg Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Phe Phe Tyr Phe Asp Tyr Trp Gly Gln Gly
            100                 105                 110

Thr Leu Val Thr Val Ser Ser Ala Ser Val Ala Ala Pro Ser Val Phe
        115                 120                 125

Ile Phe Pro Pro Ser Asp Glu Gln Leu Lys Ser Gly Thr Ala Ser Val
    130                 135                 140

Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
                165                 170                 175

Glu Gln Asp Ser Lys Asp Ser Thr Tyr Ser Leu Ser Ser Thr Leu Thr
            180                 185                 190

Leu Ser Lys Ala Asp Tyr Glu Lys His Lys Val Tyr Ala Cys Glu Val
        195                 200                 205

Thr His Gln Gly Leu Ser Ser Pro Val Thr Lys Ser Phe Asn Arg Gly
    210                 215                 220

Glu Cys
225
```

<210> SEQ ID NO 101
<211> LENGTH: 448
<212> TYPE: PRT
<213> ORGANISM: Artificial Sequence
<220> FEATURE:
<223> OTHER INFORMATION: Her2 (trastuzumab CLC) hu IgG1 VH-CH1 "EE" Fc
      hole PGLALA

<400> SEQUENCE: 101

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
```

```
            50                  55                  60
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Glu Gly Phe Tyr Ala Met Asp Tyr Trp Gly Gln
            100                 105                 110

Gly Thr Leu Val Thr Val Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Glu Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Glu Lys Val Glu Pro Lys Ser Cys Asp
210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
            355                 360                 365

Ser Cys Ala Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

<210> SEQ ID NO 102
<211> LENGTH: 437
<212> TYPE: PRT
<213> ORGANISM: Artificial Sequence
```

<220> FEATURE:
<223> OTHER INFORMATION: Her2 (trastuzumab CLC) VL-CH1 hu IgG1 Fc knob
PGLALA

<400> SEQUENCE: 102

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Arg Tyr Thr Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205

Pro Lys Ser Cys Asp Lys Thr His Thr Cys Pro Pro Cys Pro Ala Pro
210                 215                 220

Glu Ala Ala Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser His Glu Asp Pro Glu Val Lys Phe Asn Trp Tyr Val Asp
            260                 265                 270

Gly Val Glu Val His Asn Ala Lys Thr Lys Pro Arg Glu Glu Gln Tyr
        275                 280                 285

Asn Ser Thr Tyr Arg Val Val Ser Val Leu Thr Val Leu His Gln Asp
290                 295                 300

Trp Leu Asn Gly Lys Glu Tyr Lys Cys Lys Val Ser Asn Lys Ala Leu
305                 310                 315                 320

Gly Ala Pro Ile Glu Lys Thr Ile Ser Lys Ala Lys Gly Gln Pro Arg
                325                 330                 335

Glu Pro Gln Val Cys Thr Leu Pro Pro Ser Arg Asp Glu Leu Thr Lys
            340                 345                 350

Asn Gln Val Ser Leu Ser Cys Ala Val Lys Gly Phe Tyr Pro Ser Asp
        355                 360                 365

Ile Ala Val Glu Trp Glu Ser Asn Gly Gln Pro Glu Asn Asn Tyr Lys
370                 375                 380

Thr Thr Pro Pro Val Leu Asp Ser Asp Gly Ser Phe Phe Leu Val Ser
```

```
                385             390             395             400
Lys Leu Thr Val Asp Lys Ser Arg Trp Gln Gln Gly Asn Val Phe Ser
                    405             410             415

Cys Ser Val Met His Glu Ala Leu His Asn His Tyr Thr Gln Lys Ser
                420             425             430

Leu Ser Leu Ser Pro
            435

<210> SEQ ID NO 103
<211> LENGTH: 1245
<212> TYPE: PRT
<213> ORGANISM: Homo sapiens

<400> SEQUENCE: 103

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
                35                  40                  45

Leu Tyr Gln Gly Cys Gln Val Val Gln Gly Asn Leu Glu Leu Thr Tyr
50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
                100                 105                 110

Ala Leu Ala Val Leu Asp Asn Gly Asp Pro Leu Asn Asn Thr Thr Pro
                115                 120                 125

Val Thr Gly Ala Ser Pro Gly Gly Leu Arg Glu Leu Gln Leu Arg Ser
                130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
                180                 185                 190

His Pro Cys Ser Pro Met Cys Lys Gly Ser Arg Cys Trp Gly Glu Ser
                195                 200                 205

Ser Glu Asp Cys Gln Ser Leu Thr Arg Thr Val Cys Ala Gly Gly Cys
                210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
                260                 265                 270

Thr Tyr Asn Thr Asp Thr Phe Glu Ser Met Pro Asn Pro Glu Gly Arg
                275                 280                 285

Tyr Thr Phe Gly Ala Ser Cys Val Thr Ala Cys Pro Tyr Asn Tyr Leu
                290                 295                 300

Ser Thr Asp Val Gly Ser Cys Thr Leu Val Cys Pro Leu His Asn Gln
305                 310                 315                 320
```

-continued

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
                340                 345                 350

Val Arg Ala Val Thr Ser Ala Asn Ile Gln Glu Phe Ala Gly Cys Lys
                355                 360                 365

Lys Ile Phe Gly Ser Leu Ala Phe Leu Pro Glu Ser Phe Asp Gly Asp
                370                 375                 380

Pro Ala Ser Asn Thr Ala Glu Thr Leu Glu Glu Ile Thr Gly Tyr Leu
385                 390                 395                 400

Tyr Ile Ser Ala Trp Pro Asp Ser Leu Pro Asp Leu Ser Val Phe Gln
                405                 410                 415

Asn Leu Gln Val Ile Arg Gly Arg Ile Leu His Asn Gly Ala Tyr Ser
                420                 425                 430

Leu Thr Leu Gln Gly Leu Gly Ile Ser Trp Leu Gly Leu Arg Ser Leu
                435                 440                 445

Arg Glu Leu Gly Ser Gly Leu Ala Leu Ile His His Asn Thr His Leu
                450                 455                 460

Cys Phe Val His Thr Val Pro Trp Asp Gln Leu Phe Arg Asn Pro His
465                 470                 475                 480

Gln Ala Leu Leu His Thr Ala Asn Arg Pro Glu Asp Glu Cys Val Gly
                485                 490                 495

Glu Gly Leu Ala Cys His Gln Leu Cys Ala Arg Gly His Cys Trp Gly
                500                 505                 510

Pro Gly Pro Thr Gln Cys Val Asn Cys Ser Gln Phe Leu Arg Gly Gln
                515                 520                 525

Glu Cys Val Glu Glu Cys Arg Val Leu Gln Gly Leu Pro Arg Glu Tyr
                530                 535                 540

Val Asn Ala Arg His Cys Leu Pro Cys His Pro Glu Cys Gln Pro Gln
545                 550                 555                 560

Asn Gly Ser Val Thr Cys Phe Gly Pro Glu Ala Asp Gln Cys Val Ala
                565                 570                 575

Cys Ala His Tyr Lys Asp Pro Pro Phe Cys Val Ala Arg Cys Pro Ser
                580                 585                 590

Gly Val Lys Pro Asp Leu Ser Tyr Met Pro Ile Trp Lys Phe Pro Asp
                595                 600                 605

Glu Glu Gly Ala Cys Gln Pro Cys Pro Ile Asn Cys Thr His Ser Cys
                610                 615                 620

Val Asp Leu Asp Asp Lys Gly Cys Pro Ala Glu Gln Arg Ala Ser Pro
625                 630                 635                 640

Leu Thr Ser Ile Ile Ser Ala Val Val Gly Ile Leu Leu Val Val Val
                645                 650                 655

Leu Gly Val Val Phe Gly Ile Leu Ile Lys Arg Arg Gln Gln Lys Ile
                660                 665                 670

Arg Lys Tyr Thr Met Arg Arg Leu Leu Gln Glu Thr Glu Leu Val Glu
                675                 680                 685

Pro Leu Thr Pro Ser Gly Ala Met Pro Asn Gln Ala Gln Met Arg Ile
                690                 695                 700

Leu Lys Glu Thr Glu Leu Arg Lys Val Lys Val Leu Gly Ser Gly Ala
705                 710                 715                 720

Phe Gly Thr Val Tyr Lys Gly Ile Trp Ile Pro Asp Gly Glu Asn Val
                725                 730                 735

Lys Ile Pro Val Ala Ile Lys Val Leu Arg Glu Asn Thr Ser Pro Lys

-continued

```
                740                 745                 750
Ala Asn Lys Glu Ile Leu Asp Glu Ala Tyr Val Met Ala Gly Val Gly
            755                 760                 765

Ser Pro Tyr Val Ser Arg Leu Leu Gly Ile Cys Leu Thr Ser Thr Val
        770                 775                 780

Gln Leu Val Thr Gln Leu Met Pro Tyr Gly Cys Leu Leu Asp His Val
785                 790                 795                 800

Arg Glu Asn Arg Gly Arg Leu Gly Ser Gln Asp Leu Leu Asn Trp Cys
                805                 810                 815

Met Gln Ile Ala Lys Gly Met Ser Tyr Leu Glu Asp Val Arg Leu Val
            820                 825                 830

His Arg Asp Leu Ala Ala Arg Asn Val Leu Val Lys Ser Pro Asn His
        835                 840                 845

Val Lys Ile Thr Asp Phe Gly Leu Ala Arg Leu Leu Asp Ile Asp Glu
    850                 855                 860

Thr Glu Tyr His Ala Asp Gly Gly Lys Val Pro Ile Lys Trp Met Ala
865                 870                 875                 880

Leu Glu Ser Ile Leu Arg Arg Phe Thr His Gln Ser Asp Val Trp
                885                 890                 895

Ser Tyr Gly Val Thr Val Trp Glu Leu Met Thr Phe Gly Ala Lys Pro
            900                 905                 910

Tyr Asp Gly Ile Pro Ala Arg Glu Ile Pro Asp Leu Leu Glu Lys Gly
        915                 920                 925

Glu Arg Leu Pro Gln Pro Pro Ile Cys Thr Ile Asp Val Tyr Met Ile
    930                 935                 940

Met Val Lys Cys Trp Met Ile Asp Ser Glu Cys Arg Pro Arg Phe Arg
945                 950                 955                 960

Glu Leu Val Ser Glu Phe Ser Arg Met Ala Arg Asp Pro Gln Arg Phe
                965                 970                 975

Val Val Ile Gln Asn Glu Asp Leu Gly Pro Ala Ser Pro Leu Asp Ser
            980                 985                 990

Thr Phe Tyr Arg Ser Leu Leu Glu  Asp Asp Asp Met Gly  Asp Leu Val
        995                 1000                 1005

Asp Ala  Glu Glu Tyr Leu Val  Pro Gln Gln Gly Phe  Phe Cys Pro
    1010                 1015                 1020

Asp Pro  Ala Pro Gly Ala Gly  Gly Met Val His His  Arg His Arg
    1025                 1030                 1035

Ser Ser  Ser Thr Arg Ser Gly  Gly Gly Asp Leu Thr  Leu Gly Leu
    1040                 1045                 1050

Glu Pro  Ser Glu Glu Glu Ala  Pro Arg Ser Pro Leu  Ala Pro Ser
    1055                 1060                 1065

Glu Gly  Ala Gly Ser Asp Val  Phe Asp Gly Asp Leu  Gly Met Gly
    1070                 1075                 1080

Ala Ala  Lys Gly Leu Gln Ser  Leu Pro Thr His Asp  Pro Ser Pro
    1085                 1090                 1095

Leu Gln  Arg Tyr Ser Glu Asp  Pro Thr Val Pro Leu  Pro Ser Glu
    1100                 1105                 1110

Thr Asp  Gly Tyr Val Ala Pro  Leu Thr Cys Ser Pro  Gln Pro Glu
    1115                 1120                 1125

Tyr Val  Asn Gln Pro Asp Val  Arg Pro Gln Pro Pro  Ser Pro Arg
    1130                 1135                 1140

Glu Gly  Pro Leu Pro Ala Ala  Arg Pro Ala Gly Ala  Thr Leu Glu
    1145                 1150                 1155
```

-continued

Arg Pro Lys Thr Leu Ser Pro Gly Lys Asn Gly Val Val Lys Asp
    1160            1165                1170

Val Phe Ala Phe Gly Gly Ala Val Glu Asn Pro Glu Tyr Leu Thr
    1175            1180                1185

Pro Gln Gly Gly Ala Ala Pro Gln Pro His Pro Pro Pro Ala Phe
    1190            1195                1200

Ser Pro Ala Phe Asp Asn Leu Tyr Tyr Trp Asp Gln Asp Pro Pro
    1205            1210                1215

Glu Arg Gly Ala Pro Pro Ser Thr Phe Lys Gly Thr Pro Thr Ala
    1220            1225                1230

Glu Asn Pro Glu Tyr Leu Gly Leu Asp Val Pro Val
    1235            1240                1245

<210> SEQ ID NO 104
<211> LENGTH: 98
<212> TYPE: PRT
<213> ORGANISM: Homo sapiens

<400> SEQUENCE: 104

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 105
<211> LENGTH: 107
<212> TYPE: PRT
<213> ORGANISM: Homo sapiens

<400> SEQUENCE: 105

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Trp Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Glu Ser Thr Tyr Arg Trp Ser Val Leu Thr Val Leu His Gln Asp Trp
65                  70                  75                  80

Leu Asn Gly Lys Glu Tyr Lys Cys Lys Val Ser Asn Lys Ala Leu Pro
                85                  90                  95

Ala Pro Ile Glu Lys Thr Ile Ser Lys Ala Lys
                100                 105

<210> SEQ ID NO 106
<211> LENGTH: 106

<212> TYPE: PRT
<213> ORGANISM: Homo sapiens

<400> SEQUENCE: 106

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 107
<211> LENGTH: 5
<212> TYPE: PRT
<213> ORGANISM: Homo sapiens

<400> SEQUENCE: 107

Glu Pro Lys Ser Cys
1               5

<210> SEQ ID NO 108
<211> LENGTH: 10
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: X is S or P

<400> SEQUENCE: 108

Asp Lys Thr His Thr Cys Pro Xaa Cys Pro
1               5                   10

<210> SEQ ID NO 109
<211> LENGTH: 7
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: X is S or P

<400> SEQUENCE: 109

His Thr Cys Pro Xaa Cys Pro
1               5

<210> SEQ ID NO 110
<211> LENGTH: 5
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X is S or P

<400> SEQUENCE: 110

```
Cys Pro Xaa Cys Pro
1               5
```

<210> SEQ ID NO 111
<211> LENGTH: 330
<212> TYPE: PRT
<213> ORGANISM: Homo sapiens

<400> SEQUENCE: 111

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 112
<211> LENGTH: 330
<212> TYPE: PRT
<213> ORGANISM: Homo sapiens

<400> SEQUENCE: 112

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 113
<211> LENGTH: 326
<212> TYPE: PRT
<213> ORGANISM: Homo sapiens

<400> SEQUENCE: 113

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 114
<211> LENGTH: 377
<212> TYPE: PRT
<213> ORGANISM: Homo sapiens

<400> SEQUENCE: 114

Ala Ser Thr Lys Gly Pro Ser Val Phe Pro Leu Ala Pro Cys Ser Arg
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
```

```
                65                  70                  75                  80
Tyr Thr Cys Asn Val Asn His Lys Pro Ser Asn Thr Lys Val Asp Lys
                        85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 115
<211> LENGTH: 327
<212> TYPE: PRT
<213> ORGANISM: Homo sapiens

<400> SEQUENCE: 115

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

-continued

```
Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 116
<211> LENGTH: 254
<212> TYPE: PRT
<213> ORGANISM: Homo sapiens

<400> SEQUENCE: 116

Met Trp Gln Leu Leu Leu Pro Thr Ala Leu Leu Leu Leu Val Ser Ala
  1               5                  10                  15

Gly Met Arg Thr Glu Asp Leu Pro Lys Ala Val Val Phe Leu Glu Pro
             20                  25                  30

Gln Trp Tyr Arg Val Leu Glu Lys Asp Ser Val Thr Leu Lys Cys Gln
         35                  40                  45

Gly Ala Tyr Ser Pro Glu Asp Asn Ser Thr Gln Trp Phe His Asn Glu
     50                  55                  60

Ser Leu Ile Ser Ser Gln Ala Ser Ser Tyr Phe Ile Asp Ala Ala Thr
 65                  70                  75                  80

Val Asp Asp Ser Gly Glu Tyr Arg Cys Gln Thr Asn Leu Ser Thr Leu
                 85                  90                  95

Ser Asp Pro Val Gln Leu Glu Val His Ile Gly Trp Leu Leu Leu Gln
            100                 105                 110
```

```
Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
                180                 185                 190

Gly Leu Ala Val Ser Thr Ile Ser Ser Phe Phe Pro Pro Gly Tyr Gln
            195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 117
<211> LENGTH: 5
<212> TYPE: PRT
<213> ORGANISM: Artificial Sequence
<220> FEATURE:
<223> OTHER INFORMATION: Peptide linker G4S

<400> SEQUENCE: 117

Gly Gly Gly Gly Ser
1               5

<210> SEQ ID NO 118
<211> LENGTH: 10
<212> TYPE: PRT
<213> ORGANISM: Artificial Sequence
<220> FEATURE:
<223> OTHER INFORMATION: Peptide linker (G4S)2

<400> SEQUENCE: 118

Gly Gly Gly Gly Ser Gly Gly Gly Gly Ser
1               5                   10

<210> SEQ ID NO 119
<211> LENGTH: 10
<212> TYPE: PRT
<213> ORGANISM: Artificial Sequence
<220> FEATURE:
<223> OTHER INFORMATION: Peptide linker (SG4)2

<400> SEQUENCE: 119

Ser Gly Gly Gly Gly Ser Gly Gly Gly Gly
1               5                   10

<210> SEQ ID NO 120
<211> LENGTH: 14
<212> TYPE: PRT
<213> ORGANISM: Artificial Sequence
<220> FEATURE:
<223> OTHER INFORMATION: Peptide linker G4(SG4)2

<400> SEQUENCE: 120

Gly Gly Gly Gly Ser Gly Gly Gly Gly Ser Gly Gly Gly Gly
1               5                   10
```

<210> SEQ ID NO 121
<211> LENGTH: 10
<212> TYPE: PRT
<213> ORGANISM: Artificial Sequence
<220> FEATURE:
<223> OTHER INFORMATION: Peptide linker

<400> SEQUENCE: 121

Gly Ser Pro Gly Ser Ser Ser Ser Gly Ser
1               5                   10

<210> SEQ ID NO 122
<211> LENGTH: 15
<212> TYPE: PRT
<213> ORGANISM: Artificial Sequence
<220> FEATURE:
<223> OTHER INFORMATION: Peptide linker (G4S)3

<400> SEQUENCE: 122

Gly Gly Gly Gly Ser Gly Gly Gly Gly Ser Gly Gly Gly Gly Ser
1               5                   10                  15

<210> SEQ ID NO 123
<211> LENGTH: 20
<212> TYPE: PRT
<213> ORGANISM: Artificial Sequence
<220> FEATURE:
<223> OTHER INFORMATION: Peptide linker (G4S)4

<400> SEQUENCE: 123

Gly Gly Gly Gly Ser Gly Gly Gly Gly Ser Gly Gly Gly Gly Ser Gly
1               5                   10                  15

Gly Gly Gly Ser
            20

<210> SEQ ID NO 124
<211> LENGTH: 8
<212> TYPE: PRT
<213> ORGANISM: Artificial Sequence
<220> FEATURE:
<223> OTHER INFORMATION: Peptide linker

<400> SEQUENCE: 124

Gly Ser Gly Ser Gly Ser Gly Ser
1               5

<210> SEQ ID NO 125
<211> LENGTH: 8
<212> TYPE: PRT
<213> ORGANISM: Artificial Sequence
<220> FEATURE:
<223> OTHER INFORMATION: Peptide linker

<400> SEQUENCE: 125

Gly Ser Gly Ser Gly Asn Gly Ser
1               5

<210> SEQ ID NO 126
<211> LENGTH: 8
<212> TYPE: PRT
<213> ORGANISM: Artificial Sequence
<220> FEATURE:
<223> OTHER INFORMATION: Peptide linker

<400> SEQUENCE: 126

```
Gly Gly Ser Gly Ser Gly Ser Gly
1               5

<210> SEQ ID NO 127
<211> LENGTH: 6
<212> TYPE: PRT
<213> ORGANISM: Artificial Sequence
<220> FEATURE:
<223> OTHER INFORMATION: Peptide linker

<400> SEQUENCE: 127

Gly Gly Ser Gly Ser Gly
1               5

<210> SEQ ID NO 128
<211> LENGTH: 4
<212> TYPE: PRT
<213> ORGANISM: Artificial Sequence
<220> FEATURE:
<223> OTHER INFORMATION: Peptide linker

<400> SEQUENCE: 128

Gly Gly Ser Gly
1

<210> SEQ ID NO 129
<211> LENGTH: 8
<212> TYPE: PRT
<213> ORGANISM: Artificial Sequence
<220> FEATURE:
<223> OTHER INFORMATION: Peptide linker

<400> SEQUENCE: 129

Gly Gly Ser Gly Asn Gly Ser Gly
1               5

<210> SEQ ID NO 130
<211> LENGTH: 8
<212> TYPE: PRT
<213> ORGANISM: Artificial Sequence
<220> FEATURE:
<223> OTHER INFORMATION: Peptide linker

<400> SEQUENCE: 130

Gly Gly Asn Gly Ser Gly Ser Gly
1               5

<210> SEQ ID NO 131
<211> LENGTH: 6
<212> TYPE: PRT
<213> ORGANISM: Artificial Sequence
<220> FEATURE:
<223> OTHER INFORMATION: Peptide linker

<400> SEQUENCE: 131

Gly Gly Asn Gly Ser Gly
1               5

<210> SEQ ID NO 132
<211> LENGTH: 10
<212> TYPE: PRT
<213> ORGANISM: Artificial Sequence
<220> FEATURE:
<223> OTHER INFORMATION: CDR-H1, pertuzumab

<400> SEQUENCE: 132

Gly Phe Thr Phe Thr Asp Tyr Thr Met Asp
```

<210> SEQ ID NO 133
<211> LENGTH: 17
<212> TYPE: PRT
<213> ORGANISM: Artificial Sequence
<220> FEATURE:
<223> OTHER INFORMATION: CDR-H2, pertuzumab

<400> SEQUENCE: 133

Asp Val Asn Pro Asn Ser Gly Gly Ser Ile Tyr Asn Gln Arg Phe Lys
1               5                   10                  15
Gly

<210> SEQ ID NO 134
<211> LENGTH: 10
<212> TYPE: PRT
<213> ORGANISM: Artificial Sequence
<220> FEATURE:
<223> OTHER INFORMATION: CDR-H3, pertuzumab

<400> SEQUENCE: 134

Asn Leu Gly Pro Ser Phe Tyr Phe Asp Tyr
1               5                   10

<210> SEQ ID NO 135
<211> LENGTH: 11
<212> TYPE: PRT
<213> ORGANISM: Artificial Sequence
<220> FEATURE:
<223> OTHER INFORMATION: CDR-L1, pertuzumab

<400> SEQUENCE: 135

Lys Ala Ser Gln Asp Val Ser Ile Gly Val Ala
1               5                   10

<210> SEQ ID NO 136
<211> LENGTH: 7
<212> TYPE: PRT
<213> ORGANISM: Artificial Sequence
<220> FEATURE:
<223> OTHER INFORMATION: CDR-L2, pertuzumab

<400> SEQUENCE: 136

Ser Ala Ser Tyr Arg Tyr Thr
1               5

<210> SEQ ID NO 137
<211> LENGTH: 9
<212> TYPE: PRT
<213> ORGANISM: Artificial Sequence
<220> FEATURE:
<223> OTHER INFORMATION: CDR-L3, pertuzumab

<400> SEQUENCE: 137

Gln Gln Tyr Tyr Ile Tyr Pro Tyr Thr
1               5

<210> SEQ ID NO 138
<211> LENGTH: 119
<212> TYPE: PRT
<213> ORGANISM: Artificial Sequence
<220> FEATURE:
<223> OTHER INFORMATION: heavy chain variable domain VH, pertuzumab

<400> SEQUENCE: 138

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
            115
```

<210> SEQ ID NO 139
<211> LENGTH: 107
<212> TYPE: PRT
<213> ORGANISM: Artificial Sequence
<220> FEATURE:
<223> OTHER INFORMATION: light chain variable domain VL, pertuzumab

<400> SEQUENCE: 139

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105
```

<210> SEQ ID NO 140
<211> LENGTH: 10
<212> TYPE: PRT
<213> ORGANISM: Artificial Sequence
<220> FEATURE:
<223> OTHER INFORMATION: CDR-H1, trastuzumab

<400> SEQUENCE: 140

```
Gly Phe Asn Ile Lys Asp Thr Tyr Ile His
1               5                   10
```

<210> SEQ ID NO 141
<211> LENGTH: 17
<212> TYPE: PRT
<213> ORGANISM: Artificial Sequence
<220> FEATURE:
<223> OTHER INFORMATION: CDR-H2, trastuzumab

<400> SEQUENCE: 141

```
Arg Ile Tyr Pro Thr Asn Gly Tyr Thr Arg Tyr Ala Asp Ser Val Lys
```

```
1               5                   10                  15
Gly

<210> SEQ ID NO 142
<211> LENGTH: 11
<212> TYPE: PRT
<213> ORGANISM: Artificial Sequence
<220> FEATURE:
<223> OTHER INFORMATION: CDR-H3, trastuzumab

<400> SEQUENCE: 142

Trp Gly Gly Asp Gly Phe Tyr Ala Met Asp Tyr
1               5                   10

<210> SEQ ID NO 143
<211> LENGTH: 11
<212> TYPE: PRT
<213> ORGANISM: Artificial Sequence
<220> FEATURE:
<223> OTHER INFORMATION: CDR-L1, trastuzumab

<400> SEQUENCE: 143

Arg Ala Ser Gln Asp Val Asn Thr Ala Val Ala
1               5                   10

<210> SEQ ID NO 144
<211> LENGTH: 7
<212> TYPE: PRT
<213> ORGANISM: Artificial Sequence
<220> FEATURE:
<223> OTHER INFORMATION: CDR-L2, trastuzumab

<400> SEQUENCE: 144

Ser Ala Ser Phe Leu Tyr Ser
1               5

<210> SEQ ID NO 145
<211> LENGTH: 9
<212> TYPE: PRT
<213> ORGANISM: Artificial Sequence
<220> FEATURE:
<223> OTHER INFORMATION: CDR-L3, trastuzumab

<400> SEQUENCE: 145

Gln Gln His Tyr Thr Thr Pro Pro Thr
1               5

<210> SEQ ID NO 146
<211> LENGTH: 120
<212> TYPE: PRT
<213> ORGANISM: Artificial Sequence
<220> FEATURE:
<223> OTHER INFORMATION: heavy chain variable domain VH, trastuzumab

<400> SEQUENCE: 146

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
        50                  55                  60

Lys Gly Arg Phe Thr Ile Ser Ala Asp Thr Ser Lys Asn Thr Ala Tyr
```

```
                65                  70                  75                  80
Leu Gln Met Asn Ser Leu Arg Ala Glu Asp Thr Ala Val Tyr Tyr Cys
                    85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 147
<211> LENGTH: 107
<212> TYPE: PRT
<213> ORGANISM: Artificial Sequence
<220> FEATURE:
<223> OTHER INFORMATION: light chain variable domain VL, trastuzumab

<400> SEQUENCE: 147

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 148
<211> LENGTH: 5
<212> TYPE: PRT
<213> ORGANISM: Artificial Sequence
<220> FEATURE:
<223> OTHER INFORMATION: CDR-H1, CD3

<400> SEQUENCE: 148

Asn Tyr Tyr Ile His
1               5

<210> SEQ ID NO 149
<211> LENGTH: 17
<212> TYPE: PRT
<213> ORGANISM: Artificial Sequence
<220> FEATURE:
<223> OTHER INFORMATION: CDR-H2, CD3

<400> SEQUENCE: 149

Trp Ile Tyr Pro Gly Asp Gly Asn Thr Lys Tyr Asn Glu Lys Phe Lys
1               5                   10                  15

Gly

<210> SEQ ID NO 150
<211> LENGTH: 10
<212> TYPE: PRT
<213> ORGANISM: Artificial Sequence
<220> FEATURE:
<223> OTHER INFORMATION: CDR-H3, CD3

<400> SEQUENCE: 150
```

```
Asp Ser Tyr Ser Asn Tyr Tyr Phe Asp Tyr
1               5                   10

<210> SEQ ID NO 151
<211> LENGTH: 17
<212> TYPE: PRT
<213> ORGANISM: Artificial Sequence
<220> FEATURE:
<223> OTHER INFORMATION: CDR-L1, CD3

<400> SEQUENCE: 151

Lys Ser Ser Gln Ser Leu Leu Asn Ser Arg Thr Arg Lys Asn Tyr Leu
1               5                   10                  15

Ala

<210> SEQ ID NO 152
<211> LENGTH: 7
<212> TYPE: PRT
<213> ORGANISM: Artificial Sequence
<220> FEATURE:
<223> OTHER INFORMATION: CDR-L2, CD3

<400> SEQUENCE: 152

Trp Ala Ser Thr Arg Glu Ser
1               5

<210> SEQ ID NO 153
<211> LENGTH: 8
<212> TYPE: PRT
<213> ORGANISM: Artificial Sequence
<220> FEATURE:
<223> OTHER INFORMATION: CDR-L3, CD3

<400> SEQUENCE: 153

Thr Gln Ser Phe Ile Leu Arg Thr
1               5

<210> SEQ ID NO 154
<211> LENGTH: 119
<212> TYPE: PRT
<213> ORGANISM: Artificial Sequence
<220> FEATURE:
<223> OTHER INFORMATION: heavy chain variable domain VH, CD3

<400> SEQUENCE: 154

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Ile His Trp Val Arg Gln Ala Pro Gly Gln Gly Leu Glu Trp Ile
            35                  40                  45

Gly Trp Ile Tyr Pro Gly Asp Gly Asn Thr Lys Tyr Asn Glu Lys Phe
    50                  55                  60

Lys Gly Arg Ala Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Ser Tyr Ser Asn Tyr Tyr Phe Asp Tyr Trp Gly Gln Gly
                100                 105                 110

Thr Leu Val Thr Val Ser Ser
            115
```

<210> SEQ ID NO 155
<211> LENGTH: 112
<212> TYPE: PRT
<213> ORGANISM: Artificial Sequence
<220> FEATURE:
<223> OTHER INFORMATION: light chain variable domain VL, CD3

<400> SEQUENCE: 155

Asp Ile Val Met Thr Gln Ser Pro Asp Ser Leu Ala Val Ser Leu Gly
1               5                   10                  15

Glu Arg Ala Thr Ile Asn Cys Lys Ser Gln Ser Leu Leu Asn Ser
            20                  25                  30

Arg Thr Arg Lys Asn Tyr Leu Ala Trp Tyr Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
            100                 105                 110

<210> SEQ ID NO 156
<211> LENGTH: 5
<212> TYPE: PRT
<213> ORGANISM: Artificial Sequence
<220> FEATURE:
<223> OTHER INFORMATION: CDR-H1, Her2 (7C2)

<400> SEQUENCE: 156

Gly Tyr Trp Met Asn
1               5

<210> SEQ ID NO 157
<211> LENGTH: 17
<212> TYPE: PRT
<213> ORGANISM: Artificial Sequence
<220> FEATURE:
<223> OTHER INFORMATION: CDR-H2, Her2 (7C2)

<400> SEQUENCE: 157

Met Ile His Pro Ser Asp Ser Glu Ile Arg Ala Asn Gln Lys Phe Arg
1               5                   10                  15

Asp

<210> SEQ ID NO 158
<211> LENGTH: 9
<212> TYPE: PRT
<213> ORGANISM: Artificial Sequence
<220> FEATURE:
<223> OTHER INFORMATION: CDR-H3, Her2 (7C2)

<400> SEQUENCE: 158

Gly Thr Tyr Asp Gly Gly Phe Glu Tyr
1               5

<210> SEQ ID NO 159
<211> LENGTH: 15
<212> TYPE: PRT
<213> ORGANISM: Artificial Sequence
<220> FEATURE:
<223> OTHER INFORMATION: CDR-L1, Her2 (7C2)

<400> SEQUENCE: 159

Arg Ala Ser Gln Ser Val Gly Ser Arg Phe Thr Tyr Met His
1               5                   10                  15

<210> SEQ ID NO 160
<211> LENGTH: 7
<212> TYPE: PRT
<213> ORGANISM: Artificial Sequence
<220> FEATURE:
<223> OTHER INFORMATION: CDR-L2, Her2 (7C2)

<400> SEQUENCE: 160

Tyr Ala Ser Ile Leu Glu Ser
1               5

<210> SEQ ID NO 161
<211> LENGTH: 10
<212> TYPE: PRT
<213> ORGANISM: Artificial Sequence
<220> FEATURE:
<223> OTHER INFORMATION: CDR-L3, Her2 (7C2)

<400> SEQUENCE: 161

Gln His Ser Trp Glu Ile Pro Pro Trp Thr
1               5                   10

<210> SEQ ID NO 162
<211> LENGTH: 118
<212> TYPE: PRT
<213> ORGANISM: Artificial Sequence
<220> FEATURE:
<223> OTHER INFORMATION: heavy chain variable domain VH, Her2 (7C2)

<400> SEQUENCE: 162

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Ser Phe Thr Gly Tyr
                20                  25                  30

Trp Met Asn Trp Leu Lys Gln Arg Pro Gly Gln Gly Leu Glu Trp Ile
            35                  40                  45

Gly Met Ile His Pro Ser Asp Ser Glu Ile Arg Ala Asn Gln Lys Phe
        50                  55                  60

Arg Asp Lys Ala Thr Leu Thr Val Asp Lys Ser Ser Thr Thr Ala Tyr
65                  70                  75                  80

Met Gln Leu Ser Ser Pro Thr Ser Glu Asp Ser Ala Val Tyr Tyr Cys
                85                  90                  95

Ala Arg Gly Thr Tyr Asp Gly Gly Phe Glu Tyr Trp Gly Gln Gly Thr
                100                 105                 110

Thr Leu Thr Val Ser Ser
        115

<210> SEQ ID NO 163
<211> LENGTH: 112
<212> TYPE: PRT
<213> ORGANISM: Artificial Sequence
<220> FEATURE:
<223> OTHER INFORMATION: light chain variable domain VL, Her2 (7C2)

<400> SEQUENCE: 163

Asp Ile Val Leu Thr Gln Ser Pro Ala Ser Leu Val Val Ser Leu Gly
1               5                   10                  15

```
Gln Arg Ala Thr Ile Ser Cys Arg Ala Ser Gln Ser Val Gly Ser
                20                  25                  30

Arg Phe Thr Tyr Met His Trp Tyr Gln Gln Lys Pro Gly Gln Pro Pro
         35                  40                  45

Lys Leu Leu Ile Lys Tyr Ala Ser Ile Leu Glu Ser Gly Val Pro Ala
 50                      55                  60

Arg Phe Ser Gly Gly Gly Ser Gly Thr Asp Phe Thr Leu Asn Ile His
 65                  70                  75                  80

Pro Val Glu Glu Asp Asp Thr Ala Thr Tyr Tyr Cys Gln His Ser Trp
                 85                  90                  95

Glu Ile Pro Pro Trp Thr Phe Gly Gly Gly Thr Lys Leu Glu Ile Lys
                100                 105                 110
```

<210> SEQ ID NO 164
<211> LENGTH: 290
<212> TYPE: PRT
<213> ORGANISM: Homo sapiens

<400> SEQUENCE: 164

```
Met Arg Ile Phe Ala Val Phe Ile Phe Met Thr Tyr Trp His Leu Leu
 1               5                  10                  15

Asn Ala Phe Thr Val Thr Val Pro Lys Asp Leu Tyr Val Val Glu Tyr
                 20                  25                  30

Gly Ser Asn Met Thr Ile Glu Cys Lys Phe Pro Val Glu Lys Gln Leu
             35                  40                  45

Asp Leu Ala Ala Leu Ile Val Tyr Trp Glu Met Glu Asp Lys Asn Ile
 50                  55                  60

Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                 85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285
```

Glu Thr
    290

<210> SEQ ID NO 165
<211> LENGTH: 118
<212> TYPE: PRT
<213> ORGANISM: Artificial Sequence
<220> FEATURE:
<223> OTHER INFORMATION: VH (PD-L1)

<400> SEQUENCE: 165

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 166
<211> LENGTH: 107
<212> TYPE: PRT
<213> ORGANISM: Artificial Sequence
<220> FEATURE:
<223> OTHER INFORMATION: VL (PD-L1)

<400> SEQUENCE: 166

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys
            100                 105

<210> SEQ ID NO 167
<211> LENGTH: 121
<212> TYPE: PRT
<213> ORGANISM: Artificial Sequence
<220> FEATURE:
<223> OTHER INFORMATION: VH (PD-L1) 2

<400> SEQUENCE: 167

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
            115                 120

<210> SEQ ID NO 168
<211> LENGTH: 108
<212> TYPE: PRT
<213> ORGANISM: Artificial Sequence
<220> FEATURE:
<223> OTHER INFORMATION: VL (PD-L1) 2

<400> SEQUENCE: 168

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105

<210> SEQ ID NO 169
<211> LENGTH: 288
<212> TYPE: PRT
<213> ORGANISM: Homo sapiens

<400> SEQUENCE: 169

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg

```
                    85                  90                  95
Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
                115                 120                 125

Ala Pro Lys Ala Gln Ile Lys Glu Ser Leu Arg Ala Glu Leu Arg Val
                130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
                195                 200                 205

Leu Lys Glu Asp Pro Ser Ala Val Pro Val Phe Ser Val Asp Tyr Gly
                210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
                275                 280                 285

<210> SEQ ID NO 170
<211> LENGTH: 120
<212> TYPE: PRT
<213> ORGANISM: Artificial Sequence
<220> FEATURE:
<223> OTHER INFORMATION: VH (PD-1)

<400> SEQUENCE: 170

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
                35                  40                  45

Gly Gly Ile Asn Pro Ser Asn Gly Gly Thr Asn Phe Asn Glu Lys Phe
            50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
                100                 105                 110

Gly Thr Thr Val Thr Val Ser Ser
            115                 120

<210> SEQ ID NO 171
<211> LENGTH: 111
<212> TYPE: PRT
<213> ORGANISM: Artificial Sequence
<220> FEATURE:
<223> OTHER INFORMATION: VL (PD-1)
```

<400> SEQUENCE: 171

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110

<210> SEQ ID NO 172
<211> LENGTH: 113
<212> TYPE: PRT
<213> ORGANISM: Artificial Sequence
<220> FEATURE:
<223> OTHER INFORMATION: VH (PD-1) 2

<400> SEQUENCE: 172

Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 173
<211> LENGTH: 107
<212> TYPE: PRT
<213> ORGANISM: Artificial Sequence
<220> FEATURE:
<223> OTHER INFORMATION: VL (PD-1) 2

<400> SEQUENCE: 173

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys
            100                 105
```

<210> SEQ ID NO 174
<211> LENGTH: 448
<212> TYPE: PRT
<213> ORGANISM: Artificial Sequence
<220> FEATURE:
<223> OTHER INFORMATION: Her2-CD3 (4D5/40G5c) HC1 (Fc knob)

<400> SEQUENCE: 174

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
         35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
             85                  90                  95

Ser Arg Trp Gly Gly Asp Gly Phe Tyr Ala Met Asp Tyr Trp Gly Gln
         100                 105                 110

Gly Thr Leu Val Thr Val Ser Ser Ala Ser Thr Lys Gly Pro Ser Val
         115                 120                 125

Phe Pro Leu Ala Pro Ser Ser Lys Ser Thr Ser Gly Gly Thr Ala Ala
 130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
             165                 170                 175

Leu Gln Ser Ser Gly Leu Tyr Ser Leu Ser Ser Val Val Thr Val Pro
         180                 185                 190

Ser Ser Ser Leu Gly Thr Gln Thr Tyr Ile Cys Asn Val Asn His Lys
         195                 200                 205

Pro Ser Asn Thr Lys Val Asp Lys Lys Val Glu Pro Lys Ser Cys Asp
 210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
             245                 250                 255

Ser Arg Thr Pro Glu Val Thr Cys Val Val Val Asp Val Ser His Glu
         260                 265                 270

Asp Pro Glu Val Lys Phe Asn Trp Tyr Val Asp Gly Val Glu Val His
         275                 280                 285

Asn Ala Lys Thr Lys Pro Arg Glu Glu Gln Tyr Gly Ser Thr Tyr Arg
 290                 295                 300

Val Val Ser Val Leu Thr Val Leu His Gln Asp Trp Leu Asn Gly Lys
305                 310                 315                 320
```

```
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Trp Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
```

<210> SEQ ID NO 175
<211> LENGTH: 214
<212> TYPE: PRT
<213> ORGANISM: Artificial Sequence
<220> FEATURE:
<223> OTHER INFORMATION: Her2-CD3 (4D5/40G5c) LC1

<400> SEQUENCE: 175

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Asn Thr Ala
                20                  25                  30
Val Ala Trp Tyr Gln Gln Lys Pro Gly Lys Ala Pro Lys Leu Leu Ile
            35                  40                  45
Tyr Ser Ala Ser Phe Leu Tyr Ser Gly Val Pro Ser Arg Phe Ser Gly
    50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln His Tyr Thr Thr Pro Pro
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
    115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
    195                 200                 205
Phe Asn Arg Gly Glu Cys
    210
```

<210> SEQ ID NO 176
<211> LENGTH: 447

<212> TYPE: PRT
<213> ORGANISM: Artificial Sequence
<220> FEATURE:
<223> OTHER INFORMATION: Her2-CD3 (4D5/40G5c) HC2 (Fc hole)

<400> SEQUENCE: 176

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Ile
        35                  40                  45

Gly Trp Ile Tyr Pro Gly Asp Gly Asn Thr Lys Tyr Asn Glu Lys Phe
50                  55                  60

Lys Gly Arg Ala Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Ser Tyr Ser Asn Tyr Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Ser
        355                 360                 365

Cys Ala Val Lys Gly Phe Tyr Pro Ser Asp Ile Ala Val Glu Trp Glu
370                 375                 380
```

Ser Asn Gly Gln Pro Glu Asn Asn Tyr Lys Thr Thr Pro Val Leu
385                 390                 395                 400

Asp Ser Asp Gly Ser Phe Phe Leu Val Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro
        435                 440                 445

<210> SEQ ID NO 177
<211> LENGTH: 219
<212> TYPE: PRT
<213> ORGANISM: Artificial Sequence
<220> FEATURE:
<223> OTHER INFORMATION: Her2-CD3 (4D5/40G5c) LC2

<400> SEQUENCE: 177

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 178
<211> LENGTH: 448
<212> TYPE: PRT
<213> ORGANISM: Artificial Sequence
<220> FEATURE:
<223> OTHER INFORMATION: CD28(SA_Variant 8) hu IgG1 Fc hole N297G

<400> SEQUENCE: 178

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
                35                  40                  45

Gly Ser Ile Tyr Pro Gly Asn Val Gln Thr Asn Tyr Asn Glu Lys Phe
        50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Thr Ala Val Tyr Phe Cys
                85                  90                  95

Thr Arg Ser His Tyr Gly Leu Asp Phe Asn Phe Asp Val Trp Gly Gln
                100                 105                 110

Gly Thr Thr Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
                210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Gly Ser Thr Tyr Arg
                290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Ser Cys Ala Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

```
<210> SEQ ID NO 179
<211> LENGTH: 214
<212> TYPE: PRT
<213> ORGANISM: Artificial Sequence
<220> FEATURE:
<223> OTHER INFORMATION: CD28(SA_Variant 8) VL-Ckappa

<400> SEQUENCE: 179

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val Tyr
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 180
<211> LENGTH: 448
<212> TYPE: PRT
<213> ORGANISM: Artificial Sequence
<220> FEATURE:
<223> OTHER INFORMATION: Her2 (4D5) hu IgG1 knob N297G

<400> SEQUENCE: 180

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

```
Ser Arg Trp Gly Gly Asp Gly Phe Tyr Ala Met Asp Tyr Trp Gly Gln
            100                 105                 110

Gly Thr Leu Val Thr Val Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gly Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Trp Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

<210> SEQ ID NO 181
<211> LENGTH: 214
<212> TYPE: PRT
<213> ORGANISM: Artificial Sequence
<220> FEATURE:
<223> OTHER INFORMATION: Her2 (4D5) VL-Ckappa

<400> SEQUENCE: 181

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 182
<211> LENGTH: 447
<212> TYPE: PRT
<213> ORGANISM: Artificial Sequence
<220> FEATURE:
<223> OTHER INFORMATION: Her2 (2C4) hu IgG1 knob N297G

<400> SEQUENCE: 182

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
 50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Gly Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Trp
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
            435                 440                 445

<210> SEQ ID NO 183
<211> LENGTH: 214
<212> TYPE: PRT
<213> ORGANISM: Artificial Sequence
<220> FEATURE:
<223> OTHER INFORMATION: Her2 (2C4) VL-Ckappa

<400> SEQUENCE: 183

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Tyr Tyr Ile Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 184
<211> LENGTH: 447
<212> TYPE: PRT
<213> ORGANISM: Artificial Sequence
<220> FEATURE:
<223> OTHER INFORMATION: CD28 IgG4 Fc

<400> SEQUENCE: 184

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Cys Ile Tyr Pro Gly Asn Val Asn Thr Asn Tyr Asn Glu Lys Phe
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Thr Arg Ser His Tyr Gly Leu Asp Trp Asn Phe Asp Val Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220
```

```
Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
        260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
            435                 440                 445

<210> SEQ ID NO 185
<211> LENGTH: 214
<212> TYPE: PRT
<213> ORGANISM: Artificial Sequence
<220> FEATURE:
<223> OTHER INFORMATION: CD28 kappa light chain

<400> SEQUENCE: 185

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val Trp
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 186
<211> LENGTH: 443
<212> TYPE: PRT
<213> ORGANISM: Artificial Sequence
<220> FEATURE:
<223> OTHER INFORMATION: DP47 huIgG1 PGLALA heavy chain

<400> SEQUENCE: 186

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
        180                 185                 190

Thr Gln Thr Tyr Ile Cys Asn Val Asn His Lys Pro Ser Asn Thr Lys
    195                 200                 205

Val Asp Lys Lys Val Glu Pro Lys Ser Cys Asp Lys Thr His Thr Cys
210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285
```

```
Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro
    435                 440

<210> SEQ ID NO 187
<211> LENGTH: 215
<212> TYPE: PRT
<213> ORGANISM: Artificial Sequence
<220> FEATURE:
<223> OTHER INFORMATION: DP47 huIgG1 PGLALA light chain

<400> SEQUENCE: 187

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205
```

```
Ser Phe Asn Arg Gly Glu Cys
    210                 215
```

<210> SEQ ID NO 188
<211> LENGTH: 207
<212> TYPE: PRT
<213> ORGANISM: Homo sapiens

<400> SEQUENCE: 188

```
Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205
```

<210> SEQ ID NO 189
<211> LENGTH: 198
<212> TYPE: PRT
<213> ORGANISM: Macaca fascicularis

<400> SEQUENCE: 189

```
Met Gln Ser Gly Thr Arg Trp Arg Val Leu Gly Leu Cys Leu Leu Ser
1               5                   10                  15

Ile Gly Val Trp Gly Gln Asp Gly Asn Glu Glu Met Gly Ser Ile Thr
            20                  25                  30

Gln Thr Pro Tyr Gln Val Ser Ile Ser Gly Thr Thr Val Ile Leu Thr
        35                  40                  45

Cys Ser Gln His Leu Gly Ser Glu Ala Gln Trp Gln His Asn Gly Lys
    50                  55                  60

Asn Lys Glu Asp Ser Gly Asp Arg Leu Phe Leu Pro Glu Phe Ser Glu
65                  70                  75                  80

Met Glu Gln Ser Gly Tyr Tyr Val Cys Tyr Pro Arg Gly Ser Asn Pro
                85                  90                  95

Glu Asp Ala Ser His His Leu Tyr Leu Lys Ala Arg Val Cys Glu Asn
            100                 105                 110
```

```
Cys Met Glu Met Asp Val Met Ala Val Ala Thr Ile Val Ile Val Asp
        115             120                 125

Ile Cys Ile Thr Leu Gly Leu Leu Leu Val Tyr Tyr Trp Ser Lys
    130             135                 140

Asn Arg Lys Ala Lys Ala Lys Pro Val Thr Arg Gly Ala Gly Ala Gly
145             150                 155                 160

Gly Arg Gln Arg Gly Gln Asn Lys Glu Arg Pro Pro Val Pro Asn
            165                 170                 175

Pro Asp Tyr Glu Pro Ile Arg Lys Gly Gln Gln Asp Leu Tyr Ser Gly
            180             185                 190

Leu Asn Gln Arg Arg Ile
            195
```

AGONISTIC CD28 ANTIGEN BINDING MOLECULES TARGETING HER2

CROSS REFERENCE TO RELATED APPLICATIONS

This application is a continuation of European Application No. 20181730.1, filed Jun. 23, 2020 which is incorporated herein by reference in its entirety.

SEQUENCE LISTING

This application contains a Sequence Listing which has been submitted electronically in ASCII format and is hereby incorporated by reference in its entirety. Said ASCII copy, created Jun. 15, 2021, is named P36196-US_Sequence_listing_ST25.txt and is 245,760 bytes in size

FIELD OF THE INVENTION

The present invention relates to Her2-targeted bispecific agonistic CD28 antigen binding molecules characterized by monovalent binding to CD28, methods for their production, pharmaceutical compositions containing these molecules, and their use as immunomodulators and/or costiumulators in the treatment of a disease, in particular cancer.

BACKGROUND

Cancer immunotherapy is becoming an increasingly effective therapy option that can result in dramatic and durable responses in cancer types such as melanoma, non-small cell lung cancer and renal cell carcinoma. This is mostly driven by the success of several immune checkpoint blockades including anti-PD-1 (e.g. Keytruda, Merck; Opdivo, BMS), anti-CTLA-4 (e.g. Yervoy, BMS) and anti-PD-L1 (e.g. Tecentriq, Roche). These agents are likely to serve as standard of care for many cancer types, or as the backbone of combination therapies, however, only a fraction of patients (<25%) benefits from such therapies. Furthermore, various cancers (prostate cancer, colorectal cancer, pancreatic cancer, sarcomas, non-triple negative breast cancer etc.) present primary resistance to these immunomodulators. A number of reports indicate that the absence of pre-existing anti-tumor T cells contributes to the absence or poor response of some patients. In summary, despite impressive anti-cancer effects of existing immunotherapies, there is a clear medical need for addressing a large cancer patient population and for developing therapies that aim to induce and enhance novel tumor-specific T cell responses.

CD28 is the founding member of a subfamily of costimulatory molecules characterized by paired V-set immunoglobulin superfamily (IgSF) domains attached to single transmembrane domains and cytoplasmic domains that contain critical signaling motifs (Carreno and Collins, 2002). Other members of the subfamily include ICOS, CTLA-4, PD1, PD1H, TIGIT, and BTLA (Chen and Flies, 2013). CD28 expression is restricted to T cells and prevalent on all naïve and a majority of antigen-experienced subsets, including those that express PD-1 or CTLA-4. CD28 and CTLA-4 are highly homologous and compete for binding to the same B7 molecules CD80 and CD86, which are expressed on dendritic cells, B cells, macrophages, and tumor cells (Linsley et al., 1990). The higher affinity of CTLA-4 for the B7 family of ligands allows CTLA-4 to outcompete CD28 for ligand binding and suppress effector T cells responses (Engelhardt et al., 2006). In contrast, PD-1 was shown to inhibit CD28 signaling by in part dephosphorylating the cytoplasmic domain of CD28 (Hui et al., 2017). Ligation of CD28 by CD80 or CD86 on the surface of professional antigen-presenting cells is strictly required for functional de novo priming of naïve T cells, subsequent clonal expansion, cytokine production, target cell lysis, and formation of long-lived memory. Binding of CD28 ligands also promotes the expression of inducible co-stimulatory receptors such as OX-40, ICOS, and 4-1BB (reviewed in Acuto and Michel, 2003). Upon ligation of CD28, a disulfide-linked homodimer, the membrane proximal YMNM motif and the distal PYAP motif have been shown to complex with several kinases and adaptor proteins (Boomer and Green, 2010). These motifs are important for the induction of IL2 transcription, which is mediated by the CD28-dependent activation of NFAT, AP-1, and NFκB family transcription factors (Fraser et al., 1991) (June et al., 1987) (Thompson et al., 1989). However, additional poorly characterized sites for phosphorylation and ubiquitination are found within the cytoplasmic domain of CD28. As reviewed by (Esensten et al., 2016), CD28-initiated pathways have critical roles in promoting the proliferation and effector function of conventional T cells. CD28 ligation also promotes the anti-inflammatory function of regulatory T cells. CD28 co-stimulates T cells by in part augmenting signals from the T cell receptor, but was also shown to mediate unique signaling events (Acuto and Michel, 2003; Boomer and Green, 2010; June et al., 1987). Signals specifically triggered by CD28 control many important aspects of T cell function, including phosphorylation and other post-translational modifications of downstream proteins (e.g., PI3K mediated phosphorylation), transcriptional changes (eg. Bcl-xL expression), epigenetic changes (e.g. IL-2 promoter), cytoskeletal remodeling (e.g. orientation of the microtubule-organizing center) and changes in the glycolytic rate (e.g. glycolytic flux). CD28-deficient mice have reduced responses to infectious pathogens, allograft antigens, graft-versus-host disease, contact hypersensitivity and asthma (Acuto and Michel, 2003). Lack of CD28-mediated co-stimulation results in reduced T cell proliferation in vitro and in vivo, in severe inhibition of germinal-centre formation and immunoglobulin isotype-class switching, reduced T helper (Th)-cell differentiation and the expression of Th2-type cytokines. CD4-dependent cytotoxic CD8+ T-cell responses are also affected. Importantly, CD28-deficient naïve T cells showed a reduced proliferative response particularly at lower antigen concentrations. A growing body of literature supports the idea that engaging CD28 on T cells has anti-tumor potential. Recent evidence demonstrates that the anti-cancer effects of PD-L1/PD-1 and CTLA-4 checkpoint inhibitors depend on CD28 (Kamphorst et al., 2017; Tai et al., 2007). Clinical studies investigating the therapeutic effects of CTLA-4 and PD-1 blockade have shown exceptionally promising results in patients with advanced melanoma and other cancers. In addition, infusion of genetically engineered T cells expressing artificial chimeric T cell receptors comprising an extracellular antigen recognition domain fused to the intracellular TCR signaling domains (CD3z) and intracellular co-stimulatory domains (CD28 and/or 4-1BB domains) has shown high rates and durability of response in B cell cancers and other cancers.

CD28 agonistic antibodies can be divided into two categories: (i) CD28 superagonistic antibodies and (ii) CD28 conventional agonistic antibodies. Normally, for the activation of naïve T cells both engagement of the T cell antigen receptor (TCR, signal 1) and costimulatory signaling by CD28 (signal 2) is required. CD28 Superagonists (CD28SA)

are CD28-specific monoclonal antibodies, which are able to autonomously activate T cells without overt T cell receptor engagement (Hünig, 2012). In rodents, CD28SA activates conventional and regulatory T cells. CD28SA antibodies are therapeutically effective in multiple models of autoimmunity, inflammation and transplantation. However, a phase I study of the human CD28SA antibody TGN1412 resulted in a life-threatening cytokine storm in 2006. Follow-up studies have suggested that the toxicity was caused by dosing errors due to differences in the CD28 responsiveness of human T cells and T cells of preclinical animal models. TGN1412 is currently being re-evaluated in an open-label, multi-center dose escalation study in RA patients and patients with metastatic or unresectable advanced solid malignancies. CD28 conventional agonistic antibodies, such as clone 9.3, mimic CD28 natural ligands and are only able to enhance T cell activation in presence of a T cell receptor signal (signal 1). Published insights indicate that the binding epitope of the antibody has a major impact on whether the agonistic antibody is a superagonist or a conventional agonist (Beyersdorf et al., 2005). The superagonistic TGN1412 binds to a lateral motif of CD28, while the conventional agonistic molecule 9.3 binds close to the ligand binding epitope. As a consequence of the different binding epitopes, superagonistic and conventional agonistic antibodies differ in their ability to form linear complexes of CD28 molecules on the surface of T cells. Precisely, TGN1412 is able to efficiently form linear arrays of CD28, which presumably leads to aggregated signaling components which are sufficient to surpass the threshold for T cell activation. The conventional agonist 9.3, on the other hand, leads to complexes which are not linear in structure. An attempt to convert conventional agonistic binders based on the 9.3 clone has been previously published (Otz et al., 2009) using a recombinant bi-specific single-chain antibody directed to a melanoma-associated proteoglycan and CD28. The reported bispecific single chain antibody was reported to exert "supra-agonistic" activity despite the use of a conventional CD28 agonistic binder 9.3, based in the intrinsic tendency of bispecific single chain antibodies to form multimeric constructs.

The human epidermal growth factor receptor-2 (Her2; ErbB2) is a receptor tyrosine kinase and a member of the epidermal growth factor receptor (EGFR) family of transmembrane receptors. Her2 is overexpressed in a range of tumor types and it has been implicated in disease initiation and progression. It is associated with poor prognosis. For example, overexpression of Her2 is observed in approximately 30% of human breast cancers and it is implicated in the aggressive growth and poor clinical outcomes associated with these tumors (Slamon et al (1987) Science 235:177-182).

The humanized anti-Her2 monoclonal antibody trastuzumab (CAS 180288-69-1, HERCEPTIN®, huMAb4D5-8, rhuMAb Her2, Genentech) targets the extracellular domain of Her-2 (U.S. Pat. Nos. 5,677,171; 5,821, 337; 6,054,297; 6,165,464; 6,339,142; 6,407,213; 6,639, 055; 6,719,971; 6,800,738; 7,074,404; Coussens et al (1985) Science 230:1 132-9; Slamon et al (1989) Science 244:707-12; Slamon et al (2001) New Engl. J. Med. 344:783-792). Trastuzumab has been shown to inhibit the proliferation of human tumor cells that overexpress Her-2 and is a mediator of antibody-dependent cellular cytotoxicity, ADCC (Hudziak et al (1989) Mol Cell Biol 9:1 165-72; Lewis et al (1993) Cancer Immunol Immunother; 37:255-63; Baselga et al (1998) Cancer Res. 58:2825-2831; Hotaling et al (1996) [abstract]. Proc. Annual Meeting Am Assoc Cancer Res; 37:471; Pegram M D, et al (1997) [abstract]. Proc Am Assoc Cancer Res; 38:602; Sliwkowski et al (1999) Seminars in Oncology 26(4), Suppl 12:60-70; Yarden Y. and Sliwkowski, M. (2001) Nature Reviews: Molecular Cell Biology, Macmillan Magazines, Ltd., Vol. 2:127-137).

HERCEPTIN® (trastuzumab, Genentech Inc.) was approved in 1998 for the treatment of of patients with Her2-overexpressing metastatic breast cancers (Baselga et al, (1996) J. Clin. Oncol. 14:737-744). In 2006, the FDA approved HERCEPTIN® as part of a treatment regimen containing doxorubicin, cyclophosphamide and paclitaxel for the adjuvant treatment of patients with Her2-positive, node-positive breast cancer. Pertuzumab (also known as recombinant humanized monoclonal antibody 2C4, rhuMAb 2C4, PERJETA®, Genentech, Inc, South San Francisco) is another antibody treatment targeting Her2. Pertuzumab is a Her dimerization inhibitor (HDI) and functions to inhibit the ability of Her2 to form active heterodimers or homodimers with other Her receptors (such as EGFR/Her 1, Her2, Her3 and Her4). See, for example, Harari and Yarden Oncogene 19:6102-14 (2000); Yarden and Sliwkowski. Nat Rev Mol Cell Biol 2:127-37 (2001); Sliwkowski, Nat Struct Biol 10:158-9 (2003); Cho et al. Nature 421:756-60 (2003); and Malik et al., Pro Am Soc Cancer Res 44:176-7 (2003); U.S. Pat. No. 7,560,111. PERJETA® was first approved in 2012 in combination with trastuzumab and docetaxel for the treatment of patients with advanced or late-stage (metastatic) Her2-positive breast cancer. The combination therapy using trastuzumab and pertuzumab is meanwhile also approved for the neoadjuvant (before surgery) treatment off Her2-positive, locally advanced, inflammatory, or early stage breast cancer and for adjuvant (after surgery) treatment of Her2-positive early breast cancer (EBC) at high risk of recurrence. The mechanisms of action of Perjeta and Herceptin are believed to complement each other, as both bind to the Her2 receptor, but to different places. The combination of Perjeta and Herceptin is thought to provide a more comprehensive, dual blockade of HER signaling pathways, thus preventing tumor cell growth and survival. Bispecific, bivalent Her2 antibodies that are directed against domains IL III and IV of human ErbB2 are disclosed in WO 2012/143523. Bispecific HER-2 antibodies comprising optimized variants of the antibodies rhuMab 2C4 and hu4D5, called Herceptarg, have been described in WO 2015/091738.

Although the therapeutic efficacy of trastuzumab in breast carcinoma is well demonstrated, there are many patients who do not benefit from trastuzumab because of resistance. Given the lack of an effective anti-Her2 therapy in specific cancers expressing low levels of Her2, the resistance to the current therapies, and the prevalence of Her2-expressing cancers, new therapies are required to treat such cancers.

It has been found that a better T cell activation is achieved when limiting amounts of anti-CD3 bispecific antibodies, i.e. T cell bispecific antibodies (TCBs) such as a Her2-targeted CD3 antibody, are combined with agonistic anti-CD28 molecules. Given, that CD28 is expressed at baseline on T cells in various tumor indications (Lavin et al., 2017; Tirosh et al., 2016, Zheng et al., 2017) and activation of CD28 signaling enhances T cell receptor signals, the combination of a TCB molecule with a Her2-targeted CD28 antigen binding molecule is expected to act synergistically to induce strong and long-lasting anti-tumor responses. Thus, we herein describe novel Her2-targeted agonistic CD28 molecules which display synergy with TCBs and require CD28 binding monovalency for strict tumor target dependence in the presence of TCB signals.

SUMMARY

The present invention describes Her2-targeted bispecific agonistic CD28 antigen binding molecules which achieve a tumor-dependent T cell activation and tumor cell killing without the necessity to form multimers. The bispecific CD28 antigen binding molecules of the present invention are characterized by monovalent binding to CD28 and in that they comprise a second antigen binding domain capable of specific binding to human epidermal growth factor receptor-2 (Her2). Furthermore, they possess an Fc domain composed of a first and a second subunit capable of stable association comprising one or more amino acid substitution that reduces the binding affinity of the antigen binding molecule to an Fc receptor and/or effector function. Fc receptor-mediated cross-linking is thereby abrogated and tumor-specific activation is achieved by cross-linking through binding of the second antigen binding domain capable of specific binding to Her2.

Thus, the invention provides a bispecific agonistic CD28 antigen binding molecule characterized by monovalent binding to CD28, comprising
- (a) a first antigen binding domain capable of specific binding to CD28,
- (b) a second antigen binding domain capable of specific binding to an antigen binding domain capable of specific binding to human epidermal growth factor receptor-2 (Her2), and
- (c) a Fc domain composed of a first and a second subunit capable of stable association comprising one or more amino acid substitution that reduces the binding affinity of the antigen binding molecule to an Fc receptor and/or effector function.

In particular, the invention provides a bispecific agonistic CD28 antigen binding molecule characterized by monovalent binding to CD28, comprising
- (a) a first antigen binding domain capable of specific binding to CD28,
- (b) a second antigen binding domain capable of specific binding to an antigen binding domain capable of specific binding to human epidermal growth factor receptor-2 (Her2), and
- (c) a Fc domain composed of a first and a second subunit capable of stable association comprising one or more amino acid substitution that reduces the binding affinity of the antigen binding molecule to an Fc receptor and/or effector function,
wherein said second antigen binding domain capable of specific binding to Her2 comprises
- (i) a heavy chain variable region ($V_H$Her2) comprising a heavy chain complementary determining region CDR-H1 of SEQ ID NO: 2, a CDR-H2 of SEQ ID NO: 3, and a CDR-H3 of SEQ ID NO: 4, and a light chain variable region ($V_L$Her2) comprising a light chain complementary determining region CDR-L1 of SEQ ID NO: 5, a CDR-L2 of SEQ ID NO: 6 and a CDR-L3 of SEQ ID NO: 7; or
- (ii) a heavy chain variable region ($V_H$Her2) comprising a heavy chain complementary determining region CDR-H1 of SEQ ID NO: 10, a CDR-H2 of SEQ ID NO: 11, and a CDR-H3 of SEQ ID NO: 12, and a light chain variable region ($V_L$Her2) comprising a light chain complementary determining region CDR-L1 of SEQ ID NO: 13, a CDR-L2 of SEQ ID NO: 14 and a CDR-L3 of SEQ ID NO: 15; or
- (iii) a heavy chain variable region ($V_H$Her2) comprising a heavy chain complementary determining region CDR-H1 of SEQ ID NO: 132, a CDR-H2 of SEQ ID NO: 133, and a CDR-H3 of SEQ ID NO: 134, and a light chain variable region ($V_L$Her2) comprising a light chain complementary determining region CDR-L1 of SEQ ID NO: 135, a CDR-L2 of SEQ ID NO: 136 and a CDR-L3 of SEQ ID NO: 137, or
- (iv) a heavy chain variable region ($V_H$Her2) comprising a heavy chain complementary determining region CDR-H1 of SEQ ID NO: 140, a CDR-H2 of SEQ ID NO: 141, and a CDR-H3 of SEQ ID NO: 142, and a light chain variable region ($V_L$Her2) comprising a light chain complementary determining region CDR-L1 of SEQ ID NO: 143, a CDR-L2 of SEQ ID NO: 144 and a CDR-L3 of SEQ ID NO: 145.

In one aspect, the invention provides a bispecific agonistic CD28 antigen binding molecule characterized by monovalent binding to CD28, comprising
- (a) a first antigen binding domain capable of specific binding to CD28,
- (b) a second antigen binding domain capable of specific binding to an antigen binding domain capable of specific binding to human epidermal growth factor receptor-2 (Her2), and
- (c) a Fc domain composed of a first and a second subunit capable of stable association comprising one or more amino acid substitution that reduces the binding affinity of the antigen binding molecule to an Fc receptor and/or effector function,
wherein said second antigen binding domain capable of specific binding to Her2 comprises
- (i) a heavy chain variable region ($V_H$Her2) comprising a heavy chain complementary determining region CDR-H1 of SEQ ID NO: 2, a CDR-H2 of SEQ ID NO: 3, and a CDR-H3 of SEQ ID NO: 4, and a light chain variable region ($V_L$Her2) comprising a light chain complementary determining region CDR-L1 of SEQ ID NO: 5, a CDR-L2 of SEQ ID NO: 6 and a CDR-L3 of SEQ ID NO: 7; or
- (ii) a heavy chain variable region ($V_H$Her2) comprising a heavy chain complementary determining region CDR-H1 of SEQ ID NO: 10, a CDR-H2 of SEQ ID NO: 11, and a CDR-H3 of SEQ ID NO: 12, and a light chain variable region ($V_L$Her2) comprising a light chain complementary determining region CDR-L1 of SEQ ID NO: 13, a CDR-L2 of SEQ ID NO: 14 and a CDR-L3 of SEQ ID NO: 15.

In another aspect, the invention provides a bispecific agonistic CD28 antigen binding molecule characterized by monovalent binding to CD28, comprising
- (a) a first antigen binding domain capable of specific binding to CD28,
- (b) a second antigen binding domain capable of specific binding to an antigen binding domain capable of specific binding to human epidermal growth factor receptor-2 (Her2), and
- (c) a Fc domain composed of a first and a second subunit capable of stable association comprising one or more amino acid substitution that reduces the binding affinity of the antigen binding molecule to an Fc receptor and/or effector function,
wherein said second antigen binding domain capable of specific binding to Her2 comprises
- (iii) a heavy chain variable region ($V_H$Her2) comprising a heavy chain complementary determining region CDR-H1 of SEQ ID NO: 132, a CDR-H2 of SEQ ID NO: 133, and a CDR-H3 of SEQ ID NO: 134, and a light chain variable region ($V_L$Her2) comprising a light chain complementary determining region CDR-L1 of SEQ ID NO: 135, a CDR-L2 of SEQ ID NO: 136 and a CDR-L3 of SEQ ID NO: 137, or (iv) a heavy chain variable region (V$_H$Her2) comprising a heavy chain complementary determining region CDR-H1 of SEQ ID NO: 140, a CDR-H2 of SEQ ID NO: 141, and a CDR-H3 of SEQ ID NO: 142, and a light chain variable region (V$_L$Her2) comprising a light chain complementary determining region CDR-L1 of SEQ ID NO: 143, a CDR-L2 of SEQ ID NO: 144 and a CDR-L3 of SEQ ID NO: 145.

In one aspect, a bispecific agonistic CD28 antigen binding molecule as defined herein is provided, wherein the Fc domain is an IgG, particularly an IgG1 Fc domain or an IgG4 Fc domain. In one particular aspect, the Fc domain composed of a first and a second subunit capable of stable association is an IgG1 Fc domain. In one aspect, the Fc domain comprises the amino acid substitutions L234A and L235A (numbering according to Kabat EU index). In one aspect, the Fc domain is of human IgG1 subclass and comprises the amino acid mutations L234A, L235A and P329G (numbering according to Kabat EU index).

In one aspect, provided is a bispecific agonistic CD28 antigen binding molecule as defined herein before, wherein the first antigen binding domain capable of specific binding to CD28 comprises
(i) a heavy chain variable region (V$_H$CD28) comprising a heavy chain complementary determining region CDR-H1 of SEQ ID NO: 26, a CDR-H2 of SEQ ID NO: 27, and a CDR-H3 of SEQ ID NO: 28, and a light chain variable region (V$_L$CD28) comprising a light chain complementary determining region CDR-L1 of SEQ ID NO: 29, a CDR-L2 of SEQ ID NO: 30 and a CDR-L3 of SEQ ID NO: 31; or
(ii) a heavy chain variable region (V$_H$CD28) comprising a CDR-H1 of SEQ ID NO: 18, a CDR-H2 of SEQ ID NO: 19, and a CDR-H3 of SEQ ID NO: 20, and a light chain variable region (V$_L$CD28) comprising a CDR-L1 of SEQ ID NO: 21, a CDR-L2 of SEQ ID NO: 22 and a CDR-L3 of SEQ ID NO: 23.

In one aspect, the antigen binding domain capable of specific binding to CD28 of the bispecific agonistic CD28 antigen binding molecule comprises a heavy chain variable region (V$_H$CD28) comprising a CDR-H1 of SEQ ID NO: 26, a CDR-H2 of SEQ ID NO: 27, and a CDR-H3 of SEQ ID NO: 28, and a light chain variable region (V$_L$CD28) comprising a CDR-L1 of SEQ ID NO: 29, a CDR-L2 of SEQ ID NO: 30 and a CDR-L3 of SEQ ID NO: 31.

In another aspect, the antigen binding domains capable of specific binding to CD28 of the bispecific agonistic CD28 antigen binding molecule comprises a heavy chain variable region (V$_H$CD28) comprising a CDR-H1 of SEQ ID NO: 18, a CDR-H2 of SEQ ID NO: 19, and a CDR-H3 of SEQ ID NO: 20, and a light chain variable region (V$_L$CD28) comprising a CDR-L1 of SEQ ID NO: 21, a CDR-L2 of SEQ ID NO: 22 and a CDR-L3 of SEQ ID NO: 23.

In a further aspect, provided is a bispecific agonistic CD28 antigen binding molecule as defined herein before, wherein the first antigen binding domain capable of specific binding to CD28 comprises
(i) a heavy chain variable region (V$_H$CD28) comprising a heavy chain complementary determining region CDR-H1 of SEQ ID NO: 52, a CDR-H2 of SEQ ID NO: 53, and a CDR-H3 of SEQ ID NO: 54, and a light chain variable region (V$_L$CD28) comprising a light chain complementary determining region CDR-L1 of SEQ ID NO: 55, a CDR-L2 of SEQ ID NO: 56 and a CDR-L3 of SEQ ID NO: 57; or
(ii) a heavy chain variable region (V$_H$CD28) comprising a CDR-H1 of SEQ ID NO: 58, a CDR-H2 of SEQ ID NO: 59, and a CDR-H3 of SEQ ID NO: 60, and a light chain variable region (V$_L$CD28) comprising a CDR-L1 of SEQ ID NO: 61, a CDR-L2 of SEQ ID NO: 62 and a CDR-L3 of SEQ ID NO: 63; or
(ii) a heavy chain variable region (V$_H$CD28) comprising a CDR-H1 of SEQ ID NO: 64, a CDR-H2 of SEQ ID NO: 65, and a CDR-H3 of SEQ ID NO: 66, and a light chain variable region (V$_L$CD28) comprising a CDR-L1 of SEQ ID NO: 67, a CDR-L2 of SEQ ID NO: 68 and a CDR-L3 of SEQ ID NO: 69.

In one aspect, the antigen binding domain capable of specific binding to CD28 of the bispecific agonistic CD28 antigen binding molecule comprises a heavy chain variable region (V$_H$CD28) comprising a heavy chain complementary determining region CDR-H1 of SEQ ID NO: 52, a CDR-H2 of SEQ ID NO: 53, and a CDR-H3 of SEQ ID NO: 54, and a light chain variable region (V$_L$CD28) comprising a light chain complementary determining region CDR-L1 of SEQ ID NO: 55, a CDR-L2 of SEQ ID NO: 56 and a CDR-L3 of SEQ ID NO: 57.

In another aspect, the antigen binding domains capable of specific binding to CD28 of the bispecific agonistic CD28 antigen binding molecule comprises a heavy chain variable region (V$_H$CD28) comprising a CDR-H1 of SEQ ID NO: 58, a CDR-H2 of SEQ ID NO: 59, and a CDR-H3 of SEQ ID NO: 60, and a light chain variable region (V$_L$CD28) comprising a CDR-L1 of SEQ ID NO: 61, a CDR-L2 of SEQ ID NO: 62 and a CDR-L3 of SEQ ID NO: 63.

In yet another aspect, the antigen binding domains capable of specific binding to CD28 of the bispecific agonistic CD28 antigen binding molecule comprises a heavy chain variable region (V$_H$CD28) comprising a CDR-H1 of SEQ ID NO: 64, a CDR-H2 of SEQ ID NO: 65, and a CDR-H3 of SEQ ID NO: 66, and a light chain variable region (V$_L$CD28) comprising a CDR-L1 of SEQ ID NO: 67, a CDR-L2 of SEQ ID NO: 68 and a CDR-L3 of SEQ ID NO: 69.

Furthermore, provided is a bispecific agonistic CD28 antigen binding molecule as defined herein before, wherein the first antigen binding domain capable of specific binding to CD28 comprises a heavy chain variable region (V$_H$CD28) comprising an amino acid sequence that is at least about 95%, 96%, 97%, 98%, 99% or 100% identical to the amino acid sequence of SEQ ID NO:24, and a light chain variable region (V$_L$CD28) comprising an amino acid sequence that is at least about 95%, 96%, 97%, 98%, 99% or 100% identical to the amino acid sequence of SEQ ID NO:25.

In a further aspect, a bispecific agonistic CD28 antigen binding molecule is provided, wherein the first antigen binding domain capable of specific binding to CD28 comprises a heavy chain variable region (V$_H$CD28) comprising an amino acid sequence selected from the group consisting of SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40 and SEQ ID NO:41, and a light chain variable region (V$_L$CD28) comprising an amino acid sequence selected from the group consisting of SEQ ID NO:25, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50 and SEQ ID NO:51.

In another aspect, provided is a bispecific agonistic CD28 antigen binding molecule, wherein the first antigen binding domain capable of specific binding to CD28 comprises
(a) a heavy chain variable region (V$_H$CD28) comprising the amino acid sequence of SEQ ID NO:37 and a light chain variable region (V$_L$CD28) comprising the amino acid sequence of SEQ ID NO:44, or (b) a heavy chain variable region (V$_H$CD28) comprising the amino acid sequence of SEQ ID NO:37 and a light chain variable region (V$_L$CD28) comprising the amino acid sequence of SEQ ID NO:25, or (c) a heavy chain variable region (V$_H$CD28) comprising the amino acid sequence of SEQ ID NO:41 and a light chain variable region (V$_L$CD28) comprising the amino acid sequence of SEQ ID NO:51, or (d) a heavy chain variable region (V$_H$CD28) comprising the amino acid sequence of SEQ ID NO:36 and a light chain variable region (V$_L$CD28) comprising the amino acid sequence of SEQ ID NO:43, or (e) a heavy chain variable region (V$_H$CD28) comprising the amino acid sequence of SEQ ID NO:36 and a light chain variable region (V$_L$CD28) comprising the amino acid sequence of SEQ ID NO:44, or (f) a heavy chain variable region (V$_H$CD28) comprising the amino acid sequence of SEQ ID NO:36 and a light chain variable region (V$_L$CD28) comprising the amino acid sequence of SEQ ID NO:49, or (g) a heavy chain variable region (V$_H$CD28) comprising the amino acid sequence of SEQ ID NO:36 and a light chain variable region (V$_L$CD28) comprising the amino acid sequence of SEQ ID NO:25, or (h) a heavy chain variable region (V$_H$CD28) comprising the amino acid sequence of SEQ ID NO:33 and a light chain variable region (V$_L$CD28) comprising the amino acid sequence of SEQ ID NO:25, or (i) a heavy chain variable region (V$_H$CD28) comprising the amino acid sequence of SEQ ID NO:32 and a light chain variable region (V$_L$CD28) comprising the amino acid sequence of SEQ ID NO:43, or (j) a heavy chain variable region (V$_H$CD28) comprising the amino acid sequence of SEQ ID NO:32 and a light chain variable region (V$_L$CD28) comprising the amino acid sequence of SEQ ID NO:49, or (k) a heavy chain variable region (V$_H$CD28) comprising the amino acid sequence of SEQ ID NO:32 and a light chain variable region (V$_L$CD28) comprising the amino acid sequence of SEQ ID NO:25.

In one particular aspect, a bispecific agonistic CD28 antigen binding molecule is provided, wherein the first antigen binding domain capable of specific binding to CD28 comprises (i) a heavy chain variable region (V$_H$CD28) comprising a heavy chain complementary determining region CDR-H1 of SEQ ID NO: 52, a CDR-H2 of SEQ ID NO: 53, and a CDR-H3 of SEQ ID NO: 54, and a light chain variable region (V$_L$CD28) comprising a light chain complementary determining region CDR-L1 of SEQ ID NO: 55, a CDR-L2 of SEQ ID NO: 56 and a CDR-L3 of SEQ ID NO: 57. In one aspect, the first antigen binding domain capable of specific binding to CD28 comprises the CDRs of the heavy chain variable region (V$_H$CD28) comprising the amino acid sequence of SEQ ID NO:37 and the CDRs of the light chain variable region (V$_L$CD28) comprising the amino acid sequence of SEQ ID NO:44.

In another particular aspect, a bispecific agonistic CD28 antigen binding molecule is provided, wherein the antigen binding domain capable of specific binding to CD28 comprises a heavy chain variable region (V$_H$CD28) comprising the amino acid sequence of SEQ ID NO:36 and a light chain variable region (V$_L$CD28) comprising the amino acid sequence of SEQ ID NO:43. In a further particular aspect, a bispecific agonistic CD28 antigen binding molecule is provided, wherein the antigen binding domain capable of specific binding to CD28 comprises a heavy chain variable region (V$_H$CD28) comprising the amino acid sequence of SEQ ID NO:32 and a light chain variable region (V$_L$CD28) comprising the amino acid sequence of SEQ ID NO:25.

In one aspect, a bispecific agonistic CD28 antigen binding molecule is provided, wherein the antigen binding domain capable of specific binding to Her2 comprises a heavy chain variable region (V$_H$Her2) comprising a heavy chain complementary determining region CDR-H1 of SEQ ID NO: 2, a CDR-H2 of SEQ ID NO: 3, and a CDR-H3 of SEQ ID NO: 4, and a light chain variable region (V$_L$Her2) comprising a light chain complementary determining region CDR-L1 of SEQ ID NO: 5, a CDR-L2 of SEQ ID NO: 6 and a CDR-L3 of SEQ ID NO: 7. In one aspect, the antigen binding domain capable of specific binding to Her2 comprises the CDRs of the heavy chain variable region (V$_H$Her2) comprising the amino acid sequence of SEQ ID NO:8 and the CDRs of the light chain variable region (V$_L$Her2) comprising the amino acid sequence of SEQ ID NO:9. In one particular aspect, the the antigen binding domain capable of specific binding to Her2 comprises a heavy chain variable region (V$_H$Her2) comprising the amino acid sequence of SEQ ID NO: 8, and a light chain variable region (V$_L$Her2) comprising the amino acid sequence of SEQ ID NO:9.

In another aspect, provided is a bispecific agonistic CD28 antigen binding molecule as described herein, wherein the antigen binding domain capable of specific binding to Her2 comprises a heavy chain variable region (V$_H$Her2) comprising a heavy chain complementary determining region CDR-H1 of SEQ ID NO: 10, a CDR-H2 of SEQ ID NO: 11, and a CDR-H3 of SEQ ID NO: 12, and a light chain variable region (V$_L$Her2) comprising a light chain complementary determining region CDR-L1 of SEQ ID NO: 13, a CDR-L2 of SEQ ID NO: 14 and a CDR-L3 of SEQ ID NO: 15. In one aspect, the antigen binding domain capable of specific binding to Her2 comprises the CDRs of the heavy chain variable region (V$_H$Her2) comprising the amino acid sequence of SEQ ID NO:16 and the CDRs of the light chain variable region (V$_L$Her2) comprising the amino acid sequence of SEQ ID NO:17. In one particular aspect, the antigen binding domain capable of specific binding to Her2 comprises a heavy chain variable region (V$_H$Her2) comprising the amino acid sequence of SEQ ID NO:16, and a light chain variable region (V$_L$Her2) comprising the amino acid sequence of SEQ ID NO:17.

In yet another aspect, provided is a bispecific agonistic CD28 antigen binding molecule as described herein, wherein the antigen binding domain capable of specific binding to Her2 comprises a heavy chain variable region (V$_H$Her2) comprising a heavy chain complementary determining region CDR-H1 of SEQ ID NO: 132, a CDR-H2 of SEQ ID NO: 133, and a CDR-H3 of SEQ ID NO: 134, and a light chain variable region (V$_L$Her2) comprising a light chain complementary determining region CDR-L1 of SEQ ID NO: 135, a CDR-L2 of SEQ ID NO: 136 and a CDR-L3 of SEQ ID NO: 137. In one aspect, the antigen binding domain capable of specific binding to Her2 comprises the CDRs of the heavy chain variable region (V$_H$Her2) comprising the amino acid sequence of SEQ ID NO:138 and the CDRs of the light chain variable region (V$_L$Her2) comprising the amino acid sequence of SEQ ID NO:139. In one particular aspect, the antigen binding domain capable of specific binding to Her2 comprises a heavy chain variable region (V$_H$Her2) comprising the amino acid sequence of SEQ ID NO:138, and a light chain variable region (V$_L$Her2) comprising the amino acid sequence of SEQ ID NO:139.

In another aspect, provided is a bispecific agonistic CD28 antigen binding molecule as described herein, wherein the antigen binding domain capable of specific binding to Her2 comprises a heavy chain variable region (V$_H$Her2) comprising a heavy chain complementary determining region CDR-H1 of SEQ ID NO: 140, a CDR-H2 of SEQ ID NO: 141, and a CDR-H3 of SEQ ID NO: 142, and a light chain variable region (V$_L$Her2) comprising a light chain complementary determining region CDR-L1 of SEQ ID NO: 143, a CDR-L2 of SEQ ID NO: 144 and a CDR-L3 of SEQ ID NO: 145. In one aspect, the antigen binding domain capable of specific binding to Her2 comprises the CDRs of the heavy chain variable region (V$_H$Her2) comprising the amino acid sequence of SEQ ID NO:146 and the CDRs of the light chain variable region (V$_L$Her2) comprising the amino acid sequence of SEQ ID NO:147. In one particular aspect, the antigen binding domain capable of specific binding to Her2 comprises a heavy chain variable region (V$_H$Her2) comprising the amino acid sequence of SEQ ID NO:146, and a light chain variable region (V$_L$Her2) comprising the amino acid sequence of SEQ ID NO:147.

In a further aspect, provided is a bispecific agonistic CD28 antigen binding molecule as defined herein before, wherein the first antigen binding domain capable of specific binding to CD28 and/or the second antigen binding domain capable of specific binding to Her2 is a Fab fragment or a crossFab fragment. In one aspect, provided is a bispecific agonistic CD28 antigen binding molecule as described herein, comprising (a) a Fab fragment capable of specific binding to CD28, (b) a crossFab fragment capable of specific binding to Her2, and (c) a Fc domain composed of a first and a second subunit capable of stable association comprising one or more amino acid substitution that reduces the binding affinity of the antigen binding molecule to an Fc receptor and/or effector function. In another aspect, provided is a bispecific agonistic CD28 antigen binding molecule as described herein, comprising (a) a crossFab fragment capable of specific binding to CD28, (b) a Fab fragment capable of specific binding to Her2, and (c) a Fc domain composed of a first and a second subunit capable of stable association comprising one or more amino acid substitution that reduces the binding affinity of the antigen binding molecule to an Fc receptor and/or effector function.

In one aspect, the first antigen binding domain capable of specific binding to CD28 is a Fab fragment wherein the variable domains VL and VH or the constant domains CL and CH1, particularly the variable domains VL and VH, of the Fab light chain and the Fab heavy chain are replaced by each other. In one aspect, the second antigen binding domain capable of specific binding to Her2 is a conventional Fab fragment. In one aspect, the second antigen binding domain capable of specific binding to Her2 is a Fab molecule wherein in the constant domain CL the amino acid at position 123 (numbering according to Kabat EU index) is substituted by an amino acid selected from lysine (K), arginine (R) or histidine (H) and the amino acid at position 124 (numbering according to Kabat EU index) is substituted independently by lysine (K), arginine (R) or histidine (H), and wherein in the constant domain CH1 the amino acid at position 147 (numbering according to Kabat EU index) is substituted independently by glutamic acid (E) or aspartic acid (D) and the amino acid at position 213 (numbering according to Kabat EU index) is substituted independently by glutamic acid (E), or aspartic acid (D) (numbering according to Kabat EU index).

In one particular aspect, provided is a bispecific agonistic CD28 antigen binding molecule comprising
(i) a first light chain comprising the amino acid sequence of SEQ ID NO:92, a first heavy chain comprising the amino acid sequence of SEQ ID NO:91, a second heavy chain comprising the amino acid sequence of SEQ ID NO:96 and a second light chain comprising the amino acid sequence of SEQ ID NO:97, or
(ii) a first light chain comprising the amino acid sequence of SEQ ID NO:92, a first heavy chain comprising the amino acid sequence of SEQ ID NO:91, a second heavy chain comprising the amino acid sequence of SEQ ID NO:98 and a second light chain comprising the amino acid sequence of SEQ ID NO:97, or
(iii) a first light chain comprising the amino acid sequence of SEQ ID NO:92, a first heavy chain comprising the amino acid sequence of SEQ ID NO:91, a second heavy chain comprising the amino acid sequence of SEQ ID NO:101 and a second light chain comprising the amino acid sequence of SEQ ID NO:97.

In another particular aspect, provided is a bispecific agonistic CD28 antigen binding molecule comprising
(i) a first light chain comprising the amino acid sequence of SEQ ID NO:179, a first heavy chain comprising the amino acid sequence of SEQ ID NO:178, a second heavy chain comprising the amino acid sequence of SEQ ID NO:180 and a second light chain comprising the amino acid sequence of SEQ ID NO:181, or
(ii) a first light chain comprising the amino acid sequence of SEQ ID NO:179, a first heavy chain comprising the amino acid sequence of SEQ ID NO:178, a second heavy chain comprising the amino acid sequence of SEQ ID NO:182 and a second light chain comprising the amino acid sequence of SEQ ID NO:183.

In a further aspect, provided is a bispecific agonistic CD28 antigen binding molecule as described herein, wherein the second antigen binding domain capable of specific binding to Her2 is a Fab molecule wherein the variable domains VL and VH or the constant domains CL and CH1, particularly the variable domains VL and VH, of the Fab light chain and the Fab heavy chain are replaced by each other. In one aspect, the first antigen binding domain capable of specific binding to CD28 is a conventional Fab molecule. In one aspect, the first antigen binding domain capable of specific binding to CD28 is a Fab molecule wherein in the constant domain CL the amino acid at position 123 (numbering according to Kabat EU index) is substituted by an amino acid selected from lysine (K), arginine (R) or histidine (H) and the amino acid at position 124 (numbering according to Kabat EU index) is substituted independently by lysine (K), arginine (R) or histidine (H), and wherein in the constant domain CH1 the amino acid at position 147 (numbering according to Kabat EU index) is substituted independently by glutamic acid (E) or aspartic acid (D) and the amino acid at position 213 (numbering according to Kabat EU index) is substituted independently by glutamic acid (E), or aspartic acid (D) (numbering according to Kabat EU index).

In one particular aspect, provided is a bispecific agonistic CD28 antigen binding molecule comprising
(i) a first light chain comprising the amino acid sequence of SEQ ID NO:83, a first heavy chain comprising the amino acid sequence of SEQ ID NO:74, a second heavy chain comprising the amino acid sequence of SEQ ID NO:99 and a second light chain comprising the amino acid sequence of SEQ ID NO:100, or
(ii) a first light chain comprising the amino acid sequence of SEQ ID NO:83, a first heavy chain comprising the amino acid sequence of SEQ ID NO:74, a second heavy chain comprising the amino acid sequence of SEQ ID NO:102 and a second light chain comprising the amino acid sequence of SEQ ID NO:100.

In another aspect, a bispecific agonistic CD28 antigen binding molecule as disclosed herein is provided, wherein the first and the second antigen binding domain are each a Fab molecule and the Fc domain is composed of a first and a second subunit capable of stable association; and wherein (i) the first antigen binding domain is fused at the C-terminus of the Fab heavy chain to the N-terminus of the first subunit of the Fc domain and the second antigen binding domain is fused at the C-terminus of the Fab heavy chain to the N-terminus of the second subunit of the Fc domain, or (ii) the second antigen binding domain is fused at the C-terminus of the Fab heavy chain to the N-terminus of the first subunit of the Fc domain and the first antigen binding domain is fused at the C-terminus of the Fab heavy chain to the N-terminus of the second subunit of the Fc domain. In one aspect, the Fc domain comprises a modification promoting the association of the first and the second subunit of the Fc domain. In one aspect, the first subunit of the Fc domain comprises the amino acid substitutions S354C and T366W (EU numbering) and the second subunit of the Fc domain comprises the amino acid substitutions Y349C, T366S and Y407V (numbering according to Kabat EU index).

According to another aspect of the invention, there is provided one or more isolated polynucleotide(s) encoding the bispecific agonistic CD28 antigen binding molecule of the invention. The invention further provides one or more vector(s), particularly expression vector(s), comprising the isolated polynucleotide(s) of the invention, and a host cell comprising the isolated polynucleotide(s) or the expression vector(s) of the invention. In some aspects, the host cell is a eukaryotic cell, particularly a mammalian cell. In some aspects, the host cell is a prokaryotic cell. In another aspect, provided is a method of producing a bispecific agonistic CD28 antigen binding molecule as described herein comprising culturing the host cell of the invention under conditions suitable for the expression of the bispecific agonistic CD28 antigen binding molecule. Optionally, the method also comprises recovering the bispecific agonistic CD28 antigen binding molecule. The invention also encompasses a bispecific agonistic CD28 antigen binding molecule produced by the method of the invention.

The invention further provides a pharmaceutical composition comprising a bispecific agonistic CD28 antigen binding molecule of the invention and at least one pharmaceutically acceptable excipient. In one aspect, the pharmaceutical composition is for use in the treatment of a disease, particularly cancer. In one aspect, the pharmaceutical composition is for use in the treatment of Her2-positive cancer.

Also encompassed by the invention are methods of using the bispecific agonistic CD28 antigen binding molecule or the pharmaceutical composition of the invention. In one aspect, the invention provides a bispecific agonistic CD28 antigen binding molecule or a pharmaceutical composition according to the invention for use as a medicament. In one aspect, provided is a bispecific agonistic CD28 antigen binding molecule as described herein for use in (a) enhancing cell activation or (b) enhancing T cell effector functions. In one aspect, provided is a bispecific agonistic CD28 antigen binding molecule or a pharmaceutical composition according to the invention for use in the treatment of a disease. In a specific aspect, the disease is cancer, in particular Her2-positive cancer. In another aspect is provided a bispecific agonistic CD28 antigen binding molecule or pharmaceutical composition according to the invention is for use in the treatment of cancer, wherein the bispecific agonistic CD28 antigen binding molecule is for administration in combination with a chemotherapeutic agent, radiation therapy and/or other agents for use in cancer immunotherapy. In a further aspect, provided is a bispecific agonistic CD28 antigen binding molecule or a pharmaceutical composition for use in the treatment of cancer, wherein the bispecific agonistic CD28 antigen binding molecule is for administration in combination with a T-cell activating anti-CD3 bispecific antibody. In one aspect, the T-cell activating anti-CD3 bispecific antibody is an anti-Her2/anti-CD3 antibody. In yet another aspect, provided is a bispecific agonistic CD28 antigen binding molecule or a pharmaceutical composition for use in the treatment of cancer, wherein the bispecific agonistic CD28 antigen binding molecule is for administration in combination with an anti-PD-L1 antibody or an anti-PD-1 antibody.

Also provided is the use of a bispecific agonistic CD28 antigen binding molecule or the pharmaceutical composition according to the invention in the manufacture of a medicament for the treatment of a disease; as well as a method of treating a disease in an individual, comprising administering to said individual a therapeutically effective amount of a bispecific agonistic CD28 antigen binding molecule according to the invention or a composition comprising the bispecific agonistic CD28 antigen binding molecule according to the invention in a pharmaceutically acceptable form. In a specific aspect, the disease is cancer. In one aspect, provided is a method (a) enhancing T cell activation or (b) enhancing T cell effector functions in an individual, comprising administering a bispecific agonistic CD28 antigen binding molecule according to the invention or a composition comprising the bispecific agonistic CD28 antigen binding molecule according to the invention in a pharmaceutically acceptable form to said individual. In another aspect, provided is the use of a bispecific agonistic CD28 antigen binding molecule according to the invention in the manufacture of a medicament for the treatment of a disease, wherein the treatment comprises co-administration with a chemotherapeutic agent, radiation therapy and/or other agents for use in cancer immunotherapy. In a further aspect, provided is a method of treating a disease in an individual, comprising administering to said individual a therapeutically effective amount of a bispecific agonistic CD28 antigen binding molecule according to the invention or a composition comprising the bispecific agonistic CD28 antigen binding molecule according to the invention in a pharmaceutically acceptable form, wherein the method comprises co-administration with a chemotherapeutic agent, radiation therapy and/or other agents for use in cancer immunotherapy. In a further aspect, provided is a method of treating a disease in an individual, comprising administering to said individual a therapeutically effective amount of a bispecific agonistic CD28 antigen binding molecule according to the invention or a composition comprising the bispecific agonistic CD28 antigen binding molecule according to the invention in a pharmaceutically acceptable form, wherein the method comprises co-administration of a T-cell activating anti-CD3 bispecific antibody. In one aspect, the T-cell activating anti-CD3 bispecific antibody is an anti-Her2/anti-CD3 antibody. In another aspect, provided is a method of treating a disease in an individual, comprising administering to said individual a therapeutically effective amount of a bispecific agonistic CD28 antigen binding molecule according to the invention or a composition comprising the bispecific agonistic CD28 antigen binding molecule according to the invention in a pharmaceutically acceptable form, wherein the method comprises co-administration of an anti-PD-L1 antibody or an anti-PD-1 antibody. Also provided is a method of inhibiting the growth of tumor cells in an individual comprising administering to the individual an effective amount of the bispecific agonistic CD28 antigen binding molecule according to the invention, or or a composition comprising the bispecific agonistic CD28 antigen binding molecule according to the invention in a pharmaceutically acceptable form, to inhibit the growth of the tumor cells. In any of the above aspects, the individual preferably is a mammal, particularly a human.

BRIEF DESCRIPTION OF THE DRAWINGS

FIG. 1A shows a schematic illustration of the CD28 agonistic antibody variants as monovalent hu IgG1 PGLALA isotype ("Fc silent"). FIG. 1B shows a bispecific Her2-CD28 antigen binding molecule in 1+1 format, wherein in the Fab molecule comprising the CD28 antigen binding domain the VH and VL domains are exchanged with each other (VH/VL crossfab) and wherein in the Fab molecule comprising the Her2 antigen binding domain certain amino acids in the CH1 and CL domain are exchanged (Charged variants) to allow better pairing with the light chain. The Fc domain is a hu IgG1 PGLALA version. FIG. 1C shows a bispecific Her2-CD28 antigen binding molecule in 1+1 format with both heavy chains comprising the N297G mutations, wherein both Fab molecules are expressed in different cell lines, purified and assembled into the intact bispecific. FIG. 1D shows a bispecific Her2-CD28 antigen binding molecule in 1+1 format, wherein in the Fab molecule comprising the Her2 antigen binding domain the VH and VL domains are exchanged with each other (VH/VL crossfab) and wherein in the Fab molecule comprising the CD28 antigen binding domain certain amino acids in the CH1 and CL domain are exchanged (Charged variants) to allow better pairing with the light chain.

The alignment of the variable domains of CD28(SA) and variants thereof is shown in FIG. 2A to 2D. Alignment of the CD28(SA) VH domain and variants thereof in order to remove cysteine 50 and to reduce the affinity of the resulting anti-CD28 binders to different degrees is shown in FIG. 2A. Of note, in VH variants i and j, the CDRs of CD28(SA) were grafted from an IGHV1-2 framework into an IGHV3-23 framework (FIG. 2B). In FIG. 2C, alignment of the CD28 (SA) VL domain and variants thereof in order to reduce the affinity of the resulting anti-CD28 binders to different degrees is shown. In variant t, the CDRs were grafted into the framework sequence of the trastuzumab (Herceptin) VL sequence (FIG. 2D).

FIG. 9A to 9G show the effect of Her2-CD28 bispecific antigen binding molecules 2C4/CD28 and 4D5/CD28 as well as the CD28 antibody on HER2 TDB induced cytokine release as measured in supernatant samples that were harvested from the T cell activation assay 24 h after the treatments. Shown is the amount of the soluble cytokines GM-CSF (FIG. 9A), IFN-gamma (FIG. 9B), IL-10 (FIG. 9C), IL-6 (FIG. 9D), TNF-alpha (FIG. 9E), IL-2 (FIG. 9F) and IL-1b (FIG. 9G).

FIG. 10A to 10D show the effect of co-stimulation with Her2-CD28 bispecific antigen binding molecules 2C4/CD28 and 4D5/CD28 as well as the CD28 antibody on the number of immune cells on various timepoints up to 15 days after treatment with HER2-TDB. The total immune cell count is shown in FIG. 10A whereas FIG. 10B shows the $CD4^+$ cell count. FIG. 10C shows the $CD8^+$ cell count and the NK cell count is shown in FIG. 10D.

DETAILED DESCRIPTION OF THE INVENTION

Definitions

Figure 1A:
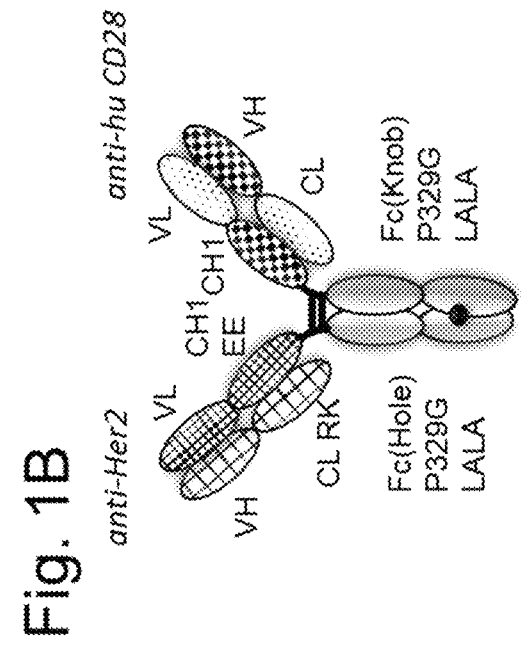
In FIG. 1A to 1D schematic illustrations of exemplary molecules as described herein are shown.

Unless defined otherwise, technical and scientific terms used herein have the same meaning as generally used in the art to which this invention belongs. For purposes of interpreting this specification, the following definitions will apply and whenever appropriate, terms used in the singular will also include the plural and vice versa.

As used herein, the term "antigen binding molecule" refers in its broadest sense to a molecule that specifically binds an antigenic determinant. Examples of antigen binding molecules are antibodies, multispecific antibodies (e.g., bispecific antibodies), antibody fragments and scaffold antigen binding proteins.

As used herein, the term "antigen binding domain that binds to a tumor-associated antigen" or "moiety capable of specific binding to a tumor-associated antigen" refers to a polypeptide molecule that specifically binds to the tumor-associated antigen Her2. In one aspect, the antigen binding domain is able to activate signaling through Her2. In a particular aspect, the antigen binding domain is able to direct the entity to which it is attached (e.g. the CD28 antibody) to a Her2-expressing cell, for example to a specific type of tumor cell. Antigen binding domains capable of specific binding to Her2 include antibodies and fragments thereof as further defined herein. In addition, antigen binding domains capable of specific binding to a tumor-associated antigen include scaffold antigen binding proteins as further defined herein, e.g. binding domains which are based on designed repeat proteins or designed repeat domains (see e.g. WO 2002/020565).

In relation to an antigen binding molecule, i.e. an antibody or fragment thereof, the term "antigen binding domain" refers to the part of the molecule that comprises the area which specifically binds to and is complementary to part or all of an antigen. An antigen binding domain capable of specific antigen binding may be provided, for example, by one or more antibody variable domains (also called antibody variable regions). Particularly, an antigen binding domain capable of specific antigen binding comprises an antibody light chain variable region (VL) and an antibody heavy chain variable region (VH). In another aspect, the "antigen binding domain capable of specific binding to a tumor-associated antigen" can also be a Fab fragment or a crossFab fragment. As used herein, the terms "first", "second" or "third" with respect to antigen binding domains etc., are used for convenience of distinguishing when there is more than one of each type of moiety. Use of these terms is not intended to confer a specific order or orientation of the moiety unless explicitly so stated.

The term "antibody" herein is used in the broadest sense and encompasses various antibody structures, including but not limited to monoclonal antibodies, polyclonal antibodies, monospecific and multispecific antibodies (e.g., bispecific antibodies), and antibody fragments so long as they exhibit the desired antigen-binding activity.

The term "monoclonal antibody" as used herein refers to an antibody obtained from a population of substantially homogeneous antibodies, i.e., the individual antibodies comprising the population are identical and/or bind the same epitope, except for possible variant antibodies, e.g. containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen.

The term "monospecific" antibody as used herein denotes an antibody that has one or more binding sites each of which bind to the same epitope of the same antigen. The term "bispecific" means that the antigen binding molecule is able to specifically bind to at least two distinct antigenic determinants. Typically, a bispecific antigen binding molecule comprises two antigen binding sites, each of which is specific for a different antigenic determinant. However, a bispecific antigen binding molecule may also comprise additional antigen binding sites which bind to further antigenic determinants. In certain aspects, the bispecific antigen binding molecule is capable of simultaneously binding two antigenic determinants, particularly two antigenic determinants expressed on two distinct cells or on the same cell. The term "bispecific" in accordance with the present invention thus may also include a trispecific molecule, e.g. a bispecific molecule comprising a CD28 antibody and two antigen binding domains directed to two different target cell antigens.

The term "valent" as used within the current application denotes the presence of a specified number of binding sites specific for one distinct antigenic determinant in an antigen binding molecule that are specific for one distinct antigenic determinant. As such, the terms "bivalent", "tetravalent", and "hexavalent" denote the presence of two binding sites, four binding sites, and six binding sites specific for a certain antigenic determinant, respectively, in an antigen binding molecule. In particular aspects of the invention, the bispecific antigen binding molecules according to the invention can be monovalent for a certain antigenic determinant, meaning that they have only one binding site for said antigenic determinant or they can be bivalent or tetravalent for a certain antigenic determinant, meaning that they have two binding sites or four binding sites, respectively, for said antigenic determinant.

The terms "full length antibody", "intact antibody", and "whole antibody" are used herein interchangeably to refer to an antibody having a structure substantially similar to a native antibody structure. "Native antibodies" or "wild type" refer to naturally occurring immunoglobulin molecules with varying structures. For example, native IgG-class antibodies are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a light chain constant domain (CL), also called a light chain constant region. The heavy chain of an antibody may be assigned to one of five types, called α (IgA), δ (IgD), ε (IgE), γ (IgG), or μ (IgM), some of which may be further divided into subtypes, e.g. γ1 (IgG1), γ2 (IgG2), γ3 (IgG3), γ4 (IgG4), α1 (IgA1) and α2 (IgA2). The light chain of an antibody may be assigned to one of two types, called kappa (κ) and lambda (λ), based on the amino acid sequence of its constant domain.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies, triabodies, tetrabodies, crossFab fragments; linear antibodies; single-chain antibody molecules (e.g. scFv); and single domain antibodies. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046. Diabodies are antibody fragments with two antigen-binding sites that may be bivalent or bispecific, see, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see e.g. U.S. Pat. No. 6,248,516 B1). Antibody fragments can be made by various techniques, including but not limited to proteolytic digestion of an intact antibody as well as production by recombinant host cells (e.g. E. coli or phage), as described herein.

Papain digestion of intact antibodies produces two identical antigen-binding fragments, called "Fab" fragments containing each the heavy- and light-chain variable domains and also the constant domain of the light chain and the first constant domain (CH1) of the heavy chain. As used herein, Thus, the term "Fab fragment" or "Fab molecule" refers to an antibody fragment comprising a light chain fragment comprising a variable light chain (VL) domain and a constant domain of a light chain (CL), and a variable heavy chain (VH) domain and a first constant domain (CH1) of a heavy chain. Fab' fragments differ from Fab fragments by the addition of a few residues at the carboxy terminus of the heavy chain CH1 domain including one or more cysteins from the antibody hinge region. Fab'-SH are Fab' fragments in which the cysteine residue(s) of the constant domains bear a free thiol group. Pepsin treatment yields an F(ab')$_2$ fragment that has two antigen-combining sites (two Fab fragments) and a part of the Fc region. A "conventional Fab fragment" is comprised of a VL-CL light chain and a VH-CH1 heavy chain.

The term "crossFab fragment" or "xFab fragment" or "crossover Fab fragment" refers to a Fab fragment, wherein either the variable regions or the constant regions of the heavy and light chain are exchanged. Two different chain compositions of a crossover Fab molecule are possible and comprised in the bispecific antibodies of the invention: On the one hand, the variable regions of the Fab heavy and light chain are exchanged, i.e. the crossover Fab molecule comprises a peptide chain composed of the light chain variable (VL) domain and the heavy chain constant domain (CH1), and a peptide chain composed of the heavy chain variable domain (VH) and the light chain constant domain (CL). This crossover Fab molecule is also referred to as CrossFab$_{(VLVH)}$. On the other hand, when the constant regions of the Fab heavy and light chain are exchanged, the crossover Fab molecule comprises a peptide chain composed of the heavy chain variable domain (VH) and the light chain constant domain (CL), and a peptide chain composed of the light chain variable domain (VL) and the heavy chain constant domain (CH1). This crossover Fab molecule is also referred to as CrossFab$_{(CLCH1)}$.

A "single chain Fab fragment" or "scFab" is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids. Said single chain Fab fragments are stabilized via the natural disulfide bond between the CL domain and the CH1 domain. In addition, these single chain Fab molecules might be further stabilized by generation of interchain disulfide bonds via insertion of cysteine residues (e.g. position 44 in the variable heavy chain and position 100 in the variable light chain according to Kabat numbering).

A "crossover single chain Fab fragment" or "x-scFab" is a is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CL-linker-VL-CH1 and b) VL-CH1-linker-VH-CL; wherein VH and VL form together an antigen-binding site which binds specifically to an antigen and wherein said linker is a polypeptide of at least 30 amino acids. In addition, these x-scFab molecules might be further stabilized by generation of interchain disulfide bonds via insertion of cysteine residues (e.g. position 44 in the variable heavy chain and position 100 in the variable light chain according to Kabat numbering).

A "single-chain variable fragment (scFv)" is a fusion protein of the variable regions of the heavy ($V_H$) and light chains ($V_L$) of an antibody, connected with a short linker peptide of ten to about 25 amino acids. The linker is usually rich in glycine for flexibility, as well as serine or threonine for solubility, and can either connect the N-terminus of the $V_H$ with the C-terminus of the $V_L$, or vice versa. This protein retains the specificity of the original antibody, despite removal of the constant regions and the introduction of the linker. scFv antibodies are, e.g. described in Houston, J. S., Methods in Enzymol. 203 (1991) 46-96). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

"Scaffold antigen binding proteins" are known in the art, for example, fibronectin and designed ankyrin repeat proteins (DARPins) have been used as alternative scaffolds for antigen-binding domains, see, e.g., Gebauer and Skerra, Engineered protein scaffolds as next-generation antibody therapeutics. Curr Opin Chem Biol 13:245-255 (2009) and Stumpp et al., Darpins: A new generation of protein therapeutics. Drug Discovery Today 13: 695-701 (2008). In one aspect of the invention, a scaffold antigen binding protein is selected from the group consisting of CTLA-4 (Evibody), Lipocalins (Anticalin), a Protein A-derived molecule such as Z-domain of Protein A (Affibody), an A-domain (Avimer/Maxibody), a serum transferrin (trans-body); a designed ankyrin repeat protein (DARPin), a variable domain of antibody light chain or heavy chain (single-domain antibody, sdAb), a variable domain of antibody heavy chain (nanobody, aVH), $V_{NAR}$ fragments, a fibronectin (AdNectin), a C-type lectin domain (Tetranectin); a variable domain of a new antigen receptor beta-lactamase ($V_{NAR}$ fragments), a human gamma-crystallin or ubiquitin (Affilin molecules); a kunitz type domain of human protease inhibitors, microbodies such as the proteins from the knottin family, peptide aptamers and fibronectin (adnectin). CTLA-4 (Cytotoxic T Lymphocyte-associated Antigen 4) is a CD28-family receptor expressed on mainly CD4$^+$ T-cells. Its extracellular domain has a variable domain—like Ig fold. Loops corresponding to CDRs of antibodies can be substituted with heterologous sequence to confer different binding properties. CTLA-4 molecules engineered to have different binding specificities are also known as Evibodies (e.g. U.S. Pat. No. 7,166,697B1). Evibodies are around the same size as the isolated variable region of an antibody (e.g. a domain antibody). For further details, see Journal of Immunological Methods 248 (1-2), 31-45 (2001). Lipocalins are a family of extracellular proteins which transport small hydrophobic molecules such as steroids, bilins, retinoids and lipids. They have a rigid beta-sheet secondary structure with a number of loops at the open end of the conical structure which can be engineered to bind to different target antigens. Anticalins are between 160-180 amino acids in size, and are derived from lipocalins. For further details, see Biochim Biophys Acta 1482: 337-350 (2000), U.S. Pat. No. 7,250,297B1 and US20070224633. An affibody is a scaffold derived from Protein A of Staphylococcus aureus which can be engineered to bind to antigen. The domain consists of a three-helical bundle of approximately 58 amino acids. Libraries have been generated by randomization of surface residues. For further details, see Protein Eng. Des. Sel. 2004, 17, 455-462 and EP 1641818A1. Avimers are multidomain proteins derived from the A-domain scaffold family. The native domains of approximately 35 amino acids adopt a defined disulfide bonded structure. Diversity is generated by shuffling of the natural variation exhibited by the family of A-domains. For further details, see Nature Biotechnology 23(12), 1556-1561 (2005) and Expert Opinion on Investigational Drugs 16(6), 909-917 (June 2007). A transferrin is a monomeric serum transport glycoprotein. Transferrins can be engineered to bind different target antigens by insertion of peptide sequences in a permissive surface loop. Examples of engineered transferrin scaffolds include the Trans-body. For further details, see J. Biol. Chem 274, 24066-24073 (1999). Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two alpha-helices and a beta-turn. They can be engineered to bind different target antigens by randomizing residues in the first alpha-helix and a beta-turn of each repeat. Their binding interface can be increased by increasing the number of modules (a method of affinity maturation). For further details, see J. Mol. Biol. 332, 489-503 (2003), PNAS 100(4), 1700-1705 (2003) and J. Mol. Biol. 369, 1015-1028 (2007) and US20040132028A1. A single-domain antibody is an antibody fragment consisting of a single monomeric variable antibody domain. The first single domains were derived from the variable domain of the antibody heavy chain from camelids (nanobodies or $V_H$H fragments). Furthermore, the term single-domain antibody includes an autonomous human heavy chain variable domain (aVH) or $V_{NAR}$ fragments derived from sharks. Fibronectin is a scaffold which can be engineered to bind to antigen. Adnectins consists of a backbone of the natural amino acid sequence of the 10th domain of the 15 repeating units of human fibronectin type III (FN3). Three loops at one end of the beta-sandwich can be engineered to enable an Adnectin to specifically recognize a therapeutic target of interest. For further details, see Protein Eng. Des. Sel. 18, 435-444 (2005), US20080139791, WO2005056764 and U.S. Pat. No. 6,818,418B1. Peptide aptamers are combinatorial recognition molecules that consist of a constant scaffold protein, typically thioredoxin (TrxA) which contains a constrained variable peptide loop inserted at the active site. For further details, see Expert Opin. Biol. Ther. 5, 783-797 (2005). Microbodies are derived from naturally occurring microproteins of 25-50 amino acids in length which contain 3-4 cysteine bridges—examples of microproteins include KalataBI and conotoxin and knottins. The microproteins have a loop which can be engineered to include up to 25 amino acids without affecting the overall fold of the microprotein. For further details of engineered knottin domains, see WO2008098796.

An "antigen binding molecule that binds to the same epitope" as a reference molecule refers to an antigen binding molecule that blocks binding of the reference molecule to its antigen in a competition assay by 50% or more, and conversely, the reference molecule blocks binding of the antigen binding molecule to its antigen in a competition assay by 50% or more.

The term "antigen binding domain" refers to the part of an antigen binding molecule that comprises the area which specifically binds to and is complementary to part or all of an antigen. Where an antigen is large, an antigen binding molecule may only bind to a particular part of the antigen, which part is termed an epitope. An antigen binding domain may be provided by, for example, one or more variable domains (also called variable regions). Preferably, an antigen binding domain comprises an antibody light chain variable domain (VL) and an antibody heavy chain variable domain (VH).

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins useful as antigens herein can be any native form the proteins from any vertebrate source, including mammals such as primates (e.g. humans) and rodents (e.g. mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g. splice variants or allelic variants.

The term "capable of specific binding to Her2" refers to an antigen binding molecule that is capable of binding to Her2 with sufficient affinity such that the antigen binding molecule is useful as a diagnostic and/or therapeutic agent in targeting Her2. The antigen binding molecule includes but is not limited to, antibodies, Fab molecules, crossover Fab molecules, single chain Fab molecules, Fv molecules, scFv molecules, single domain antibodies, and VH and scaffold antigen binding protein. In one aspect, the extent of binding of an anti-Her2 antigen binding molecule to an unrelated, non-Her2 protein is less than about 10% of the binding of the antigen binding molecule to Her2 as measured, e.g., by surface plasmon resonance (SPR). In particular, an antigen binding molecule that is capable of specific binding to Her2 has a dissociation constant ($K_d$) of ≤1 μM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M). In certain aspects, an anti-Her2 antigen binding molecule binds to Her2 from different species. In particular, the anti-Her2 antigen binding molecule binds to human and cynomolgus Her2.

The term "epitope" denotes the site on an antigen, either proteinaceous or non-proteinaceous, to which an antibody binds. Epitopes can be formed from contiguous amino acid stretches (linear epitope) or comprise non-contiguous amino acids (conformational epitope), e.g., coming in spatial proximity due to the folding of the antigen, i.e. by the tertiary folding of a proteinaceous antigen. Linear epitopes are typically still bound by an antibody after exposure of the proteinaceous antigen to denaturing agents, whereas conformational epitopes are typically destroyed upon treatment with denaturing agents. An epitope comprises at least 3, at least 4, at least 5, at least 6, at least 7, or 8-10 amino acids in a unique spatial conformation.

The "epitope 4D5" or "4D5 epitope" or "4D5" is the region in the extracellular domain of HER2 to which the antibody 4D5 (ATCC CRL 10463) and trastuzumab bind. This epitope is close to the transmembrane domain of HER2, and within domain IV of HER2. To screen for antibodies which bind to the 4D5 epitope, a routine cross-blocking assay such as that described in Antibodies, A Laboratory Manual, Cold Spring Harbor Laboratory, Ed Harlow and David Lane (1988), can be performed. Alternatively, epitope mapping can be performed to assess whether the antibody binds to the 4D5 epitope of HER2 (e.g. any one or more residues in the region from about residue 550 to about residue 610, inclusive, of human HER2 (SEQ ID NO: 54).

The "epitope 2C4" or "2C4 epitope" is the region in the extracellular domain of HER2 to which the antibody 2C4 binds. In order to screen for antibodies which bind to the 2C4 epitope, a routine cross-blocking assay such as that described in Antibodies, A Laboratory Manual, Cold Spring Harbor Laboratory, Ed Harlow and David Lane (1988), can be performed. Alternatively, epitope mapping can be performed to assess whether the antibody binds to the 2C4 epitope of HER2. Epitope 2C4 comprises residues from domain II in the extracellular domain of HER2. The 2C4 antibody and pertuzumab bind to the extracellular domain of HER2 at the junction of domains I, II and III (Franklin et al. Cancer Cell 5:317-328 (2004)).

By "specific binding" is meant that the binding is selective for the antigen and can be discriminated from unwanted or non-specific interactions. The ability of an antigen binding molecule to bind to a specific antigen can be measured either through an enzyme-linked immunosorbent assay (ELISA) or other techniques familiar to one of skill in the art, e.g. Surface Plasmon Resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of an antigen binding molecule to an unrelated protein is less than about 10% of the binding of the antigen binding molecule to the antigen as measured, e.g. by SPR. In certain embodiments, an molecule that binds to the antigen has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g. from $10^{-9}$ M to $10^{-13}$ M).

"Affinity" or "binding affinity" refers to the strength of the sum total of non-covalent interactions between a single binding site of a molecule (e.g. an antibody) and its binding partner (e.g. an antigen). Unless indicated otherwise, as used herein, "binding affinity" refers to intrinsic binding affinity which reflects a 1:1 interaction between members of a binding pair (e.g. antibody and antigen). The affinity of a molecule X for its partner Y can generally be represented by the dissociation constant (Kd), which is the ratio of dissociation and association rate constants (koff and kon, respectively). Thus, equivalent affinities may comprise different rate constants, as long as the ratio of the rate constants remains the same. Affinity can be measured by common methods known in the art, including those described herein. A particular method for measuring affinity is Surface Plasmon Resonance (SPR).

A "tumor-associated antigen" or TAA as used herein refers to an antigenic determinant presented on the surface of a target cell, for example a cell in a tumor such as a cancer cell or a cell of the tumor stroma. In certain aspects, the target cell antigen is an antigen on the surface of a tumor cell. In one particular aspect, TAA is Her2.

The term "Her2", also known as "ErbB2", "ErbB2 receptor", or "c-Erb-B2", refers to any native, mature HER2 which results from processing of a HER2 precursor protein in a cell. The term includes HER2 from any vertebrate source, including mammals such as primates (e.g. humans and cynomolgus monkeys) and rodents (e.g., mice and rats), unless otherwise indicated. The term also includes naturally occurring variants of HER2, e.g., splice variants or allelic variants. The amino acid sequence of an exemplary human HER2 protein is shown in SEQ ID NO:103.

The term "CD28" (Cluster of differentiation 28, Tp44) refers to any CD28 protein from any vertebrate source, including mammals such as primates (e.g. humans) non-human primates (e.g. cynomolgus monkeys) and rodents (e.g. mice and rats), unless otherwise indicated. CD28 is expressed on T cells and provides co-stimulatory signals required for T cell activation and survival. T cell stimulation through CD28 in addition to the T-cell receptor (TCR) can provide a potent signal for the production of various interleukins. CD28 is the receptor for CD80 (B7.1) and CD86 (B7.2) proteins and is the only B7 receptor constitutively expressed on naive T cells. The amino acid sequence of human CD28 is shown in UniProt (www.uniprot.org) accession no. P10747 (SEQ ID NO:1).

An "agonistic antibody" refers to an antibody that comprises an agonistic function against a given receptor. In general, when an agonist ligand (factor) binds to a receptor, the tertiary structure of the receptor protein changes, and the receptor is activated (when the receptor is a membrane protein, a cell growth signal or such is usually transducted). If the receptor is a dimer-forming type, an agonistic antibody can dimerize the receptor at an appropriate distance and angle, thus acting similarly to a ligand. An appropriate anti-receptor antibody can mimic dimerization of receptors performed by ligands, and thus can become an agonistic antibody.

A "CD28 agonistic antigen binding molecule" or "CD28 conventional agonistic antigen binding molecule" is an antigen binding molecule that mimicks CD28 natural ligands (CD80 or CD86) in their role to enhance T cell activation in presence of a T cell receptor signal ("signal 2"). A T cell needs two signals to become fully activated. Under physiological conditions "signal 1" arises form the interaction of T cell receptor (TCR) molecules with peptide/major histocompatibility complex (MHC) complexes on antigen presenting cells (APCs) and "signal 2" is provided by engagement of a costimulatory receptor, e.g. CD28. A CD28 agonistic antigen binding molecule is able to costimulate T cells (signal 2). It is also able to induce T cell proliferation and cytokine secretion in combination with a molecule with specificity for the TCR complex, however the CD28 agonistic antigen binding molecule is not capable of fully activating T cells without additional stimulation of the TCR. There is however a subclass of CD28 specific antigen binding molecules, the so-called CD28 superagonistic antigen binding molecules. A "CD28 superagonistic antigen binding molecule" is a CD28 antigen binding molecule which is capable of fully activating T cells without additional stimulation of the TCR. A CD28 superagonistic antigen binding molecule is capable to induce T cell proliferation and cytokine secretion without prior T cell activation (signal 1).

A "T-cell antigen" as used herein refers to an antigenic determinant presented on the surface of a T lymphocyte, particularly a cytotoxic T lymphocyte.

A "T cell activating therapeutic agent" as used herein refers to a therapeutic agent capable of inducing T cell activation in a subject, particularly a therapeutic agent designed for inducing T-cell activation in a subject. Examples of T cell activating therapeutic agents include bispecific antibodies that specifically bind an activating T cell antigen, such as CD3, and a target cell antigen, such as CEA or Folate Receptor.

An "activating T cell antigen" as used herein refers to an antigenic determinant expressed by a T lymphocyte, particularly a cytotoxic T lymphocyte, which is capable of inducing or enhancing T cell activation upon interaction with an antigen binding molecule. Specifically, interaction of an antigen binding molecule with an activating T cell antigen may induce T cell activation by triggering the signaling cascade of the T cell receptor complex. An exemplary activating T cell antigen is CD3.

The term "CD3" refers to any native CD3 from any vertebrate source, including mammals such as primates (e.g. humans), non-human primates (e.g. cynomolgus monkeys) and rodents (e.g. mice and rats), unless otherwise indicated. The term encompasses "full-length," unprocessed CD3 as well as any form of CD3 that results from processing in the cell. The term also encompasses naturally occurring variants of CD3, e.g., splice variants or allelic variants. In one embodiment, CD3 is human CD3, particularly the epsilon subunit of human CD3 (CD3ε). The amino acid sequence of human CD3ε is shown in UniProt (www.uniprot.org) accession no. P07766 (version 144), or NCBI (www.ncbi.nlm.nih.gov/) RefSeq NP_000724.1. See also SEQ ID NO: 188. The amino acid sequence of cynomolgus [Macaca fascicularis] CD3ε is shown in UniProt (www.uniprot.org) accession no. Q95LI5. See also SEQ ID NO: 189.

The term "variable domain" or "variable region" refers to the domain of an antibody heavy or light chain that is involved in binding the antigen binding molecule to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6th ed., W. H. Freeman and Co., page 91 (2007). A single VH or VL domain may be sufficient to confer antigen-binding specificity.

The term "hypervariable region" or "HVR" as used herein refers to each of the regions of an antigen binding variable domain which are hypervariable in sequence and which determine antigen binding specificity, for example "complementarity determining regions" ("CDRs"). Generally, antigen binding domains comprise six CDRs: three in the VH (CDR-H1, CDR-H2, CDR-H3), and three in the VL (CDR-L1, CDR-L2, CDR-L3). Exemplary CDRs herein include:
  (a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));
  (b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest,* 5th Ed. Public Health Service, National Institutes of Health, Bethesda, MD (1991)); and
  (c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)).

Unless otherwise indicated, the CDRs are determined according to Kabat et al., supra. One of skill in the art will understand that the CDR designations can also be determined according to Chothia, supra, McCallum, supra, or any other scientifically accepted nomenclature. Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

As used herein, the term "affinity matured" in the context of antigen binding molecules (e.g., antibodies) refers to an antigen binding molecule that is derived from a reference antigen binding molecule, e.g., by mutation, binds to the same antigen, preferably binds to the same epitope, as the reference antibody; and has a higher affinity for the antigen than that of the reference antigen binding molecule. Affinity maturation generally involves modification of one or more amino acid residues in one or more CDRs of the antigen binding molecule. Typically, the affinity matured antigen binding molecule binds to the same epitope as the initial reference antigen binding molecule.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g. $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\varepsilon$, $\delta$, and $\mu$ respectively.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

A "human" antibody is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "CH1 domain" denotes the part of an antibody heavy chain polypeptide that extends approximately from EU position 118 to EU position 215 (EU numbering system according to Kabat). In one aspect, a CH1 domain has the amino acid sequence of ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKV (SEQ ID NO: 104). Usually, a segment having the amino acid sequence of EPKSC (SEQ ID NO:107) is following to link the CH1 domain to the hinge region, The term "hinge region" denotes the part of an antibody heavy chain polypeptide that joins in a wild-type antibody heavy chain the CH1 domain and the CH2 domain, e. g. from about position 216 to about position 230 according to the EU number system of Kabat, or from about position 226 to about position 230 according to the EU number system of Kabat. The hinge regions of other IgG subclasses can be determined by aligning with the hinge-region cysteine residues of the IgG1 subclass sequence. The hinge region is normally a dimeric molecule consisting of two polypeptides with identical amino acid sequence. The hinge region generally comprises up to 25 amino acid residues and is flexible allowing the associated target binding sites to move independently. The hinge region can be subdivided into three domains: the upper, the middle, and the lower hinge domain (see e.g. Roux, et al., J. Immunol. 161 (1998) 4083).

In one aspect, the hinge region has the amino acid sequence DKTHTCPXCP (SEQ ID NO: 108), wherein X is either S or P. In one aspect, the hinge region has the amino acid sequence HTCPXCP (SEQ ID NO: 109), wherein X is either S or P. In one aspect, the hinge region has the amino acid sequence CPXCP (SEQ ID NO:110), wherein X is either S or P.

The term "Fc domain" or "Fc region" herein is used to define a C-terminal region of an antibody heavy chain that contains at least a portion of the constant region. The term includes native sequence Fc regions and variant Fc regions. An IgG Fc region comprises an IgG CH2 and an IgG CH3 domain.

The "CH2 domain" of a human IgG Fc region usually extends from an amino acid residue at about EU position 231 to an amino acid residue at about EU position 340 (EU numbering system according to Kabat). In one aspect, a CH2 domain has the amino acid sequence of APELLGGPSV FLFPPKPKDT LMISRTPEVT CVWDVSHEDP EVKFNWYVDG VEVHNAKTKP REEQESTYRW SVLTVLHQDW LNGKEYKCKV SNKALPAPIE KTISKAK (SEQ ID NO: 105). The CH2 domain is unique in that it is not closely paired with another domain. Rather, two N-linked branched carbohydrate chains are interposed between the two CH2 domains of an intact native Fc-region. It has been speculated that the carbohydrate may provide a substitute for the domain-domain pairing and help stabilize the CH2 domain. Burton, Mol. Immunol. 22 (1985) 161-206. In one embodiment, a carbohydrate chain is attached to the CH2 domain. The CH2 domain herein may be a native sequence CH2 domain or variant CH2 domain.

The "CH3 domain" comprises the stretch of residues C-terminal to a CH2 domain in an Fc region denotes the part of an antibody heavy chain polypeptide that extends approximately from EU position 341 to EU position 446 (EU numbering system according to Kabat). In one aspect, the CH3 domain has the amino acid sequence of GQPREPQVYT LPPSRDELTK NQVSLTCLVK GFYPS-DIAVE WESNGQPENN YKTTPPVLDS DGSFFLYSKL TVDKSRWQQG NVFSCSVMHE ALHNHYTQKS LSL-SPG (SEQ ID NO: 106). The CH3 region herein may be a native sequence CH3 domain or a variant CH3 domain (e.g. a CH3 domain with an introduced "protuberance" ("knob") in one chain thereof and a corresponding introduced "cavity" ("hole") in the other chain thereof; see U.S. Pat. No. 5,821,333, expressly incorporated herein by reference). Such variant CH3 domains may be used to promote heterodimerization of two non-identical antibody heavy chains as herein described. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991.

The "knob-into-hole" technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine). The protuberance and cavity can be made by altering the nucleic acid encoding the polypeptides, e.g. by site-specific mutagenesis, or by peptide synthesis. In a specific embodiment a knob modification comprises the amino acid substitution T366W in one of the two subunits of the Fc domain, and the hole modification comprises the amino acid substitutions T366S, L368A and Y407V in the other one of the two subunits of the Fc domain. In a further specific embodiment, the subunit of the Fc domain comprising the knob modification additionally comprises the amino acid substitution S354C, and the subunit of the Fc domain comprising the hole modification additionally comprises the amino acid substitution Y349C. Introduction of these two cysteine residues results in the formation of a disulfide bridge between the two subunits of the Fc region, thus further stabilizing the dimer (Carter, J Immunol Methods 248, 7-15 (2001)).

A "region equivalent to the Fc region of an immunoglobulin" is intended to include naturally occurring allelic variants of the Fc region of an immunoglobulin as well as variants having alterations which produce substitutions, additions, or deletions but which do not decrease substantially the ability of the immunoglobulin to mediate effector functions (such as antibody-dependent cellular cytotoxicity). For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, J. U. et al., Science 247:1306-10 (1990)).

The term "wild-type Fc domain" denotes an amino acid sequence identical to the amino acid sequence of an Fc domain found in nature. Wild-type human Fc domains include a native human IgG1 Fc-region (non-A and A allotypes), native human IgG2 Fc-region, native human IgG3 Fc-region, and native human IgG4 Fc-region as well as naturally occurring variants thereof. Wild-type Fc-regions are denoted in SEQ ID NO: 111 (IgG1, caucasian allotype), SEQ ID NO: 112 (IgG1, afroamerican allotype), SEQ ID NO: 113 (IgG2), SEQ ID NO: 114 (IgG3) and SEQ ID NO:115 (IgG4).

The term "variant (human) Fc domain" denotes an amino acid sequence which differs from that of a "wild-type" (human) Fc domain amino acid sequence by virtue of at least one "amino acid mutation". In one aspect, the variant Fc-region has at least one amino acid mutation compared to a native Fc-region, e.g. from about one to about ten amino acid mutations, and in one aspect from about one to about five amino acid mutations in a native Fc-region. In one aspect, the (variant) Fc-region has at least about 95% homology with a wild-type Fc-region.

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

Fc receptor binding dependent effector functions can be mediated by the interaction of the Fc-region of an antibody with Fc receptors (FcRs), which are specialized cell surface receptors on hematopoietic cells. Fc receptors belong to the immunoglobulin superfamily, and have been shown to mediate both the removal of antibody-coated pathogens by phagocytosis of immune complexes, and the lysis of erythrocytes and various other cellular targets (e.g. tumor cells) coated with the corresponding antibody, via antibody dependent cell mediated cytotoxicity (ADCC) (see e.g. Van de Winkel, J. G. and Anderson, C. L., J. Leukoc. Biol. 49 (1991) 511-524). FcRs are defined by their specificity for immunoglobulin isotypes: Fc receptors for IgG antibodies are referred to as FcγR. Fc receptor binding is described e.g. in Ravetch, J. V. and Kinet, J. P., Annu. Rev. Immunol. 9 (1991) 457-492; Capel, P. J., et al., Immunomethods 4 (1994) 25-34; de Haas, M., et al., J. Lab. Clin. Med. 126 (1995) 330-341; and Gessner, J. E., et al., Ann. Hematol. 76 (1998) 231-248.

Cross-linking of receptors for the Fc-region of IgG antibodies (FcγR) triggers a wide variety of effector functions including phagocytosis, antibody-dependent cellular cytotoxicity, and release of inflammatory mediators, as well as immune complex clearance and regulation of antibody production. In humans, three classes of FcγR have been characterized, which are:

FcγRI (CD64) binds monomeric IgG with high affinity and is expressed on macrophages, monocytes, neutrophils and eosinophils. Modification in the Fc-region IgG at least at one of the amino acid residues E233-G236, P238, D265, N297, A327 and P329 (numbering according to EU index of Kabat) reduce binding to FcγRI. IgG2 residues at positions 233-236, substituted into IgG1 and IgG4, reduced binding to FcγRI by $10^3$-fold and eliminated the human monocyte response to antibody-sensitized red blood cells (Armour, K. L., et al., Eur. J. Immunol. 29 (1999) 2613-2624).

FcγRII (CD32) binds complexed IgG with medium to low affinity and is widely expressed. This receptor can be divided into two sub-types, FcγRIIA and FcγRIIB. FcγRIIA is found on many cells involved in killing (e.g. macrophages, monocytes, neutrophils) and seems able to activate the killing process. FcγRIIB seems to play a role in inhibitory processes and is found on B cells, macrophages and on mast cells and eosinophils. On B-cells it seems to function to suppress further immunoglobulin production and isotype switching to, for example, the IgE class. On macrophages, FcγRIIB acts to inhibit phagocytosis as mediated through FcγRIIA. On eosinophils and mast cells the B-form may help to suppress activation of these cells through IgE binding to its separate receptor. Reduced binding for FcγRIIA is found e.g. for antibodies comprising an IgG Fc-region with mutations at least at one of the amino acid residues E233-G236, P238, D265, N297, A327, P329, D270, Q295, A327, R292, and K414 (numbering according to EU index of Kabat).

FcγRIII (CD16) binds IgG with medium to low affinity and exists as two types. FcγRIIIA is found on NK cells, macrophages, eosinophils and some monocytes and T cells and mediates ADCC. FcγRIIIB is highly expressed on neutrophils. Reduced binding to FcγRIIIA is found e.g. for antibodies comprising an IgG Fc-region with mutation at least at one of the amino acid residues E233-G236, P238, D265, N297, A327, P329, D270, Q295, A327, 5239, E269, E293, Y296, V303, A327, K338 and D376 (numbering according to EU index of Kabat).

Mapping of the binding sites on human IgG1 for Fc receptors, the above mentioned mutation sites and methods for measuring binding to FcγRI and FcγRIIA are described in Shields, R. L., et al. J. Biol. Chem. 276 (2001) 6591-6604.

The term "ADCC" or "antibody-dependent cellular cytotoxicity" is an immune mechanism leading to lysis of antibody-coated target cells by immune effector cells. The target cells are cells to which antibodies or derivatives thereof comprising an Fc region specifically bind, generally via the protein part that is N-terminal to the Fc region. As used herein, the term "reduced ADCC" is defined as either a reduction in the number of target cells that are lysed in a given time, at a given concentration of antibody in the medium surrounding the target cells, by the mechanism of ADCC defined above, and/or an increase in the concentration of antibody in the medium surrounding the target cells, required to achieve the lysis of a given number of target cells in a given time, by the mechanism of ADCC. The reduction in ADCC is relative to the ADCC mediated by the same antibody produced by the same type of host cells, using the same standard production, purification, formulation and storage methods (which are known to those skilled in the art), but that has not been engineered. For example, the reduction in ADCC mediated by an antibody comprising in its Fc domain an amino acid substitution that reduces ADCC, is relative to the ADCC mediated by the same antibody without this amino acid substitution in the Fc domain. Suitable assays to measure ADCC are well known in the art (see e.g. PCT publication no. WO 2006/082515 or PCT publication no. WO 2012/130831). For example, the capacity of the antibody to induce the initial steps mediating ADCC is investigated by measuring their binding to Fcγ receptors expressing cells, such as cells, recombinantly expressing FcγRI and/or FcγRIIA or NK cells (expressing essentially FcγRIIIA). In particular, binding to FcγR on NK cells is measured.

An "activating Fc receptor" is an Fc receptor that following engagement by an Fc region of an antibody elicits signaling events that stimulate the receptor-bearing cell to perform effector functions. Activating Fc receptors include FcγRIIIa (CD16a), FcγRI (CD64), FcγRIIa (CD32), and FcαRI (CD89). A particular activating Fc receptor is human FcγRIIIa (UniProt accession no. P08637, version 141).

An "ectodomain" is the domain of a membrane protein that extends into the extracellular space (i.e. the space outside the target cell). Ectodomains are usually the parts of proteins that initiate contact with surfaces, which leads to signal transduction.

The term "peptide linker" refers to a peptide comprising one or more amino acids, typically about 2 to 20 amino acids. Peptide linkers are known in the art or are described herein. Suitable, non-immunogenic linker peptides are, for example, $(G_4S)_n$, $(SG_4)_n$ or $G_4(SG_4)_n$ peptide linkers, wherein "n" is generally a number between 1 and 5, typically between 2 and 4, in particular 2, i.e. the peptides selected from the group consisting of GGGGS (SEQ ID NO:117) GGGGSGGGGS (SEQ ID NO:118), SGGGGSGGGG (SEQ ID NO:119) and GGGGSGGGGSGGGG (SEQ ID NO:120), but also include the sequences GSPGSSSSGS (SEQ ID NO:121), $(G4S)_3$ (SEQ ID NO:122), $(G4S)_4$ (SEQ ID NO:123), GSGSGSGS (SEQ ID NO:124), GSGSGNGS (SEQ ID NO:125), GGSGSGSG (SEQ ID NO:126), GGSGSG (SEQ ID NO:127), GGSG (SEQ ID NO:128), GGSGNGSG (SEQ ID NO:129), GGNGSGSG (SEQ ID NO:130) and GGNGSG (SEQ ID NO:131). Peptide linkers of particular interest are (G4S) (SEQ ID NO:117), $(G4S)_2$ or GGGGSGGGGS (SEQ ID NO:118), $(G4S)_3$ (SEQ ID NO:122) and $(G4S)_4$ (SEQ ID NO:123).

The term "amino acid" as used within this application denotes the group of naturally occurring carboxy a-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

By "fused" or "connected" is meant that the components (e.g. a polypeptide and an ectodomain of said TNF ligand family member) are linked by peptide bonds, either directly or via one or more peptide linkers.

"Percent (%) amino acid sequence identity" with respect to a reference polypeptide (protein) sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN. SAWI or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

In certain embodiments, amino acid sequence variants of the CD28 antigen binding molecules provided herein are contemplated. For example, it may be desirable to improve the binding affinity and/or other biological properties of the CD28 antigen binding molecules. Amino acid sequence variants of the CD28 antigen binding molecules may be prepared by introducing appropriate modifications into the nucleotide sequence encoding the molecules, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding. Sites of interest for substitutional mutagenesis include the HVRs and Framework (FRs). Conservative substitutions are provided in Table B under the heading "Preferred Substitutions" and further described below in reference to amino acid side chain classes (1) to (6). Amino acid substitutions may be introduced into the molecule of interest and the products screened for a desired activity, e.g., retained/improved antigen binding, decreased immunogenicity, or improved ADCC or CDC.

TABLE A

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

The term "amino acid sequence variants" includes substantial variants wherein there are amino acid substitutions in one or more hypervariable region residues of a parent antigen binding molecule (e.g. a humanized or human antibody). Generally, the resulting variant(s) selected for further study will have modifications (e.g., improvements) in certain biological properties (e.g., increased affinity, reduced immunogenicity) relative to the parent antigen binding molecule and/or will have substantially retained certain biological properties of the parent antigen binding molecule. An exemplary substitutional variant is an affinity matured antibody, which may be conveniently generated, e.g., using phage display-based affinity maturation techniques such as those described herein. Briefly, one or more HVR residues are mutated and the variant antigen binding molecules displayed on phage and screened for a particular biological activity (e.g. binding affinity). In certain embodiments, substitutions, insertions, or deletions may occur within one or more HVRs so long as such alterations do not substantially reduce the ability of the antigen binding molecule to bind antigen. For example, conservative alterations (e.g., conservative substitutions as provided herein) that do not substantially reduce binding affinity may be made in HVRs. A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antigen binding molecule complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of insertions include CD28 antigen binding molecules with a fusion to the N- or C-terminus to a polypeptide which increases the serum half-life of the CD28 antigen binding molecules.

In certain embodiments, the CD28 antigen binding molecules provided herein are altered to increase or decrease the extent to which the antibody is glycosylated. Glycosylation variants of the molecules may be conveniently obtained by altering the amino acid sequence such that one or more glycosylation sites is created or removed. Where the agonistic CD28 antigen binding molecule comprises an Fc domain, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in agonistic ICOS-binding molecules may be made in order to create variants with certain improved properties. In one aspect, variants of agonistic CD28-binding molecules are provided having a carbohydrate structure that lacks fucose attached (directly or indirectly) to an Fc region. Such fucosylation variants may have improved ADCC function, see e.g. US Patent Publication Nos. US 2003/0157108 (Presta, L.) or US 2004/0093621 (Kyowa Hakko Kogyo Co., Ltd). Further variants of the CD28 antigen binding molecules of the invention include those with bisected oligosaccharides, e.g., in which a biantennary oligosaccharide attached to the Fc region is bisected by GlcNAc. Such variants may have reduced fucosylation and/or improved ADCC function, see for example WO 2003/011878 (Jean-Mairet et al.); U.S. Pat. No. 6,602,684 (Umana et al.); and US 2005/0123546 (Umana et al.). Variants with at least one galactose residue in the oligosaccharide attached to the Fc region are also provided. Such antibody variants may have improved CDC function and are described, e.g., in WO 1997/30087 (Patel et al.); WO 1998/58964 (Raju, S.); and WO 1999/22764 (Raju, S.).

In certain embodiments, it may be desirable to create cysteine engineered variants of the CD28 antigen binding molecules of the invention, e.g., "thioMAbs," in which one or more residues of the molecule are substituted with cysteine residues. In particular embodiments, the substituted residues occur at accessible sites of the molecule. By substituting those residues with cysteine, reactive thiol groups are thereby positioned at accessible sites of the antibody and may be used to conjugate the antibody to other moieties, such as drug moieties or linker-drug moieties, to create an immunoconjugate. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antigen binding molecules may be generated as described, e.g., in U.S. Pat. No. 7,521,541.

In certain aspects, the CD28 antigen binding molecules provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the bispecific antibody derivative will be used in a therapy under defined conditions, etc. In another aspect, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed. In another aspect, immunoconjugates of the CD28 antigen binding molecules provided herein maybe obtained. An "immunoconjugate" is an antibody conjugated to one or more heterologous molecule(s), including but not limited to a cytotoxic agent.

The term "polynucleotide" refers to an isolated nucleic acid molecule or construct, e.g. messenger RNA (mRNA), virally-derived RNA, or plasmid DNA (pDNA). A polynucleotide may comprise a conventional phosphodiester bond or a non-conventional bond (e.g. an amide bond, such as found in peptide nucleic acids (PNA). The term "nucleic acid molecule" refers to any one or more nucleic acid segments, e.g. DNA or RNA fragments, present in a polynucleotide. Each nucleotide is composed of a base, specifically a purine- or pyrimidine base (i.e. cytosine (C), guanine (G), adenine (A), thymine (T) or uracil (U)), a sugar (i.e. deoxyribose or ribose), and a phosphate group. Often, the nucleic acid molecule is described by the sequence of bases, whereby said bases represent the primary structure (linear structure) of a nucleic acid molecule. The sequence of bases is typically represented from 5' to 3'. Herein, the term nucleic acid molecule encompasses deoxyribonucleic acid (DNA) including e.g., complementary DNA (cDNA) and genomic DNA, ribonucleic acid (RNA), in particular messenger RNA (mRNA), synthetic forms of DNA or RNA, and mixed polymers comprising two or more of these molecules. The nucleic acid molecule may be linear or circular. In addition, the term nucleic acid molecule includes both, sense and antisense strands, as well as single stranded and double stranded forms. Moreover, the herein described nucleic acid molecule can contain naturally occurring or non-naturally occurring nucleotides. Examples of non-naturally occurring nucleotides include modified nucleotide bases with derivatized sugars or phosphate backbone linkages or chemically modified residues. Nucleic acid molecules also encompass DNA and RNA molecules which are suitable as a vector for direct expression of an antibody of the invention in vitro and/or in vivo, e.g., in a host or patient. Such DNA (e.g., cDNA) or RNA (e.g., mRNA) vectors, can be unmodified or modified. For example, mRNA can be chemically modified to enhance the stability of the RNA vector and/or expression of the encoded molecule so that mRNA can be injected into a subject to generate the antibody in vivo (see e.g., Stadler et al. (2017) Nature Medicine 23:815-817, or EP 2 101 823 B1).

By "isolated" nucleic acid molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode bispecific antigen binding molecules of the invention or fragments thereof.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode bispecific antigen binding molecules of the invention or fragments thereof.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the bispecific antigen binding molecules of the present invention. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable excipient" refers to an ingredient in a pharmaceutical composition, other than an active ingredient, which is nontoxic to a subject. A pharmaceutically acceptable excipient includes, but is not limited to, a buffer, a stabilizer, or a preservative.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, the molecules of the invention are used to delay development of a disease or to slow the progression of a disease.

The term "combination treatment" or "co-administration" as noted herein encompasses combined administration (where two or more therapeutic agents are included in the same or separate formulations), and separate administration, in which case, administration of an antibody as reported herein can occur prior to, simultaneously, and/or following, administration of the additional therapeutic agent or agents, preferably an antibody or antibodies.

The term "cancer" refers to or describes the physiological condition in mammals that is typically characterized by unregulated cell growth/proliferation. Thus, the term cancer as used herein refers to proliferative diseases, such as carcinoma, lymphomas (e.g., Hodgkin's and non-Hodgkin's lymphoma), blastoma, sarcoma, and leukemia. In particular, the term cancer includes lymphocytic leukemias, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, including refractory versions of any of the above cancers, or a combination of one or more of the above cancers. In one aspect, the cancer is a solid tumor. In another aspect, the cancer is a haematological cancer, particularly leukemia, most particularly acute lymphoblastic leukemia (ALL) or acute myelogenous leukemia (AML).

A "Her2-positive" cancer comprises cancer cells which have higher than normal levels of Her2. Examples of Her2-positive cancer include Her2-positive breast cancer and Her2-positive gastric cancer. Optionally, Her2-positive cancer has an immunohistochemistry (IHC) score of 2+ or 3+ and/or an in situ hybridization (ISH) amplification ratio>2.0.

The term "early stage breast cancer (EBC)" or "early breast cancer" is used herein to refer to breast cancer that has not spread beyond the breast or the axillary lymph nodes. This includes ductal carcinoma in situ and stage I, stage IIA, stage IIB, and stage IIIA breast cancers.

Reference to a tumor or cancer as a "Stage 0", "Stage I", "Stage II", "Stage III", or "Stage IV", and various sub-stages within this classification, indicates classification of the tumor or cancer using the Overall Stage Grouping or Roman Numeral Staging methods known in the art. Although the actual stage of the cancer is dependent on the type of cancer, in general, a Stage 0 cancer is an in situ lesion, a Stage I cancer is small localized tumor, a Stage II and III cancer is a local advanced tumor which exhibits involvement of the local lymph nodes, and a Stage IV cancer represents metastatic cancer. The specific stages for each type of tumor is known to the skilled clinician.

The term "metastatic breast cancer" means the state of breast cancer where the cancer cells are transmitted from the original site to one or more sites elsewhere in the body, by the blood vessels or lymphatics, to form one or more secondary tumors in one or more organs besides the breast.

An "advanced" cancer is one which has spread outside the site or organ of origin, either by local invasion or metastasis. Accordingly, the term "advanced" cancer includes both locally advanced and metastatic disease.

A "recurrent" cancer is one which has regrown, either at the initial site or at a distant site, after a response to initial therapy, such as surgery. A "locally recurrent" cancer is cancer that returns after treatment in the same place as a previously treated cancer. An "operable" or "resectable" cancer is cancer which is confined to the primary organ and suitable for surgery (resection). A "non-resectable" or "unresectable" cancer is not able to be removed (resected) by surgery.

Bispecific Agonistic CD28 Antigen Binding Molecules of The Invention

The invention provides novel bispecific agonistic CD28 antigen binding molecules with particularly advantageous properties such as producibility, stability, binding affinity, biological activity, targeting efficiency, reduced toxicity, an extended dosage range that can be given to a patient and thereby a possibly enhanced efficacy. The novel bispecific agonistic CD28 antigen binding molecules comprise an Fc domain composed of a first and a second subunit capable of stable association comprising one or more amino acid substitution that reduces the binding affinity of the antigen binding molecule to an Fc receptor and/or effector function (Fc silent) and thus unspecific cross-linking via Fc receptors is avoided. Instead, they comprise at least one antigen binding domain capable of specific binding to Her2 which causes cross-linking at the tumor site. Thus, tumor-specific T cell activation is achieved.

Herein provided is a bispecific agonistic CD28 antigen binding molecule with monovalent binding to CD28, comprising (a) a first antigen binding domain capable of specific binding to CD28,
(b) a second antigen binding domain capable of specific binding to an antigen binding domain capable of specific binding to human epidermal growth factor receptor-2 (Her2), and
(c) a Fc domain composed of a first and a second subunit capable of stable association comprising one or more amino acid substitution that reduces the binding affinity of the antigen binding molecule to an Fc receptor and/or effector function,
wherein said second antigen binding domain capable of specific binding to Her2 comprises
(i) a heavy chain variable region ($V_H$Her2) comprising a heavy chain complementary determining region CDR-H1 of SEQ ID NO: 2, a CDR-H2 of SEQ ID NO: 3, and a CDR-H3 of SEQ ID NO: 4, and a light chain variable region ($V_L$Her2) comprising a light chain complementary determining region CDR-L1 of SEQ ID NO: 5, a CDR-L2 of SEQ ID NO: 6 and a CDR-L3 of SEQ ID NO: 7; or
(ii) a heavy chain variable region ($V_H$Her2) comprising a heavy chain complementary determining region CDR-H1 of SEQ ID NO: 10, a CDR-H2 of SEQ ID NO: 11, and a CDR-H3 of SEQ ID NO: 12, and a light chain variable region ($V_L$Her2) comprising a light chain complementary determining region CDR-L1 of SEQ ID NO: 13, a CDR-L2 of SEQ ID NO: 14 and a CDR-L3 of SEQ ID NO: 15; or
(iii) a heavy chain variable region ($V_H$Her2) comprising a heavy chain complementary determining region CDR-H1 of SEQ ID NO: 132, a CDR-H2 of SEQ ID NO: 133, and a CDR-H3 of SEQ ID NO: 134, and a light chain variable region ($V_L$Her2) comprising a light chain complementary determining region CDR-L1 of SEQ ID NO: 135, a CDR-L2 of SEQ ID NO: 136 and a CDR-L3 of SEQ ID NO: 137, or
(iv) a heavy chain variable region ($V_H$Her2) comprising a heavy chain complementary determining region CDR-H1 of SEQ ID NO: 140, a CDR-H2 of SEQ ID NO: 141, and a CDR-H3 of SEQ ID NO: 142, and a light chain variable region ($V_L$Her2) comprising a light chain complementary determining region CDR-L1 of SEQ ID NO: 143, a CDR-L2 of SEQ ID NO: 144 and a CDR-L3 of SEQ ID NO: 145.

Herein provided is a bispecific agonistic CD28 antigen binding molecule with monovalent binding to CD28, comprising
(a) a first antigen binding domain capable of specific binding to CD28,
(b) a second antigen binding domain capable of specific binding to an antigen binding domain capable of specific binding to human epidermal growth factor receptor-2 (Her2), and
(c) a Fc domain composed of a first and a second subunit capable of stable association comprising one or more amino acid substitution that reduces the binding affinity of the antigen binding molecule to an Fc receptor and/or effector function,
wherein said second antigen binding domain capable of specific binding to Her2 comprises
(i) a heavy chain variable region ($V_H$Her2) comprising a heavy chain complementary determining region CDR-H1 of SEQ ID NO: 2, a CDR-H2 of SEQ ID NO: 3, and a CDR-H3 of SEQ ID NO: 4, and a light chain variable region ($V_L$Her2) comprising a light chain complementary determining region CDR-L1 of SEQ ID NO: 5, a CDR-L2 of SEQ ID NO: 6 and a CDR-L3 of SEQ ID NO: 7; or
(ii) a heavy chain variable region ($V_H$Her2) comprising a heavy chain complementary determining region CDR-H1 of SEQ ID NO: 10, a CDR-H2 of SEQ ID NO: 11, and a CDR-H3 of SEQ ID NO: 12, and a light chain variable region ($V_L$Her2) comprising a light chain complementary determining region CDR-L1 of SEQ ID NO: 13, a CDR-L2 of SEQ ID NO: 14 and a CDR-L3 of SEQ ID NO: 15.

In another aspect, the invention provides a bispecific agonistic CD28 antigen binding molecule characterized by monovalent binding to CD28, comprising
(a) a first antigen binding domain capable of specific binding to CD28,
(b) a second antigen binding domain capable of specific binding to an antigen binding domain capable of specific binding to human epidermal growth factor receptor-2 (Her2), and
(c) a Fc domain composed of a first and a second subunit capable of stable association comprising one or more amino acid substitution that reduces the binding affinity of the antigen binding molecule to an Fc receptor and/or effector function,
wherein said second antigen binding domain capable of specific binding to Her2 comprises
(iii) a heavy chain variable region ($V_H$Her2) comprising a heavy chain complementary determining region CDR-H1 of SEQ ID NO: 132, a CDR-H2 of SEQ ID NO: 133, and a CDR-H3 of SEQ ID NO: 134, and a light chain variable region ($V_L$Her2) comprising a light chain complementary determining region CDR-L1 of SEQ ID NO: 135, a CDR-L2 of SEQ ID NO: 136 and a CDR-L3 of SEQ ID NO: 137, or
(iv) a heavy chain variable region ($V_H$Her2) comprising a heavy chain complementary determining region CDR-H1 of SEQ ID NO: 140, a CDR-H2 of SEQ ID NO: 141, and a CDR-H3 of SEQ ID NO: 142, and a light chain variable region ($V_L$Her2) comprising a light chain complementary determining region CDR-L1 of SEQ ID NO: 143, a CDR-L2 of SEQ ID NO: 144 and a CDR-L3 of SEQ ID NO: 145.

In one aspect, a bispecific agonistic CD28 antigen binding molecule as defined herein before is provided, wherein the Fc domain is an IgG, particularly an IgG1 Fc domain or an IgG4 Fc domain. In one particular aspect, the Fc domain composed of a first and a second subunit capable of stable association is an IgG1 Fc domain. The Fc domain comprises one or more amino acid substitution that reduces the binding affinity of the antigen binding molecule to an Fc receptor and/or reduces or abolishes effector function. In one aspect, the Fc domain comprises the amino acid substitutions L234A and L235A (numbering according to Kabat EU index). In one aspect, the Fc domain is of human IgG1 subclass and comprises the amino acid mutations L234A, L235A and P329G (numbering according to Kabat EU index). In one aspect, a bispecific agonistic CD28 antigen binding molecule is provided, wherein the antigen binding molecule comprises an Fc domain composed of a first and a second subunit capable of stable association, wherein the first subunit comprises the amino acid sequence of SEQ ID NO:70 (Fc hole PGLALA) and the second subunit comprise the amino acid sequence of SEQ ID NO:71 (Fc knob PGLALA).

In one aspect, provided is a bispecific agonistic CD28 antigen binding molecule as defined herein before, wherein the first antigen binding domain capable of specific binding to CD28 comprises
(i) a heavy chain variable region ($V_H$CD28) comprising a heavy chain complementary determining region CDR-H1 of SEQ ID NO: 26, a CDR-H2 of SEQ ID NO: 27, and a CDR-H3 of SEQ ID NO: 28, and a light chain variable region ($V_L$CD28) comprising a light chain complementary determining region CDR-L1 of SEQ ID NO: 29, a CDR-L2 of SEQ ID NO: 30 and a CDR-L3 of SEQ ID NO: 31; or
(ii) a heavy chain variable region ($V_H$CD28) comprising a CDR-H1 of SEQ ID NO: 18, a CDR-H2 of SEQ ID NO: 19, and a CDR-H3 of SEQ ID NO: 20, and a light chain variable region ($V_L$CD28) comprising a CDR-L1 of SEQ ID NO: 21, a CDR-L2 of SEQ ID NO: 22 and a CDR-L3 of SEQ ID NO: 23.

In one aspect, the antigen binding domain capable of specific binding to CD28 of the bispecific agonistic CD28 antigen binding molecule comprises a heavy chain variable region ($V_H$CD28) comprising a CDR-H1 of SEQ ID NO: 26, a CDR-H2 of SEQ ID NO: 27, and a CDR-H3 of SEQ ID NO: 28, and a light chain variable region ($V_L$CD28) comprising a CDR-L1 of SEQ ID NO: 29, a CDR-L2 of SEQ ID NO: 30 and a CDR-L3 of SEQ ID NO: 31.

In another aspect, the antigen binding domain capable of specific binding to CD28 of the bispecific agonistic CD28 antigen binding molecule comprises a heavy chain variable region ($V_H$CD28) comprising a CDR-H1 of SEQ ID NO: 18, a CDR-H2 of SEQ ID NO: 19, and a CDR-H3 of SEQ ID NO: 20, and a light chain variable region ($V_L$CD28) comprising a CDR-L1 of SEQ ID NO: 21, a CDR-L2 of SEQ ID NO: 22 and a CDR-L3 of SEQ ID NO: 23.

In a further aspect, provided is a bispecific agonistic CD28 antigen binding molecule as defined herein before, wherein the first antigen binding domain capable of specific binding to CD28 comprises
(i) a heavy chain variable region ($V_H$CD28) comprising a heavy chain complementary determining region CDR-H1 of SEQ ID NO: 52, a CDR-H2 of SEQ ID NO: 53, and a CDR-H3 of SEQ ID NO: 54, and a light chain variable region ($V_L$CD28) comprising a light chain complementary determining region CDR-L1 of SEQ ID NO: 55, a CDR-L2 of SEQ ID NO: 56 and a CDR-L3 of SEQ ID NO: 57; or
(ii) a heavy chain variable region ($V_H$CD28) comprising a CDR-H1 of SEQ ID NO: 58, a CDR-H2 of SEQ ID NO: 59, and a CDR-H3 of SEQ ID NO: 60, and a light chain variable region ($V_L$CD28) comprising a CDR-L1 of SEQ ID NO: 61, a CDR-L2 of SEQ ID NO: 62 and a CDR-L3 of SEQ ID NO: 63; or
(ii) a heavy chain variable region ($V_H$CD28) comprising a CDR-H1 of SEQ ID NO: 64, a CDR-H2 of SEQ ID NO: 65, and a CDR-H3 of SEQ ID NO: 66, and a light chain variable region ($V_L$CD28) comprising a CDR-L1 of SEQ ID NO: 67, a CDR-L2 of SEQ ID NO: 68 and a CDR-L3 of SEQ ID NO: 69.

In one aspect, the antigen binding domain capable of specific binding to CD28 of the bispecific agonistic CD28 antigen binding molecule comprises a heavy chain variable region ($V_H$CD28) comprising a heavy chain complementary determining region CDR-H1 of SEQ ID NO: 52, a CDR-H2 of SEQ ID NO: 53, and a CDR-H3 of SEQ ID NO: 54, and a light chain complementary determining region CDR-L1 of SEQ ID NO: 55, a CDR-L2 of SEQ ID NO: 56 and a CDR-L3 of SEQ ID NO: 57.

In another aspect, the antigen binding domains capable of specific binding to CD28 of the bispecific agonistic CD28 antigen binding molecule comprises a heavy chain variable region ($V_H$CD28) comprising a CDR-H1 of SEQ ID NO: 58, a CDR-H2 of SEQ ID NO: 59, and a CDR-H3 of SEQ ID NO: 60, and a light chain variable region ($V_L$CD28) comprising a CDR-L1 of SEQ ID NO: 61, a CDR-L2 of SEQ ID NO: 62 and a CDR-L3 of SEQ ID NO: 63.

In yet another aspect, the antigen binding domains capable of specific binding to CD28 of the bispecific agonistic CD28 antigen binding molecule comprises a heavy chain variable region ($V_H$CD28) comprising a CDR-H1 of SEQ ID NO: 64, a CDR-H2 of SEQ ID NO: 65, and a CDR-H3 of SEQ ID NO: 66, and a light chain variable region ($V_L$CD28) comprising a CDR-L1 of SEQ ID NO: 67, a CDR-L2 of SEQ ID NO: 68 and a CDR-L3 of SEQ ID NO: 69.

Furthermore, provided is a bispecific agonistic CD28 antigen binding molecule as defined herein before, wherein the antigen binding domain capable of specific binding to CD28 comprises a heavy chain variable region ($V_H$CD28) comprising an amino acid sequence that is at least about 95%, 96%, 97%, 98%, 99% or 100% identical to the amino acid sequence of SEQ ID NO:24, and a light chain variable region ($V_L$CD28) comprising an amino acid sequence that is at least about 95%, 96%, 97%, 98%, 99% or 100% identical to the amino acid sequence of SEQ ID NO:25. In one aspect, the first antigen binding domain capable of specific binding to CD28 comprises a heavy chain variable region ($V_H$CD28) comprising an amino acid sequence selected from the group consisting of SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40 and SEQ ID NO:41, and a light chain variable region ($V_L$CD28) comprising an amino acid sequence selected from the group consisting of SEQ ID NO:25, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50 and SEQ ID NO:51.

In another aspect, provided is bispecific agonistic CD28 antigen binding molecule, wherein the first antigen binding domain capable of specific binding to CD28 comprises
(a) a heavy chain variable region ($V_H$CD28) comprising the amino acid sequence of SEQ ID NO:37 and a light chain variable region ($V_L$CD28) comprising the amino acid sequence of SEQ ID NO:44, or
(b) a heavy chain variable region ($V_H$CD28) comprising the amino acid sequence of SEQ ID NO:37 and a light chain variable region ($V_L$CD28) comprising the amino acid sequence of SEQ ID NO:25, or
(c) a heavy chain variable region ($V_H$CD28) comprising the amino acid sequence of SEQ ID NO:41 and a light chain variable region ($V_L$CD28) comprising the amino acid sequence of SEQ ID NO:51, or
(d) a heavy chain variable region ($V_H$CD28) comprising the amino acid sequence of SEQ ID NO:36 and a light chain variable region ($V_L$CD28) comprising the amino acid sequence of SEQ ID NO:43, or
(e) a heavy chain variable region ($V_H$CD28) comprising the amino acid sequence of SEQ ID NO:36 and a light chain variable region ($V_L$CD28) comprising the amino acid sequence of SEQ ID NO:44, or
(f) a heavy chain variable region ($V_H$CD28) comprising the amino acid sequence of SEQ ID NO:36 and a light chain variable region (V$_L$CD28) comprising the amino acid sequence of SEQ ID NO:49, or (g) a heavy chain variable region (V$_H$CD28) comprising the amino acid sequence of SEQ ID NO:36 and a light chain variable region (V$_L$CD28) comprising the amino acid sequence of SEQ ID NO:25, or (h) a heavy chain variable region (V$_H$CD28) comprising the amino acid sequence of SEQ ID NO:33 and a light chain variable region (V$_L$CD28) comprising the amino acid sequence of SEQ ID NO:25, or (i) a heavy chain variable region (V$_H$CD28) comprising the amino acid sequence of SEQ ID NO:32 and a light chain variable region (V$_L$CD28) comprising the amino acid sequence of SEQ ID NO:43, or (j) a heavy chain variable region (V$_H$CD28) comprising the amino acid sequence of SEQ ID NO:32 and a light chain variable region (V$_L$CD28) comprising the amino acid sequence of SEQ ID NO:49, or (k) a heavy chain variable region (V$_H$CD28) comprising the amino acid sequence of SEQ ID NO:32 and a light chain variable region (V$_L$CD28) comprising the amino acid sequence of SEQ ID NO:25.

In one aspect, provided is a bispecific agonistic CD28 antigen binding molecule, wherein the first antigen binding domain capable of specific binding to CD28 comprises the CDRs of the heavy chain variable region (V$_H$CD28) comprising the amino acid sequence of SEQ ID NO:37 and the CDRs of the light chain variable region (V$_L$CD28) comprising the amino acid sequence of SEQ ID NO:44. In another aspect, the first antigen binding domain capable of specific binding to CD28 of the bispecific agonistic CD28 antigen binding molecule comprises a heavy chain variable region (V$_H$CD28) comprising a CDR-H1 of SEQ ID NO: 52, a CDR-H2 of SEQ ID NO: 53, and a CDR-H3 of SEQ ID NO: 54, and a light chain variable region (V$_L$CD28) comprising a CDR-L1 of SEQ ID NO: 55, a CDR-L2 of SEQ ID NO: 56 and a CDR-L3 of SEQ ID NO: 57.

In another aspect, provided is a bispecific agonistic CD28 antigen binding molecule, wherein the antigen binding domain capable of specific binding to CD28 comprises the CDRs of the heavy chain variable region (V$_H$CD28) comprising the amino acid sequence of SEQ ID NO:36 and the CDRs of the light chain variable region (V$_L$CD28) comprising the amino acid sequence of SEQ ID NO:43. In another aspect, the antigen binding domain capable of specific binding to CD28 of the bispecific agonistic CD28 antigen binding molecule comprises a heavy chain variable region (V$_H$CD28) comprising a CDR-H1 of SEQ ID NO: 58, a CDR-H2 of SEQ ID NO: 59, and a CDR-H3 of SEQ ID NO: 60, and a light chain variable region (V$_L$CD28) comprising a CDR-L1 of SEQ ID NO: 61, a CDR-L2 of SEQ ID NO: 62 and a CDR-L3 of SEQ ID NO: 63.

In another aspect, provided is a bispecific agonistic CD28 antigen binding molecule, wherein the antigen binding domain capable of specific binding to CD28 comprises the CDRs of the heavy chain variable region (V$_H$CD28) comprising the amino acid sequence of SEQ ID NO:32 and the CDRs of the light chain variable region (V$_L$CD28) comprising the amino acid sequence of SEQ ID NO:25. In another aspect, the antigen binding domain capable of specific binding to CD28 of the bispecific agonistic CD28 antigen binding molecule comprises a heavy chain variable region (V$_H$CD28) comprising a CDR-H1 of SEQ ID NO: 64, a CDR-H2 of SEQ ID NO: 65, and a CDR-H3 of SEQ ID NO: 66, and a light chain variable region (V$_L$CD28) comprising a CDR-L1 of SEQ ID NO: 67, a CDR-L2 of SEQ ID NO: 68 and a CDR-L3 of SEQ ID NO: 69.

In one aspect, a bispecific agonistic CD28 antigen binding molecule is provided, wherein the antigen binding domain capable of specific binding to CD28 binds to CD28 with an reduced affinity compared to an antigen binding domain comprising a heavy chain variable region (V$_H$CD28) comprising the amino acid sequence of SEQ ID NO:24 and a light chain variable region (V$_L$CD28) comprising the amino acid sequence of SEQ ID NO:25. The affinity is measured by flow cytometry as binding to CHO cells expressing CD28. In one aspect, the antigen binding domain capable of specific binding to CD28 binds to CD28 with an reduced affinity compared to an antigen binding domain comprising a heavy chain variable region (V$_H$CD28) comprising the amino acid sequence of SEQ ID NO:24 and a light chain variable region (V$_L$CD28) comprising the amino acid sequence of SEQ ID NO:25 and comprises the CDR-H1, CDR-H2 and CDR-H3 of the heavy chain variable region (V$_H$CD28) comprising the amino acid sequence of SEQ ID NO:37 and the CDR-L1, CDR-L2 and CDR-L3 of the light chain variable region (V$_L$CD28) comprising the amino acid sequence of SEQ ID NO:44. In one aspect, the antigen binding domain capable of specific binding to CD28 with reduced affinity compared to an antigen binding domain comprising a heavy chain variable region (V$_H$CD28) comprising the amino acid sequence of SEQ ID NO:24 and a light chain variable region (V$_L$CD28) comprising the amino acid sequence of SEQ ID NO:25 comprises a heavy chain variable region (V$_H$CD28) comprising an amino acid sequence that is at least about 95%, 96%, 97%, 98%, 99% or 100% identical to the amino acid sequence of SEQ ID NO:37, and a light chain variable region (V$_L$CD28) comprising an amino acid sequence that is at least about 95%, 96%, 97%, 98%, 99% or 100% identical to the amino acid sequence of SEQ ID NO:44.

In one particular aspect, a bispecific agonistic CD28 antigen binding molecule is provided, wherein the antigen binding domain capable of specific binding to CD28 comprises a heavy chain variable region (V$_H$CD28) comprising the amino acid sequence of SEQ ID NO:37 and a light chain variable region (V$_L$CD28) comprising the amino acid sequence of SEQ ID NO:44.

In another particular aspect, a bispecific agonistic CD28 antigen binding molecule is provided, wherein the antigen binding domain capable of specific binding to CD28 comprises a heavy chain variable region (V$_H$CD28) comprising the amino acid sequence of SEQ ID NO:36 and a light chain variable region (V$_L$CD28) comprising the amino acid sequence of SEQ ID NO:43.

In further particular aspect, a bispecific agonistic CD28 antigen binding molecule is provided, wherein the antigen binding domain capable of specific binding to CD28 comprises a heavy chain variable region (V$_H$CD28) comprising the amino acid sequence of SEQ ID NO:32 and a light chain variable region (V$_L$CD28) comprising the amino acid sequence of SEQ ID NO:25.

Her2-Targeting Bispecific Agonistic CD28 Antigen Binding Molecules

A bispecific agonistic CD28 antigen binding molecule is provided herein, wherein the antigen binding domain capable of specific binding to a tumor-associated antigen is an antigen binding domain capable of specific binding to human epidermal growth factor receptor-2 (Her2).

In one aspect, provided is a bispecific agonistic CD28 antigen binding molecule as described herein, wherein the antigen binding domain capable of specific binding to Her2 comprises a heavy chain variable region (V$_H$Her2) comprising a CDR-H1 comprising the amino acid sequence of SEQ ID NO:2, a CDR-H2 comprising the amino acid sequence of SEQ ID NO:3, and a CDR-H3 comprising the amino acid sequence of SEQ ID NO:4, and a light chain variable region ($V_L$Her2) comprising a CDR-L1 comprising the amino acid sequence of SEQ ID NO:5, a CDR-L2 comprising the amino acid sequence of SEQ ID NO:6, and a CDR-L3 comprising the amino acid sequence of SEQ ID NO:7. In one aspect, the antigen binding domain capable of specific binding to Her2 comprises the CDRs of the heavy chain variable region ($V_H$Her2) comprising the amino acid sequence of SEQ ID NO: 8 and the CDRs of the light chain variable region ($V_L$Her2) comprising the amino acid sequence of SEQ ID NO:9. In one aspect, a bispecific agonistic CD28 antigen binding molecule is provided, wherein the antigen binding domain capable of specific binding to Her2 comprises a heavy chain variable region ($V_H$Her2) comprising an amino acid sequence that is at least about 95%, 96%, 97%, 98%, 99% or 100% identical to the amino acid sequence of SEQ ID NO: 8, and a light chain variable region ($V_L$Her2) comprising an amino acid sequence that is at least about 95%, 96%, 97%, 98%, 99% or 100% identical to the amino acid sequence of SEQ ID NO:9. Particularly, the antigen binding domain capable of specific binding to Her2 comprises a heavy chain variable region ($V_H$Her2) comprising the amino acid sequence of SEQ ID NO:8 and a light chain variable region ($V_L$Her2) comprising the amino acid sequence of SEQ ID NO:9.

In another aspect, provided is a bispecific agonistic CD28 antigen binding molecule as described herein, wherein the antigen binding domain capable of specific binding to Her2 comprises a heavy chain variable region ($V_H$Her2) comprising a CDR-H1 comprising the amino acid sequence of SEQ ID NO:10, a CDR-H2 comprising the amino acid sequence of SEQ ID NO:11, and a CDR-H3 comprising the amino acid sequence of SEQ ID NO:12, and a light chain variable region ($V_L$Her2) comprising a CDR-L1 comprising the amino acid sequence of SEQ ID NO:13, a CDR-L2 comprising the amino acid sequence of SEQ ID NO:14, and a CDR-L3 comprising the amino acid sequence of SEQ ID NO:15. In one aspect, the antigen binding domain capable of specific binding to Her2 comprises the CDRs of the heavy chain variable region ($V_H$Her2) comprising the amino acid sequence of SEQ ID NO:16 and the CDRs of the light chain variable region ($V_L$Her2) comprising the amino acid sequence of SEQ ID NO:17. In one aspect, a bispecific agonistic CD28 antigen binding molecule is provided, wherein the antigen binding domain capable of specific binding to Her2 comprises a heavy chain variable region ($V_H$Her2) comprising an amino acid sequence that is at least about 95%, 96%, 97%, 98%, 99% or 100% identical to the amino acid sequence of SEQ ID NO:16, and a light chain variable region ($V_L$Her2) comprising an amino acid sequence that is at least about 95%, 96%, 97%, 98%, 99% or 100% identical to the amino acid sequence of SEQ ID NO:17. Particularly, the antigen binding domain capable of specific binding to Her2 comprises a heavy chain variable region ($V_H$Her2) comprising the amino acid sequence of SEQ ID NO:16 and a light chain variable region ($V_L$Her2) comprising the amino acid sequence of SEQ ID NO:17.

Also herein disclosed is a bispecific agonistic CD28 antigen binding molecule as described herein, wherein the antigen binding domain capable of specific binding to Her2 comprises a heavy chain variable region ($V_H$Her2) comprising (i) CDR-H1 comprising the amino acid sequence of SEQ ID NO:132, (ii) CDR-H2 comprising the amino acid sequence of SEQ ID NO:133, and (iii) CDR-H3 comprising the amino acid sequence of SEQ ID NO:134, and a light chain variable region ($V_L$Her2) comprising (iv) CDR-L1 comprising the amino acid sequence of SEQ ID NO:135, (v) CDR-L2 comprising the amino acid sequence of SEQ ID NO:136, and (vi) CDR-L3 comprising the amino acid sequence of SEQ ID NO:137. In one aspect, the antigen binding domain capable of specific binding to Her2 comprises a heavy chain variable region ($V_H$Her2) comprising an amino acid sequence that is at least about 95%, 96%, 97%, 98%, 99% or 100% identical to the amino acid sequence of SEQ ID NO:138, and a light chain variable region ($V_L$Her2) comprising an amino acid sequence that is at least about 95%, 96%, 97%, 98%, 99% or 100% identical to the amino acid sequence of SEQ ID NO:139. Particularly, the antigen binding domain capable of specific binding to Her2 comprises a heavy chain variable region ($V_H$Her2) comprising the amino acid sequence of SEQ ID NO:138 and a light chain variable region ($V_L$her2) comprising the amino acid sequence of SEQ ID NO:139 (pertuzumab, 2C4).

Furthermore, herein disclosed is a bispecific agonistic CD28 antigen binding molecule as described herein, wherein the antigen binding domain capable of specific binding to Her2 comprises a heavy chain variable region ($V_H$Her2) comprising (i) CDR-H1 comprising the amino acid sequence of SEQ ID NO:140, (ii) CDR-H2 comprising the amino acid sequence of SEQ ID NO:141, and (iii) CDR-H3 comprising the amino acid sequence of SEQ ID NO:142, and a light chain variable region ($V_L$Her2) comprising (iv) CDR-L1 comprising the amino acid sequence of SEQ ID NO:143, (v) CDR-L2 comprising the amino acid sequence of SEQ ID NO:144, and (vi) CDR-L3 comprising the amino acid sequence of SEQ ID NO:145. In one aspect, the antigen binding domain capable of specific binding to Her2 comprises a heavy chain variable region ($V_H$Her2) comprising an amino acid sequence that is at least about 95%, 96%, 97%, 98%, 99% or 100% identical to the amino acid sequence of SEQ ID NO:146, and a light chain variable region ($V_L$Her2) comprising an amino acid sequence that is at least about 95%, 96%, 97%, 98%, 99% or 100% identical to the amino acid sequence of SEQ ID NO:147. Particularly, the antigen binding domain capable of specific binding to Her2 comprises a heavy chain variable region ($V_H$Her2) comprising the amino acid sequence of SEQ ID NO:146 and a light chain variable region ($V_L$Her2) comprising the amino acid sequence of SEQ ID NO:147 (trastuzumab, 4D5).

In addition, herein disclosed is a bispecific agonistic CD28 antigen binding molecule as described herein, wherein the antigen binding domain capable of specific binding to Her2 comprises a heavy chain variable region ($V_H$Her2) comprising (i) CDR-H1 comprising the amino acid sequence of SEQ ID NO:156, (ii) CDR-H2 comprising the amino acid sequence of SEQ ID NO:157, and (iii) CDR-H3 comprising the amino acid sequence of SEQ ID NO:158, and a light chain variable region ($V_L$Her2) comprising (iv) CDR-L1 comprising the amino acid sequence of SEQ ID NO:159, (v) CDR-L2 comprising the amino acid sequence of SEQ ID NO:160, and (vi) CDR-L3 comprising the amino acid sequence of SEQ ID NO:161. In one aspect, the antigen binding domain capable of specific binding to Her2 comprises a heavy chain variable region ($V_H$Her2) comprising an amino acid sequence that is at least about 95%, 96%, 97%, 98%, 99% or 100% identical to the amino acid sequence of SEQ ID NO:162, and a light chain variable region ($V_L$Her2) comprising an amino acid sequence that is at least about 95%, 96%, 97%, 98%, 99% or 100% identical to the amino acid sequence of SEQ ID NO:163. Particularly, the antigen binding domain capable of specific binding to Her2 comprises a heavy chain variable region ($V_H$Her2) comprising the amino acid sequence of SEQ ID NO:162 and a light chain variable region (V_LHer2) comprising the amino acid sequence of SEQ ID NO:163 (7C2).

Bispecific Agonistic CD28 Antigen Binding Molecules Monovalent for Binding to CD28 and Monovalent for Binding to Her2 (1+1 Format)

In one aspect, a bispecific agonistic CD28 antigen binding molecule is provided, wherein the first antigen binding domain capable of specific binding to CD28 and/or the second antigen binding domain capable of specific binding to Her2 is a Fab fragment. In one particular aspect, both the first antigen binding domain capable of specific binding to CD28 and the second antigen binding domain capable of specific binding to Her2 are Fab fragments.

In one aspect, provided is a bispecific agonistic CD28 antigen binding molecule as described herein, comprising (a) a crossFab fragment capable of specific binding to CD28, (b) a conventional Fab fragment capable of specific binding to Her2, and (c) a Fc domain composed of a first and a second subunit capable of stable association comprising one or more amino acid substitution that reduces the binding affinity of the antigen binding molecule to an Fc receptor and/or effector function. In another aspect, provided is a bispecific agonistic CD28 antigen binding molecule as described herein, comprising (a) a conventional Fab fragment capable of specific binding to CD28, (b) a crossFab fragment capable of specific binding to Her2, and (c) a Fc domain composed of a first and a second subunit capable of stable association comprising one or more amino acid substitution that reduces the binding affinity of the antigen binding molecule to an Fc receptor and/or effector function.

In one aspect, provided is a bispecific agonistic CD28 antigen binding molecule as described herein, wherein the first antigen binding domain capable of specific binding to CD28 is a Fab fragment wherein the variable domains VL and VH or the constant domains CL and CH1, particularly the variable domains VL and VH, of the Fab light chain and the Fab heavy chain are replaced by each other (crossfab fragment). In one aspect, the first antigen binding domain capable of specific binding to CD28 is a Fab fragment wherein the variable domains VL and VH or the constant domains CL and CH1, particularly the variable domains VL and VH, of the Fab light chain and the Fab heavy chain are replaced by each other and the second antigen binding domain capable of specific binding to Her2 is a conventional Fab fragment. In one aspect, the second antigen binding domain capable of specific binding to Her2 is a Fab fragment wherein in the constant domain CL the amino acid at position 123 (numbering according to Kabat EU index) is substituted by an amino acid selected from lysine (K), arginine (R) or histidine (H) and the amino acid at position 124 (numbering according to Kabat EU index) is substituted independently by lysine (K), arginine (R) or histidine (H), and wherein in the constant domain CH1 the amino acid at position 147 (numbering according to Kabat EU index) is substituted independently by glutamic acid (E) or aspartic acid (D) and the amino acid at position 213 (numbering according to Kabat EU index) is substituted independently by glutamic acid (E), or aspartic acid (D) (numbering according to Kabat EU index).

In one particular aspect, provided is a bispecific agonistic CD28 antigen binding molecule comprising a first light chain comprising the amino acid sequence of SEQ ID NO:92, a first heavy chain comprising the amino acid sequence of SEQ ID NO:91, a second heavy chain comprising the amino acid sequence of SEQ ID NO:96 and a second light chain comprising the amino acid sequence of SEQ ID NO:97 (Molecule A). In a further particular aspect, provided is a bispecific agonistic CD28 antigen binding molecule comprising a first light chain comprising the amino acid sequence of SEQ ID NO:92, a first heavy chain comprising the amino acid sequence of SEQ ID NO:91, a second heavy chain comprising the amino acid sequence of SEQ ID NO:98 and a second light chain comprising the amino acid sequence of SEQ ID NO:97 (Molecule B). In another particular aspect, provided is a bispecific agonistic CD28 antigen binding molecule comprising a first light chain comprising the amino acid sequence of SEQ ID NO:92, a first heavy chain comprising the amino acid sequence of SEQ ID NO:91, a second heavy chain comprising the amino acid sequence of SEQ ID NO:101 and a second light chain comprising the amino acid sequence of SEQ ID NO:97 (Molecule D).

In another particular aspect, provided is a bispecific agonistic CD28 antigen binding molecule comprising a first light chain comprising the amino acid sequence of SEQ ID NO:179, a first heavy chain comprising the amino acid sequence of SEQ ID NO:178, a second heavy chain comprising the amino acid sequence of SEQ ID NO:180 and a second light chain comprising the amino acid sequence of SEQ ID NO:181 (Molecule F). In another particular aspect, provided is a bispecific agonistic CD28 antigen binding molecule comprising a first light chain comprising the amino acid sequence of SEQ ID NO:179, a first heavy chain comprising the amino acid sequence of SEQ ID NO:178, a second heavy chain comprising the amino acid sequence of SEQ ID NO:182 and a second light chain comprising the amino acid sequence of SEQ ID NO:183 (Molecule G).

In one aspect, provided is a bispecific agonistic CD28 antigen binding molecule as described herein, wherein the second antigen binding domain capable of specific binding to Her2 is a Fab fragment wherein the variable domains VL and VH or the constant domains CL and CH1, particularly the variable domains VL and VH, of the Fab light chain and the Fab heavy chain are replaced by each other (crossfab fragment). In one aspect, the second antigen binding domain capable of specific binding to Her2 is a Fab fragment wherein the variable domains VL and VH or the constant domains CL and CH1, particularly the variable domains VL and VH, of the Fab light chain and the Fab heavy chain are replaced by each other and the first antigen binding domain capable of specific binding to CD28 is a conventional Fab fragment. In one aspect, the antigen binding domain capable of specific binding to CD28 is a Fab fragment wherein in the constant domain CL the amino acid at position 123 (numbering according to Kabat EU index) is substituted by an amino acid selected from lysine (K), arginine (R) or histidine (H) and the amino acid at position 124 (numbering according to Kabat EU index) is substituted independently by lysine (K), arginine (R) or histidine (H), and wherein in the constant domain CH1 the amino acid at position 147 (numbering according to Kabat EU index) is substituted independently by glutamic acid (E) or aspartic acid (D) and the amino acid at position 213 (numbering according to Kabat EU index) is substituted independently by glutamic acid (E), or aspartic acid (D) (numbering according to Kabat EU index).

In one particular aspect, provided is a bispecific agonistic CD28 antigen binding molecule comprising a first light chain comprising the amino acid sequence of SEQ ID NO:83, a first heavy chain comprising the amino acid sequence of SEQ ID NO:74, a second heavy chain comprising the amino acid sequence of SEQ ID NO:99 and a second light chain comprising the amino acid sequence of SEQ ID NO:100 (Molecule C). In one particular aspect, provided is a bispecific agonistic CD28 antigen binding molecule comprising a first light chain comprising the amino acid sequence of SEQ ID NO:83, a first heavy chain comprising the amino acid sequence of SEQ ID NO:74, a second heavy chain comprising the amino acid sequence of SEQ ID NO:102 and a second light chain comprising the amino acid sequence of SEQ ID NO:100 (Molecule E).

Fc Domain Modifications Reducing Fc Receptor Binding and/or Effector Function

The Fc domain of the bispecific agonistic CD28 antigen binding molecule of the invention consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other. The Fc domain confers favorable pharmacokinetic properties to the antigen binding molecules of the invention, including a long serum half-life which contributes to good accumulation in the target tissue and a favorable tissue-blood distribution ratio. On the other side, it may, however, lead to undesirable targeting of the bispecific antibodies of the invention to cells expressing Fc receptors rather than to the preferred antigen-bearing cells.

Accordingly, the Fc domain of the bispecific agonistic CD28 antigen binding molecule of the invention exhibits reduced binding affinity to an Fc receptor and/or reduced effector function, as compared to a native IgG1 Fc domain. In one aspect, the Fc does not substantially bind to an Fc receptor and/or does not induce effector function. In a particular aspect the Fc receptor is an Fcγ receptor. In one aspect, the Fc receptor is a human Fc receptor. In a specific aspect, the Fc receptor is an activating human Fcγ receptor, more specifically human FcγRIIIa, FcγRI or FcγRIIa, most specifically human FcγRIIIa. In one aspect, the Fc domain does not induce effector function. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced dendritic cell maturation, or reduced T cell priming.

In certain aspects, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In one particular aspect, the invention provides an antigen binding molecule, wherein the Fc region comprises one or more amino acid substitution that reduces binding to an Fc receptor, in particular towards Fcγ receptor. In one aspect, the invention provides an antibody, wherein the Fc region comprises one or more amino acid substitution and wherein the ADCC induced by the antibody is reduced to 0-20% of the ADCC induced by an antibody comprising the wild-type human IgG1 Fc region.

In one aspect, the Fc domain of the antigen binding molecule of the invention comprises one or more amino acid mutation that reduces the binding affinity of the Fc domain to an Fc receptor and/or effector function. Typically, the same one or more amino acid mutation is present in each of the two subunits of the Fc domain. In particular, the Fc domain comprises an amino acid substitution at a position of E233, L234, L235, N297, P331 and P329 (EU numbering). In particular, the Fc domain comprises amino acid substitutions at positions 234 and 235 (EU numbering) and/or 329 (EU numbering) of the IgG heavy chains. More particularly, provided is an antigen binding molecule according to the invention which comprises an Fc domain with the amino acid substitutions L234A, L235A and P329G ("P329G LALA", EU numbering) in the IgG heavy chains. The amino acid substitutions L234A and L235A refer to the so-called LALA mutation. The "P329G LALA" combination of amino acid substitutions almost completely abolishes Fcγ receptor binding of a human IgG1 Fc domain and is described in International Patent Appl. Publ. No. WO 2012/130831 A1 which also describes methods of preparing such mutant Fc domains and methods for determining its properties such as Fc receptor binding or effector functions.

Fc domains with reduced Fc receptor binding and/or effector function also include those with substitution of one or more of Fc domain residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In another aspect, the Fc domain is an IgG4 Fc domain. IgG4 antibodies exhibit reduced binding affinity to Fc receptors and reduced effector functions as compared to IgG1 antibodies. In a more specific aspect, the Fc domain is an IgG4 Fc domain comprising an amino acid substitution at position S228 (Kabat numbering), particularly the amino acid substitution S228P. In a more specific aspect, the Fc domain is an IgG4 Fc domain comprising amino acid substitutions L235E and S228P and P329G (EU numbering). Such IgG4 Fc domain mutants and their Fcγ receptor binding properties are also described in WO 2012/130831.

Additionally or alternatively, the one or more substitution mutations comprise an aglycosylation site mutation (e.g., an aglycosylation site mutation at amino acid residue N297 (EU numbering), e.g., an aglycosylation site mutation of N297G or N297A (EU numbering), that also reduces binding to an Fc receptor and/or effector function. In a particular aspect, the Fc domain is an IgG1 Fc domain comprising amino acid substitutions N297G according to EU numbering.

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. Alternatively, binding affinity of Fc domains or cell activating antibodies comprising an Fc domain for Fc receptors may be evaluated using cell lines known to express particular Fc receptors, such as human NK cells expressing FcγIIIa receptor.

Effector function of an Fc domain, or antigen binding molecules of the invention comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTITM non-radioactive cytotoxicity assay for flow cytometry (CellTechnology, Inc. Mountain View, CA); and CytoTox 96® non-radioactive cytotoxicity assay (Promega, Madison, WI)). Useful effector cells for such assays include peripheral blood mononuclear cells (PBMC) and Natural Killer (NK) cells. Alternatively, or additionally, ADCC activity of the molecule of interest may be assessed in vivo, e.g. in an animal model such as that disclosed in Clynes et al., Proc Natl Acad Sci USA 95, 652-656 (1998).

In some aspects, binding of the Fc domain to a complement component, specifically to C1q, is reduced. Accordingly, in some aspects wherein the Fc domain is engineered to have reduced effector function, said reduced effector function includes reduced CDC. C1q binding assays may be carried out to determine whether the bispecific antibodies of the invention are able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

In one particular aspect, the Fc domain exhibiting reduced binding affinity to an Fc receptor and/or reduced effector function, as compared to a native IgG1 Fc domain, is a human IgG1 Fc domain comprising the amino acid substitutions L234A, L235A and optionally P329G, or a human IgG4 Fc domain comprising the amino acid substitutions S228P, L235E and optionally P329G (numberings according to Kabat EU index). More particularly, it is a human IgG1 Fc domain comprising the amino acid substitutions L234A, L235A and P329G (numbering according to Kabat EU index).

In another aspect, the Fc domain is an IgG1 or IgG4 Fc domain, wherein the the one or more amino acid substitutions that reduces binding to an Fc receptor and/or effector function is at N297. In a particular aspect, the Fc domain is an IgG1 Fc domain comprising amino acid substitutions N297G according to EU numbering.

Fc Domain Modifications Promoting Heterodimerization

The bispecific agonistic CD28 antigen binding molecules of the invention comprise different antigen-binding sites, fused to one or the other of the two subunits of the Fc domain, thus the two subunits of the Fc domain may be comprised in two non-identical polypeptide chains. Recombinant co-expression of these polypeptides and subsequent dimerization leads to several possible combinations of the two polypeptides. To improve the yield and purity of the bispecific antigen binding molecules of the invention in recombinant production, it will thus be advantageous to introduce in the Fc domain of the bispecific antigen binding molecules of the invention a modification promoting the association of the desired polypeptides.

Accordingly, in particular aspects the invention relates to the bispecific agonistic CD28 antigen binding molecule with monovalent binding to CD28 comprising (a) one antigen binding domain capable of specific binding to CD28, (b) at least one antigen binding domain capable of specific binding to a tumor-associated antigen, and (c) a Fc domain composed of a first and a second subunit capable of stable association comprising one or more amino acid substitution that reduces the binding affinity of the antigen binding molecule to an Fc receptor and/or effector function, wherein the Fc domain comprises a modification promoting the association of the first and second subunit of the Fc domain. The site of most extensive protein-protein interaction between the two subunits of a human IgG Fc domain is in the CH3 domain of the Fc domain. Thus, in one aspect said modification is in the CH3 domain of the Fc domain.

In a specific aspect said modification is a so-called "knob-into-hole" modification, comprising a "knob" modification in one of the two subunits of the Fc domain and a "hole" modification in the other one of the two subunits of the Fc domain. Thus, the invention relates to the bispecific agonistic CD28 antigen binding molecule with monovalent binding to CD28 comprising (a) one antigen binding domain capable of specific binding to CD28, (b) at least one antigen binding domain capable of specific binding to a tumor-associated antigen, and (c) a Fc domain composed of a first and a second subunit capable of stable association comprising one or more amino acid substitution that reduces the binding affinity of the antigen binding molecule to an Fc receptor and/or effector function, wherein the first subunit of the Fc domain comprises knobs and the second subunit of the Fc domain comprises holes according to the knobs into holes method. In a particular aspect, the first subunit of the Fc domain comprises the amino acid substitutions S354C and/or T366W (EU numbering) and the second subunit of the Fc domain comprises the amino acid substitutions Y349C, T366S and Y407V (numbering according to Kabat EU index).

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in one aspect, in the CH3 domain of the first subunit of the Fc domain of the bispecific antigen binding molecules of the invention an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable. The protuberance and cavity can be made by altering the nucleic acid encoding the polypeptides, e.g. by site-specific mutagenesis, or by peptide synthesis. In a specific aspect, in the CH3 domain of the first subunit of the Fc domain the threonine residue at position 366 is replaced with a tryptophan residue (T366W), and in the CH3 domain of the second subunit of the Fc domain the tyrosine residue at position 407 is replaced with a valine residue (Y407V). In one aspect, in the second subunit of the Fc domain additionally the threonine residue at position 366 is replaced with a serine residue (T366S) and the leucine residue at position 368 is replaced with an alanine residue (L368A).

In yet a further aspect, in the first subunit of the Fc domain additionally the serine residue at position 354 is replaced with a cysteine residue (S354C), and in the second subunit of the Fc domain additionally the tyrosine residue at position 349 is replaced by a cysteine residue (Y349C). Introduction of these two cysteine residues results in formation of a disulfide bridge between the two subunits of the Fc domain, further stabilizing the dimer (Carter (2001), J Immunol Methods 248, 7-15). In a particular aspect, the first subunit of the Fc domain comprises the amino acid substitutions S354C and T366W (EU numbering) and the second subunit of the Fc domain comprises the amino acid substitutions Y349C, T366S and Y407V (numbering according to Kabat EU index).

In an alternative aspect, a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable.

The C-terminus of the heavy chain of the bispecific agonistic CD28 antigen binding molecule as reported herein can be a complete C-terminus ending with the amino acid residues PGK. The C-terminus of the heavy chain can be a shortened C-terminus in which one or two of the C terminal amino acid residues have been removed. In one preferred aspect, the C-terminus of the heavy chain is a shortened C-terminus ending P. In one preferred aspect, the C-terminus of the heavy chain is a shortened C-terminus ending PG. In one aspect of all aspects as reported herein, a CD28 antigen binding molecule comprising a heavy chain including a C-terminal CH3 domain as specified herein, comprises the C-terminal glycine-lysine dipeptide (G446 and K447, numbering according to Kabat EU index). In one aspect of all aspects as reported herein, a CD28 antigen binding molecule comprising a heavy chain including a C-terminal CH3 domain, as specified herein, comprises a C-terminal glycine residue (G446, numbering according to Kabat EU index).

Modifications in the Fab Domains

In one aspect, the invention relates to a bispecific agonistic CD28 antigen binding molecule characterized by monovalent binding to CD28 comprising (a) a first antigen binding domain capable of specific binding to CD28, (b) a second antigen binding domain capable of specific binding to Her2, and (c) a Fc domain composed of a first and a second subunit capable of stable association comprising one or more amino acid substitution that reduces the binding affinity of the antigen binding molecule to an Fc receptor and/or effector function, wherein the second antigen binding domain capable of specific binding to Her2 is a Fab fragment and in the Fab fragment either the variable domains VH and VL or the constant domains CH1 and CL are exchanged according to the Crossmab technology.

Multispecific antibodies with a domain replacement/exchange in one binding arm (CrossMabVH-VL or CrossMabCH-CL) are described in detail in WO2009/080252 and Schaefer, W. et al, PNAS, 108 (2011) 11187-1191. They clearly reduce the byproducts caused by the mismatch of a light chain against a first antigen with the wrong heavy chain against the second antigen (compared to approaches without such domain exchange).

In one aspect, the invention relates to a bispecific agonistic CD28 antigen binding molecule characterized by monovalent binding to CD28 comprising (a) a first antigen binding domain capable of specific binding to CD28, (b) a second antigen binding domain capable of specific binding to Her2, and (c) a Fc domain composed of a first and a second subunit capable of stable association comprising one or more amino acid substitution that reduces the binding affinity of the antigen binding molecule to an Fc receptor and/or effector function, wherein in the Fab fragment capable of specific binding to CD28 the variable domains VL and VH are replaced by each other so that the VH domain is part of the light chain and the VL domain is part of the heavy chain.

In another aspect, and to further improve correct pairing, the bispecific agonistic CD28 antigen binding molecule characterized by monovalent binding to CD28 comprising (a) a first antigen binding domain capable of specific binding to CD28, (b) a second antigen binding domains capable of specific binding to a Her2, and (c) a Fc domain composed of a first and a second subunit capable of stable association comprising one or more amino acid substitution that reduces the binding affinity of the antigen binding molecule to an Fc receptor and/or effector function, can contain different charged amino acid substitutions (so-called "charged residues"). These modifications are introduced in the crossed or non-crossed CH1 and CL domains. In a particular aspect, the invention relates to a bispecific agonistic CD28 antigen binding molecule, wherein in one of CL domains the amino acid at position 123 (EU numbering) has been replaced by arginine (R) and the amino acid at position 124 (EU numbering) has been substituted by lysine (K) and wherein in one of the CH1 domains the amino acids at position 147 (EU numbering) and at position 213 (EU numbering) have been substituted by glutamic acid (E). In one particular aspect, in the CL domain of the Fab fragment capable of specific binding to CD28 the amino acid at position 123 (EU numbering) has been replaced by arginine (R) and the amino acid at position 124 (EU numbering) has been substituted by lysine (K) and in the CH1 domain of the Fab fragment capable of specific binding to CD28 the amino acids at position 147 (EU numbering) and at position 213 (EU numbering) have been substituted by glutamic acid (E).

Polynucleotides

The invention further provides isolated polynucleotides encoding a bispecific agonistic CD28 antigen binding molecule as described herein or a fragment thereof. The one or more isolated polynucleotides encoding the bispecific agonistic CD28 antigen binding molecule of the invention may be expressed as a single polynucleotide that encodes the entire antigen binding molecule or as multiple (e.g., two or more) polynucleotides that are co-expressed. Polypeptides encoded by polynucleotides that are co-expressed may associate through, e.g., disulfide bonds or other means to form a functional antigen binding molecule. For example, the light chain portion of an immunoglobulin may be encoded by a separate polynucleotide from the heavy chain portion of the immunoglobulin. When co-expressed, the heavy chain polypeptides will associate with the light chain polypeptides to form the immunoglobulin. In some aspects, the isolated polynucleotide encodes the entire bispecific agonistic CD28 antigen binding molecule according to the invention as described herein. In other aspects, the isolated polynucleotide encodes a polypeptide comprised in the bispecific agonistic CD28 antigen binding molecule according to the invention as described herein. In certain aspects the polynucleotide or nucleic acid is DNA. In other aspects, a polynucleotide of the present invention is RNA, for example, in the form of messenger RNA (mRNA). RNA of the present invention may be single stranded or double stranded.

Recombinant Methods

Bispecific agonistic CD28 antigen binding molecules of the invention may be obtained, for example, by solid-state peptide synthesis (e.g. Merrifield solid phase synthesis) or recombinant production. For recombinant production one or more polynucleotide encoding the bispecific agonistic CD28 antigen binding molecule or polypeptide fragments thereof, e.g., as described above, is isolated and inserted into one or more vectors for further cloning and/or expression in a host cell. Such polynucleotide may be readily isolated and sequenced using conventional procedures. In one aspect of the invention, a vector, preferably an expression vector, comprising one or more of the polynucleotides of the invention is provided. Methods which are well known to those skilled in the art can be used to construct expression vectors containing the coding sequence of the antibody (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y. (1989). The expression vector can be part of a plasmid, virus, or may be a nucleic acid fragment. The expression vector includes an expression cassette into which the polynucleotide encoding the antibody or polypeptide fragments thereof (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the antibody of the invention or polypeptide fragments thereof, or variants or derivatives thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription.

Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit â-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the antibody or polypeptide fragments thereof is desired, DNA encoding a signal sequence may be placed upstream of the nucleic acid an antibody of the invention or polypeptide fragments thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the bispecific agonistic CD28 antigen binding molecule may be included within or at the ends of the polynucleotide encoding an antibody of the invention or polypeptide fragments thereof.

In a further aspect of the invention, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one aspect, a host cell comprises (e.g. has been transformed or transfected with) a vector comprising a polynucleotide that encodes (part of) an antibody of the invention of the invention. As used herein, the term "host cell" refers to any kind of cellular system which can be engineered to generate the fusion proteins of the invention or fragments thereof. Host cells suitable for replicating and for supporting expression of antigen binding molecules are well known in the art. Such cells may be transfected or transduced as appropriate with the particular expression vector and large quantities of vector containing cells can be grown for seeding large scale fermenters to obtain sufficient quantities of the antigen binding molecule for clinical applications. Suitable host cells include prokaryotic microorganisms, such as E. coli, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006).

Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells. Plant cell cultures can also be utilized as hosts. See e.g. U.S. Pat. Nos. 5,959,177, 6,040, 498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr-CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B. K. C. Lo, ed., Humana Press, Totowa, NJ), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., Y0, NS0, Sp20 cell). Standard technologies are known in the art to express foreign genes in these systems. Cells expressing a polypeptide comprising either the heavy or the light chain of an immunoglobulin, may be engineered so as to also express the other of the immunoglobulin chains such that the expressed product is an immunoglobulin that has both a heavy and a light chain.

In one aspect, a method of producing a bispecific agonistic CD28 antigen binding molecule of the invention or polypeptide fragments thereof is provided, wherein the method comprises culturing a host cell comprising polynucleotides encoding the antibody of the invention or polypeptide fragments thereof, as provided herein, under conditions suitable for expression of the antibody of the invention or polypeptide fragments thereof, and recovering the antibody of the invention or polypeptide fragments thereof from the host cell (or host cell culture medium).

In certain aspects the antigen binding domain capable of specific binding to Her2 (e.g. a Fab fragment) forming part of the antigen binding molecule comprises at least an immunoglobulin variable region capable of binding to an antigen. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108 to McCafferty).

Any animal species of immunoglobulin can be used in the invention. Non-limiting immunoglobulins useful in the present invention can be of murine, primate, or human origin. If the fusion protein is intended for human use, a chimeric form of immunoglobulin may be used wherein the constant regions of the immunoglobulin are from a human. A humanized or fully human form of the immunoglobulin can also be prepared in accordance with methods well known in the art (see e.g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling). Particular immunoglobulins according to the invention are human immunoglobulins. Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005). Human antibodies and human variable regions may also be generated by isolating Fv clone variable region sequences selected from human-derived phage display libraries (see e.g., Hoogenboom et al. in Methods in Molecular Biology 178, 1-37 (O'Brien et al., ed., Human Press, Totowa, NJ, 2001); and McCafferty et al., Nature 348, 552-554; Clackson et al., Nature 352, 624-628 (1991)). Phage typically display antibody fragments, either as single-chain Fv (scFv) fragments or as Fab fragments.

In certain aspects, the antigen binding domains comprised in the bispecific agonistic CD28 antigen binding molecules are engineered to have enhanced binding affinity according to, for example, the methods disclosed in PCT publication WO 2012/020006 (see Examples relating to affinity maturation) or U.S. Pat. Appl. Publ. No. 2004/0132066. The ability of the antigen binding molecules of the invention to bind to a specific antigenic determinant can be measured either through an enzyme-linked immunosorbent assay (ELISA) or other techniques familiar to one of skill in the art, e.g. surface plasmon resonance technique (Liljeblad, et al., Glyco J 17, 323-329 (2000)), and traditional binding assays (Heeley, Endocr Res 28, 217-229 (2002)). Competition assays may be used to identify an antigen binding molecule that competes with a reference antibody for binding to a particular antigen. In certain embodiments, such a competing antigen binding molecule binds to the same epitope (e.g. a linear or a conformational epitope) that is bound by the reference antigen binding molecule. Detailed exemplary methods for mapping an epitope to which an antigen binding molecule binds are provided in Morris (1996) "Epitope Mapping Protocols", in Methods in Molecular Biology vol. 66 (Humana Press, Totowa, NJ). In an exemplary competition assay, immobilized antigen is incubated in a solution comprising a first labeled antigen binding molecule that binds to the antigen and a second unlabeled antigen binding molecule that is being tested for its ability to compete with the first antigen binding molecule for binding to the antigen. The second antigen binding molecule may be present in a hybridoma supernatant. As a control, immobilized antigen is incubated in a solution comprising the first labeled antigen binding molecule but not the second unlabeled antigen binding molecule. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antigen binding molecule is competing with the first antigen binding molecule for binding to the antigen. See Harlow and Lane (1988) Antibodies: A Laboratory Manual ch. 14 (Cold Spring Harbor Laboratory, Cold Spring Harbor, NY).

Bispecific agonistic CD28 antigen binding molecules of the invention prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the antigen binding molecule binds. For example, for affinity chromatography purification of antigen binding molecules of the invention, a matrix with protein A or protein G may be used. Sequential Protein A or G affinity chromatography and size exclusion chromatography can be used to isolate an antigen binding molecule essentially as described in the Examples. The purity of the CD28 antigen binding molecule or fragments thereof can be determined by any of a variety of well-known analytical methods including gel electrophoresis, high pressure liquid chromatography, and the like. For example, the CD28 antigen binding molecule expressed as described in the Examples were shown to be intact and properly assembled as demonstrated by reducing and non-reducing SDS-PAGE.

Assays

The bispecific agonistic CD28 antigen binding molecules provided herein may be identified, screened for, or characterized for their physical/chemical properties and/or biological activities by various assays known in the art.

1. Affinity Assays

The affinity of the antigen binding molecule provided herein for the corresponding target can be determined in accordance with the methods set forth in the Examples by surface plasmon resonance (SPR), using standard instrumentation such as a Proteon instrument (Bio-rad), and receptors or target proteins such as may be obtained by recombinant expression. The affinity of the antigen binding molecule for the target cell antigen can also be determined by surface plasmon resonance (SPR), using standard instrumentation such as a Proteon instrument (Bio-rad), and receptors or target proteins such as may be obtained by recombinant expression. According to one aspect, $K_D$ is measured by surface plasmon resonance using a Proteon® machine (Bio-Rad) at 25° C.

2. Binding Assays and Other Assays

Binding of the bispecific antigen binding molecule provided herein to the corresponding receptor expressing cells may be evaluated using cell lines expressing the particular receptor or target antigen, for example by flow cytometry (FACS). In one aspect, CHO cells expressing human CD28 (parental cell line CHO-k1 ATCC #CCL-61, modified to stably overexpress human CD28) are used in the binding assay.

In a further aspect, cancer cell lines expressing Her2 (e.g. human breast cancer cell line KPL-4, Kawasaki Medical School) were used to demonstrate the binding of the bispecific antigen binding molecules to the target cell antigen.

3. Activity Assays

In one aspect, assays are provided for identifying CD28 antigen binding molecules having biological activity. Biological activity may include, e.g. T cell activation and cytokine secretion or tumor cell killing as measured with the methods as described in Example 3. Antigen binding molecules having such biological activity in vivo and/or in vitro are also provided.

Pharmaceutical Compositions, Formulations and Routes of Administration

In a further aspect, the invention provides pharmaceutical compositions comprising any of the bispecific agonistic CD28 antigen binding molecules provided herein, e.g., for use in any of the below therapeutic methods. In one embodiment, a pharmaceutical composition comprises a bispecific agonistic CD28 antigen binding molecule provided herein and at least one pharmaceutically acceptable excipient. In another aspect, a pharmaceutical composition comprises a bispecific agonistic CD28 antigen binding molecule provided herein and at least one additional therapeutic agent, e.g., as described below.

Pharmaceutical compositions of the present invention comprise a therapeutically effective amount of one or more bispecific antigen binding molecules dissolved or dispersed in a pharmaceutically acceptable excipient. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains at least one bispecific agonistic CD28 antigen binding molecule and optionally an additional active ingredient will be known to those of skill in the art in light of the present disclosure, as exemplified by Remington's Pharmaceutical Sciences, 18th Ed. Mack Printing Company, 1990, incorporated herein by reference. In particular, the compositions are lyophilized formulations or aqueous solutions. As used herein, "pharmaceutically acceptable excipient" includes any and all solvents, buffers, dispersion media, coatings, surfactants, antioxidants, preservatives (e.g. antibacterial agents, anti-fungal agents), isotonic agents, salts, stabilizers and combinations thereof, as would be known to one of ordinary skill in the art.

Parenteral compositions include those designed for administration by injection, e.g. subcutaneous, intradermal, intralesional, intravenous, intraarterial intramuscular, intrathecal or intraperitoneal injection. For injection, the TNF family ligand trimer-containing antigen binding molecules of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the bispecific agonistic CD28 antigen binding molecule may be in powder form for constitution with a suitable vehicle, e.g., sterile pyrogen-free water, before use. Sterile injectable solutions are prepared by incorporating the fusion proteins of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein. Suitable pharmaceutically acceptable excipients include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof. Exemplary pharmaceutically acceptable excipients herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases. Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer. In addition to the compositions described previously, the bispecific agonistic CD28 antigen binding molecule may also be formulated as a depot preparation. Such long acting formulations may be administered by implantation (for example subcutaneously or intramuscularly) or by intramuscular injection. Thus, for example, the bispecific agonistic CD28 antigen binding molecule may be formulated with suitable polymeric or hydrophobic materials (for example as emulsion in an acceptable oil) or ion exchange resins, or as sparingly soluble derivatives, for example, as a sparingly soluble salt.

Pharmaceutical compositions comprising the bispecific agonistic CD28 antigen binding molecule of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen. The bispecific agonistic CD28 antigen binding molecule of the invention may be formulated into a composition in a free acid or base, neutral or salt form. Pharmaceutically acceptable salts are salts that substantially retain the biological activity of the free acid or base. These include the acid addition salts, e.g. those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms. The composition herein may also contain more than one active ingredients as necessary for the particular indication being treated, preferably those with complementary activities that do not adversely affect each other. Such active ingredients are suitably present in combination in amounts that are effective for the purpose intended. The formulations to be used for in vivo administration are generally sterile. Sterility may be readily accomplished, e.g., by filtration through sterile filtration membranes.

Therapeutic Methods and Compositions

Any of the bispecific agonistic CD28 antigen binding molecules provided herein may be used in therapeutic methods, either alone or in combination.

In one aspect, a bispecific agonistic CD28 antigen binding molecule for use as a medicament is provided. In further aspects, a bispecific agonistic CD28 antigen binding molecule for use in treating cancer is provided. In certain aspects, a bispecific agonistic CD28 antigen binding molecule for use in a method of treatment is provided. In certain aspects, herein is provided a bispecific agonistic CD28 antigen binding molecule for use in a method of treating an individual having cancer comprising administering to the individual an effective amount of the bispecific agonistic CD28 antigen binding molecule. In one such embodiment, the method further comprises administering to the individual an effective amount of at least one additional therapeutic agent.

In one aspect, the bispecific agonistic CD28 antigen binding molecule is for use in inhibiting the growth of Her2-expressing cancer cells. Thus, in particular aspects, the bispecific agonistic CD28 antigen binding molecule is for use in treating Her2-positive cancer. Examples of Her2-positive cancers include breast cancer, ovarian cancer, gastric cancer, bladder cancer, salivary gland, endometrial cancer, pancreatic cancer and non-small-cell lung cancer (NSCLC). In one aspect, the Her2-positive cancer is Her2+ positive breast cancer, for instance early or locally advanced Her2+ positive breast cancer. Thus, a bispecific agonistic CD28 antigen binding molecule as described herein for use in the treatment of these cancers is provided. The subject, patient, or "individual" in need of treatment is typically a mammal, more specifically a human.

In certain aspects, a bispecific agonistic CD28 antigen binding molecule for use in a method of treatment is provided. In certain aspects, herein is provided a bispecific agonistic CD28 antigen binding molecule for use in a method of treating an individual having cancer comprising administering to the individual an effective amount of the bispecific agonistic CD28 antigen binding molecule. In another aspect, provided is a bispecific agonistic CD28 antigen binding molecule for use in a method of treating an individual having her2-positive cancer, in particular breast cancer, ovarian cancer, gastric cancer, bladder cancer, salivary gland, endometrial cancer, pancreatic cancer and non-small-cell lung cancer (NSCLC), comprising administering to the individual an effective amount of the bispecific agonistic CD28 antigen binding molecule. In one such embodiment, the method further comprises administering to the individual an effective amount of at least one additional therapeutic agent.

In a further aspect, herein is provided for the use of a bispecific agonistic CD28 antigen binding molecule as described herein in the manufacture or preparation of a medicament. In one embodiment, the medicament is for treatment of cancer, particularly Her2-positive cancer. In a further aspect, the medicament is for use in a method of treating cancer comprising administering to an individual having cancer an effective amount of the medicament. In one such aspect, the method further comprises administering to the individual an effective amount of at least one additional therapeutic agent, e.g., as described below. In another aspect, the medicament is for treatment of Her2-positive cancer. In a further aspect, the medicament is for use in a method of treating cancer, in particular Her2-positive cancer, comprising administering to an individual having cancer an effective amount of the medicament. In a further aspect, herein is provided a method for treating a cancer, in particular Her2-positive cancer. In one aspect, the method comprises administering to an individual having cancer an effective amount of a bispecific agonistic CD28 antigen binding molecule. In one such aspect, the method further comprises administering to the individual an effective amount of at least one additional therapeutic agent, as described below. An "individual" according to any of the above aspects may be a human.

In a further aspect, herein are provided pharmaceutical formulations comprising any of the bispecific agonistic CD28 antigen binding molecules as reported herein, e.g., for use in any of the above therapeutic methods. In one aspect, a pharmaceutical formulation comprises any of the bispecific agonistic CD28 antigen binding molecules as reported herein and a pharmaceutically acceptable carrier. In another aspect, a pharmaceutical formulation comprises any of the bispecific agonistic CD28 antigen binding molecules as reported herein and at least one additional therapeutic agent.

Bispecific agonistic CD28 antigen binding molecules as reported herein can be used either alone or in combination with other agents in a therapy. For instance, a bispecific agonistic CD28 antigen binding molecule as reported herein may be co-administered with at least one additional therapeutic agent. Thus, a bispecific agonistic CD28 antigen binding molecule as described herein for use in cancer immunotherapy is provided. In certain embodiments, a bispecific agonistic CD28 antigen binding molecule for use in a method of cancer immunotherapy is provided. An "individual" according to any of the above aspects is preferably a human.

Such combination therapies noted above encompass combined administration (where two or more therapeutic agents are included in the same or separate formulations), and separate administration, in which case, administration of the antibody as reported herein can occur prior to, simultaneously, and/or following, administration of the additional therapeutic agent or agents. In one aspect, administration of the bispecific agonistic CD28 antigen binding molecule and administration of an additional therapeutic agent occur within about one month, or within about one, two or three weeks, or within about one, two, three, four, five, or six days, of each other.

An antigen binding molecule as reported herein (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Bispecific agonistic CD28 antigen binding molecules as described herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The bispecific agonistic CD28 antigen binding molecule need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a bispecific agonistic CD28 antigen binding molecule as described herein (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The bispecific agonistic CD28 antigen binding molecule is suitably administered to the patient at one time or over a series of treatments. Depending on the type and severity of the disease, about 1 µg/kg to 15 mg/kg (e.g. 0.5 mg/kg-10 mg/kg) of bispecific agonistic CD28 antigen binding molecule can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

Other Agents and Treatments

As described before, the bispecific agonistic CD28 antigen binding molecules of the invention may be administered in combination with one or more other agents in therapy. For instance, an antigen binding molecule of the invention may be co-administered with at least one additional therapeutic agent. The term "therapeutic agent" encompasses any agent that can be administered for treating a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is another anti-cancer agent, for example a microtubule disruptor, an antimetabolite, a topoisomerase inhibitor, a DNA intercalator, an alkylating agent, a hormonal therapy, a kinase inhibitor, a receptor antagonist, an activator of tumor cell apoptosis, or an antiangiogenic agent. In certain aspects, an additional therapeutic agent is an immunomodulatory agent, a cytostatic agent, an inhibitor of cell adhesion, a cytotoxic or cytostatic agent, an activator of cell apoptosis, or an agent that increases the sensitivity of cells to apoptotic inducers.

Thus, provided are bispecific agonistic CD28 antigen binding molecules of the invention or pharmaceutical compositions comprising them for use in the treatment of cancer, wherein the bispecific antigen binding molecule is administered in combination with a chemotherapeutic agent, radiation and/or other agents for use in cancer immunotherapy.

Such other agents are suitably present in combination in amounts that are effective for the purpose intended. The effective amount of such other agents depends on the amount of fusion protein used, the type of disorder or treatment, and other factors discussed above. The bispecific antigen binding molecule or antibody of the invention are generally used in the same dosages and with administration routes as described herein, or about from 1 to 99% of the dosages described herein, or in any dosage and by any route that is empirically/clinically determined to be appropriate. Such combination therapies noted above encompass combined administration (where two or more therapeutic agents are included in the same or separate compositions), and separate administration, in which case, administration of the bispecific antigen binding molecule or antibody of the invention can occur prior to, simultaneously, and/or following, administration of the additional therapeutic agent and/or adjuvant.

In a further aspect, provided is the bispecific agonistic CD28 antigen binding molecule as described herein before for use in the treatment of cancer, in particular Her2-positive cancer, wherein the bispecific antigen binding molecule is administered in combination with another immunomodulator. The term "immunomodulator" refers to any substance including a monoclonal antibody that effects the immune system. The molecules of the inventions can be considered immunomodulators. Immunomodulators can be used as antineoplastic agents for the treatment of cancer. In one aspect, immunomodulators include, but are not limited to anti-CTLA4 antibodies (e.g. ipilimumab), anti-PD1 antibodies (e.g. nivolumab or pembrolizumab), PD-L1 antibodies (e.g. atezolizumab, avelumab or durvalumab), OX-40 antibodies, 4-1BB antibodies and GITR antibodies. Such combination therapies noted above encompass combined administration (where two or more therapeutic agents are included in the same or separate compositions), and separate administration, in which case, administration of the bispecific antigen binding molecule can occur prior to, simultaneously, and/or following, administration of the additional therapeutic agent and/or adjuvant.

Combination with T Cell Bispecific Antibodies

In one aspect, the bispecific agonistic CD28 antigen binding molecule of the invention may be administered in combination with T-cell activating anti-CD3 bispecific antibodies. In one aspect, the T-cell activating anti-CD3 bispecific antibody specific for a tumor-associated antigen is an anti-Her2/anti-CD3 bispecific antibody. In one aspect, a bispecific agonistic CD28 antigen binding molecule comprising at least one antigen binding domain capable of specific binding to Her2 is suitable for administration in combination with an anti-Her2/anti-CD3 bispecific antibody. In one aspect, the anti-Her2/anti-CD3 antibody comprises a first antigen binding domain that binds to CD3, and a second antigen binding domain that binds to Her2. In a particular aspect the second binding domain binding to Her2 binds to a different epitope on Her2 than the 4-1BBL trimer-containing antigen binding molecule.

In one aspect, the anti-Her2/anti-CD3 bispecific antibody as used herein comprises a first antigen binding domain comprising a heavy chain variable region ($V_H$CD3) comprising CDR-H1 sequence of SEQ ID NO:148, CDR-H2 sequence of SEQ ID NO:149, and CDR-H3 sequence of SEQ ID NO:150; and/or a light chain variable region ($V_L$CD3) comprising CDR-L1 sequence of SEQ ID NO:151, CDR-L2 sequence of SEQ ID NO:152, and CDR-L3 sequence of SEQ ID NO:153. More particularly, the anti-Her²/anti-CD3 bispecific antibody comprises a first antigen binding domain comprising a heavy chain variable region ($V_H$CD3) that is at least 90%, 95%, 96%, 97%, 98%, or 99% identical to the amino acid sequence of SEQ ID NO:154 and/or a light chain variable region ($V_L$CD3) that is at least 90%, 95%, 96%, 97%, 98%, or 99% identical to the amino acid sequence of SEQ ID NO:155. In a further aspect, the anti-Her2/anti-CD3 bispecific antibody comprises a heavy chain variable region ($V_H$CD3) comprising the amino acid sequence of SEQ ID NO:154 and/or a light chain variable region ($V_L$CD3) comprising the amino acid sequence of SEQ ID NO: 155.

In one aspect, the anti-Her2/anti-CD3 bispecific antibody comprises a second antigen binding domain that binds to the same epitope as the antibody 4D5 (humanized version thereof known as trastuzumab). In another aspect, the anti-Her2/anti-CD3 bispecific antibody comprises a second antigen binding domain that binds to the same epitope as the antibody 2C4 (humanized version thereof known as pertuzumab). In yet another aspect, anti-Her2/anti-CD3 bispecific antibody comprises a second antigen binding domain that binds to the same epitope as the antibody 7C2 (U.S. Pat. No. 9,518,118).

In another aspect, the anti-Her2/anti-CD3 bispecific antibody comprises a second antigen binding domain comprising (a) a heavy chain variable region ($V_H$Her2) comprising CDR-H1 sequence of SEQ ID NO:140, CDR-H2 sequence of SEQ ID NO:141, and CDR-H3 sequence of SEQ ID NO:142, and/or a light chain variable region ($V_L$Her2) comprising CDR-L1 sequence of SEQ ID NO:143, CDR-L2 sequence of SEQ ID NO:144, and CDR-L3 sequence of SEQ ID NO:145, or (b) a heavy chain variable region ($V_H$Her2) comprising CDR-H1 sequence of SEQ ID NO:132, CDR-H2 sequence of SEQ ID NO:133, and CDR-H3 sequence of SEQ ID NO:134, and/or a light chain variable region ($V_L$Her2) comprising CDR-L1 sequence of SEQ ID NO:135, CDR-L2 sequence of SEQ ID NO:136, and CDR-L3 sequence of SEQ ID NO:137, or (c) a heavy chain variable region ($V_H$Her2) comprising CDR-H1 sequence of SEQ ID NO:156, CDR-H2 sequence of SEQ ID NO:157, and CDR-H3 sequence of SEQ ID NO:158, and/or a light chain variable region ($V_L$Her2) comprising CDR-L1 sequence of SEQ ID NO:159, CDR-L2 sequence of SEQ ID NO:160, and CDR-L3 sequence of SEQ ID NO:161.

In one aspect, the anti-Her²/anti-CD3 bispecific comprises a second antigen binding domain comprising a heavy chain variable region ($V_H$Her2) that is at least 90%, 95%, 96%, 97%, 98%, or 99% identical to the amino acid sequence of SEQ ID NO:146 and/or a light chain variable region ($V_L$Her2) that is at least 90%, 95%, 96%, 97%, 98%, or 99% identical to the amino acid sequence of SEQ ID NO:147. In a further aspect, the anti-Her²/anti-CD3 bispecific comprises a second antigen binding domain comprising a heavy chain variable region ($V_H$Her2) comprising the amino acid sequence of SEQ ID NO:146 and/or a light chain variable region ($V_L$Her2) comprising the amino acid sequence of SEQ ID NO:147.

In one aspect, the anti-Her2/anti-CD3 bispecific antibody comprises a first antigen binding domain comprising a heavy chain variable region ($V_H$CD3) comprising the amino acid sequence of SEQ ID NO:154 and/or a light chain variable region (V$_L$CD3) comprising the amino acid sequence of SEQ ID NO:155 and a second antigen binding domain comprising a heavy chain variable region (V$_H$Her2) comprising the amino acid sequence of SEQ ID NO:146 and/or a light chain variable region (V$_L$Her2) comprising the amino acid sequence of SEQ ID NO:147.

In one aspect, anti-Her2/anti-CD3 bispecific antibody comprises a first heavy chain comprising the amino acid sequence of SEQ ID NO:174 and/or a light chain comprising the amino acid sequence of SEQ ID NO:175 and a second heavy chain comprising the amino acid sequence of SEQ ID NO:176 and/or a light chain comprising the amino acid sequence of SEQ ID NO:177 (HER2 TDB).

In another aspect, the anti-Her2/anti-CD3 bispecific comprises a second antigen binding domain comprising a heavy chain variable region (V$_H$Her2) that is at least 90%, 95%, 96%, 97%, 98%, or 99% identical to the amino acid sequence of SEQ ID NO:138 and/or a light chain variable region (V$_L$Her2) that is at least 90%, 95%, 96%, 97%, 98%, or 99% identical to the amino acid sequence of SEQ ID NO:139. In a further aspect, the anti-Her2/anti-CD3 bispecific comprises a second antigen binding domain comprising a heavy chain variable region (V$_H$Her2) comprising the amino acid sequence of SEQ ID NO:138 and/or a light chain variable region (V$_L$Her2) comprising the amino acid sequence of SEQ ID NO:139. In another aspect, the anti-Her2/anti-CD3 bispecific comprises a second antigen binding domain comprising a heavy chain variable region (V$_H$Her2) that is at least 90%, 95%, 96%, 97%, 98%, or 99% identical to the amino acid sequence of SEQ ID NO:162 and/or a light chain variable region (V$_L$Her2) that is at least 90%, 95%, 96%, 97%, 98%, or 99% identical to the amino acid sequence of SEQ ID NO:163. In a further aspect, the anti-Her2/anti-CD3 bispecific comprises a second antigen binding domain comprising a heavy chain variable region (V$_H$Her2) comprising the amino acid sequence of SEQ ID NO:162 and/or a light chain variable region (V$_L$Her2) comprising the amino acid sequence of SEQ ID NO:163.

In one aspect, the anti-Her2/anti-CD3 bispecific antibody comprises a first antigen binding domain comprising a heavy chain variable region (V$_H$CD3) comprising the amino acid sequence of SEQ ID NO:154 and/or a light chain variable region (V$_L$CD3) comprising the amino acid sequence of SEQ ID NO:155 and a second antigen binding domain comprising a heavy chain variable region (V$_H$Her2) comprising the amino acid sequence of SEQ ID NO:162 and/or a light chain variable region (V$_L$Her2) comprising the amino acid sequence of SEQ ID NO:163.

In a further aspect, the bispecific agonistic CD28 antigen binding molecule is for use in combination with a T-cell activating anti-CD3 bispecific antibody and the T-cell activating anti-CD3 bispecific antibody is administered concurrently with, prior to, or subsequently to bispecific agonistic CD28 antigen binding molecule.

In a further aspect, provided is the use of the bispecific agonistic CD28 antigen binding molecule for the manufacture of a medicament for the treatment of cancer, wherein the bispecific agonistic CD28 antigen binding molecules is for use in combination with a T-cell activating anti-CD3 bispecific antibody, in particular an anti-Her2/anti-CD3 bispecific antibody. In certain aspects, the disease to be treated is Her2-positive cancers. Examples of Her2-positive cancers include breast cancer, ovarian cancer, gastric cancer, bladder cancer, salivary gland, endometrial cancer, pancreatic cancer and non-small-cell lung cancer (NSCLC). In certain aspects, cancers to be treated are Her2-positive breast cancer, in particular Her2-positive metastatic breast cancer.

In a further aspect, the invention provides a method for treating cancer in an individual, comprising administering to said individual a therapeutically effective amount of a bispecific agonistic CD28 antigen binding molecule and an effective amount a T-cell activating anti-CD3 bispecific antibody, in particular an anti-Her2/anti-CD3 bispecific antibody as defined above. In certain aspects, the method is for the treatment of Her2-positive cancers. Examples of Her2-positive cancers include breast cancer, ovarian cancer, gastric cancer, bladder cancer, salivary gland, endometrial cancer, pancreatic cancer and non-small-cell lung cancer (NSCLC). In one aspect, the method is for treating Her2-positive metastatic breast cancer.

In another aspect, provided is a combination product comprising a bispecific agonistic CD28 antigen binding molecule as described herein and a T-cell activating anti-CD3 bispecific antibody. In one aspect, the T-cell activating anti-CD3 bispecific antibody specific for a tumor-associated antigen is an anti-Her2/anti-CD3 bispecific antibody.

Combination with Agents Blocking PD-L1/PD-1 Interaction

In one aspect, the bispecific agonistic CD28 antigen binding molecules of the invention may be administered in combination with agents blocking PD-L1/PD-1 interaction such as a PD-L1 binding antagonist or a PD-1 binding antagonist, in particular an anti-PD-L1 antibody or an anti-PD-1 antibody.

In one aspect, the agent blocking PD-L1/PD-1 interaction is an anti-PD-L1 antibody. The term "PD-L1", also known as CD274 or B7-H1, refers to any native PD-L1 from any vertebrate source, including mammals such as primates (e.g. humans) non-human primates (e.g. cynomolgus monkeys) and rodents (e.g. mice and rats), in particular to "human PD-L1". The amino acid sequence of complete human PD-L1 is shown in UniProt (www.uniprot.org) accession no. Q9NZQ7 (SEQ ID NO:164). The term "PD-L1 binding antagonist" refers to a molecule that decreases, blocks, inhibits, abrogates or interferes with signal transduction resulting from the interaction of PD-L1 with either one or more of its binding partners, such as PD-1, B7-1. In some aspects, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some aspects, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one aspect, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In particular, a PD-L1 binding antagonist is an anti-PD-L1 antibody. The term "anti-PD-L1 antibody" or "antibody binding to human PD-L1" or "antibody that specifically binds to human PD-L1" or "antagonistic anti-PD-L1" refers to an antibody specifically binding to the human PD-L1 antigen with a binding affinity of KD-value of $1.0 \times 10^{-8}$ mol/l or lower, in one aspect of a K$_D$-value of $1.0 \times 10^{-9}$ mol/l or lower. The binding affinity is determined with a standard binding assay, such as surface plasmon resonance technique (BIAcore®, GE-Healthcare Uppsala, Sweden). In a particular aspect, the agent blocking PD-L1/PD-1 interaction is an anti-PD-L1 antibody. In a specific aspect, the anti-PD-L1 antibody is selected from the group consisting of atezolizumab (MPDL3280A, RG7446), durvalumab (MEDI4736), avelumab (MSB0010718C) and MDX-1105. In a specific aspect, an anti-PD-L1 antibody is YW243.55.S70 described herein. In another specific aspect, an anti-PD-L1 antibody is MDX-1105 described herein. In still another specific aspect, an anti-PD-L1 antibody is MEDI4736 (durvalumab). In yet a further aspect, an anti-PD-L1 antibody is MSB0010718C (avelumab). More particularly, the agent blocking PD-L1/PD-1 interaction is atezolizumab (MPDL3280A). In another aspect, the agent blocking PD-L1/PD-1 interaction is an anti-PD-L1 antibody comprising a heavy chain variable domain VH(PDL-1) of SEQ ID NO:165 and a light chain variable domain VL(PDL-1) of SEQ ID NO:166. In another aspect, the agent blocking PD-L1/PD-1 interaction is an anti-PD-L1 antibody comprising a heavy chain variable domain VH(PDL-1) of SEQ ID NO:167 and a light chain variable domain VL(PDL-1) of SEQ ID NO:168.

The term "PD-1", also known as CD279, PD1 or programmed cell death protein 1, refers to any native PD-L1 from any vertebrate source, including mammals such as primates (e.g. humans) non-human primates (e.g. cynomolgus monkeys) and rodents (e.g. mice and rats), in particular to the human protein PD-1 with the amino acid sequence as shown in UniProt (www.uniprot.org) accession no. Q15116 (SEQ ID NO:1691). The term "PD-1 binding antagonist" refers to a molecule that inhibits the binding of PD-1 to its ligand binding partners. In some embodiments, the PD-1 binding antagonist inhibits the binding of PD-1 to PD-L1. In some embodiments, the PD-1 binding antagonist inhibits the binding of PD-1 to PD-L2. In some embodiments, the PD-1 binding antagonist inhibits the binding of PD-1 to both PD-L1 and PD-L2. In particular, a PD-L1 binding antagonist is an anti-PD-L1 antibody. The term "anti-PD-1 antibody" or "antibody binding to human PD-1" or "antibody that specifically binds to human PD-1" or "antagonistic anti-PD-1" refers to an antibody specifically binding to the human PD1 antigen with a binding affinity of KD-value of $1.0 \times 10^{-8}$ mol/1 or lower, in one aspect of a KD-value of $1.0 \times 10^{-9}$ mol/1 or lower. The binding affinity is determined with a standard binding assay, such as surface plasmon resonance technique (BIAcore®, GE-Healthcare Uppsala, Sweden). In one aspect, the agent blocking PD-L1/PD-1 interaction is an anti-PD-1 antibody. In a specific aspect, the anti-PD-1 antibody is selected from the group consisting of MDX 1106 (nivolumab), MK-3475 (pembrolizumab), CT-011 (pidilizumab), MEDI-0680 (AMP-514), PDR001, REGN2810, and BGB-108, in particular from pembrolizumab and nivolumab. In another aspect, the agent blocking PD-L1/PD-1 interaction is an anti-PD-1 antibody comprising a heavy chain variable domain VH(PD-1) of SEQ ID NO:170 and a light chain variable domain VL(PD-1) of SEQ ID NO:171. In another aspect, the agent blocking PD-L1/PD-1 interaction is an anti-PD-1 antibody comprising a heavy chain variable domain VH(PD-1) of SEQ ID NO:172 and a light chain variable domain VL(PD-1) of SEQ ID NO:173.

In another aspect, provided is a combination product comprising a bispecific agonistic CD28 antigen binding molecule as described herein and an agents blocking PD-L1/PD-1 interaction such as a PD-L1 binding antagonist or a PD-1 binding antagonist, in particular an anti-PD-L1 antibody or an anti-PD-1 antibody.

Such combination therapies noted above encompass combined administration (where two or more therapeutic agents are included in the same or separate formulations), and separate administration, in which case, administration of the therapeutic agent can occur prior to, simultaneously, and/or following, administration of an additional therapeutic agent or agents. In one embodiment, administration of the therapeutic agent and administration of an additional therapeutic agent occur within about one month, or within about one, two or three weeks, or within about one, two, three, four, five, or six days, of each other.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper that is pierceable by a hypodermic injection needle). At least one active agent in the composition is a bispecific agonistic CD28 antigen binding molecule of the invention. The label or package insert indicates that the composition is used for treating the condition of choice. Moreover, the article of manufacture may comprise (a) a first container with a composition contained therein, wherein the composition comprises a bispecific agonistic CD28 antigen binding molecule of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

TABLE B (Sequences):

| SEQ ID NO: | Name | Sequence |
|---|---|---|
| 1 | hu CD28 UniProt no. P10747, version 1 | MLRLLLALNL FPSIQVTGNK ILVKQSPMLV AYDNAVNLSC KYSYNLFSRE FRASLHKGLD SAVEVCVVYG NYSQQLQVYS KTGFNCDGKL GNESVTFYLQ NLYVNQTDIY FCKIEVMYPP |

TABLE B-continued (Sequences):

| SEQ ID NO: | Name | Sequence |
|---|---|---|
|  |  | PYLDNEKSNG TIIHVKGKHL CPSPLFPGPS KPFWVLVVVG GVLACYSLLV TVAFIIFWVR SKRSRLLHSD YMNMTPRRPG PTRKHYQPYA PPRDFAAYRS |
| 2 | heavy chain CDR-H1, pertuzumab CLC | DYTMD |
| 3 | heavy chain CDR-H2, pertuzumab CLC | DVNPNSGGSIVNRRFKG |
| 4 | heavy chain CDR-H3, pertuzumab CLC | NLGPFFYFDY |
| 5 | light chain CDR-L1, pertuzumab CLC | KASQDVSTA |
| 6 | light chain CDR-L2, pertuzumab CLC | SASFRYT |
| 7 | light chain CDR-L3, pertuzumab CLC | QQHYTTPPT |
| 8 | heavy chain variable domain VH, pertuzumab CLC | EVQLVESGGGLVQPGGSLRLSCAASGFTFNDYTM DWVRQAPGKGLEWVADVNPNSGGSIVNRRFKGRF TLSVDRSKNTLYLQMNSLRAEDTAVYYCARNLGP FFYFDYWGQGTLVTVSS |
| 9 | light chain variable domain VL, pertuzumab CLC | DIQMTQSPSSLSASVGDRVTITCKASQDVSTAVA WYQQKPGKAPKLLIYSASFRYTGVPSRFSGSRSG TDFTLTISSLQPEDFATYYCQQHYTTPPTFGQGT KVEIK |
| 10 | heavy chain CDR-H1, trastuzumab CLC | GFNIKDTYIH |
| 11 | heavy chain CDR-H2, trastuzumab CLC | RIYPTNGYTRYADSVKG |
| 12 | heavy chain CDR-H3, trastuzumab CLC | WGGEGFYAMDY |
| 13 | light chain CDR-L1, trastuzumab CLC | KASQDVSTA |
| 14 | light chain CDR-L2, trastuzumab CLC | SASFRYT |
| 15 | light chain CDR-L3, trastuzumab CLC | QQHYTTPPT |
| 16 | heavy chain variable domain VH, trastuzumab CLC | EVQLVESGGGLVQPGGSLRLSCAASGFNIKDTYI HWVRQAPGKGLEWVARIYPTNGYTRYADSVKGRF TISADTSKNTAYLQMNSLRAEDTAVYYCSRWGGE GFYAMDYWGQGTLVTVSS |
| 17 | light chain variable domain VL, trastuzumab CLC | DIQMTQSPSSLSASVGDRVTITCKASQDVSTAVA WYQQKPGKAPKLLIYSASFRYTGVPSRFSGSRSG TDFTLTISSLQPEDFATYYCQQHYTTPPTFGQGT KVEIK |
| 18 | CD28(SA) CDR-H1 | SYYIH |
| 19 | CD28(SA) CDR-H2 | CIYPGNVNTNYNEKFKD |
| 20 | CD28(SA) CDR-H3 | SHYGLDWNFDV |
| 21 | CD28(SA) CDR-L1 | HASQNIYVWLN |
| 22 | CD28(SA) CDR-L2 | KASNLHT |
| 23 | CD28(SA) CDR-L3 | QQGQTYPYT |

TABLE B-continued (Sequences):

| SEQ ID NO: | Name | Sequence |
|---|---|---|
| 24 | CD28(SA) VH | QVQLVQSGAEVKKPGASVKVSCKASGYTFTSYYI HWVRQAPGQGLEWIGCIYPGNVNTNYNEKFKDRA TLTVDTSISTAYMELSRLRSDDTAVYFCTRSHYG LDWNFDVWGQGTTVTVSS |
| 25 | CD28(SA) VL | DIQMTQSPSSLSASVGDRVTITCHASQNIYVWLN WYQQKPGKAPKLLIYKASNLHTGVPSRFSGSGSG TDFTLTISSLQPEDFATYYCQQGQTYPYTFGGGT KVEIK |
| 26 | CD28 CDR-H1 consensus | SYYIH |
| 27 | CD28 CDR-H2 consensus | SIYPX$_1$X$_2$X$_3$X$_4$TNYNEKFKD, wherein<br>X$_1$ is G or R<br>X$_2$ is N or D<br>X$_3$ is V or G<br>X$_4$ is N or Q or A |
| 28 | CD28 CDR-H3 consensus | SHYGX$_5$DX$_6$NFDV, wherein<br>X$_5$ is L or A<br>X$_6$ is W or H or Y or F |
| 29 | CD28 CDR-L1 consensus | X$_7$ASQX$_8$IX$_9$X$_{10}$X$_{11}$LN, wherein<br>X$_7$ is H or R<br>X$_8$ is N or G<br>X$_9$ is Y or S<br>X$_{10}$ is V or N<br>X$_{11}$ is W or H or F or Y |
| 30 | CD28 CDR-L2 consensus | X$_{12}$X$_{13}$SX$_{14}$LX$_{15}$X$_{16}$, wherein<br>X$_{12}$ is K or Y<br>X$_{13}$ is A or T<br>X$_{14}$ is N or S<br>X$_{15}$ is H or Y<br>X$_{16}$ is T or S |
| 31 | CD28 CDR-L3 consensus | QQX$_{17}$QTYPYT, wherein<br>X$_{17}$ is G or A |
| 32 | CD28 VH variant a | QVQLVQSGAEVKKPGASVKVSCKASGYTFTSYYI HWVRQAPGQGLEWIGSIYPGNVNTNYNEKFKDRA TLTVDTSISTAYMELSRLRSDDTAVYFCTRSHYG LDWNFDVWGQGTTVTVSS |
| 33 | CD28 VH variant b | QVQLVQSGAEVKKPGASVKVSCKASGYTFTSYYI HWVRQAPGQGLEWIGSIYPGNVQTNYNEKFKDRA TLTVDTSISTAYMELSRLRSDDTAVYFCTRSHYG LDHNFDVWGQGTTVTVSS |
| 34 | CD28 VH variant c | QVQLVQSGAEVKKPGASVKVSCKASGYTFTSYYI HWVRQAPGQGLEWIGSIYPGNVQTNYNEKFKDRA TLTVDTSISTAYMELSRLRSDDTAVYFCTRSHYG ADHNFDVWGQGTTVTVSS |
| 35 | CD28 VH variant d | QVQLVQSGAEVKKPGASVKVSCKASGYTFTSYYI HWVRQAPGQGLEWIGSIYPRDGQTNYNEKFKDRA TLTVDTSISTAYMELSRLRSDDTAVYFCTRSHYG LDYNFDVWGQGTTVTVSS |
| 36 | CD28 VH variant e | QVQLVQSGAEVKKPGASVKVSCKASGYTFTSYYI HWVRQAPGQGLEWIGSIYPGNVQTNYNEKFKDRA TLTVDTSISTAYMELSRLRSDDTAVYFCTRSHYG LDWNFDVWGQGTTVTVSS |
| 37 | CD28 VH variant f | QVQLVQSGAEVKKPGASVKVSCKASGYTFTSYYI HWVRQAPGQGLEWIGSIYPGNVQTNYNEKFKDRA TLTVDTSISTAYMELSRLRSDDTAVYFCTRSHYG LDFNFDVWGQGTTVTVSS |
| 38 | CD28 VH variant g | QVQLVQSGAEVKKPGASVKVSCKASGYTFTSYYI HWVRQAPGQGLEWIGSIYPRNVQTNYNEKFKDRA TLTVDTSISTAYMELSRLRSDDTAVYFCTRSHYG LDHNFDVWGQGTTVTVSS |

TABLE B-continued (Sequences):

| SEQ ID NO: | Name | Sequence |
|---|---|---|
| 39 | CD28 VH variant h | QVQLVQSGAEVKKPGASVKVSCKASGYTFTSYYIHWVRQAPGQGLEWIGSIYPRDVQTNYNEKFKDRATLTVDTSISTAYMELSRLRSDDTAVYFCTRSHYGLDHNFDVWGQGTTVTVSS |
| 40 | CD28 VH variant i | EVQLVESGGGLVQPGGSLRLSCAASGFTFTSYYIHWVRQAPGKGLEWVASIYPGNVNTRYADSVKGRFTISADTSKNTAYLQMNSLRAEDTAVYYCTRSHYGLDWNFDVWGQGTTVTVSS |
| 41 | CD28 VH variant j | EVQLVESGGGLVQPGGSLRLSCAASGFTFTSYYIHWVRQAPGKGLEWVASIYPGNVATRYADSVKGRFTISADTSKNTAYLQMNSLRAEDTAVYYCTRSHYGLDWNFDVWGQGTTVTVSS |
| 42 | CD28 VL variant k | DIQMTQSPSSLSASVGDRVTITCHASQNIYVHLNWYQQKPGKAPKLLIYKASNLHTGVPSRFSGSGSGTDFTLTISSLQPEDFATYYCQQAQTYPYTFGGGTKVEIK |
| 43 | CD28 VL variant l | DIQMTQSPSSLSASVGDRVTITCHASQNIYVFLNWYQQKPGKAPKLLIYKASNLHTGVPSRFSGSGSGTDFTLTISSLQPEDFATYYCQQGQTYPYTFGGGTKVEIK |
| 44 | CD28 VL variant m | DIQMTQSPSSLSASVGDRVTITCHASQNIYVYLNWYQQKPGKAPKLLIYKASNLHTGVPSRFSGSGSGTDFTLTISSLQPEDFATYYCQQGQTYPYTFGGGTKVEIK |
| 45 | CD28 VL variant n | DIQMTQSPSSLSASVGDRVTITCHASQGISNYLNWYQQKPGKAPKLLIYKASNLHTGVPSRFSGSGSGTDFTLTISSLQPEDFATYYCQQGQTYPYTFGGGTKVEIK |
| 46 | CD28 VL variant o | DIQMTQSPSSLSASVGDRVTITCHASQNIYVWLNWYQQKPGKAPKLLIYYTSSLHSGVPSRFSGSGSGTDFTLTISSLQPEDFATYYCQQGQTYPYTFGGGTKVEIK |
| 47 | CD28 VL variant p | DIQMTQSPSSLSASVGDRVTITCHASQGISNYLNWYQQKPGKAPKLLIYYTSSLHSGVPSRFSGSGSGTDFTLTISSLQPEDFATYYCQQGQTYPYTFGGGTKVEIK |
| 48 | CD28 VL variant q | DIQMTQSPSSLSASVGDRVTITCHASQGISNHLNWYQQKPGKAPKLLIYKASNLHTGVPSRFSGSGSGTDFTLTISSLQPEDFATYYCQQGQTYPYTFGGGTKVEIK |
| 49 | CD28 VL variant r | DIQMTQSPSSLSASVGDRVTITCHASQGIYVYLNWYQQKPGKAPKLLIYKASNLHTGVPSRFSGSGSGTDFTLTISSLQPEDFATYYCQQGQTYPYTFGGGTKVEIK |
| 50 | CD28 VL variant s | DIQMTQSPSSLSASVGDRVTITCHASQGISVYLNWYQQKPGKAPKLLIYKASNLHTGVPSRFSGSGSGTDFTLTISSLQPEDFATYYCQQGQTYPYTFGGGTKVEIK |
| 51 | CD28 VL variant t | DIQMTQSPSSLSASVGDRVTITCRASQNIYVWLNWYQQKPGKAPKLLIYKASNLYSGVPSRFSGSRSGTDFTLTISSLQPEDFATYYCQQGQTYPYTFGQGTKLEIK |
| 52 | CD28(variant 8) CDR-H1 | SYYIH |
| 53 | CD28(variant 8) CDR-H2 | SIYPGNVQTNYNEKFKD |
| 54 | CD28(variant 8) CDR-H3 | SHYGLDWNFDV |
| 55 | CD28(variant 8) CDR-L1 | HASQNIYVYLN |
| 56 | CD28(variant 8) CDR-L2 | KASNLHT |

TABLE B-continued (Sequences):

| SEQ ID NO: | Name | Sequence |
|---|---|---|
| 57 | CD28(variant 8) CDR-L3 | QQGQTYPYT |
| 58 | CD28(variant 15) CDR-H1 | SYYIH |
| 59 | CD28(variant 15) CDR-H2 | SIYPGNVQTNYNEKFKD |
| 60 | CD28(variant 15) CDR-H3 | SHYGLDWNFDV |
| 61 | CD28(variant 15) CDR-L1 | HASQNIYVELN |
| 62 | CD28(variant 15) CDR-L2 | KASNLHT |
| 63 | CD28(variant 15) CDR-L3 | QQGQTYPYT |
| 64 | CD28(variant 29) CDR-H1 | SYYIH |
| 65 | CD28(variant 29) CDR-H2 | STYPGNVTNYNEKEKD |
| 66 | CD28(variant 29) CDR-H3 | SHYGLDWNFDV |
| 67 | CD28(variant 29) CDR-L1 | HASQNIYVWLN |
| 68 | CD28(variant 29) CDR-L2 | KASNLHT |
| 69 | CD28(variant 29) CDR-L3 | QQGQTYPYT |
| 70 | Fc hole PGLALA | DKTHTCPPCPAPEAAGGPSVFLEPPKPKDTLMIS RTPEVTCVVVDVSHEDPEVKFNWYVDGVEVHNAK TKPREEQYNSTYRVVSVLTVLHQDWLNGKEYKCK VSNKALGAPIEKTISKAKGQPREPQVCTLPPSRD ELTKNQVSLSCAVKGFYPSDIAVEWESNGQPENN YKTTPPVLDSDGSFFLVSKLTVDKSRWQQGNVFS CSVMHEALHNHYTQKSLSLSP |
| 71 | Fc knob PGLALA | DKTHTCPPCPAPEAAGGPSVFLEPPKPKDTLMIS RTPEVTCVVVDVSHEDPEVKFNWYVDGVEVHNAK TKPREEQYNSTYRVVSVLTVLHQDWLNGKEYKCK VSNKALGAPIEKTISKAKGQPREPQVYTLPPCRD ELTKNQVSLWCLVKGFYPSDIAVEWESNGQPENN YKTTPPVLDSDGSFFLYSKLTVDKSRWQQGNVFS CSVMHEALHNHYTQKSLSLSP |
| 72 | VH (CD28 SA) CH1 (EE)- Fc knob PGLALA | QVQLVQSGAEVKKPGASVKVSCKASGYTFTSYYI HWVRQAPGQGLEWIGCTYPGNVNTNYNEKEKDRA TLTVDTSISTAYMELSRLRSDDTAVYFCTRSHYG LDWNEDVWGQGTTVTVSSASTKGPSVFPLAPSSK STSGGTAALGCLVEDYFPEPVTVSWNSGALTSGV HTFPAVLQSSGLYSLSSVVTVPSSSLGTQTYICN VNHKPSNTKVDEKVEPKSCDKTHTCPPCPAPEAA GGPSVFLEPPKPKDTLMISRTPEVTCVVVDVSHE DPEVKFNWYVDGVEVHNAKTKPREEQYNSTYRVV SVLTVLHQDWLNGKEYKCKVSNKALGAPIEKTIS KAKGQPREPQVYTLPPCRDELTKNQVSLWCLVKG FYPSDIAVEWESNGQPENNYKTTPPVLDSDGSFF LYSKLTVDKSRWQQGNVFSCSVMHEALHNHYTQK SLSLSP |
| 73 | VH (CD28 variant g) CH1 (EE) - Fc knob PGLALA | QVQLVQSGAEVKKPGASVKVSCKASGYTFTSYYI HWVRQAPGQGLEWIGSTYPRNVQTNYNEKEKDRA TLTVDTSISTAYMELSRLRSDDTAVYFCTRSHYG LDHNEDVWGQGTTVTVSSASTKGPSVFPLAPSSK STSGGTAALGCLVEDYFPEPVTVSWNSGALTSGV HTFPAVLQSSGLYSLSSVVTVPSSSLGTQTYICN VNHKPSNTKVDEKVEPKSCDKTHTCPPCPAPEAA GGPSVFLEPPKPKDTLMISRTPEVTCVVVDVSHE DPEVKFNWYVDGVEVHNAKTKPREEQYNSTYRVV SVLTVLHQDWLNGKEYKCKVSNKALGAPIEKTIS KAKGQPREPQVYTLPPCRDELTKNQVSLWCLVKG FYPSDIAVEWESNGQPENNYKTTPPVLDSDGSFF LYSKLTVDKSRWQQGNVFSCSVMHEALHNHYTQK SLSLSP |

TABLE B-continued (Sequences):

| SEQ ID NO: | Name | Sequence |
|---|---|---|
| 74 | VH (CD28 variant f) CH1 (EE) - Fc knob PGLALA | QVQLVQSGAEVKKPGASVKVSCKASGYTFTSYYI HWVRQAPGQGLEWIGSTYPGNVQTNYNEKEKDRA TLTVDTSISTAYMELSRLRSDDTAVYFCTRSHYG LDFNEDVWGQGTTVTVSSASTKGPSVFPLAPSSK STSGGTAALGCLVEDYFPEPVTVSWNSGALTSGV HTFPAVLQSSGLYSLSSVVTVPSSSLGTQTYICN VNHKPSNTKVDEKVEPKSCDKTHTCPPCPAPEAA GGPSVFLEPPKPKDTLMISRTPEVTCVVVDVSHE DPEVKFNWYVDGVEVHNAKTKPREEQYNSTYRVV SVLTVLHQDWLNGKEYKCKVSNKALGAPIEKTIS KAKGQPREPQVYTLPPCRDELTKNQVSLWCLVKG FYPSDIAVEWESNGQPENNYKTTPPVLDSDGSFF LYSKLTVDKSRWQQGNVFSCSVMHEALHNHYTQK SLSLSP |
| 75 | VH (CD28 variant j) CH1 (EE) - Fc knob PGLALA | EVQLVESGGGLVQPGGSLRLSCAASGETFTSYYI HWVRQAPGKGLEWVASTYPGNVATRYADSVKGRF TISADTSKNTAYLQMNSLRAEDTAVYYCTRSHYG LDWNEDVWGQGTTVTVSSASTKGPSVFPLAPSSK STSGGTAALGCLVEDYFPEPVTVSWNSGALTSGV HTFPAVLQSSGLYSLSSVVTVPSSSLGTQTYICN VNHKPSNTKVDEKVEPKSCDKTHTCPPCPAPEAA GGPSVFLEPPKPKDTLMISRTPEVTCVVVDVSHE DPEVKFNWYVDGVEVHNAKTKPREEQYNSTYRVV SVLTVLHQDWLNGKEYKCKVSNKALGAPIEKTIS KAKGQPREPQVYTLPPCRDELTKNQVSLWCLVKG FYPSDIAVEWESNGQPENNYKTTPPVLDSDGSFF LYSKLTVDKSRWQQGNVFSCSVMHEALHNHYTQK SLSLSP |
| 76 | VH (CD28 variant e) CH1 (EE)- Fc knob PGLALA | QVQLVQSGAEVKKPGASVKVSCKASGYTFTSYYI HWVRQAPGQGLEWIGSTYPGNVQTNYNEKEKDRA TLTVDTSISTAYMELSRLRSDDTAVYFCTRSHYG LDWNEDVWGQGTTVTVSSASTKGPSVFPLAPSSK STSGGTAALGCLVEDYFPEPVTVSWNSGALTSGV HTFPAVLQSSGLYSLSSVVTVPSSSLGTQTYICN VNHKPSNTKVDEKVEPKSCDKTHTCPPCPAPEAA GGPSVFLEPPKPKDTLMISRTPEVTCVVVDVSHE DPEVKFNWYVDGVEVHNAKTKPREEQYNSTYRVV SVLTVLHQDWLNGKEYKCKVSNKALGAPIEKTIS KAKGQPREPQVYTLPPCRDELTKNQVSLWCLVKG FYPSDIAVEWESNGQPENNYKTTPPVLDSDGSFF LYSKLTVDKSRWQQGNVFSCSVMHEALHNHYTQK SLSLSP |
| 77 | VH (CD28 variant b) CH1 (EE) - Fc knob PGLALA | QVQLVQSGAEVKKPGASVKVSCKASGYTFTSYYI HWVRQAPGQGLEWIGSTYPGNVQTNYNEKEKDRA TLTVDTSISTAYMELSRLRSDDTAVYFCTRSHYG LDHNEDVWGQGTTVTVSSASTKGPSVFPLAPSSK STSGGTAALGCLVEDYFPEPVTVSWNSGALTSGV HTFPAVLQSSGLYSLSSVVTVPSSSLGTQTYICN VNHKPSNTKVDEKVEPKSCDKTHTCPPCPAPEAA GGPSVFLEPPKPKDTLMISRTPEVTCVVVDVSHE DPEVKFNWYVDGVEVHNAKTKPREEQYNSTYRVV SVLTVLHQDWLNGKEYKCKVSNKALGAPIEKTIS KAKGQPREPQVYTLPPCRDELTKNQVSLWCLVKG FYPSDIAVEWESNGQPENNYKTTPPVLDSDGSFF LYSKLTVDKSRWQQGNVFSCSVMHEALHNHYTQK SLSLSP |
| 78 | VH (CD28 variant a) CH1 (EE) - Fc knob PGLALA | QVQLVQSGAEVKKPGASVKVSCKASGYTFTSYYI HWVRQAPGQGLEWIGSTYPGNVNTNYNEKEKDRA TLTVDTSISTAYMELSRLRSDDTAVYFCTRSHYG LDWNEDVWGQGTTVTVSSASTKGPSVFPLAPSSK STSGGTAALGCLVEDYFPEPVTVSWNSGALTSGV HTFPAVLQSSGLYSLSSVVTVPSSSLGTQTYICN VNHKPSNTKVDEKVEPKSCDKTHTCPPCPAPEAA GGPSVFLEPPKPKDTLMISRTPEVTCVVVDVSHE DPEVKFNWYVDGVEVHNAKTKPREEQYNSTYRVV SVLTVLHQDWLNGKEYKCKVSNKALGAPIEKTIS KAKGQPREPQVYTLPPCRDELTKNQVSLWCLVKG FYPSDIAVEWESNGQPENNYKTTPPVLDSDGSFF LYSKLTVDKSRWQQGNVFSCSVMHEALHNHYTQK SLSLSP |

TABLE B-continued (Sequences):

| SEQ ID NO: | Name | Sequence |
|---|---|---|
| 79 | VH (CD28 variant i) CH1 (EE) - Fc knob PGLALA | EVQLVESGGGLVQPGGSLRLSCAASGETFTSYYI HWVRQAPGKGLEWVASTYPGNVNTRYADSVKGRF TISADTSKNTAYLQMNSLRAEDTAVYYCTRSHYG LDWNEDVWGQGTTVTVSSASTKGPSVFPLAPSSK STSGGTAALGCLVEDYFPEPVTVSWNSGALTSGV HTFPAVLQSSGLYSLSSVVTVPSSSLGTQTYICN VNHKPSNTKVDEKVEPKSCDKTHTCPPCPAPEAA GGPSVFLEPPKPKDTLMISRTPEVTCVVVDVSHE DPEVKFNWYVDGVEVHNAKTKPREEQYNSTYRVV SVLTVLHQDWLNGKEYKCKVSNKALGAPIEKTIS KAKGQPREPQVYTLPPCRDELTKNQVSLWCLVKG FYPSDIAVEWESNGQPENNYKTTPPVLDSDGSFF LYSKLTVDKSRWQQGNVFSCSVMHEALHNHYTQK SLSLSP |
| 80 | VL-CD28(SA)-CL"RK" | DIQMTQSPSSLSASVGDRVTITCHASQNIYVWLN WYQQKPGKAPKLLIYKASNLHTGVPSRFSGSGSG TDFTLTISSLQPEDFATYYCQQGQTYPYTEGGGT KVEIKRTVAAPSVFIFPPSDRKLKSGTASVVCLL NNFYPREAKVQWKVDNALQSGNSQESVTEQDSKD STYSLSSTLTLSKADYEKHKVYACEVTHQGLSSP VTKSFNRGEC |
| 81 | VL (CD28 variant k)-CL (RK) | DIQMTQSPSSLSASVGDRVTITCHASQNIYVHLN WYQQKPGKAPKLLIYKASNLHTGVPSRFSGSGSG TDFTLTISSLQPEDFATYYCQQAQTYPYTEGGGT KVEIKRTVAAPSVFIFPPSDRKLKSGTASVVCLL NNFYPREAKVQWKVDNALQSGNSQESVTEQDSKD STYSLSSTLTLSKADYEKHKVYACEVTHQGLSSP VTKSFNRGEC |
| 82 | VL (CD28 variant l)-CL (RK) | DIQMTQSPSSLSASVGDRVTITCHASQNIYVELN WYQQKPGKAPKLLIYKASNLHTGVPSRFSGSGSG TDFTLTISSLQPEDFATYYCQQGQTYPYTEGGGT KVEIKRTVAAPSVFIFPPSDRKLKSGTASVVCLL NNFYPREAKVQWKVDNALQSGNSQESVTEQDSKD STYSLSSTLTLSKADYEKHKVYACEVTHQGLSSP VTKSFNRGEC |
| 83 | VL (CD28 variant m)-CL (RK) | DIQMTQSPSSLSASVGDRVTITCHASQNIYVYLN WYQQKPGKAPKLLIYKASNLHTGVPSRFSGSGSG TDFTLTISSLQPEDFATYYCQQGQTYPYTEGGGT KVEIKRTVAAPSVFIFPPSDRKLKSGTASVVCLL NNFYPREAKVQWKVDNALQSGNSQESVTEQDSKD STYSLSSTLTLSKADYEKHKVYACEVTHQGLSSP VTKSFNRGEC |
| 84 | VL (CD28 variant r)-CL (RK) | DIQMTQSPSSLSASVGDRVTITCHASQGIYVYLN WYQQKPGKAPKLLIYKASNLHTGVPSRFSGSGSG TDFTLTISSLQPEDFATYYCQQGQTYPYTEGGGT KVEIKRTVAAPSVFIFPPSDRKLKSGTASVVCLL NNFYPREAKVQWKVDNALQSGNSQESVTEQDSKD STYSLSSTLTLSKADYEKHKVYACEVTHQGLSSP VTKSFNRGEC |
| 85 | VL (CD28 variant s)-CL (RK) | DIQMTQSPSSLSASVGDRVTITCHASQGISVYLN WYQQKPGKAPKLLIYKASNLHTGVPSRFSGSGSG TDFTLTISSLQPEDFATYYCQQGQTYPYTEGGGT KVEIKRTVAAPSVFIFPPSDRKLKSGTASVVCLL NNFYPREAKVQWKVDNALQSGNSQESVTEQDSKD STYSLSSTLTLSKADYEKHKVYACEVTHQGLSSP VTKSFNRGEC |
| 86 | VL (CD28 variant t)-CL (RK) | DIQMTQSPSSLSASVGDRVTITCRASQNIYVWLN WYQQKPGKAPKLLIYKASNLYSGVPSRFSGSRSG TDFTLTISSLQPEDFATYYCQQGQTYPYTEGQGT KLEIKRTVAAPSVFIFPPSDRKLKSGTASVVCLL NNFYPREAKVQWKVDNALQSGNSQESVTEQDSKD STYSLSSTLTLSKADYEKHKVYACEVTHQGLSSP VTKSFNRGEC |
| 87 | Fc hole PGLALA, HYRF | DKTHTCPPCPAPEAAGGPSVFLEPPKPKDTLMIS RTPEVTCVVVDVSHEDPEVKFNWYVDGVEVHNAK TKPREEQYNSTYRVVSVLTVLHQDWLNGKEYKCK |

TABLE B-continued (Sequences):

| SEQ ID NO: | Name | Sequence |
|---|---|---|
| | | VSNKALGAPIEKTISKAKGQPREPQVCTLPPSRD ELTKNQVSLSCAVKGFYPSDIAVEWESNGQPENN YKTTPPVLDSDGSFFLVSKLTVDKSRWQQGNVFS CSVMHEALHNRFTQKSLSLSP |
| 88 | Avi tag | GLNDIFEAQKIEWHE |
| 89 | CD28(SA) VL-CH1 hu IgG1 Fc knob PGLALA | DIQMTQSPSSLSASVGDRVTITCHASQNIYVWLN WYQQKPGKAPKLLIYKASNLHTGVPSRFSGSGSG TDFTLTISSLQPEDFATYYCQQGQTYPYTEGGGT KVEIKSSASTKGPSVFPLAPSSKSTSGGTAALGC LVKDYFPEPVTVSWNSGALTSGVHTFPAVLQSSG LYSLSSVVTVPSSSLGTQTYICNVNHKPSNTKVD KKVEPKSCDKTHTCPPCPAPEAAGGPSVFLFPPK PKDTLMISRTPEVTCVVVDVSHEDPEVKFNWYVD GVEVHNAKTKPREEQYNSTYRVVSVLTVLHQDWL NGKEYKCKVSNKALGAPIEKTISKAKGQPREPQV YTLPPCRDELTKNQVSLWCLVKGFYPSDIAVEWE SNGQPENNYKTTPPVLDSDGSFFLYSKLTVDKSR WQQGNVFSCSVMHEALHNHYTQKSLSLSP |
| 90 | CD28(SA) VH-Ckappa | QVQLVQSGAEVKKPGASVKVSCKASGYTFTSYYI HWVRQAPGQGLEWIGCTYPGNVNTNYNEKEKDRA TLTVDTSISTAYMELSRLRSDDTAVYFCTRSHYG LDWNEDVWGQGTTVTVSSASVAAPSVFIFPPSDE QLKSGTASVVCLLNNFYPREAKVQWKVDNALQSG NSQESVTEQDSKDSTYSLSSTLTLSKADYEKHKV YACEVTHQGLSSPVTKSFNRGEC |
| 91 | CD28(SA_Variant 8) VL-CH1 hu IgG1 Fc knob PGLALA | DIQMTQSPSSLSASVGDRVTITCHASQNIYVYLN WYQQKPGKAPKLLIYKASNLHTGVPSRFSGSGSG TDFTLTISSLQPEDFATYYCQQGQTYPYTFGGGT KVEIKSSASTKGPSVFPLAPSSKSTSGGTAALGC LVKDYFPEPVTVSWNSGALTSGVHTFPAVLQSSG LYSLSSVVTVPSSSLGTQTYICNVNHKPSNTKVD KKVEPKSCDKTHTCPPCPAPEAAGGPSVFLFPPK PKDTLMISRTPEVTCVVVDVSHEDPEVKFNWYVD GVEVHNAKTKPREEQYNSTYRVVSVLTVLHQDWL NGKEYKCKVSNKALGAPIEKTISKAKGQPREPQV YTLPPCRDELTKNQVSLWCLVKGFYPSDIAVEWE SNGQPENNYKTTPPVLDSDGSFFLYSKLTVDKSR WQQGNVFSCSVMHEALHNHYTQKSLSLSP |
| 92 | CD28(SA_Variant 8) VH-Ckappa | QVQLVQSGAEVKKPGASVKVSCKASGYTFTSYYI HWVRQAPGQGLEWIGSIYPGNVQTNYNEKFKDRA TLTVDTSISTAYMELSRLRSDDTAVYFCTRSHYG LDFNFDVWGQGTTVTVSSASVAAPSVFIFPPSDE QLKSGTASVVCLLNNFYPREAKVQWKVDNALQSG NSQESVTEQDSKDSTYSLSSTLTLSKADYEKHKV YACEVTHQGLSSPVTKSFNRGEC |
| 93 | CD28(SA_Variant 15) VL-CH1 hu IgG1 Fc knob PGLALA | DIQMTQSPSSLSASVGDRVTITCHASQNIYVFLN WYQQKPGKAPKLLIYKASNLHTGVPSRFSGSGSG TDFTLTISSLQPEDFATYYCQQGQTYPYTFGGGT KVEIKSSASTKGPSVFPLAPSSKSTSGGTAALGC LVKDYFPEPVTVSWNSGALTSGVHTFPAVLQSSG LYSLSSVVTVPSSSLGTQTYICNVNHKPSNTKVD KKVEPKSCDKTHTCPPCPAPEAAGGPSVFLFPPK PKDTLMISRTPEVTCVVVDVSHEDPEVKFNWYVD GVEVHNAKTKPREEQYNSTYRVVSVLTVLHQDWL NGKEYKCKVSNKALGAPIEKTISKAKGQPREPQV YTLPPCRDELTKNQVSLWCLVKGFYPSDIAVEWE SNGQPENNYKTTPPVLDSDGSFFLYSKLTVDKSR WQQGNVFSCSVMHEALHNHYTQKSLSLSP |
| 94 | CD28(SA_Variant 15) VH-Ckappa | QVQLVQSGAEVKKPGASVKVSCKASGYTFTSYYI HWVRQAPGQGLEWIGSIYPGNVNTNYNEKFKDRA TLTVDTSISTAYMELSRLRSDDTAVYFCTRSHYG LDWNFDVWGQGTTVTVSSASVAAPSVFIFPPSDE QLKSGTASVVCLLNNFYPREAKVQWKVDNALQSG NSQESVTEQDSKDSTYSLSSTLTLSKADYEKHKV YACEVTHQGLSSPVTKSFNRGEC |

TABLE B-continued (Sequences):

| SEQ ID NO: | Name | Sequence |
|---|---|---|
| 95 | CD28(SA_Variant 29) VH-Ckappa | QVQLVQSGAEVKKPGASVKVSCKASGYTFTSYYI HWVRQAPGQGLEWIGSIYPGNVNTNYNEKFKDRA TLTVDTSISTAYMELSRLRSDDTAVYFCTRSHYG LDWNFDVWGQGTTVTVSSASVAAPSVFIFPPSDE QLKSGTASVVCLLNNFYPREAKVQWKVDNALQSG NSQESVTEQDSKDSTYSLSSTLTLSKADYEKHKV YACEVTHQGLSSPVTKSFNRGEC |
| 96 | Her2 (pertuzumab CLC) hu IgG1 VH-CH1 "EE" Fc hole wildtype | EVQLVESGGGLVQPGGSLRLSCAASGFTFNDYTM DWVRQAPGKGLEWVADVNPNSGGSIVNRRFKGRF TLSVDRSKNTLYLQMNSLRAEDTAVYYCARNLGP FFYFDYWGQGTLVTVSSASTKGPSVFPLAPSSKS TSGGTAALGCLVEDYFPEPVTVSWNSGALTSGVH TFPAVLQSSGLYSLSSVVTVPSSSLGTQTYICNV NHKPSNTKVDEKVEPKSCDKTHTCPPCPAPELLG GPSVFLEPPKPKDTLMISRTPEVTCVVVDVSHED PEVKFNWYVDGVEVHNAKTKPREEQYNSTYRVVS VLTVLHQDWLNGKEYKCKVSNKALPAPIEKTISK AKGQPREPQVCTLPPSRDELTKNQVSLSCAVKGF YPSDIAVEWESNGQPENNYKTTPPVLDSDGSFFL VSKLTVDKSRWQQGNVFSCSVMHEALHNHYTQKS LSLSP |
| 97 | Her2 (pertuzumab CLC) VL-Ckappa "RK" | DIQMTQSPSSLSASVGDRVTITCKASQDVSTAVA WYQQKPGKAPKLLIYSASFRYTGVPSRFSGSRSG TDFTLTISSLQPEDFATYYCQQHYTTPPTFGQGT KVEIKRTVAAPSVFIFPPSDRKLKSGTASVVCLL NNFYPREAKVQWKVDNALQSGNSQESVTEQDSKD STYSLSSTLTLSKADYEKHKVYACEVTHQGLSSP VTKSFNRGEC |
| 98 | Her2 (pertuzumab CLC) hu IgG1 VH-CH1 "EE" Fc hole PGLALA | EVQLVESGGGLVQPGGSLRLSCAASGFTFNDYTM DWVRQAPGKGLEWVADVNPNSGGSIVNRRFKGRF TLSVDRSKNTLYLQMNSLRAEDTAVYYCARNLGP FFYFDYWGQGTLVTVSSASTKGPSVFPLAPSSKS TSGGTAALGCLVEDYFPEPVTVSWNSGALTSGVH TFPAVLQSSGLYSLSSVVTVPSSSLGTQTYICNV NHKPSNTKVDEKVEPKSCDKTHTCPPCPAPEAAG GPSVFLEPPKPKDTLMISRTPEVTCVVVDVSHED PEVKFNWYVDGVEVHNAKTKPREEQYNSTYRVVS VLTVLHQDWLNGKEYKCKVSNKALGAPIEKTISK AKGQPREPQVCTLPPSRDELTKNQVSLSCAVKGF YPSDIAVEWESNGQPENNYKTTPPVLDSDGSFFL VSKLTVDKSRWQQGNVFSCSVMHEALHNHYTQKS LSLSP |
| 99 | Her2 (pertuzumab CLC) VL-CH1 hu IgG1 Fc knob PGLALA | DIQMTQSPSSLSASVGDRVTITCKASQDVSTAVA WYQQKPGKAPKLLIYSASFRYTGVPSRFSGSRSG TDFTLTISSLQPEDFATYYCQQHYTTPPTFGQGT KVEIKSSASTKGPSVFPLAPSSKSTSGGTAALGC LVKDYFPEPVTVSWNSGALTSGVHTFPAVLQSSG LYSLSSVVTVPSSSLGTQTYICNVNHKPSNTKVD KKVEPKSCDKTHTCPPCPAPEAAGGPSVFLFPPK PKDTLMISRTPEVTCVVVDVSHEDPEVKFNWYVD GVEVHNAKTKPREEQYNSTYRVVSVLTVLHQDWL NGKEYKCKVSNKALGAPIEKTISKAKGQPREPQV CTLPPSRDELTKNQVSLSCAVKGFYPSDIAVEWE SNGQPENNYKTTPPVLDSDGSFFLVSKLTVDKSR WQQGNVFSCSVMHEALHNHYTQKSLSLSP |
| 100 | Her2 (pertuzumab CLC) VH-Ckappa | EVQLVESGGGLVQPGGSLRLSCAASGFTFNDYTM DWVRQAPGKGLEWVADVNPNSGGSIVNRRFKGRF TLSVDRSKNTLYLQMNSLRAEDTAVYYCARNLGP FFYFDYWGQGTLVTVSSASVAAPSVFIFPPSDEQ LKSGTASVVCLLNNFYPREAKVQWKVDNALQSGN SQESVTEQDSKDSTYSLSSTLTLSKADYEKHKVY ACEVTHQGLSSPVTKSFNRGEC |
| 101 | Her2 (trastuzumab CLC) hu IgG1 VH-CH1 "EE" Fc hole PGLALA | EVQLVESGGGLVQPGGSLRLSCAASGENIKDTYI HWVRQAPGKGLEWVARIYPTNGYTRYADSVKGRF TISADTSKNTAYLQMNSLRAEDTAVYYCSRWGGE GFYAMDYWGQGTLVTVSSASTKGPSVFPLAPSSK STSGGTAALGCLVEDYFPEPVTVSWNSGALTSGV HTFPAVLQSSGLYSLSSVVTVPSSSLGTQTYICN VNHKPSNTKVDEKVEPKSCDKTHTCPPCPAPEAA |

TABLE B-continued (Sequences):

| SEQ ID NO: | Name | Sequence |
|---|---|---|
| | | GGPSVFLFPPKPKDTLMISRTPEVTCVVVDVSHE DPEVKFNWYVDGVEVHNAKTKPREEQYNSTYRVV SVLTVLHQDWLNGKEYKCKVSNKALGAPIEKTIS KAKGQPREPQVCTLPPSRDELTKNQVSLSCAVKG FYPSDIAVEWESNGQPENNYKTTPPVLDSDGSFF LVSKLTVDKSRWQQGNVFSCSVMHEALHNHYTQK SLSLSP |
| 102 | Her2 (trastuzumab CLC) VL-CH1 hu IgG1 Fc knob PGLALA | DIQMTQSPSSLSASVGDRVTITCKASQDVSTAVA WYQQKPGKAPKLLIYSASFRYTGVPSRFSGSRSG TDFTLTISSLQPEDFATYYCQQHYTTPPTFGQGT KVEIKSSASTKGPSVFPLAPSSKSTSGGTAALGC LVKDYFPEPVTVSWNSGALTSGVHTFPAVLQSSG LYSLSSVVTVPSSSLGTQTYICNVNHKPSNTKVD KKVEPKSCDKTHTCPPCPAPEAAGGPSVFLFPPK PKDTLMISRTPEVTCVVVDVSHEDPEVKFNWYVD GVEVHNAKTKPREEQYNSTYRVVSVLTVLHQDWL NGKEYKCKVSNKALGAPIEKTISKAKGQPREPQV CTLPPSRDELTKNQVSLSCAVKGFYPSDIAVEWE SNGQPENNYKTTPPVLDSDGSFFLVSKLTVDKSR WQQGNVFSCSVMHEALHNHYTQKSLSLSP |
| 103 | human Her2, UniProt Acc. No. P04626-1 | MELAALCRWGLLLALLPPGAASTQVCTGTDMKLR LPASPETHLDMLRHLYQGCQVVQGNLELTYLPTN ASLSFLQDIQEVQGYVLIAHNQVRQVPLQRLRIV RGTQLFEDNYALAVLDNGDPLNNTTPVTGASPGG LRELQLRSLTEILKGGVLIQRNPQLCYQDTILWK DIFHKNNQLALTLIDTNRSRACHPCSPMCKGSRC WGESSEDCQSLTRTVCAGGCARCKGPLPTDCCHE QCAAGCTGPKHSDCLACLHFNHSGICELHCPALV TYNTDTFESMPNPEGRYTFGASCVTACPYNYLST DVGSCTLVCPLHNQEVTAEDGTQRCEKCSKPCAR VCYGLGMEHLREVRAVTSANIQEFAGCKKIFGSL AFLPESFDGDPASNTAETLEEITGYLYISAWPDS LPDLSVFQNLQVIRGRILHNGAYSLTLQGLGISW LGLRSLRELGSGLALIHHNTHLCFVHTVPWDQLF RNPHQALLHTANRPEDECVGEGLACHQLCARGHC WGPGPTQCVNCSQFLRGQECVEECRVLQGLPREY VNARHCLPCHPECQPQNGSVTCFGPEADQCVACA HYKDPPFCVARCPSGVKPDLSYMPIWKFPDEEGA CQPCPINCTHSCVDLDDKGCPAEQRASPLTSIIS AVVGILLVVVLGVVFGILIKRRQQKIRKYTMRRL LQETELVEPLTPSGAMPNQAQMRILKETELRKVK VLGSGAFGTVYKGIWIPDGENVKIPVAIKVLREN TSPKANKEILDEAYVMAGVGSPYVSRLLGICLTS TVQLVTQLMPYGCLLDHVRENRGRLGSQDLLNWC MQIAKGMSYLEDVRLVHRDLAARNVLVKSPNHVK ITDFGLARLLDIDETEYHADGGKVPIKWMALESI LRRRFTHQSDVWSYGVTVWELMTFGAKPYDGIPA REIPDLLEKGERLPQPPICTIDVYMIMVKCWMID SECRPRFRELVSEFSRMARDPQRFVVIQNEDLGP ASPLDSTFYRSLLEDDDMGDLVDAEEYLVPQQGF FCPDPAPGAGGMVHHRHRSSSTRSGGGDLTLGLE PSEEEAPRSPLAPSEGAGSDVFDGDLGMGAAKGL QSLPTHDPSPLQRYSEDPTVPLPSETDGYVAPLT CSPQPEYVNQPDVRPQPPSPREGPLPAARPAGAT LERPKTLSPGKNGVVKDVFAFGGAVENPEYLTPQ GGAAPQPHPPPAFSPAFDNLYYWDQDPPERGAPP STFKGTPTAENPEYLGLDVPV |
| 104 | IgG CH1 domain | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKKV |
| 105 | IgG CH2 domain | APELLGGPSVFLFPPKPKDTLMISRTPEVTCVWD VSHEDPEVKFNWYVDGVEVHNAKTKPREEQESTY RWSVLTVLHQDWLNGKEYKCKVSNKALPAPIEKT ISKAK |
| 106 | IgG CH3 domain | GQPREPQVYTLPPSRDELTKNQVSLTCLVKGFYP SDIAVEWESNGQPENNYKTTPPVLDSDGSFFLYS KLTVDKSRWQQGNVFSCSVMHEALHNHYTQKSLS LSPG |
| 107 | CH1 connector | EPKSC |

TABLE B-continued (Sequences):

| SEQ ID NO: | Name | Sequence |
|---|---|---|
| 108 | Hinge full | DKTHTCPXCP with X being S or P |
| 109 | Hinge middle | HTCPXCP with X being S or P |
| 110 | Hinge short | CPXCP with X being S or P |
| 111 | IgG1, caucasian allotype | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKKVEPKS CDKTHTCPPCPAPELLGGPSVFLFPPKPKDTLMI SRTPEVTCVVVDVSHEDPEVKFNWYVDGVEVHNA KTKPREEQYNSTYRVVSVLTVLHQDWLNGKEYKC KVSNKALPAPIEKTISKAKGQPREPQVYTLPPSR DELTKNQVSLTCLVKGFYPSDIAVEWESNGQPEN NYKTTPPVLDSDGSFFLYSKLTVDKSRWQQGNVF SCSVMHEALHNHYTQKSLSLSPGK |
| 112 | IgG1, afromnerican allotype | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKKVEPKS CDKTHTCPPCPAPELLGGPSVFLFPPKPKDTLMI SRTPEVTCVVVDVSHEDPEVKFNWYVDGVEVHNA KTKPREEQYNSTYRVVSVLTVLHQDWLNGKEYKC KVSNKALPAPIEKTISKAKGQPREPQVYTLPPSR EEMTKNQVSLTCLVKGFYPSDIAVEWESNGQPEN NYKTTPPVLDSDGSFFLYSKLTVDKSRWQQGNVF SCSVMHEALHNHYTQKSLSLSPGK |
| 113 | IgG2 | ASTKGPSVFPLAPCSRSTSESTAALGCLVKDYFP EPVTVSWNSGALTSGVHTFPAVLQSSGLYSLSSV VTVPSSNFGTQTYTCNVDHKPSNTKVDKTVERKC CVECPPCPAPPVAGPSVFLFPPKPKDTLMISRTP EVTCVVVDVSHEDPEVQFNWYVDGVEVHNAKTKP REEQFNSTFRVVSVLTVVHQDWLNGKEYKCKVSN KGLPAPIEKTISKTKGQPREPQVYTLPPSREEMT KNQVSLTCLVKGFYPSDISVEWESNGQPENNYKT TPPMLDSDGSFFLYSKLTVDKSRWQQGNVFSCSV MHEALHNHYTQKSLSLSPGK |
| 114 | IgG3 | ASTKGPSVFPLAPCSRSTSGGTAALGCLVKDYFP EPVTVSWNSGALTSGVHTFPAVLQSSGLYSLSSV VTVPSSSLGTQTYTCNVNHKPSNTKVDKRVELKT PLGDTTHTCPRCPEPKSCDTPPPCPRCPEPKSCD TPPPCPRCPEPKSCDTPPPCPRCPAPELLGGPSV FLFPPKPKDTLMISRTPEVTCVVVDVSHEDPEVQ FKWYVDGVEVHNAKTKPREEQYNSTFRVVSVLTV LHQDWLNGKEYKCKVSNKALPAPIEKTISKTKGQ PREPQVYTLPPSREEMTKNQVSLTCLVKGFYPSD IAVEWESSGQPENNYNTTPPMLDSDGSFELYSKL TVDKSRWQQGNIFSCSVMHEALHNRFTQKSLSLS PGK |
| 115 | IgG4 | ASTKGPSVFPLAPCSRSTSESTAALGCLVKDYFP EPVTVSWNSGALTSGVHTFPAVLQSSGLYSLSSV VTVPSSSLGTKTYTCNVDHKPSNTKVDKRVESKY GPPCPSCPAPEFLGGPSVFLEPPKPKDTLMISRT PEVTCVVVDVSQEDPEVQFNWYVDGVEVHNAKTK PREEQFNSTYRVVSVLTVLHQDWLNGKEYKCKVS NKGLPSSIEKTISKAKGQPREPQVYTLPPSQEEM TKNQVSLTCLVKGFYPSDIAVEWESNGQPENNYK TTPPVLDSDGSFFLYSRLTVDKSRWQEGNVFSCS VMHEALHNHYTQKSLSLSLGK |
| 116 | human FcγRIIIa UniProt accession no. P08637 | MWQLLLPTALLLLVSAGMRTEDLPKAVVFLEPQW YRVLEKDSVTLKCQGAYSPEDNSTQWFHNESLIS SQASSYFIDAATVDDSGEYRCQTNLSTLSDPVQL EVHIGWLLLQAPRWVFKEEDPIHLRCHSWKNTAL HKVTYLQNGKGRKYFHHNSDFYIPKATLKDSGSY FCRGLFGSKNVSSETVNITITQGLAVSTISSFFP PGYQVSFCLVMVLLFAVDTGLYFSVKTNIRSSTR DWKDHKFKWRKDPQDK |
| 117 | Peptide linker (G4S) | GGGGS |

TABLE B-continued (Sequences):

| SEQ ID NO: | Name | Sequence |
|---|---|---|
| 118 | Peptide linker (G4S)2 | GGGGSGGGGS |
| 119 | Peptide linker (SG4)2 | SGGGGSGGGG |
| 120 | Peptide linker G4(SG4)2 | GGGGSGGGGSGGGG |
| 121 | peptide linker | GSPGSSSSGS |
| 122 | (G4S)3 peptide linker | GGGGSGGGGSGGGGS |
| 123 | (G4S)4 peptide linker | GGGGSGGGGSGGGGSGGGGS |
| 124 | peptide linker | GSGSGSGS |
| 125 | peptide linker | GSGSGNGS |
| 126 | peptide linker | GGSGSGSG |
| 127 | peptide linker | GGSGSG |
| 128 | peptide linker | GGSG |
| 129 | peptide linker | GGSGNGSG |
| 130 | peptide linker | GGNGSGSG |
| 131 | peptide linker | GGNGSG |
| 132 | CDR-H1, pertuzumab | GFTFTDYTMD |
| 133 | CDR-H2, pertuzumab | DVNPNSGGSIYNQRFKG |
| 134 | CDR-H3, pertuzumab | NLGPSFYFDY |
| 135 | CDR-L1, pertuzumab | KASQDVSIGVA |
| 136 | CDR-L2, pertuzumab | SASYRYT |
| 137 | CDR-L3, pertuzumab | QQYYIYPYT |
| 138 | heavy chain variable domain VH, pertuzumab | EVQLVESGGGLVQPGGSLRLSCAASGFTFTDYTMDWVRQAPGKGLEWVADVNPNSGGSIYNQRFKGRFTLSVDRSKNTLYLQMNSLRAEDTAVYYCARNLGPSFYFDYWGQGTLVTVSS |
| 139 | light chain variable domain VL, pertuzumab | DIQMTQSPSSLSASVGDRVTITCKASQDVSIGVAWYQQKPGKAPKLLIYSASYRYTGVPSRFSGSGSGTDFTLTISSLQPEDFATYYCQQYYIYPYTFGQGTKVEIK |
| 140 | CDR-H1, trastuzumab | GFNIKDTYIH |
| 141 | CDR-H2, trastuzumab | RIYPTNGYTRYADSVKG |
| 142 | CDR-H3, trastuzumab | WGGDGFYAMDY |
| 143 | CDR-L1, trastuzumab | RASQDVNTAVA |
| 144 | CDR-L2, trastuzumab | SASFLYS |
| 145 | CDR-L3, trastuzumab | QQHYTTPPT |
| 146 | heavy chain variable domain VH, trastuzumab | EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVSS |
| 147 | light chain variable domain VL, trastuzumab | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIK |
| 148 | CDR-H1, CD3 | NYYIH |
| 149 | CDR-H2, CD3 | WIYPGDGNTK YNEKFKG |

TABLE B-continued (Sequences):

| SEQ ID NO: | Name | Sequence |
|---|---|---|
| 150 | CDR-H3, CD3 | DSYSNYYFDY |
| 151 | CDR-L1, CD3 | KSSQSLLNSR TRKNYLA |
| 152 | CDR-L2, CD3 | WASTRES |
| 153 | CDR-L3, CD3 | TQSFILRT |
| 154 | heavy chain variable domain VH, CD3 | EVQLVQSGAEVKKPGASVKVSCKASGYTFTNYYI HWVRQAPGQGLEWIGWIYPGDGNTKYNEKFKGRA TLTADTSTSTAYLELSSLRSEDTAVYYCARDSYS NYYFDYWGQGTLVTVSS |
| 155 | light chain variable domain VL, CD3 | DIVMTQSPDSLAVSLGERATINCKSSQSLLNSRT RKNYLAWYQQKPGQPPKLLIYWASTRESGVPDRF SGSGSGTDFTLTISSLQAEDVAVYYCTQSFILRT FGQGTKVEIK |
| 156 | CDR-H1, Her2 (7C2) | GYWMN |
| 157 | CDR-H2, Her2 (7C2) | MIHPSDSEIR ANQKFRD |
| 158 | CDR-H3, Her2 (7C2) | GTYDGGFEY |
| 159 | CDR-L1, Her2 (7C2) | RASQSVSGSR FTYMH |
| 160 | CDR-L2, Her2 (7C2) | YASILES |
| 161 | CDR-L3, Her2 (7C2) | QHSWEIPPWT |
| 162 | heavy chain variable domain VH, Her2 (7C2) | QVQLQQPGAELVRPGASVKLSCKASGYSFTGYWM NWLKQRPGQGLEWIGMIHPSDSEIRANQKFRDKA TLTVDKSSTTAYMQLSSPTSEDSAVYYCARGTYD GGFEYWGQGTTLTVSS |
| 163 | light chain variable domain VL, Her2 (7C2) | DIVLTQSPASLVVSLGQRATISCRASQSVSGSRF TYMHWYQQKPGQPPKLLIKYASILESGVPARFSG GGSGTDFTLNIHPVEEDDTATYYCQHSWEIPPWT FGGGTKLEIK |
| 164 | Human PD-L1 Uniprot accession no. Q9NZQ7 | MRIFAVFIFMTYWHLLNAFTVTVPKDLYVVEYGS NMTIECKFPVEKQLDLAALIVYWEMEDKNIIQFV HGEEDLKVQHSSYRQRARLLKDQLSLGNAALQIT DVKLQDAGVYRCMISYGGADYKRITVKVNAPYNK INQRILVVDPVTSEHELTCQAEGYPKAEVIWTSS DHQVLSGKTTTTNSKREEKLFNVTSTLRINTTTN EIFYCTFRRLDPEENHTAELVIPELPLAHPPNER THLVILGAILLCLGVALTFIFRLRKGRMMDVKKC GIQDTNSKKQSDTHLEET |
| 165 | VH (PD-L1) | EVQLVESGGGLVQPGGSLRLSCAASGFTFSDSWI HWVRQAPGKGLEWVAWISPYGGSTYYADSVKGRF TISADTSKNTAYLQMNSLRAEDTAVYYCARRHWP GGFDYWGQGTLVTVSS |
| 166 | VL (PD-L1) | DIQMTQSPSSLSASVGDRVTITCRASQDVSTAVA WYQQKPGKAPKLLIYSASFLYSGVPSRFSGSGSG TDFTLTISSLQPEDFATYYCQQYLYHPATFGQGT KVEIK |
| 167 | VH (PD-L1) | EVQLVESGGGLVQPGGSLRLSCAASGFTFSRYWM SWVRQAPGKGLEWVANIKQDGSEKYYVDSVKGRF TISRDNAKNSLYLQMNSLRAEDTAVYYCAREGGW FGELAFDYWGQGTLVTVSS |
| 168 | VL (PD-L1) | EIVLTQSPGTLSLSPGERATLSCRASQRVSSSYL AWYQQKPGQAPRLLIYDASSRATGIPDRFSGSGS GTDFTLTISRLEPEDFAVYYCQQYGSLPWTFGQG TKVEIK |
| 169 | human PD-1 Uniprot accession no. Q15116 | MQIPQAPWPVVWAVLQLGWRPGWFLDSPDRPWNP PTFSPALLVVTEGDNATFTCSFSNTSESFVLNWY RMSPSNQTDKLAAFPEDRSQPGQDCRFRVTQLPN GRDFHMSVVRARRNDSGTYLCGAISLAPKAQIKE |

TABLE B-continued (Sequences):

| SEQ ID NO: | Name | Sequence |
|---|---|---|
| | | SLRAELRVTERRAEVPTAHPSPSPRPAGQFQTLV VGVVGGLLGSLVLLVWVLAVICSRAARGTIGARR TGQPLKEDPSAVPVFSVDYGELDFQWREKTPEPP VPCVPEQTEYATIVFPSGMGTSSPARRGSADGPR SAQPLRPEDGHCSWPL |
| 170 | VH (PD-1) | QVQLVQSGVEVKKPGASVKVSCKASGYTFTNYYM YWVRQAPGQGLEWMGGINPSNGGTNENEKEKNRV TLTTDSSTTTAYMELKSLQFDDTAVYYCARRDYR FDMGFDYWGQGTTVTVSS |
| 171 | VL (PD-1) | EIVLTQSPATLSLSPGERATLSCRASKGVSTSGY SYLHWYQQKPGQAPRLLIYLASYLESGVPARFSG SGSGTDFTLTISSLEPEDFAVYYCQHSRDLPLTF GGGTKVEIK |
| 172 | VH (PD-1) | QVQLVESGGGVVQPGRSLRLDCKASGITFSNSGM HWVRQAPGKGLEWVAVIWYDGSKRYYADSVKGRF TISRDNSKNTLFLQMNSLRAEDTAVYYCATNDDY WGQGTLVTVSS |
| 173 | VL (PD-1) | EIVLTQSPATLSLSPGERATLSCRASQSVSSYLA WYQQKPGQAPRLLIYDASNRATGIPARFSGSGSG TDFTLTISSLEPEDFAVYYCQQSSNWPRTFGQGT KVEIK |
| 174 | Her2-CD3 (4D5/40G5c) HC1 (Fc knob) | EVQLVESGGGLVQPGGSLRLSCAASGFNIKDTYI HWVRQAPGKGLEWVARIYPTNGYTRYADSVKGRF TISADTSKNTAYLQMNSLRAEDTAVYYCSRWGGD GFYAMDYWGQGTLVTVSSASTKGPSVFPLAPSSK STSGGTAALGCLVKDYFPEPVTVSWNSGALTSGV HTFPAVLQSSGLYSLSSVVTVPSSSLGTQTYICN VNHKPSNTKVDKKVEPKSCDKTHTCPPCPAPELL GGPSVFLFPPKPKDTLMISRTPEVTCVVVDVSHE DPEVKFNWYVDGVEVHNAKTKPREEQYGSTYRVV SVLTVLHQDWLNGKEYKCKVSNKALPAPIEKTIS KAKGQPREPQVYTLPPSREEMTKNQVSLWCLVKG FYPSDIAVEWESNGQPENNYKTTPPVLDSDGSFF LYSKLTVDKSRWQQGNVFSCSVMHEALHNHYTQK SLSLSP |
| 175 | Her2-CD3 (4D5/40G5c) LC1 | DIQMTQSPSSLSASVGDRVTITCRASQDVNTAVA WYQQKPGKAPKLLIYSASFLYSGVPSRFSGSRSG TDFTLTISSLQPEDFATYYCQHYTTPPTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| 176 | Her2-CD3 (4D5/40G5c) HC2 (Fc hole) | EVQLVQSGAEVKKPGASVKVSCKASGYTFTNYYI HWVRQAPGQGLEWIGWIYPGDGNTKYNEKFKGRA TLTADTSTSTAYLELSSLRSEDTAVYYCARDSYS NYYFDYWGQGTLVTVSSASTKGPSVFPLAPSSKS TSGGTAALGCLVKDYFPEPVTVSWNSGALTSGVH TFPAVLQSSGLYSLSSVVTVPSSSLGTQTYICNV NHKPSNTKVDKKVEPKSCDKTHTCPPCPAPELLG GPSVFLFPPKPKDTLMISRTPEVTCVVVDVSHED PEVKFNWYVDGVEVHNAKTKPREEQYGSTYRVVS VLTVLHQDWLNGKEYKCKVSNKALPAPIEKTISK AKGQPREPQVYTLPPSREEMTKNQVSLSCAVKGF YPSDIA VEWESNGQPENNYKTTPPVLDSDGSFFLVSKLTV DKSRWQQGNVFSCSVMHEALHNHYTQKSLSLSP |
| 177 | Her2-CD3 (4D5/40G5c) LC2 | DIVMTQSPDSLAVSLGERATINCKSSQSLLNSRT RKNYLAWYQQKPGQPPKLLIYWASTRESGVPDRF SGSGSGTDFTLTISSLQAEDVAVYYCTQSFILRT FGQGTKVEIKRTVAAPSVFIFPPSDEQLKSGTAS VVCLLNNFYPREAKVQWKVDNALQSGNSQESVTE QDSKDSTYSLSSTLTLSKAD YEKHKVYACEVTHQGLSSPVTKSFNRGEC |
| 178 | CD28(SA_Variant 8) hu IgG1 Fc hole N297G | QVQLVQSGAEVKKPGASVKVSCKASGYTFSYYI HWVRQAPGQGLEWIGSIYPGNVQTNYNEKFKDRA TLTVDTSISTAYMELSRLRSDDTAVYFCTRSHYG |

TABLE B-continued (Sequences):

| SEQ ID NO: | Name | Sequence |
|---|---|---|
| | | LDFNFDVWGQGTTVTVSSASTKGPSVFPLAPSSK STSGGTAALGCLVKDYFPEPVTVSWNSGALTSGV HTFPAVLQSSGLYSLSSVVTVPSSSLGTQTYICN VNHKPSNTKVDKKVEPKSCDKTHTCPPCPAPELL GGPSVFLFPPKPKDTLMISRTPEVTCVVVDVSHE DPEVKFNWYVDGVEVHNAKTKPREEQYGSTYRVV SVLTVLHQDWLNGKEYKCKVSNKALPAPIEKTIS KAKGQPREPQVYTLPPSREEMTKNQVSLSCAVKG FYPSDIAVEWESNGQPENNYKTTPPVLDSDGSFF LVSKLTVDKSRWQQGNVFSCSVMHEALHNHYTQK SLSLSP |
| 179 | CD28(SA_Variant 8) VL-Ckappa | DIQMTQSPSSLSASVGDRVTITCHASQNIYVYLN WYQQKPGKAPKLLIYKASNLHTGVPSRFSGSGSG TDFTLTISSLQPEDFATYYCQQGQTYPYTFGGGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| 180 | Her2 (4D5) hu IgG1 knob N297G | EVQLVESGGGLVQPGGSLRLSCAASGFNIKDTYI HWVRQAPGKGLEWVARIYPTNGYTRYADSVKGRF TISADTSKNTAYLQMNSLRAEDTAVYYCSRWGGD GFYAMDYWGQGTLVTVSSASTKGPSVFPLAPSSK STSGGTAALGCLVKDYFPEPVTVSWNSGALTSGV HTFPAVLQSSGLYSLSSVVTVPSSSLGTQTYICN VNHKPSNTKVDKKVEPKSCDKTHTCPPCPAPELL GGPSVFLFPPKPKDTLMISRTPEVTCVVVDVSHE DPEVKFNWYVDGVEVHNAKTKPREEQYGSTYRVV SVLTVLHQDWLNGKEYKCKVSNKALPAPIEKTIS KAKGQPREPQVYTLPPSREEMTKNQVSLWCLVKG FYPSDIAVEWESNGQPENNYKTTPPVLDSDGSFF LYSKLTVDKSRWQQGNVFSCSVMHEALHNHYTQK SLSLSP |
| 181 | Her2 (4D5) VL-Ckappa | DIQMTQSPSSLSASVGDRVTITCRASQDVNTAVA WYQQKPGKAPKLLIYSASFLYSGVPSRFSGSRSG TDFTLTISSLQPEDFATYYCQQHYTTPPTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| 182 | Her2 (2C4) hu IgG1 knob N297G | EVQLVESGGGLVQPGGSLRLSCAASGFTFTDYTM DWVRQAPGKGLEWVADVNPNSGGSIYNQRFKGRF TLSVDRSKNTLYLQMNSLRAEDTAVYYCARNLGP SFYFDYWGQGTLVTVSSASTKGPSVFPLAPSSKS TSGGTAALGCLVKDYFPEPVTVSWNSGALTSGVH TFPAVLQSSGLYSLSSVVTVPSSSLGTQTYICNV NHKPSNTKVDKKVEPKSCDKTHTCPPCPAPELLG GPSVFLFPPKPKDTLMISRTPEVTCVVVDVSHED PEVKFNWYVDGVEVHNAKTKPREEQYGSTYRVVS VLTVLHQDWLNGKEYKCKVSNKALPAPIEKTISK AKGQPREPQVYTLPPSREEMTKNQVSLWCLVKGF YPSDIAVEWESNGQPENNYKTTPPVLDSDGSFFL YSKLTVDKSRWQQGNVFSCSVMHEALHNHYTQKS LSLSP |
| 183 | Her2 (2C4) VL-Ckappa | DIQMTQSPSSLSASVGDRVTITCKASQDVSIGVA WYQQKPGKAPKLLIYSASYRYTGVPSRFSGSGSG TDFTLTISSLQPEDFATYYCQQYYTYPYTEGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| 184 | CD28 IgG4 Fc | QVQLVQSGAEVKKPGASVKVSCKASGYTFTSYYI HWVRQAPGQGLEWIGCTYPGNVNTNYNEKEKDRA TLTVDTSISTAYMELSRLRSDDTAVYFCTRSHYG LDWNEDVWGQGTTVTVSSASTKGPSVFPLAPCSR STSESTAALGCLVKDYFPEPVTVSWNSGALTSGV HTFPAVLQSSGLYSLSSVVTVPSSSLGTKTYTCN VDHKPSNTKVDKRVESKYGPPCPPCPAPEFLGGP SVFLFPPKPKDTLMISRTPEVTCVVVDVSQEDPE VQFNWYVDGVEVHNAKTKPREEQFNSTYRVVSVL |

TABLE B-continued (Sequences):

| SEQ ID NO: | Name | Sequence |
|---|---|---|
| | | TVLHQDWLNGKEYKCKVSNKGLPSSIEKTISKAK GQPREPQVYTLPPSQEEMTKNQVSLTCLVKGFYP SDIAVEWESNGQPENNYKTTPPVLDSDGSFFLYS RLTVDKSRWQEGNVFSCSVMHEALHNHYTQKSLS LSLGK |
| 185 | CD28 kappa light chain | DIQMTQSPSSLSASVGDRVTITCHASQNIYVWLN WYQQKPGKAPKLLIYKASNLHTGVPSRFSGSGSG TDFTLTISSLQPEDFATYYCQQGQTYPYTEGGGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| 186 | DP47 huIgG1 PGLALA heavy chain | EVQLLESGGGLVQPGGSLRLSCAASGFTFSSYAM SWVRQAPGKGLEWVSAISGSGGSTYYADSVKGRF TISRDNSKNTLYLQMNSLRAEDTAVYYCAKGSGF DYWGQGTLVTVSSASTKGPSVFPLAPSSKSTSGG TAALGCLVKDYFPEPVTVSWNSGALTSGVHTFPA VLQSSGLYSLSSVVTVPSSSLGTQTYICNVNHKP SNTKVDKKVEPKSCDKTHTCPPCPAPEAAGGPSV FLFPPKPKDTLMISRTPEVTCVVVDVSHEDPEVK FNWYVDGVEVHNAKTKPREEQYNSTYRVVSVLTV LHQDWLNGKEYKCKVSNKALGAPIEKTISKAKGQ PREPQVYTLPPSRDELTKNQVSLTCLVKGFYPSD IAVEWESNGQPENNYKTTPPVLDSDGSFELYSKL TVDKSRWQQGNVFSCSVMHEALHNHYTQKSLSLS P |
| 187 | DP47 huIgG1 PGLALA light chain | EIVLTQSPGTLSLSPGERATLSCRASQSVSSSYL AWYQQKPGQAPRLLIYGASSRATGIPDRFSGSGS GTDFTLTISRLEPEDFAVYYCQQYGSSPLTFGQG TKVEIKRTVAAPSVFIFPPSDEQLKSGTASVVCL LNNFYPREAKVQWKVDNALQSGNSQESVTEQDSK DSTYSLSSTLTLSKADYEKHKVYACEVTHQGLSS PVTKSFNRGEC |
| 188 | human CD3ε Uniprot No. P07766 | MQSGTHWRVLGLCLLSVGVWGQDGNEEMGGITQT PYKVSISGTTVILTCPQYPGSEILWQHNDKNIGG DEDDKNIGSDEDHLSLKEFSELEQSGYYVCYPRG SKPEDANFYLYLRARVCENCMEMDVMSVATIVIV DICITGGLLLLVYYWSKNRKAKAKPVTRGAGAGG RQRGQNKERPPPVPNPDYEPIRKGQRDLYSGLNQ RRI |
| 189 | Cynomolgus CD3ε Uniprot No. Q95LI5 | MQSGTRWRVLGLCLLSIGVWGQDGNEEMGSITQT PYQVSISGTIVILTCSQHLGSEAQWQHNGKNKED SGDRLFLPEFSEMEQSGYYVCYPRGSNPEDASHH LYLKARVCENCMEMDVMAVATIVIVDICITLGLL LLVYYWSKNRKAKAKPVTRGAGAGGRQRGQNKER PPPVPNPDYEPIRKGQQDLYSGLNQRRI |

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, MD (1991). Amino acids of antibody chains are numbered and referred to according to the numbering systems according to Kabat (Kabat, E. A., et al., Sequences of Proteins of Immunological Interest, 5th ed., Public Health Service, National Institutes of Health, Bethesda, MD (1991)) as defined above.

The following numbered paragraphs (paras) describe aspects of the present invention:

1. A bispecific agonistic CD28 antigen binding molecule characterized by monovalent binding to CD28, comprising
   (a) a first antigen binding domain capable of specific binding to CD28,
   (b) a second antigen binding domain capable of specific binding to an antigen binding domain capable of specific binding to human epidermal growth factor receptor-2 (Her2), and
   (c) a Fc domain composed of a first and a second subunit capable of stable association comprising one or more amino acid substitution that reduces the binding affinity of the antigen binding molecule to an Fc receptor and/or effector function,
   wherein said second antigen binding domain capable of specific binding to Her2 comprises
   (i) a heavy chain variable region ($V_H$Her2) comprising a heavy chain complementary determining region CDR-H1 of SEQ ID NO: 2, a CDR-H2 of SEQ ID NO: 3, and a CDR-H3 of SEQ ID NO: 4, and a light chain variable region ($V_L$Her2) comprising a light chain complementary determining region CDR-L1 of SEQ ID NO: 5, a CDR-L2 of SEQ ID NO: 6 and a CDR-L3 of SEQ ID NO: 7; or (ii) a heavy chain variable region ($V_H$Her2) comprising a heavy chain complementary determining region CDR-H1 of SEQ ID NO: 10, a CDR-H2 of SEQ ID NO: 11, and a CDR-H3 of SEQ ID NO: 12, and a light chain variable region ($V_L$Her2) comprising a light chain complementary determining region CDR-L1 of SEQ ID NO: 13, a CDR-L2 of SEQ ID NO: 14 and a CDR-L3 of SEQ ID NO: 15.

2. The bispecific agonistic CD28 antigen binding molecule of para 1, wherein the Fc domain is of human IgG1 subclass and comprises the amino acid mutations L234A, L235A and P329G (numbering according to Kabat EU index).

3. The bispecific agonistic CD28 antigen binding molecule of paras 1 or 2, wherein the first antigen binding domain capable of specific binding to CD28 comprises
   (i) a heavy chain variable region ($V_H$CD28) comprising a heavy chain complementary determining region CDR-H1 of SEQ ID NO: 26, a CDR-H2 of SEQ ID NO: 27, and a CDR-H3 of SEQ ID NO: 28, and a light chain variable region ($V_L$CD28) comprising a light chain complementary determining region CDR-L1 of SEQ ID NO: 29, a CDR-L2 of SEQ ID NO: 30 and a CDR-L3 of SEQ ID NO: 31; or
   (ii) a heavy chain variable region ($V_H$CD28) comprising a CDR-H1 of SEQ ID NO: 18, a CDR-H2 of SEQ ID NO: 19, and a CDR-H3 of SEQ ID NO: 20, and a light chain variable region ($V_L$CD28) comprising a CDR-L1 of SEQ ID NO: 21, a CDR-L2 of SEQ ID NO: 22 and a CDR-L3 of SEQ ID NO: 23.

4. The bispecific agonistic CD28 antigen binding molecule of any one of paras 1 to 3, wherein the first antigen binding domain capable of specific binding to CD28 comprises a heavy chain variable region ($V_H$CD28) comprising an amino acid sequence that is at least about 95%, 96%, 97%, 98%, 99% or 100% identical to the amino acid sequence of SEQ ID NO:24, and a light chain variable region ($V_L$CD28) comprising an amino acid sequence that is at least about 95%, 96%, 97%, 98%, 99% or 100% identical to the amino acid sequence of SEQ ID NO:25.

5. The bispecific agonistic CD28 antigen binding molecule of any one of paras 1 to 4, wherein the first antigen binding domain capable of specific binding to CD28 comprises a heavy chain variable region ($V_H$CD28) comprising an amino acid sequence selected from the group consisting of SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40 and SEQ ID NO:41, and a light chain variable region ($V_L$CD28) comprising an amino acid sequence selected from the group consisting of SEQ ID NO:25, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50 and SEQ ID NO:51.

6. The bispecific agonistic CD28 antigen binding molecule of any one of paras 1 to 3 or 5, wherein the first antigen binding domain capable of specific binding to CD28 comprises
   (a) a heavy chain variable region ($V_H$CD28) comprising the amino acid sequence of SEQ ID NO:37 and a light chain variable region ($V_L$CD28) comprising the amino acid sequence of SEQ ID NO:44, or
   (b) a heavy chain variable region ($V_H$CD28) comprising the amino acid sequence of SEQ ID NO:37 and a light chain variable region ($V_L$CD28) comprising the amino acid sequence of SEQ ID NO:25, or
   (c) a heavy chain variable region ($V_H$CD28) comprising the amino acid sequence of SEQ ID NO:41 and a light chain variable region ($V_L$CD28) comprising the amino acid sequence of SEQ ID NO:51, or
   (d) a heavy chain variable region ($V_H$CD28) comprising the amino acid sequence of SEQ ID NO:36 and a light chain variable region ($V_L$CD28) comprising the amino acid sequence of SEQ ID NO:43, or
   (e) a heavy chain variable region ($V_H$CD28) comprising the amino acid sequence of SEQ ID NO:36 and a light chain variable region ($V_L$CD28) comprising the amino acid sequence of SEQ ID NO:44, or
   (f) a heavy chain variable region ($V_H$CD28) comprising the amino acid sequence of SEQ ID NO:36 and a light chain variable region ($V_L$CD28) comprising the amino acid sequence of SEQ ID NO:49, or
   (g) a heavy chain variable region ($V_H$CD28) comprising the amino acid sequence of SEQ ID NO:36 and a light chain variable region ($V_L$CD28) comprising the amino acid sequence of SEQ ID NO:25, or
   (h) a heavy chain variable region ($V_H$CD28) comprising the amino acid sequence of SEQ ID NO:33 and a light chain variable region ($V_L$CD28) comprising the amino acid sequence of SEQ ID NO:25, or
   (i) a heavy chain variable region ($V_H$CD28) comprising the amino acid sequence of SEQ ID NO:32 and a light chain variable region ($V_L$CD28) comprising the amino acid sequence of SEQ ID NO:43, or
   (j) a heavy chain variable region ($V_H$CD28) comprising the amino acid sequence of SEQ ID NO:32 and a light chain variable region ($V_L$CD28) comprising the amino acid sequence of SEQ ID NO:49, or
   (k) a heavy chain variable region ($V_H$CD28) comprising the amino acid sequence of SEQ ID NO:32 and a light chain variable region ($V_L$CD28) comprising the amino acid sequence of SEQ ID NO:25.

7. The bispecific agonistic CD28 antigen binding molecule of any one of paras 1 to 6, wherein the first antigen binding domain capable of specific binding to CD28 comprises
   (i) a heavy chain variable region ($V_H$CD28) comprising a heavy chain complementary determining region CDR-H1 of SEQ ID NO: 52, a CDR-H2 of SEQ ID NO: 53, and a CDR-H3 of SEQ ID NO: 54, and a light chain variable region ($V_L$CD28) comprising a light chain complementary determining region CDR-L1 of SEQ ID NO: 55, a CDR-L2 of SEQ ID NO: 56 and a CDR-L3 of SEQ ID NO: 57.

8. The bispecific agonistic CD28 antigen binding molecule of any one of paras 1 to 6, wherein the first antigen binding domain capable of specific binding to CD28 comprises the CDRs of the heavy chain variable region ($V_H$CD28) comprising the amino acid sequence of SEQ ID NO:37 and the CDRs of the light chain variable region ($V_L$CD28) comprising the amino acid sequence of SEQ ID NO:44.

9. The bispecific agonistic CD28 antigen binding molecule of any one of paras 1 to 8, wherein the antigen binding domain capable of specific binding to Her2 comprises the CDRs of the heavy chain variable region ($V_H$Her2) comprising the amino acid sequence of SEQ ID NO:8 and the CDRs of the light chain variable region ($V_L$Her2) comprising the amino acid sequence of SEQ ID NO:9.

10. The bispecific agonistic CD28 antigen binding molecule of any one of paras 1 to 9, wherein the antigen binding domain capable of specific binding to Her2 comprises a heavy chain variable region ($V_H$Her2) comprising the amino acid sequence of SEQ ID NO:8, and a light chain variable region ($V_L$Her2) comprising the amino acid sequence of SEQ ID NO:9.

11. The bispecific agonistic CD28 antigen binding molecule of any one of paras 1 to 8, wherein the antigen binding domain capable of specific binding to Her2 comprises the CDRs of the heavy chain variable region ($V_H$Her2) comprising the amino acid sequence of SEQ ID NO:16 and the CDRs of the light chain variable region ($V_L$Her2) comprising the amino acid sequence of SEQ ID NO:17.

12. The bispecific agonistic CD28 antigen binding molecule of any one of paras 1 to 8 or 11, wherein the antigen binding domain capable of specific binding to Her2 comprises a heavy chain variable region ($V_H$Her2) comprising the amino acid sequence of SEQ ID NO:16, and a light chain variable region ($V_L$Her2) comprising the amino acid sequence of SEQ ID NO:17.

13. The bispecific agonistic CD28 antigen binding molecule of any one of paras 1 to 12, wherein the first antigen binding domain capable of specific binding to CD28 and/or the second antigen binding domain capable of specific binding to Her2 is a Fab molecule.

14. The bispecific agonistic CD28 antigen binding molecule of any one of paras 1 to 13, wherein the first antigen binding domain capable of specific binding to CD28 is a Fab molecule wherein the variable domains VL and VH or the constant domains CL and CH1, particularly the variable domains VL and VH, of the Fab light chain and the Fab heavy chain are replaced by each other.

15. The bispecific agonistic CD28 antigen binding molecule of any one of paras 1 to 14, wherein the second antigen binding domain capable of specific binding to Her2 is a conventional Fab molecule.

16. The bispecific agonistic CD28 antigen binding molecule of any one of paras 1 to 15, wherein the second antigen binding domain capable of specific binding to Her2 is a Fab molecule wherein in the constant domain CL the amino acid at position 123 (numbering according to Kabat EU index) is substituted by an amino acid selected from lysine (K), arginine (R) or histidine (H) and the amino acid at position 124 (numbering according to Kabat EU index) is substituted independently by lysine (K), arginine (R) or histidine (H), and wherein in the constant domain CH1 the amino acid at position 147 (numbering according to Kabat EU index) is substituted independently by glutamic acid (E) or aspartic acid (D) and the amino acid at position 213 (numbering according to Kabat EU index) is substituted independently by glutamic acid (E), or aspartic acid (D) (numbering according to Kabat EU index).

17. The bispecific agonistic CD28 antigen binding molecule of any one of paras 1 to 16, comprising
(i) a first light chain comprising the amino acid sequence of SEQ ID NO:92, a first heavy chain comprising the amino acid sequence of SEQ ID NO:91, a second heavy chain comprising the amino acid sequence of SEQ ID NO:96 and a second light chain comprising the amino acid sequence of SEQ ID NO:97, or
(ii) a first light chain comprising the amino acid sequence of SEQ ID NO:92, a first heavy chain comprising the amino acid sequence of SEQ ID NO:91, a second heavy chain comprising the amino acid sequence of SEQ ID NO:98 and a second light chain comprising the amino acid sequence of SEQ ID NO:97, or
(iii) a first light chain comprising the amino acid sequence of SEQ ID NO:92, a first heavy chain comprising the amino acid sequence of SEQ ID NO:91, a second heavy chain comprising the amino acid sequence of SEQ ID NO:101 and a second light chain comprising the amino acid sequence of SEQ ID NO:97.

18. The bispecific agonistic CD28 antigen binding molecule of any one of paras 1 to 13, wherein the second antigen binding domain capable of specific binding to Her2 is a Fab molecule wherein the variable domains VL and VH or the constant domains CL and CH1, particularly the variable domains VL and VH, of the Fab light chain and the Fab heavy chain are replaced by each other.

19. The bispecific agonistic CD28 antigen binding molecule of any one of paras 1 to 13 or 18, wherein the first antigen binding domain capable of specific binding to CD28 is a conventional Fab molecule.

20. The bispecific agonistic CD28 antigen binding molecule of any one of paras 1 to 13 or 18 or 19, wherein the first antigen binding domain capable of specific binding to CD28 is a Fab molecule wherein in the constant domain CL the amino acid at position 123 (numbering according to Kabat EU index) is substituted by an amino acid selected from lysine (K), arginine (R) or histidine (H) and the amino acid at position 124 (numbering according to Kabat EU index) is substituted independently by lysine (K), arginine (R) or histidine (H), and wherein in the constant domain CH1 the amino acid at position 147 (numbering according to Kabat EU index) is substituted independently by glutamic acid (E) or aspartic acid (D) and the amino acid at position 213 (numbering according to Kabat EU index) is substituted independently by glutamic acid (E), or aspartic acid (D) (numbering according to Kabat EU index).

21. The bispecific agonistic CD28 antigen binding molecule of any one of paras 1 to 13 or 18 to 20, comprising
(i) a first light chain comprising the amino acid sequence of SEQ ID NO:83, a first heavy chain comprising the amino acid sequence of SEQ ID NO:74, a second heavy chain comprising the amino acid sequence of SEQ ID NO:99 and a second light chain comprising the amino acid sequence of SEQ ID NO:100, or
(ii) a first light chain comprising the amino acid sequence of SEQ ID NO:83, a first heavy chain comprising the amino acid sequence of SEQ ID NO:74, a second heavy chain comprising the amino acid sequence of SEQ ID NO:102 and a second light chain comprising the amino acid sequence of SEQ ID NO:100.

22. The bispecific agonistic CD28 antigen binding molecule of any one of paras 1 to 21, wherein the first and the second antigen binding domain are each a Fab molecule and the Fc domain is composed of a first and a second subunit capable of stable association; and wherein (i) the first antigen binding domain is fused at the C-terminus of the Fab heavy chain to the N-terminus of the first subunit of the Fc domain and the second antigen binding domain is fused at the C-terminus of the Fab heavy chain to the N-terminus of the second subunit of the Fc domain, or (ii) the second antigen binding domain is fused at the C-terminus of the Fab heavy chain to the N-terminus of the first subunit of the Fc domain and the first antigen binding domain is fused at the C-terminus of the Fab heavy chain to the N-terminus of the second subunit of the Fc domain.

23. The bispecific agonistic CD28 antigen binding molecule of any one of paras 1 to 22, wherein the Fc domain comprises a modification promoting the association of the first and the second subunit of the Fc domain.

24. The bispecific agonistic CD28 antigen binding molecule of any one of paras 1 to 23, wherein the first subunit of the Fc domain comprises the amino acid substitutions S354C and T366W (EU numbering) and the second subunit of the Fc domain comprises the amino acid substitutions Y349C, T366S and Y407V (numbering according to Kabat EU index).

25. One or more isolated polynucleotide encoding the bispecific agonistic CD28 antigen binding molecule of any one of paras 1 to 24.

26. One or more vector, particularly expression vector, comprising the polynucleotide(s) of para 25.

27. A host cell comprising the polynucleotide(s) of para 25 or the vector(s) of para 26.

28. A method of producing a bispecific agonistic CD28 antigen binding molecule, comprising the steps of a) culturing the host cell of para 27 under conditions suitable for the expression of the bispecific agonistic CD28 antigen binding molecule and b) optionally recovering the bispecific agonistic CD28 antigen binding molecule.

29. A bispecific agonistic CD28 antigen binding molecule produced by the method of para 28.

30. A pharmaceutical composition comprising the bispecific agonistic CD28 antigen binding molecule of any one of paras 1 to 24 and at least one pharmaceutically acceptable excipient.

31. The bispecific agonistic CD28 antigen binding molecule of any one of paras 1 to 24, or the pharmaceutical composition of para 30, for use as a medicament.

32. The bispecific agonistic CD28 antigen binding molecule of any one of paras 1 to 24, or the pharmaceutical composition of para 30, for use in enhancing (a) T cell activation or (b) T cell effector functions.

33. The bispecific agonistic CD28 antigen binding molecule of any one of paras 1 to 24, or the pharmaceutical composition of para 30, for use in the treatment of a disease.

34. The bispecific agonistic CD28 antigen binding molecule or the pharmaceutical composition for use of para 33, wherein the disease is cancer.

35. The bispecific agonistic CD28 antigen binding molecule of any one of paras 1 to 24, or the pharmaceutical composition of para 30, for use in the treatment of cancer, wherein the use is for administration in combination with a chemotherapeutic agent, radiation therapy and/or other agents for use in cancer immunotherapy.

36. The bispecific agonistic CD28 antigen binding molecule of any one of paras 1 to 24, or the pharmaceutical composition of para 30, for use in the treatment of cancer, wherein the use is for administration in combination with a T-cell activating anti-CD3 bispecific antibody.

37. The bispecific agonistic CD28 antigen binding molecule of any one of paras 1 to 24, or the pharmaceutical composition of para 30, for use in the treatment of cancer, wherein the use is for administration in combination with an anti-PD-L1 antibody or an anti-PD-1 antibody.

38. Use of the bispecific agonistic CD28 antigen binding molecule of any one of claims 1 to 24, or the pharmaceutical composition of para 30, in the manufacture of a medicament for the treatment of a disease, particularly for the treatment of cancer.

39. A method of treating a disease, particularly cancer, in an individual, comprising administering to said individual an effective amount of the bispecific agonistic CD28 antigen binding molecule of any one of paras 1 to 24, or the pharmaceutical composition of para 30.

40. The method of para 39, further comprising administration in combination with a chemotherapeutic agent, radiation therapy and/or other agents for use in cancer immunotherapy, particularly a T-cell activating anti-CD3 bispecific antibody or an anti-PD-L1 antibody or an anti-PD-1 antibody.

EXAMPLES

The following are examples of methods and compositions of the invention. It is understood that various other embodiments may be practiced, given the general description provided above.

Recombinant DNA Techniques

Standard methods were used to manipulate DNA as described in Sambrook et al., Molecular cloning: A laboratory manual; Cold Spring Harbor Laboratory Press, Cold Spring Harbor, New York, 1989. The molecular biological reagents were used according to the manufacturer's instructions. General information regarding the nucleotide sequences of human immunoglobulin light and heavy chains is given in: Kabat, E. A. et al., (1991) Sequences of Proteins of Immunological Interest, Fifth Ed., NIH Publication No 91-3242.

DNA Sequencing

DNA sequences were determined by double strand sequencing.

Gene Synthesis

Desired gene segments, where required, were either generated by PCR using appropriate templates or were synthesized at Geneart AG (Regensburg, Germany) or Genscript (New Jersey, USA) from synthetic oligonucleotides and PCR products by automated gene synthesis. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow subcloning into the respective expression vectors. All constructs were designed with a 5'-end DNA sequence coding for a leader peptide which targets proteins for secretion in eukaryotic cells.

Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

Protein Purification

Proteins were purified from filtered cell culture supernatants referring to standard protocols. In brief, antibodies were applied to a Protein A Sepharose column (GE healthcare) and washed with PBS. Elution of antibodies was achieved at pH 2.8 followed by immediate neutralization of the sample. Aggregated protein was separated from monomeric antibodies by size exclusion chromatography (Superdex 200, GE Healthcare) in PBS or in 20 mM Histidine, 150 mM NaCl pH 6.0. Monomeric antibody fractions were pooled, concentrated (if required) using e.g., a MILLIPORE Amicon Ultra (30 MWCO) centrifugal concentrator, frozen and stored at −20° C. or −80° C. Part of the samples were provided for subsequent protein analytics and analytical characterization e.g. by SDS-PAGE, size exclusion chromatography (SEC) or mass spectrometry.

SDS-PAGE

The NuPAGE® Pre-Cast gel system (Invitrogen) was used according to the manufacturer's instruction. In particular, 10% or 4-12% NuPAGE® Novex® Bis-TRIS Pre-Cast gels (pH 6.4) and a NuPAGE® MES (reduced gels, with NuPAGE® Antioxidant running buffer additive) or MOPS (non-reduced gels) running buffer was used.

Analytical Size Exclusion Chromatography

Size exclusion chromatography (SEC) for the determination of the aggregation and oligomeric state of antibodies was performed by HPLC chromatography. Briefly, Protein A purified antibodies were applied to a Tosoh TSKgel G3000SW column in 300 mM NaCl, 50 mM $KH_2PO_4$/$K_2HPO_4$, pH 7.5 on an Agilent HPLC 1100 system or to a Superdex 200 column (GE Healthcare) in 2×PBS on a Dionex HPLC-System. The eluted protein was quantified by UV absorbance and integration of peak areas. BioRad Gel Filtration Standard 151-1901 served as a standard.

Mass Spectrometry

This section describes the characterization of the multispecific antibodies with VH/VL exchange (VH/VL CrossMabs) with emphasis on their correct assembly. The expected primary structures were analyzed by electrospray ionization mass spectrometry (ESI-MS) of the deglycosylated intact CrossMabs and deglycosylated/plasmin digested or alternatively deglycosylated/limited LysC digested CrossMabs.

The VH/VL CrossMabs were deglycosylated with N-Glycosidase F in a phosphate or Tris buffer at 37° C. for up to 17 h at a protein concentration of 1 mg/ml. The plasmin or limited LysC (Roche) digestions were performed with 100 µg deglycosylated VH/VL CrossMabs in a Tris buffer pH 8 at room temperature for 120 hours and at 37° C. for 40 min, respectively. Prior to mass spectrometry the samples were desalted via HPLC on a Sephadex G25 column (GE Healthcare). The total mass was determined via ESI-MS on a maXis 4G UHR-QTOF MS system (Bruker Daltonik) equipped with a TriVersa NanoMate source (Advion).

Determination of Binding and Binding Affinity of Multispecific Antibodies to the Respective Antigens using Surface Plasmon Resonance (SPR) (BIACORE)

Binding of the generated antibodies to the respective antigens is investigated by surface plasmon resonance using a BIACORE instrument (GE Healthcare Biosciences AB, Uppsala, Sweden). Briefly, for affinity measurements Goat-Anti-Human IgG, MR 109-005-098 antibodies are immobilized on a CM5 chip via amine coupling for presentation of the antibodies against the respective antigen. Binding is measured in HBS buffer (HBS-P (10 mM HEPES, 150 mM NaCl, 0.005% Tween 20, ph 7.4), 25° C. (or alternatively at 37° C.). Antigen (R&D Systems or in house purified) was added in various concentrations in solution. Association was measured by an antigen injection of 80 seconds to 3 minutes; dissociation was measured by washing the chip surface with HBS buffer for 3-10 minutes and a KD value was estimated using a 1:1 Langmuir binding model. Negative control data (e.g. buffer curves) are subtracted from sample curves for correction of system intrinsic baseline drift and for noise signal reduction. The respective Biacore Evaluation Software is used for analysis of sensorgrams and for calculation of affinity data.

Example 1

Generation and Production of Bispecific Antigen Binding Molecules Targeting CD28 and Human Epidermal Growth Factor Receptor-2 (Her2)

1.1 Cloning of Bispecific Antigen Binding Molecules Targeting CD28 and Human Epidermal Growth Factor Receptor-2 (Her2)

Cloning of the Antigen:

A DNA fragment encoding the extracellular domain (amino acids 1 to 134 of matured protein) of human CD28 (Uniprot: P10747) was inserted in frame into two different mammalian recipient vectors upstream of a fragment encoding a hum IgG1 Fc fragment which serves as solubility—and purification tag. One of the expression vectors contained the "hole" mutations in the Fc region, the other one the "knob" mutations as well as a C-terminal avi tag (GLNDIFEAQK-TEWHE, SEQ ID NO:88) allowing specific biotinylation during co-expression with Bir A biotin ligase. In addition, both Fc fragments contained the PG-LALA mutations. Both vectors were co-transfected in combination with a plasmid coding for the BirA biotin ligase in order to get a dimeric CD28-Fc construct with a monovalent biotinylated avi-tag at the C-terminal end of the Fc-knob chain.

Generation and Characterization of CD28 (SA) Variants Devoid of Hotspots and Reduced in Affinity The CD28 superagonistic antibody (SA) with a VH comprising the amino acid sequence of SEQ ID NO:24 and a VL comprising the amino acid sequences of SEQ ID NO:25 is described in WO 2006/050949.

Removal of an Unpaired Cysteine Residue, Tryptophan Residues, a Deamidation Site and Generation of Affinity-reduced CD28 (SA) Variants As part of our detailed binder characterization, a computational analysis of the CD28(SA) variable domain sequences was performed. This analysis revealed an unpaired cysteine in the CDR2 region of VH (position 50, Kabat numbering), tryptophan residues in CDR3 of VH (position 100a, Kabat numbering) and CDR1 of VL (position 32, Kabat numbering), and a potential asparagine deamidation site in CDR2 of VH (position 56, Kabat numbering). While oxidation of tryptophan is a rather slow process and can be prevented by adding reducing compounds, the presence of unpaired cysteines in an antibody variable domain can be critical. Free cysteines are reactive and can form stable bonds with other unpaired cysteines of other proteins or components of the cell or media. As a consequence, this can lead to a heterogeneous and instable product with unknown modifications which are potentially immunogenic and therefore may pose a risk for the patients. In addition, deamidation of asparagine and the resulting formation of iso-aspartate and succinimide can affect both in vitro stability and in vivo biological functions. A crystal structure analysis of the parental murine binder 5.11A revealed that C50 is not involved in binding to human CD28 and therefore can be replaced by a similar amino acid such as serine without affecting the affinity to CD28. Both tryptophan residues as well as asparagine at position 50, however, are close to or involved in the binding interface and a replacement by a similar amino acid can therefore lead to a reduction of the binding affinity. In this example, we particularly aimed at reducing the affinity of CD28(SA) to human CD28 because of the following reason: The affinity of CD28(SA) is in the range of 1-2 nM with a binding half-life of about 32 minutes. This strong affinity can lead to a sink effect in tissue containing large amounts of CD28- expressing cells such as blood and lymphatic tissue when injected intravenously into patients. As a consequence, site-specific targeting of the compound via the targeting component may be reduced and the efficacy of the construct can be diminished.

In order to minimize such an effect, several VH and VL variants were generated in order to reduce to affinities to different degrees (FIGS. 2A and 2C). Besides the previously mentioned positions that represent potential stability hotspots, additional residues involved directly or indirectly in the binding to human CD28 were replaced either by the original murine germline amino acid or by a similar amino acid. In addition, the CDRs of both CD28(SA) VL and VH were also grafted into the respective framework sequences of trastuzumab (FIGS. 2B and 2D). Several combinations of VH and VL variants were then expressed as monovalent one-armed anti-CD28 IgG-like constructs and binding was characterized by SPR.

Analysis of the Dissociation Rate Constants (kw) of Reduced One-armed Anti-cd28 Variants by SPR In order to characterize the anti-CD28 binder variants in a first step, all binders were expressed as monovalent one-armed IgG-like constructs (FIG. 1A). This format was chosen in order to characterize the binding to CD28 in a 1:1 model. 5 days after transfection into HEK cells, the supernatant was harvested and the titer of the expressed constructs was determined.

The off-rate of the anti-CD28 binder variants was determined by surface plasmon resonance (SPR) using a ProteOn XPR36 instrument (Biorad) at 25° C. with biotinylated huCD28-Fc antigen immobilized on NLC chips by neutravidin capture. For the immobilization of recombinant antigen (ligand), huCD28-Fc was diluted with PBST (Phophate buffered saline with Tween 20 consisting of 10 mM phosphate, 150 mM sodium chloride pH 7.4, 0.005% Tween 20) to concentrations ranging from 100 to 500 nM, then injected at 25 µl/minute at varying contact times. This resulted in immobilization levels between 1000 to 3000 response units (RU) in vertical orientation.

For one-shot kinetics measurements, injection direction was changed to horizontal orientation. Based on the titer of the produced supernatants, the monovalent one-armed IgGs were diluted with PBST to get two-fold dilution series ranging from 100 nM to 6.25 nM. Injection was performed simultaneously at 50 µl/min along separate channels 1-5, with association times of 120 s, and dissociation times of 300 s. Buffer (PBST) was injected along the sixth channel to provide an "in-line" blank for referencing. Since the binding interaction was measured with monovalent one-armed IgGs from supernatant without purification and biochemical characterization, only the off-rates of the protein:protein interaction was used for further conclusions. Off-rates were calculated using a simple one-to-one Langmuir binding model in ProteOn Manager v3.1 software by fitting the dissociation sensorgrams. The dissociation rate constants ($k_{off}$) values of all clones are summarized in Table 1. Comparison of the produced variants revealed $k_{off}$ values with an up to 30-fold decrease compared to the parental sequence.

TABLE 1

Summary of all expressed monovalent anti-CD28 variants with dissociation rate constants ($k_{off}$) values

| Binder variants | Tapir ID | SEQ ID NO: | SEQ ID NO: | SEQ ID NO: | $k_{off}(10^{-4}/M)$ |
|---|---|---|---|---|---|
| CD28(SA)_variant_1 (parental CD28) | P1AE4441 | 72 | 80 | 87 | 3.0 |
| CD28(SA)_variant_2 | P1AE3058 | 73 | 81 | 87 | N/A |
| CD28(SA)_variant_3 | P1AE3059 | 73 | 82 | 87 | N/A |
| CD28(SA)_variant_4 | P1AE3060 | 73 | 83 | 87 | N/A |
| CD28(SA)_variant_5 | P1AE3061 | 73 | 80 | 87 | N/A |
| CD28(SA)_variant_6 | P1AE3062 | 74 | 81 | 87 | N/A |
| CD28(SA)_variant_7 | P1AE3063 | 74 | 82 | 87 | 100 |
| CD28(SA)_variant_8 | P1AE3064 | 74 | 83 | 87 | 68 |
| CD28(SA)_variant_9 | P1AE3065 | 74 | 84 | 87 | 78 |
| CD28(SA)_variant_10 | P1AE3066 | 74 | 85 | 87 | N/A |
| CD28(SA)_variant_11 | P1AE3067 | 74 | 80 | 87 | 37 |
| CD28(SA)_variant_12 | P1AE3068 | 75 | 86 | 87 | 2.4 |
| CD28(SA)_variant_13 | P1AE3069 | 75 | 80 | 87 | 1.9 |
| CD28(SA)_variant_14 | P1AE3070 | 76 | 81 | 87 | 100 |
| CD28(SA)_variant_15 | P1AE3071 | 76 | 82 | 87 | 24 |
| CD28(SA)_variant_16 | P1AE3072 | 76 | 83 | 87 | 10 |
| CD28(SA)_variant_17 | P1AE3073 | 76 | 84 | 87 | 14 |
| CD28(SA)_variant_18 | P1AE3074 | 76 | 85 | 87 | 82 |
| CD28(SA)_variant_19 | P1AE3075 | 76 | 80 | 87 | 2.9 |
| CD28(SA)_variant_20 | P1AE3076 | 77 | 81 | 87 | N/A |
| CD28(SA)_variant_21 | P1AE3077 | 77 | 82 | 87 | N/A |
| CD28(SA)_variant_22 | P1AE3078 | 77 | 83 | 87 | 61 |
| CD28(SA)_variant_23 | P1AE3079 | 77 | 80 | 87 | 43 |
| CD28(SA)_variant_24 | P1AE3080 | 78 | 81 | 87 | 80 |
| CD28(SA)_variant_25 | P1AE3081 | 78 | 82 | 87 | 3.51 |
| CD28(SA)_variant_26 | P1AE3082 | 78 | 83 | 87 | 9.7 |
| CD28(SA)_variant_27 | P1AE3083 | 78 | 84 | 87 | 14 |
| CD28(SA)_variant_28 | P1AE3084 | 78 | 85 | 87 | 69 |
| CD28(SA)_variant_29 | P1AE3085 | 78 | 80 | 87 | 2.5 |
| CD28(SA)_variant_30 | P1AE3086 | 79 | 86 | 87 | 3.22 |
| CD28(SA)_variant_31 | P1AE3087 | 79 | 80 | 87 | 2.5 |

Figure 3A:
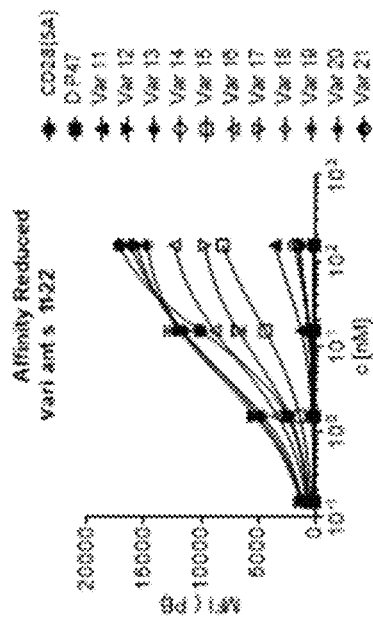
In FIG. 3A to 3C the binding of affinity-reduced CD28 agonistic antibody variants in monospecific, monovalent IgG formats from supernatants to human CD28 on cells is shown. Median fluorescence intensities of binding to CHO cells expressing human CD28 (parental cell line CHO-k1 ATCC #CCL-61, modified to stably overexpress human CD28) compared to the negative control (anti-DP47) and the original CD28 antibody CD28(SA), were assessed by flow cytometry. The binding curves of variants 1-10 are shown in FIG. 3A, those of variants 11 to 22 in FIG. 3B and those of variants 23 to 31 in FIG. 3C. Depicted are technical duplicates with SD.
Figure 3B:
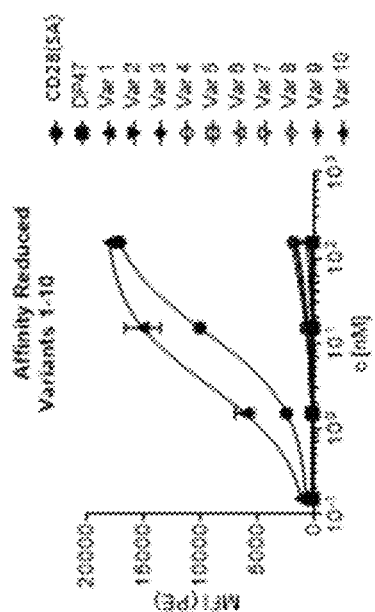
Figure 3C:
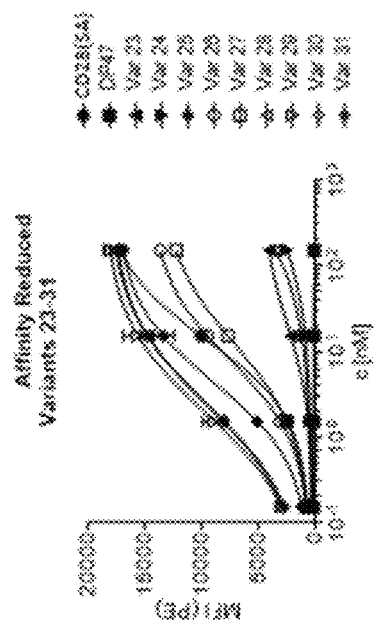

Binding to human CD28 was tested with CHO cells expressing human CD28 (parental cell line CHO-k1 ATCC #CCL-61, modified to stably overexpress human CD28). To assess binding, cells were harvested, counted, checked for viability and re-suspended at $2.5 \times 10^5$/ml in FACS buffer (eBioscience, Cat No 00-4222-26). $5 \times 10^4$ cells were incubated in round-bottom 96-well plates for 2 h at 4° C. with increasing concentrations of the CD28 binders (1 pM-100 nM). Then, cells were washed three times with cold FACS buffer, incubated for further 60 min at 4° C. with PE-conjugated, goat-anti human PE (Jackson ImmunoResearch, Cat No 109-116-098), washed once with cold FACS buffer, centrifuged and resuspended in 100 ul FACS buffer. To monitor unspecific binding interactions between constructs and cells, an anti-DP47 IgG was included as negative control. Binding was assessed by flow cytometry with a FACS Fortessa (BD, Software FACS Diva). Binding curves were obtained using GraphPadPrism6. The monovalent one-armed IgG-like CD28 variant constructs showed differences in binding as can be seen from FIG. 3A to 3C.

Cloning of Bispecific Antigen Binding Molecules Targeting CD28 and Her2

For the generation of the expression plasmids, the sequences of the respective variable domains were used and sub-cloned in frame with the respective constant regions which are pre-inserted in the respective recipient mammalian expression vector. In the Fc domain, Pro329Gly, Leu234Ala and Leu235Ala mutations (PG-LALA) have been introduced in the constant region of the human IgG1 heavy chains to abrogate binding to Fc gamma receptors according to the method described in International Patent Appl. Publ. No. WO 2012/130831. For the generation of bispecific antibodies, Fc fragments contained either the "knob" (T366W mutation, numbering according to EU index, optionally also the S354C mutation, numbering according to EU index) or "hole" mutations (T366S/L368A/Y407V mutations according to EU index, optionally also the Y349C mutation according to EU index) to avoid mispairing of the heavy chains. In some cases, the knob and hole antibodies were expressed in separate cells, purified, and assembled into the intact bispecific antibody as described previously. In order to avoid mispairing of light chains in the bispecific antigen binding molecules, exchange of VH/VL or CH1/Ckappa domains was introduced in one binding moiety (CrossFab technology). In another binding moiety, charges were introduced into the CH1 and Ckappa domains as described in International Patent Appl. Publ. No. WO 2015/150447.

The generation and preparation of the Her2 antibodies pertuzumab CLC and trastuzumab CLC is described in WO 2015/091738.

Figure 1B:
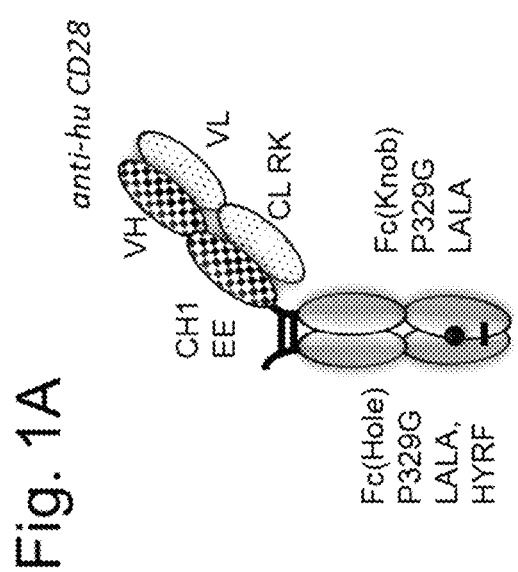
Figure 1C:
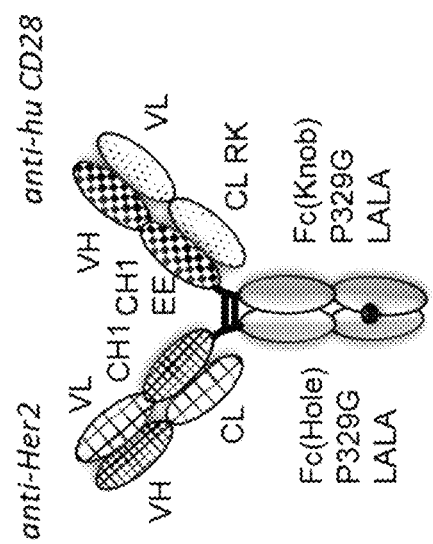
Figure 1D:
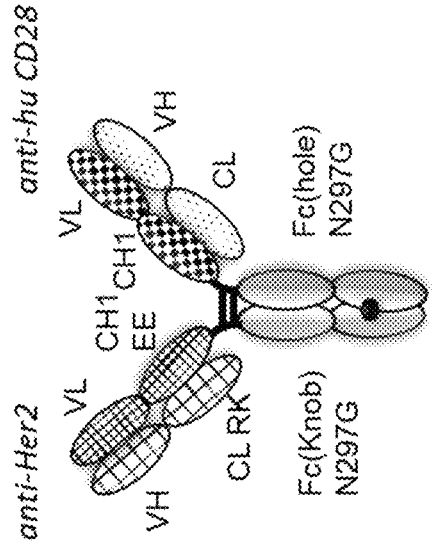

The following molecules were cloned, a schematic illustration thereof is shown in FIG. 1B, 1C or 1D:

Molecule A: Her2 (pertuzumab CLC_WT)-CD28 (SA_Variant 8) 1+1 format, bispecific huIgG1 wild-type/PG-LALA chimeric CrossFab molecule with VH/VL exchange in the CD28(SA_Variant 8) Fab fragment (knob) and charged modifications in the Her2 (pertuzumab CLC_WT) Fab fragment (hole) (FIG. 1B, however only the Fc knob chain comprises the PG-LALA mutations) comprising the heavy chain amino acid sequences of SEQ ID NOs: 91 and 96 and the light chain amino acid sequences of SEQ ID NOs: 92 and 97 (P1AF6741).

Molecule B: Her2 (pertuzumab CLC)-CD28 (SA_Variant 8) 1+1 format, bispecific huIgG1 PG-LALA CrossFab molecule with VH/VL exchange in the CD28(SA_Variant 8) Fab fragment (knob) and charged modifications in the Her2 (pertuzumab CLC) Fab fragment (hole) (FIG. 1B) comprising the heavy chain amino acid sequences of SEQ ID NOs: 91 and 98 and the light chain amino acid sequences of SEQ ID NOs: 92 and 97 (P1AF8305).

Molecule C: Her2 (pertuzumab CLC)-CD28 (SA_variant 8) 1+1, bispecific huIgG1 PG-LALA CrossFab molecule with charged modifications in the CD28(SA_Variant 8) Fab fragment (knob) and VH/VL exchange in the Her2 (pertuzumab CLC)-Fab fragment (hole) (FIG. 1D) comprising the heavy chain amino acid sequences of SEQ ID NOs: 74 and 99 and the light chain amino acid sequences of SEQ ID NOs: 83 and 100.

Molecule D: Her2 (trastuzumab CLC)-CD28 (SA_variant 8) 1+1, bispecific huIgG1 PG-LALA CrossFab molecule with VH/VL exchange in the CD28(SA_Variant 8) Fab fragment (knob) and charged modifications in the Her2 (trastuzumab CLC)-Fab fragment (hole) (FIG. 1B) comprising the heavy chain amino acid sequences of SEQ ID NOs: 91 and 101 and the light chain amino acid sequences of SEQ ID NOs: 92 and 97 (P1AF8338).

Molecule E: Her2 (trastuzumab CLC)-CD28 (SA_variant 8) 1+1, bispecific huIgG1 PG-LALA CrossFab molecule with charged modifications in the CD28(SA_Variant 8) Fab fragment (knob) and VH/VL exchange in the Her2 (trastuzumab CLC)Fab fragment (hole) (FIG. 1D) comprising the heavy chain amino acid sequences of SEQ ID NOs: 74 and 102 and the light chain amino acid sequences of SEQ ID NOs: 83 and 100.

Molecule F: Her2 (4D5)-CD28 (SA_variant 8) 1+1, bispecific huIgG1 N297G (FIG. 1C) comprising the heavy chain amino acid sequences of SEQ ID NOs: 178 and 180 and the light chain amino acid sequences of SEQ ID NOs: 179 and 181.

Molecule G: Her2 (2C4)-CD28 (SA_variant 8) 1+1, bispecific huIgG1 N297G (FIG. 1C) comprising the heavy chain amino acid sequences of SEQ ID NOs: 178 and 182 and the light chain amino acid sequences of SEQ ID NOs: 179 and 183.

1.2 Production of Bispecific Antigen Binding Molecules Targeting CD28 and Her2

Expression of the above-mentioned molecules is either driven by a chimeric MPSV promoter or a CMV promoter. Polyadenylation is driven by a synthetic polyA signal sequence located at the 3' end of the CDS. In addition, each vector contains an EBV OriP sequence for autosomal replication.

Antibodies and bispecific antibodies were generated by transient transfection of HEK293 EBNA cells or CHO EBNA cells. Cells were centrifuged and, medium was replaced by pre-warmed CD CHO medium (Thermo Fisher, Cat N° 10743029). Expression vectors were mixed in CD CHO medium, PEI (Polyethylenimine, Polysciences, Inc, Cat N° 23966-1) was added, the solution vortexed and incubated for 10 minutes at room temperature. Afterwards, cells (2 Mio/ml) were mixed with the vector/PEI solution, transferred to a flask and incubated for 3 hours at 37° C. in a shaking incubator with a 5% $CO_2$ atmosphere. After the incubation, Excell medium with supplements (80% of total volume) was added (W. Zhou and A. Kantardjieff, Mammalian Cell Cultures for Biologics Manufacturing, DOI: 10.1007/978-3-642-54050-9; 2014). One day after transfection, supplements (Feed, 12% of total volume) were added.

Cell supernatants were harvested after 7 days by centrifugation and subsequent filtration (0.2 µm filter), and proteins were purified from the harvested supernatant by standard methods as indicated below.

Alternatively, the antibodies and bispecific antibodies described herein were prepared by Evitria using their proprietary vector system with conventional (non-PCR based) cloning techniques and using suspension-adapted CHO K1 cells (originally received from ATCC and adapted to serum-free growth in suspension culture at Evitria). For the production, Evitria used its proprietary, animal-component free and serum-free media (eviGrow and eviMake2) and its proprietary transfection reagent (eviFect). Supernatant was harvested by centrifugation and subsequent filtration (0.2 µm filter) and, proteins were purified from the harvested supernatant by standard methods.

1.3 Purification of Bispecific Antigen Binding Molecules Targeting CD28 and Her2

Proteins were purified from filtered cell culture supernatants referring to standard protocols. In brief, Fc containing proteins were purified from cell culture supernatants by Protein A-affinity chromatography (equilibration buffer: 20 mM sodium citrate, 20 mM sodium phosphate, pH 7.5; elution buffer: 20 mM sodium citrate, pH 3.0). Elution was achieved at pH 3.0 followed by immediate pH neutralization of the sample. The protein was concentrated by centrifugation (Millipore Amicon® ULTRA-15 (Art.Nr.: UFC903096), and aggregated protein was separated from monomeric protein by size exclusion chromatography in 20 mM histidine, 140 mM sodium chloride, pH 6.0.

1.4 Analytical Data of Bispecific Antibodies Targeting CD28 and Her2

The concentrations of purified proteins were determined by measuring the absorption at 280 nm using the mass extinction coefficient calculated on the basis of the amino acid sequence according to Pace, et al., Protein Science, 1995, 4, 2411-1423. Purity and molecular weight of the proteins were analyzed by CE-SDS in the presence and absence of a reducing agent using a LabChipGXII or LabChip GX Touch (Perkin Elmer) (Perkin Elmer). Determination of the aggregate content was performed by HPLC chromatography at 25° C. using analytical size-exclusion column (TSKgel G3000 SW XL or UP-SW3000) equilibrated in running buffer (200 mM $KH_2PO_4$, 250 mM KCl pH 6.2, 0.02% $NaN_3$). A summary of the purification parameters of all molecules is given in Table 2.

Example 2

Binding of Bispecific CD28 Agonistic Antigen Binding Molecules Targeting Her2 to Her2- and CD28-Expressing Cells The binding of Her2-CD28 bispecific antigen binding molecules to Her2 was tested using human breast cancer cell line KPL-4 (Kawasaki Medical School) and the binding to human CD28 was tested with CHO cells expressing human CD28 (parental cell line CHO-k1 ATCC #CCL-61, modified to stably overexpress human CD28).

To assess binding, cells were harvested, counted, checked for viability and re-suspended at 2 Mio cells/ml in PBS $2×10^5$ cells were incubated in round-bottom 96-well plates (greiner bio-one, cellstar, Cat.-No. 650185) for 60 min at 4° C. with increasing concentrations of the Her2-CD28 construct or control molecule (DP47 huIgG1 P329G LALA comprising heavy chains of SEQ ID NO:186 and light chains of SEQ ID NO:187). Then, cells were washed twice with PBS, incubated for further 30 min at 4° C. with secondary binding R-Phycoerythrin AffiniPure F(ab')₂ Fragment Goat Anti-Human IgG, Fcγ fragment specific (Jackson ImmunoResearch, Cat. No. 109-116-098), washed twice with PBS, centrifuged and resuspended in 150 µl PBS+Dapi (4',6-Diamidine-2'-phenylindole dihydrochloride, 1:10000 dilution in PBS, 10236276001 Roche). Binding was assessed by flow cytometry with a FACS Fortessa (BD, Software FACS Diva). Binding curves were obtained using GraphPadPrism 7 (Graph Pad Software Inc.)

Figure 4A:
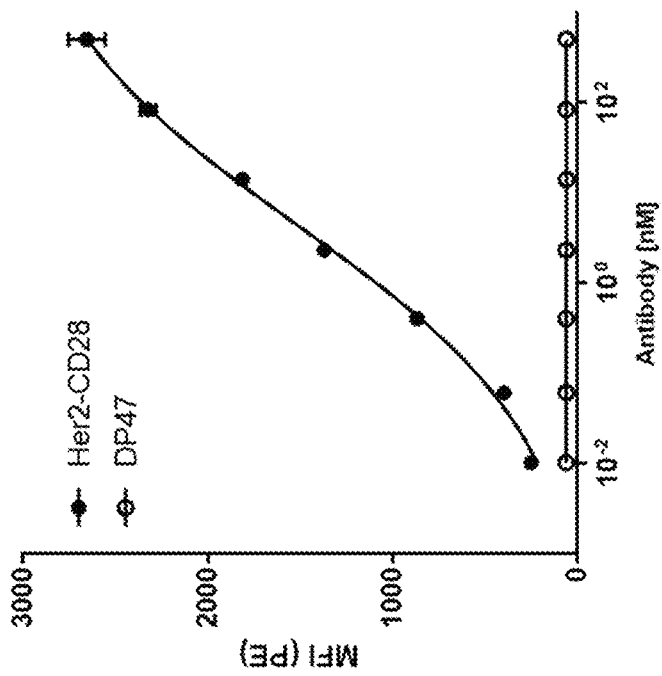
FIG. 4A shows the binding of the Her2-CD28 bispecific antigen binding molecules to Her2 expressed on the cell surface by human breast cancer cell line KPL-4. Her2-CD28 (P1AF6741) or control molecule (DP47 huIgG1 P329G LALA antibody) were incubated with Her2-expressing cell line KPL-4 at different concentrations as indicated in the X-axis. Afterwards excessive and not bound molecules were washed of and bound molecules were detected with a secondary binding R-Phycoerythrin AffiniPure F(ab')$_2$ Fragment Goat Anti-Human IgG, Fcγ fragment specific. The median of fluorescence intensity (MFI) was measured by flow cytometry and indicates the affinity of the tested molecules in a dose dependent manner. Values shown is the mean of technical duplicates+/−SEM.
Figure 4B:
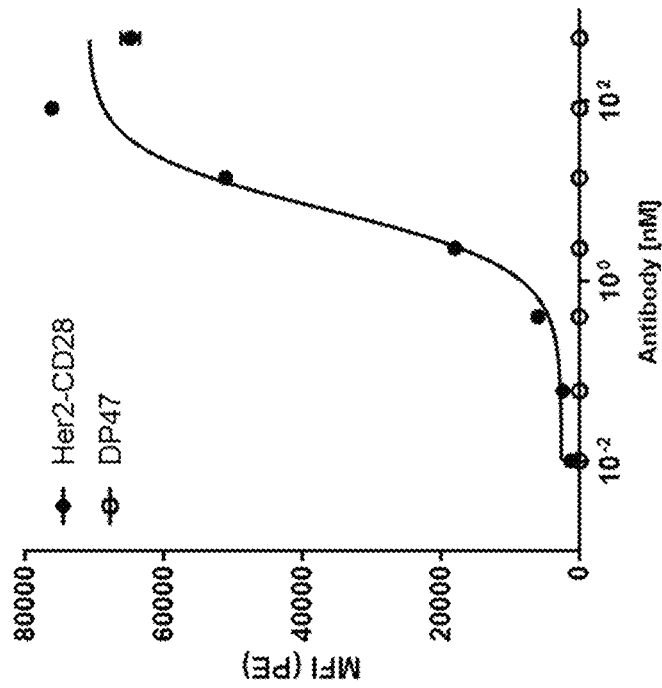
FIG. 4B shows the binding of the Her2-CD28 bispecific antigen binding molecules to CD28 expressed on the cell surface of CHOk1-huCD28 cell line. Her2-CD28 (P1AF6741) or control molecule (DP47 huIgG1 P329G LALA antibody) were incubated with CHOk1-huCD28 cell line at different concentrations as indicated in the X-axis. Afterwards excessive and not bound molecules were washed of and bound molecules were detected with a secondary binding R-Phycoerythrin AffiniPure F(ab')$_2$ Fragment Goat Anti-Human IgG, Fcγ fragment specific. The median of fluorescence intensity (MFI) was measured by flow cytometry and indicates the affinity of the tested molecules in a dose dependent manner. Values shown is the mean of technical duplicates+/−SEM.
Figure 6A:
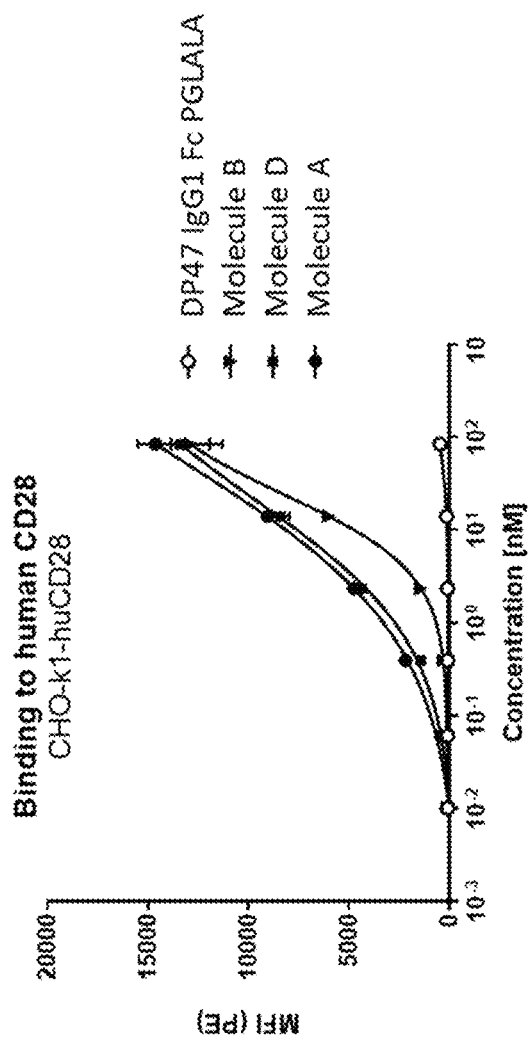
FIG. 6A shows the binding of Her2-CD28 bispecific antigen binding molecules B, D and A to Her2 expressed on the cell surface of the human breast cancer cell line KPL-4. All molecules, including the negative control (germline control DP47 IgG1 Fc PGLALA) were incubated in a concentration range of 0.01-500 nM in a 5-fold dilution. Afterwards, excessive and unbound molecules were washed of and bound molecules were detected with a Fcγ fragment specific, goat anti-human IgG R-Phycoerythrin AffiniPure F(ab')$_2$ secondary antibody. The median fluorescence intensity (MFI) was measured by flow cytometry and indicates the affinity of the tested molecules in a dose dependent manner. All values are depicted as the mean of technical triplicates+/−SEM.
Figure 6B:
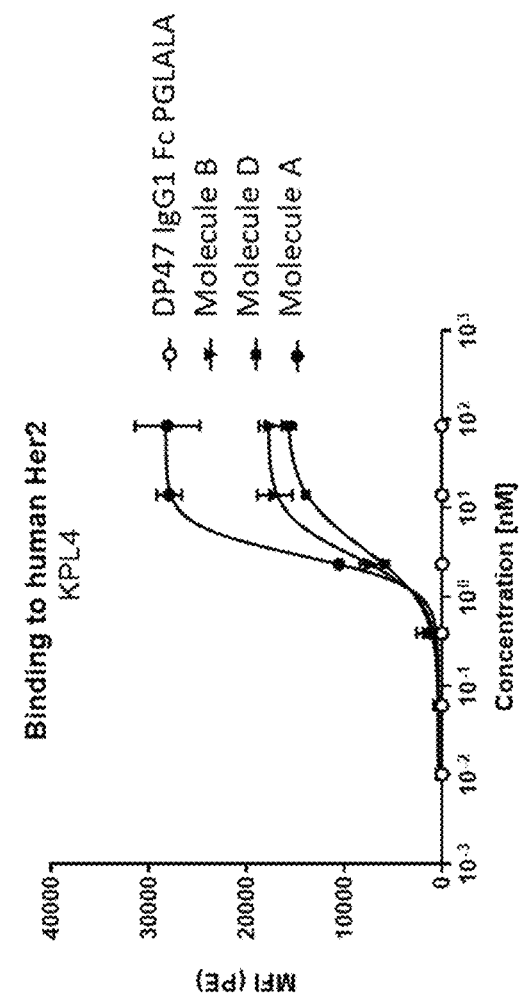
FIG. 6B shows the binding of Her2-CD28 bispecific antigen binding molecules B, D and A to CD28 expressed on the cell surface of CHOk1 huCD28. All molecules, including the negative control (DP47 IgG1 Fc PGLALA) were incubated in a concentration range of 0.01-500 nM in a 5-fold dilution. Afterwards, excessive and unbound molecules were washed of and bound molecules were detected with a Fcγ fragment specific, goat anti-human IgG R-Phycoerythrin AffiniPure F(ab')$_2$ secondary antibody. The median fluorescence intensity (MFI) was measured by flow cytometry and indicates the affinity of the tested molecules in a dose dependent manner. All values are depicted as the mean of technical triplicates+/−SEM.

As shown in FIGS. 4A and 4B and in FIGS. 6A and 6B, Her2-CD28 bispecific antigen binding molecules show binding to Her2 on KPL-4 cells and binding to CD28 on CHO-k1 (ATCC #CCL-61) cells expressing human CD28.

Example 3

In Vitro Functional Characterization of Bispecific CD28 Agonistic Antigen Binding Molecules Targeting Her2

3.1 In Vitro Functional Characterization of Bispecific CD28 Agonistic Antigen Binding Molecules Targeting Her2 Based on IL-2 Reporter Assay—Stimulation with CD3-IgG To assess the ability of Her2-CD28 bispecific antigen binding molecules to support anti-CD3-mediated T cell activation, Her2-CD28 bispecific antigen binding molecules were tested in an IL-2 reporter cell assay. IL-2 reporter cells

TABLE 2

Summary of the production and purification of bispecific CD28 antigen binding molecules

| Molecule | Description | Yield [mg/l] | Analytical SEC (HMW/Monomer/LMW) [%] | Purity measured by CE-SDS [%] |
|---|---|---|---|---|
| A | Her2 (Pertuzumab CLC_WT) - CD28 (SA_Variant 8) 1 + 1 | n.d. | 4.6/93.6/1.7 | 88.61 |
| B | Her2 (Pertuzumab CLC) - CD28 (SA_Variant 8) 1 + 1 | 68.16 | 3.3/93.6/3.1 | 80.71 |
| D | Her2 (Trastuzumab CLC) - CD28 (SA_Variant 8) 1 + 1 | 48.1 | 1.5/98.5/0 | 98.35 |

(Promega, Ca No J1651) served as effector cells (Jurkat T cell line that expresses a luciferase reporter driven by the IL-2 promoter) and KPL-4 cells served as tumor targets. DP47 huIgG1 P329G LALA antibody was included as non-binding control. 10000 tumor target cells were incubated in white & flat bottom 96 well plate (Greiner 655083) for 6 h at 37° C. with 50000 IL-2 reporter cells (E:T 5:1) in presence of 10 nM anti-CD3 (eBioscience #16-0037-85) alone or in combination with increasing concentrations of the Her2-CD28 bispecific antibodies (2.44 pM-10 nM). Prior to the measurement, plates were incubated at room temperature for 15 min, and then 100 µl of substrate (ONE-Glo solution, Promega, Ca No E6120) was added to the cells. After 10 min of incubation at room temperature in the dark, luminescence (counts/sec) was measured with a Tecan Spark 10M.

Figure 5:
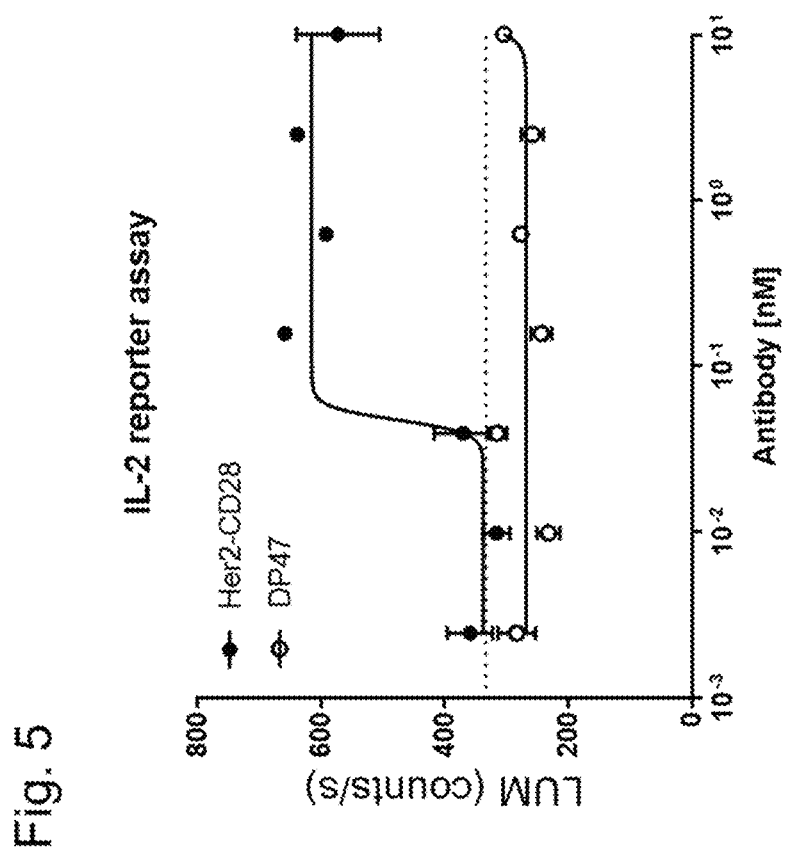
FIG. 5 shows that Her2-CD28 bispecific antigen binding molecules enhance T cell response to anti-CD3 stimulus in the IL-2 reporter assay in presence of KPL-4 cells. Shown is the IL-2 reporter cell activation measured by luminescence readout after 6 hours of co-incubation with KPL-4 cells in presence of suboptimal concentrations of anti-CD3 IgG clone OKT3 (10 nM) and increasing concentrations of Her2-CD28 (P1AF6741) or control molecule (DP47). Dotted line shows anti-CD3 only. Values shown is the mean of technical duplicates+/−SEM.
Figure 7A:
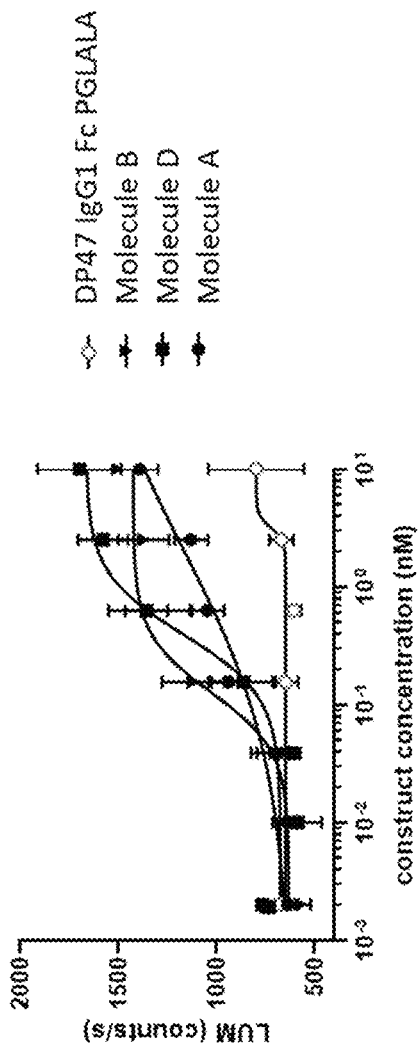
FIG. 7A and FIG. 7B show a comparison between crossed variants of Trastuzumab CLC-CD28 (Molecule D) and Pertuzumab CLC-CD28 (Molecules A and B) in the presence (FIG. 7A) or absence (FIG. 7B) of KPL4 tumor target cells. DP47 IgG1 Fc PGLALA was included as non-binding control. Reporter and target cells were plated in with an E:T ratio of 5:1. After addition of anti-CD3 to a concentration of 10 nM, the molecules were incubated in concentrations ranging from 0.002 to 10 nM with a dilution factor of 4. Upon 6 hours of incubation, substrate buffer was added and luminescence measured. All values are depicted as the mean of technical duplicates+/−SEM.
Figure 7B:
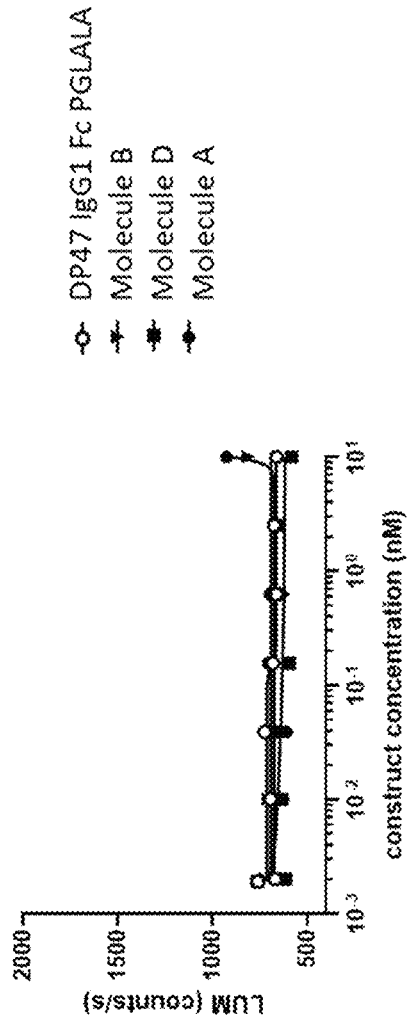

As depicted in FIG. 5 and FIG. 7A, Her2-CD28 bispecific antigen binding molecules were able to enhance T cell activation, as judged by increased IL-2 production in T cells exposed to suboptimal CD3 stimulation in a concentration dependent manner. No T cell activation could be observed for DP47 huIgG1 P329G LALA antibody or in the absence of Her2-expressing KPL4 tumor cells (FIG. 7B).

3.2 In Vitro Assessment of T Cell Activation by Bispecific CD28 Agonistic Antigen Binding Molecules Targeting Her2 using Peripheral Blood Mononuclear Cells (PBMCs)

The effect of Her2-CD28 bispecific antigen binding molecules on HER2 TDB induced T cell activation was tested by treating healthy donor PBMC and Her2 amplified KPL-4 breast cancer cells with HER2 TDB in the presence or absence of mono- or bispecific CD28 agonist antibodies. Activation of CD4 and CD8 T cells was measured by flow cytometry.

Figure 8A:
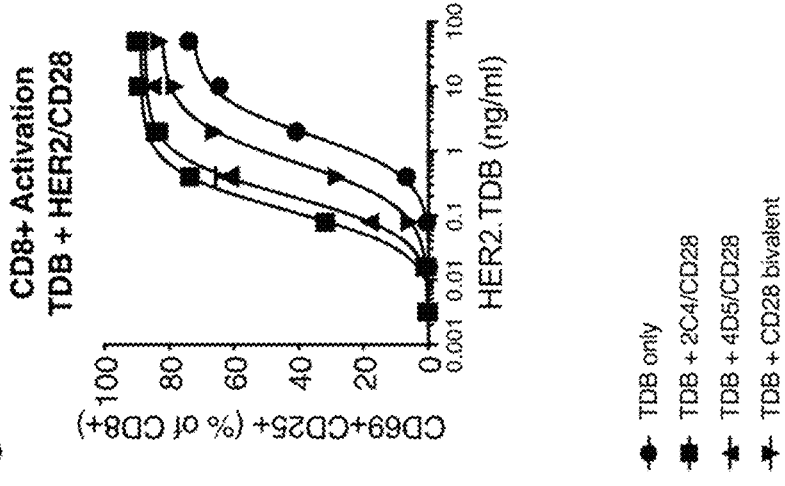
FIG. 8A is a graph showing the effect of Her2-CD28 bispecific antigen binding molecules 2C4/CD28 (Molecule F) and 4D5/CD28 (Molecule G) as well as the CD28 antibody at a concentration of 500 ng/mL on HER2 TDB induced activation of human $CD4^+$ T cells cultured with high Her2-expressing cell line KPL4. T cell activation was measured by dual expression of CD69 and CD25.
Figure 8B:
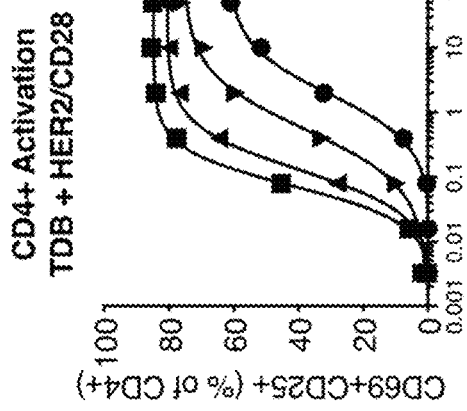
FIG. 8B is a graph showing the effect of Her2-CD28 bispecific antigen binding molecules 2C4/CD28 and 4D5/CD28 as well as the CD28 antibody at a concentration of 500 ng/mL on HER2 TDB induced activation of human $CD8^+$ T cells cultured with high Her2-expressing cell line KPL4. T cell activation was measured by dual expression of CD69 and CD25.

Human PBMC and tumor target cells (KPL-4) (in 10:1 ratio) were incubated in the presence of HER2 TDB (a Her2-CD3 bispecific antibody comprising a heavy chain HC1 of SEQ ID NO: 174, a light chain LC1 of SEQ ID NO: 175, a second heavy chain HC2 of SEQ ID NO: 176 and a second light chain of SEQ ID NO: 177) with Her2-CD28 bispecific antigen binding molecules Her2(4D5)/CD28 or Her2 (2C4)/CD28 (500 ng/ml) or monospecific anti-CD28 antibody (CD28 bivalent, 500 ng/ml) for 24 hours in flat-bottom 96-well plate (BD). After incubation, cells were transferred to a new V-bottom 96-well plate. Cells were stained with CD4-PE-Cy7, CD8-FITC, CD69-PE, and CD25-APC. CD69 and CD25 surface expression was detected on CD4$^+$ or CD8$^+$ T cells by flow cytometry. The percentages of CD4$^+$CD69$^+$CD25$^+$ and CD8$^+$CD69$^+$CD25$^+$ T cells were reported as CD4$^+$ (FIG. 8A) and CD8$^+$ T cell activation (FIG. 8B).

As expected, single agent treatment with HER2 TDB resulted in a robust activation of both CD4 and CD8 cells. Combination treatment of HER2 TDB with any of the three CD28 agonists further increased both the fraction activated T cells and the potency of T cell activation. The Her2-targeted bispecific antigen binding molecules enhanced the T cell activation more potently compared to the non-targeted bivalent CD28 antibody.

3.3 In Vitro Assessment of Tumor Cell Killing by Bispecific CD28 Agonistic Antigen Binding Molecules Targeting Her2 in the Presence of Her2 TDB The same experimental set-up as in Example 3.2 was used to analyze the effect of CD28 co-stimulation on HER2 TDB induced tumor cell killing. Loss of tumor cell viability was detected by Cell Titer-Glow Luminescent Cell Viability assay. To assess the ability of bispecific Her2-CD28 antigen binding molecules to achieve tumor cell killing or support TDB-mediated tumor cell killing, Her2-expressing KPL-4 cells served as tumor targets. Target cells KPL-4 were plated in black, clear-bottomed 96-well plates at density of 10,000 cells per well. Human PBMC were added to the wells in 10:1 E:T ratio. HER2 TDB as indicated concentrations were added to the wells with Her2-CD28 bispecific antigen binding molecules Her2(4D5)/CD28 or Her2 (2C4)/CD28 (500 ng/ml). After 48 hours, the plates were washed twice with PBS. 100 uL Cell Titer-Glow Luminescent Cell Viability reagent (Promega cat #G7570) was added and plates were read on luminometer as described in the instructions.

Figure 8C:
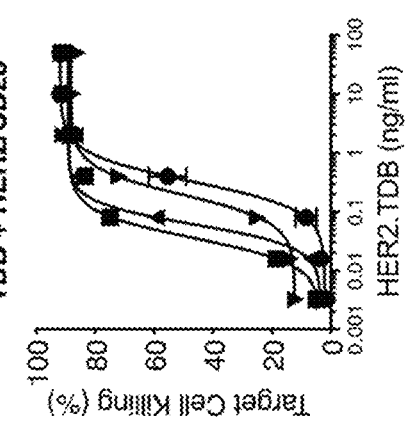
FIG. 8C is a graph showing the effect of Her2-CD28 bispecific antigen binding molecules 2C4/CD28 and 4D5/CD28 as well as the CD28 antibody on HER2 TDB mediated target cell killing of KPL-4 tumor cells.

Combination treatment with any of the three CD28 agonists increased the potency of HER2 TDB in mediating killing of KPL-4 cells (FIG. 8C). Similar to T cell activation, the effect of HER2 targeted bispecific CD28 antigen binding molecules was stronger compared to the non-targeted bivalent CD28 antibody. Her2 targeting using anti-HER2 clone 2C4 resulted in enhanced responses compared to Her2 targeting using anti-HER2 clone 4D5 in both T cell activation and tumor cell killing, likely due to a non-competitive binding with 4D5 targeted HER2 TDB.

3.4 In Vitro Cytokine Release Assay

Supernatants were harvested from the T cell activation assay 24 h after the treatments for analysis of soluble cytokines. The supernatant samples collected from the in vitro T cell activation assay (described in Example 3.2) were studied using the Bio-Plex Pro Human Cytokine Assay (Biorad; Hercules, CA) following the manufacturer's instructions.

Addition of bivalent CD28 antibody had only a minor effect on HER2 TDB induced cytokine release whereas the addition of either HER2-targeted CD28 bispecific antigen binding molecule resulted in substantial increase of all measured cytokines. In FIGS. 9A to 9G, the cytokine release of GM-CSF (FIG. 9A), IFN-gamma (FIG. 9B), IL-10 (FIG. 9C), IL-6 (FIG. 9D), TNF-alpha (FIG. 9E), IL-2 (FIG. 9F) and IL-1b (FIG. 9G) is shown.

3.5 In Vitro T Cell and NK Cell Numbers Count

The effect of CD28 co-stimulation on immune cell numbers was measured by flow cytometry on various timepoints up to weeks after treatment with HER2-TDB. Human PBMC were labeled with carboxyfluorescein succinimidyl ester (CFSE; ThermoFisher Scientific; Waltham, MA) following the manufacturer's instructions. CFSE labeled PBMC and target cells (KPL-4) (in 10:1 ratio) were incubated in the presence or the absence of 50 ng of HER2 TDB and 500 ng/ml of Her2-CD28 bispecific antigen binding molecules Her2(4D5)/CD28 or Her2 (2C4)/CD28 in flat-bottom 96-well plate (BD) for 3, 7, 10 or 14 days. In the end of the incubation time, cells were stained for CD4-PE-Cy7, CD8-pacific blue, CD56-APC and cell numbers were counted using counting beads with flow cytometry.

Co-treatment with any of the three CD28 agonist molecules resulted in increased numbers of CD4$^+$ cells at days 7-14 compared to samples treated with HER2 TDB only (FIG. 10B). All CD28 agonist molecules also clearly increased CD8$^+$ cell numbers at day 14, whereas NK cell numbers were only slightly increased by the two Her2-targeted bispecific CD28 antigen binding molecules (FIG. 10D). Similarly to T cell activation, tumor cell killing and cytokine release, co-treatment with HER2-targeted bispecific antigen binding molecules resulted in a more robust increase in immune cell numbers compared to the bivalent CD28 antibody.

REFERENCES

Acuto, O., and Michel, F. (2003). CD28-mediated co-stimulation: a quantitative support for TCR signalling. Nat Rev Immunol 3, 939-951.

Bahlis N. J., King A. M., Kolonias D. Carlson L. M., Liu H. Y., Hussein M. A., Terebelo H. R., Byrne G. E. Jr, Levine B. L., Boise L. H., Lee K. P. (2007). CD28-mediated regulation of multiple myeloma cell proliferation and survival. Blood 109 (11), 5002-5010.

Boomer, J. S., and Green, J. M. (2010). An enigmatic tail of CD28 signaling. Cold Spring Harb Perspect Biol 2, a002436.

Carreno, B. M., and Collins, M. (2002). The B7 family of ligands and its receptors: new pathways for costimulation and inhibition of immune responses. Annu Rev Immunol 20, 29-53.

Chen, L., and Flies, D. B. (2013). Molecular mechanisms of T cell co-stimulation and co-inhibition. Nat Rev Immunol 13, 227-242.

Engelhardt, J. J., Sullivan, T. J., and Allison, J. P. (2006). CTLA-4 overexpression inhibits T cell responses through a CD28-B7-dependent mechanism. J Immunol 177, 1052-1061.

Esensten, J. H., Helou, Y. A., Chopra, G., Weiss, A., and Bluestone, J. A. (2016). CD28 Costimulation: From Mechanism to Therapy. Immunity 44, 973-988.

Fraser, J. D., Irving, B. A., Crabtree, G. R., and Weiss, A. (1991). Regulation of interleukin-2 gene enhancer activity by the T cell accessory molecule CD28. Science 251, 313-316.

Gao Y., Wang X., Yan H., Zeng J., Ma S., Niu Y., Zhou G., Jiang Y., Chen Y. (2016). Comparative Transcriptome Analysis of Fetal Skin Reveals Key Genes Related to Hair Follicle Morphogenesis in Cashmere Goats. PLoS One 11(3), e0151118.

Hui, E., Cheung, J., Zhu, J., Su, X., Taylor, M. J., Wallweber, H. A., Sasmal, D. K., Huang, J., Kim, J. M., Mellman, I., and Vale, R. D. (2017). T cell costimulatory receptor CD28 is a primary target for PD-1-mediated inhibition. Science 355, 1428-1433.

Hunig, T. (2012). The storm has cleared: lessons from the CD28 superagonist TGN1412 trial. Nat Rev Immunol 12, 317-318.

June, C. H., Ledbetter, J. A., Gillespie, M. M., Lindsten, T., and Thompson, C. B. (1987). T-cell proliferation involving the CD28 pathway is associated with cyclosporine-resistant interleukin 2 gene expression. Mol Cell Biol 7, 4472-4481.

Kamphorst, A. O., Wieland, A., Nasti, T., Yang, S., Zhang, R., Barber, D. L., Konieczny, B. T., Daugherty, C. Z., Koenig, L., Yu, K., et al. (2017). Rescue of exhausted CD8 T cells by PD-1-targeted therapies is CD28-dependent. Science 355, 1423-1427.

Lavin, Y., Kobayashi, S., Leader, A., Amir, E. D., Elefant, N., Bigenwald, C., Remark, R., Sweeney, R., Becker, C. D., Levine, J. H., et al. (2017). Innate Immune Landscape in Early Lung Adenocarcinoma by Paired Single-Cell Analyses. Cell 169, 750-765 e717.

Linsley, P. S., Clark, E. A., and Ledbetter, J. A. (1990). T-cell antigen CD28 mediates adhesion with B cells by interacting with activation antigen B7/BB-1. Proc Natl Acad Sci USA 87, 5031-5035.

Murray M. E., Gavile C. M., Nair J. R., Koorella C., Carlson L. M., Buac D., Utley A., Chesi M., Bergsagel P. L., Boise L. H., Lee K. P. (2014). CD28-mediated pro-survival signaling induces chemotherapeutic resistance in multiple myeloma. Blood 123 (24), 3770-3779.

Römer, P. S., Berr, S., Avota, E., Na, S. Y., Battaglia, M., ten Berge, I., Einsele, H., and Hunig, T. (2011). Preculture of PBMCs at high cell density increases sensitivity of T-cell responses, revealing cytokine release by CD28 superagonist TGN1412. Blood 118, 6772-6782.

Tai, X., Van Laethem, F., Sharpe, A. H., and Singer, A. (2007). Induction of autoimmune disease in CTLA-4-/- mice depends on a specific CD28 motif that is required for in vivo costimulation. Proc Natl Acad Sci USA 104, 13756-13761.

Thompson, C. B., Lindsten, T., Ledbetter, J. A., Kunkel, S. L., Young, H. A., Emerson, S. G., Leiden, J. M., and June, C. H. (1989). CD28 activation pathway regulates the production of multiple T-cell-derived lymphokines/cytokines. Proc Natl Acad Sci USA 86, 1333-1337.

Zheng, C., Zheng, L., Yoo, J. K., Guo, H., Zhang, Y., Guo, X., Kang, B., Hu, R., Huang, J. Y., Zhang, Q., et al. (2017). Landscape of Infiltrating T Cells in Liver Cancer Revealed by Single-Cell Sequencing. Cell 169, 1342-1356 e1316.

The invention claimed is:

1. A bispecific agonistic CD28 antigen binding molecule characterized by monovalent binding to CD28, comprising
   (a) a first antigen binding domain capable of specific binding to CD28,
   (b) a second antigen binding domain capable of specific binding to an antigen binding domain capable of specific binding to human epidermal growth factor receptor-2 (Her2), and
   (c) a Fc domain composed of a first and a second subunit capable of stable association comprising one or more amino acid substitution that reduces the binding affinity of the antigen binding molecule to an Fc receptor and/or effector function,
   wherein said second antigen binding domain capable of specific binding to Her2 comprises
   (i) a heavy chain variable region (VHHer2) comprising a heavy chain complementary determining region CDR-H1 of SEQ ID NO: 2, a CDR-H2 of SEQ ID NO: 3, and a CDR-H3 of SEQ ID NO: 4, and a light chain variable region (VLHer2) comprising a light chain complementary determining region CDR-L1 of SEQ ID NO: 5, a CDR-L2 of SEQ ID NO: 6 and a CDR-L3 of SEQ ID NO: 7; or
   (ii) a heavy chain variable region (VHHer2) comprising a heavy chain complementary determining region CDR-H1 of SEQ ID NO: 10, a CDR-H2 of SEQ ID NO: 11, and a CDR-H3 of SEQ ID NO: 12, and a light chain variable region (VLHer2) comprising a light chain complementary determining region CDR-L1 of SEQ ID NO: 13, a CDR-L2 of SEQ ID NO: 14 and a CDR-L3 of SEQ ID NO: 15; or
   (iii) a heavy chain variable region (VHHer2) comprising a heavy chain complementary determining region CDR-H1 of SEQ ID NO: 132, a CDR-H2 of SEQ ID NO: 133, and a CDR-H3 of SEQ ID NO: 134, and a light chain variable region (VLHer2) comprising a light chain complementary determining region CDR-L1 of SEQ ID NO: 135, a CDR-L2 of SEQ ID NO: 136 and a CDR-L3 of SEQ ID NO: 137, or
   (iv) a heavy chain variable region (VHHer2) comprising a heavy chain complementary determining region CDR-H1 of SEQ ID NO: 140, a CDR-H2 of SEQ ID NO: 141, and a CDR-H3 of SEQ ID NO: 142, and a light chain variable region (VLHer2) comprising a light chain complementary determining region CDR-L1 of SEQ ID NO: 143, a CDR-L2 of SEQ ID NO: 144 and a CDR-L3 of SEQ ID NO: 145; and wherein the first antigen binding domain capable of specific binding to CD28 comprises
   (i) a heavy chain variable region (VHCD28) comprising a heavy chain complementary determining region CDR-H1 of SEQ ID NO: 26, a CDR-H2 of SEQ ID NO: 27, and a CDR-H3 of SEQ ID NO: 28, and a light chain variable region (VLCD28) comprising a light chain complementary determining region CDR-L1 of SEQ ID NO: 29, a CDR-L2 of SEQ ID NO: 30 and a CDR-L3 of SEQ ID NO: 31; or
   (ii) a heavy chain variable region (VHCD28) comprising a CDR-H1 of SEQ ID NO: 18, a CDR-H2 of SEQ ID NO: 19, and a CDR-H3 of SEQ ID NO: 20, and a light chain variable region (VLCD28) comprising a CDR-L1 of SEQ ID NO: 21, a CDR-L2 of SEQ ID NO: 22 and a CDR-L3 of SEQ ID NO: 23; or
   (iii) a heavy chain variable region (VHCD28) comprising a CDR-H1 of SEQ ID NO: 58, a CDR-H2 of SEQ ID NO: 59, and a CDR-H3 of SEQ ID NO: 60, and a light chain variable region (VLCD28) comprising a CDR-L1 of SEQ ID NO: 61, a CDR-L2 of SEQ ID NO: 62 and a CDR-L3 of SEQ ID NO: 63; or
   (iv) a heavy chain variable region (VHCD28) comprising a CDR-H1 of SEQ ID NO: 64, a CDR-H2 of SEQ ID NO: 65, and a CDR-H3 of SEQ ID NO: 66, and a light chain variable region (VLCD28) comprising a CDR-L1 of SEQ ID NO: 67, a CDR-L2 of SEQ ID NO: 68 and a CDR-L3 of SEQ ID NO: 69.

2. The bispecific agonistic CD28 antigen binding molecule of claim 1, wherein the Fc domain is of human IgG1 subclass and comprises amino acid mutations L234A, L235A and P329G, wherein the numbering in each case is according to the Kabat EU index.

3. The bispecific agonistic CD28 antigen binding molecule of claim 1 or claim 2, wherein the first antigen binding domain capable of specific binding to CD28 comprises a heavy chain variable region ($V_H$CD28) comprising an amino acid sequence that is at least about 95%, 96%, 97%, 98%, 99% or 100% identical to the amino acid sequence of SEQ ID NO:24, and a light chain variable region ($V_L$CD28) comprising an amino acid sequence that is at least about 95%, 96%, 97%, 98%, 99% or 100% identical to the amino acid sequence of SEQ ID NO:25.

4. The bispecific agonistic CD28 antigen binding molecule of claim 3, wherein the first antigen binding domain capable of specific binding to CD28 comprises a heavy chain variable region ($V_H$CD28) comprising an amino acid sequence selected from the group consisting of SEQ ID NO:32, SEQ ID NO:33, SEQ ID NO:34, SEQ ID NO:35, SEQ ID NO:36, SEQ ID NO:38, SEQ ID NO:39, SEQ ID NO:40 and SEQ ID NO:41, and a light chain variable region (V$_L$CD28) comprising an amino acid sequence selected from the group consisting of SEQ ID NO:25, SEQ ID NO:42, SEQ ID NO:43, SEQ ID NO:45, SEQ ID NO:46, SEQ ID NO:47, SEQ ID NO:48, SEQ ID NO:49, SEQ ID NO:50 and SEQ ID NO:51.

5. The bispecific agonistic CD28 antigen binding molecule of claim 4, wherein the first antigen binding domain capable of specific binding to CD28 comprises
(a) a heavy chain variable region (V$_H$CD28) comprising the amino acid sequence of SEQ ID NO:37 and a light chain variable region (V$_L$CD28) comprising the amino acid sequence of SEQ ID NO:25, or
(b) a heavy chain variable region (V$_H$CD28) comprising the amino acid sequence of SEQ ID NO:41 and a light chain variable region (V$_L$CD28) comprising the amino acid sequence of SEQ ID NO:51, or
(c) a heavy chain variable region (V$_H$CD28) comprising the amino acid sequence of SEQ ID NO:36 and a light chain variable region (V$_L$CD28) comprising the amino acid sequence of SEQ ID NO:43, or
(d) a heavy chain variable region (V$_H$CD28) comprising the amino acid sequence of SEQ ID NO:36 and a light chain variable region (V$_L$CD28) comprising the amino acid sequence of SEQ ID NO:44, or
(e) a heavy chain variable region (V$_H$CD28) comprising the amino acid sequence of SEQ ID NO:36 and a light chain variable region (V$_L$CD28) comprising the amino acid sequence of SEQ ID NO:49, or
(f) a heavy chain variable region (V$_H$CD28) comprising the amino acid sequence of SEQ ID NO:36 and a light chain variable region (V$_L$CD28) comprising the amino acid sequence of SEQ ID NO:25, or
(g) a heavy chain variable region (V$_H$CD28) comprising the amino acid sequence of SEQ ID NO:33 and a light chain variable region (V$_L$CD28) comprising the amino acid sequence of SEQ ID NO:25, or
(h) a heavy chain variable region (V$_H$CD28) comprising the amino acid sequence of SEQ ID NO:32 and a light chain variable region (V$_L$CD28) comprising the amino acid sequence of SEQ ID NO:43, or
(i) a heavy chain variable region (V$_H$CD28) comprising the amino acid sequence of SEQ ID NO:32 and a light chain variable region (V$_L$CD28) comprising the amino acid sequence of SEQ ID NO:49, or
(j) a heavy chain variable region (V$_H$CD28) comprising the amino acid sequence of SEQ ID NO:32 and a light chain variable region (V$_L$CD28) comprising the amino acid sequence of SEQ ID NO:25.

6. The bispecific agonistic CD28 antigen binding molecule of claim 1, wherein the first antigen binding domain capable of specific binding to CD28 comprises a heavy chain variable region (VHCD28) comprising a heavy chain complementary determining region CDR-H1 of SEQ ID NO: 52, a CDR-H2 of SEQ ID NO: 53, and a CDR-H3 of SEQ ID NO: 54, and a light chain variable region (VLCD28) comprising a light chain complementary determining region of CDR-L1 of SEQ ID NO: 55, a CDR-L2 of SEQ ID NO: 56 and a CDRL-3 of SEQ ID NO: 57.

7. The bispecific agonistic CD28 antigen binding molecule of claim 1, wherein the antigen binding domain capable of specific binding to Her2 comprises the CDRs of the heavy chain variable region (V$_H$Her2) comprising the amino acid sequence of SEQ ID NO:8 and the CDRs of the light chain variable region (V$_L$Her2) comprising the amino acid sequence of SEQ ID NO:9.

8. The bispecific agonistic CD28 antigen binding molecule of claim 7, wherein the antigen binding domain capable of specific binding to Her2 comprises a heavy chain variable region (V$_H$Her2) comprising the amino acid sequence of SEQ ID NO:8, and a light chain variable region (V$_L$Her2) comprising the amino acid sequence of SEQ ID NO:9.

9. The bispecific agonistic CD28 antigen binding molecule of claim 1, wherein the antigen binding domain capable of specific binding to Her2 comprises the CDRs of the heavy chain variable region (V$_H$Her2) comprising the amino acid sequence of SEQ ID NO:16 and the CDRs of the light chain variable region (V$_L$Her2) comprising the amino acid sequence of SEQ ID NO: 17.

10. The bispecific agonistic CD28 antigen binding molecule of claim 9, wherein the antigen binding domain capable of specific binding to Her2 comprises a heavy chain variable region (V$_H$Her2) comprising the amino acid sequence of SEQ ID NO:16, and a light chain variable region (V$_L$Her2) comprising the amino acid sequence of SEQ ID NO:17.

11. The bispecific agonistic CD28 antigen binding molecule of claim 1, wherein the antigen binding domain capable of specific binding to Her2 comprises the CDRs of the heavy chain variable region (V$_H$Her2) comprising the amino acid sequence of SEQ ID NO:138 and the CDRs of the light chain variable region (V$_L$Her2) comprising the amino acid sequence of SEQ ID NO: 139.

12. The bispecific agonistic CD28 antigen binding molecule of claim 11, wherein the antigen binding domain capable of specific binding to Her2 comprises a heavy chain variable region (V$_H$Her2) comprising the amino acid sequence of SEQ ID NO: 138, and a light chain variable region (V$_L$Her2) comprising the amino acid sequence of SEQ ID NO: 139.

13. The bispecific agonistic CD28 antigen binding molecule of claim 1, wherein the antigen binding domain capable of specific binding to Her2 comprises the CDRs of the heavy chain variable region (V$_H$Her2) comprising the amino acid sequence of SEQ ID NO:146 and the CDRs of the light chain variable region (V$_L$Her2) comprising the amino acid sequence of SEQ ID NO:147.

14. The bispecific agonistic CD28 antigen binding molecule of any one of claim 1 or 13, wherein the antigen binding domain capable of specific binding to Her2 comprises a heavy chain variable region (V$_H$Her2) comprising the amino acid sequence of SEQ ID NO:146, and a light chain variable region (V$_L$Her2) comprising the amino acid sequence of SEQ ID NO: 147.

15. The bispecific agonistic CD28 antigen binding molecule of any one of claim 1, wherein the first antigen binding domain capable of specific binding to CD28 or the second antigen binding domain capable of specific binding to Her2 is a Fab molecule, or both the first and second antigen binding domains are Fab molecules.

16. The bispecific agonistic CD28 antigen binding molecule of claim 1, wherein the first antigen binding domain capable of specific binding to CD28 is a Fab molecule wherein the variable domains VL and VH or the constant domains CL and CH1 of the Fab light chain and the Fab heavy chain are replaced by each other.

17. The bispecific agonistic CD28 antigen binding molecule of claim 1, wherein the second antigen binding domain capable of specific binding to Her2 is a conventional Fab molecule.

18. The bispecific agonistic CD28 antigen binding molecule of any one of claim 1, wherein the second antigen binding domain capable of specific binding to Her2 is a Fab molecule
   wherein in the constant domain CL the amino acid at position 123 is substituted by an amino acid selected from lysine (K), arginine (R) or histidine (H) and the amino acid at position 124 is substituted independently by lysine (K), arginine (R) or histidine (H), and
   wherein in the constant domain CH1 the amino acid at position 147 is substituted independently by glutamic acid (E) or aspartic acid (D) and the amino acid at position 213 is substituted independently by glutamic acid (E), or aspartic acid (D), wherein the numbering in each case is according to the Kabat EU index.

19. The bispecific agonistic CD28 antigen binding molecule of claim 1, comprising
   (i) a first light chain comprising the amino acid sequence of SEQ ID NO:179, a first heavy chain comprising the amino acid sequence of SEQ ID NO:178, a second heavy chain comprising the amino acid sequence of SEQ ID NO:180 and a second light chain comprising the amino acid sequence of SEQ ID NO:181, or
   (ii) a first light chain comprising the amino acid sequence of SEQ ID NO:179, a first heavy chain comprising the amino acid sequence of SEQ ID NO:178, a second heavy chain comprising the amino acid sequence of SEQ ID NO:182 and a second light chain comprising the amino acid sequence of SEQ ID NO:183.

20. The bispecific agonistic CD28 antigen binding molecule of claim 1, wherein the second antigen binding domain capable of specific binding to Her2 is a Fab molecule wherein the variable domains VL and VH or the constant domains CL and CH1 of the Fab light chain and the Fab heavy chain are replaced by each other.

21. The bispecific agonistic CD28 antigen binding molecule of any one of claim 1 or 20, wherein the first antigen binding domain capable of specific binding to CD28 is a conventional Fab molecule.

22. The bispecific agonistic CD28 antigen binding molecule of any one of claims 1, 2, 6, 7-13, 15-18, 19, or 20, wherein the first antigen binding domain capable of specific binding to CD28 is a Fab molecule
   wherein in the constant domain CL the amino acid at position 123 is substituted by an amino acid selected from lysine (K), arginine (R) or histidine (H) and the amino acid at position 124 is substituted independently by lysine (K), arginine (R) or histidine (H), and
   wherein in the constant domain CH1 the amino acid at position 147 is substituted independently by glutamic acid (E) or aspartic acid (D) and the amino acid at position 213) is substituted independently by glutamic acid (E), or aspartic acid (D).

23. The bispecific agonistic CD28 antigen binding molecule of claim 1, comprising
   (i) a first light chain comprising the amino acid sequence of SEQ ID NO:83, a first heavy chain comprising the amino acid sequence of SEQ ID NO:74, a second heavy chain comprising the amino acid sequence of SEQ ID NO:99 and a second light chain comprising the amino acid sequence of SEQ ID NO: 100, or
   (ii) a first light chain comprising the amino acid sequence of SEQ ID NO:83, a first heavy chain comprising the amino acid sequence of SEQ ID NO:74, a second heavy chain comprising the amino acid sequence of SEQ ID NO:102 and a second light chain comprising the amino acid sequence of SEQ ID NO:100.

24. The bispecific agonistic CD28 antigen binding molecule of claim 1, wherein the first and the second antigen binding domains are each a Fab molecule and the Fc domain is composed of a first and a second subunit capable of stable association; and wherein
   (i) the first antigen binding domain is fused at the C-terminus of the Fab heavy chain to the N-terminus of the first subunit of the Fc domain and the second antigen binding domain is fused at the C-terminus of the Fab heavy chain to the N-terminus of the second subunit of the Fc domain, or
   (ii) the second antigen binding domain is fused at the C-terminus of the Fab heavy chain to the N-terminus of the first subunit of the Fc domain and the first antigen binding domain is fused at the C-terminus of the Fab heavy chain to the N-terminus of the second subunit of the Fc domain.

25. The bispecific agonistic CD28 antigen binding molecule of claim 1, wherein the Fc domain comprises a modification promoting the association of the first and the second subunit of the Fc domain.

26. The bispecific agonistic CD28 antigen binding molecule claim 1, wherein the first subunit of the Fc domain comprises the amino acid substitutions S354C and/or T366W, according to EU numbering and the second subunit of the Fc domain comprises the amino acid substitutions Y349C, T366S and Y407V, wherein in each case the numbering is according to the Kabat EU index.

27. One or more isolated polynucleotides encoding the bispecific agonistic CD28 antigen binding molecule of claim 1.

28. One or more vectors, comprising the one or more polynucleotides of claim 27.

29. A host cell comprising the one or more polynucleotides of claim 27 or the one or more vectors of claim 28.

30. A method of producing a bispecific agonistic CD28 antigen binding molecule, comprising culturing the host cell of claim 29 under conditions suitable for the expression of the bispecific agonistic CD28 antigen binding molecule.

31. A bispecific agonistic CD28 antigen binding molecule produced by the method of claim 30.

32. A pharmaceutical composition comprising the bispecific agonistic CD28 antigen binding molecule of claim 1 and at least one pharmaceutically acceptable excipient.

33. The bispecific agonistic CD28 antigen binding molecule of claim 16, wherein the variable domains VL and VH of the Fab light chain and the Fab heavy chain are replaced by each other.

34. The bispecific agonistic CD28 antigen binding molecule of claim 20, wherein the second antigen binding domain capable of specific binding to Her2 is a Fab molecule wherein the variable domains VL and VH of the Fab light chain and the Fab heavy chain are replaced by each other.

35. The one or more vectors of claim 28, wherein the one or more vectors are expression vectors.

36. The method of producing a bispecific agonistic CD28 antigen binding molecule of claim 30, further comprising recovering the expressed bispecific agonistic CD28 antigen binding molecule.

37. A bispecific agonistic CD28 antigen binding molecule produced by the method of claim 36.

\* \* \* \* \*